United States Patent
Hillebrand et al.

(10) Patent No.: US 9,023,844 B2
(45) Date of Patent: May 5, 2015

(54) HETEROCYCLYLPYRI (MI) DINYLPYRAZOLE AS FUNGICIDALS

(71) Applicant: Bayer Intellectual Property GmbH, Monheim (DE)

(72) Inventors: Stefan Hillebrand, Neuss (DE); Amos Mattes, Langenfeld (DE); Alexander Sudau, Langenfeld (DE); Pierre Wasnaire, Düsseldorf (DE); Jürgen Benting, Leichlingen (DE); Peter Dahmen, Neuss (DE); Ulrike Wachendorff-Neumann, Neuwied (DE); Haruko Sawada, Langenfeld (DE); Philippe Desbordes, Lyons (FR); Anne-Sophie Rebstock, Lyons (FR); Stéphane Brunet, Saint André de Corcy (FR); Hélène Lachaise, Lyons (FR); Philippe Rinolfi, Châtillon d'Azergues (FR)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/349,144

(22) PCT Filed: Oct. 4, 2012

(86) PCT No.: PCT/EP2012/069561
§ 371 (c)(1),
(2) Date: Apr. 2, 2014

(87) PCT Pub. No.: WO2013/050437
PCT Pub. Date: Apr. 11, 2013

(65) Prior Publication Data
US 2014/0256677 A1    Sep. 11, 2014

(30) Foreign Application Priority Data
Oct. 6, 2011    (EP) .................................. 11184137

(51) Int. Cl.
| | | |
|---|---|---|
| *C07D 471/04* | (2006.01) | |
| *C07D 487/04* | (2006.01) | |
| *C07D 498/04* | (2006.01) | |
| *A01N 43/90* | (2006.01) | |
| *C07D 513/04* | (2006.01) | |
| *A01N 53/00* | (2006.01) | |
| *A01N 55/00* | (2006.01) | |

(52) U.S. Cl.
CPC .............. *A01N 43/90* (2013.01); *C07D 471/04* (2013.01); *C07D 487/04* (2013.01); *C07D 498/04* (2013.01); *C07D 513/04* (2013.01); *A01N 53/00* (2013.01); *A01N 55/00* (2013.01)

(58) Field of Classification Search
CPC .. C07D 471/04; C07D 487/04; C07D 498/04; C07D 513/04; A01N 43/90; A01N 53/00; A01N 55/00

USPC .............. 544/91, 281; 546/271.7; 514/230.5, 514/259.3, 338
See application file for complete search history.

(56) References Cited

U.S. PATENT DOCUMENTS

2013/0281455 A1    10/2013 Sudau et al.

FOREIGN PATENT DOCUMENTS

| EP | 1 553 096 | 7/2005 |
|---|---|---|
| EP | 2 308 866 | 4/2011 |
| EP | 2 402 337 | 1/2012 |
| EP | 2 402 338 | 1/2012 |

(Continued)

OTHER PUBLICATIONS

Townes et al. "The Development of New Bicyclic Pyrazole-Based Cytokine Synthesis Inhibitors", Bioorg. Med. Chem. Lett. (2004) vol. 14, pp. 4945-4948.

(Continued)

*Primary Examiner* — Deepak Rao
(74) *Attorney, Agent, or Firm* — Miles & Stockbridge P.C.

(57) ABSTRACT

Heterocyclylpyri(mi)dinylpyrazole of the formula (I)

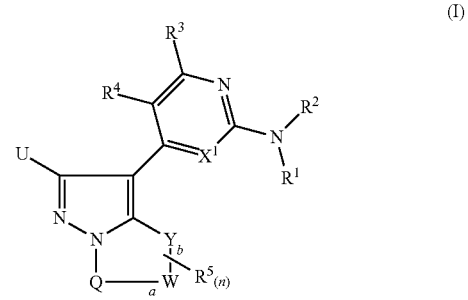

(I)

in which $R^1$ to $R^5$, $X^1$, U, Q, W, Y, n, a, b have the meanings given in the description, and agrochemically active salts, to their use and to methods and compositions for controlling phytopathogenic harmful fungi in and/or on plants or in and/or on seed of plants and for reducing mycotoxins in plants and parts of the plants, to processes for preparing such compounds and compositions and treated seed and also to their use for controlling phytopathogenic harmful fungi in agriculture, horticulture, forestry, in animal husbandry, in the protection of materials, in the domestic and hygiene field and for the reduction of mycotoxins in plants and parts of the plants.

7 Claims, No Drawings

(56) References Cited

FOREIGN PATENT DOCUMENTS

| | | |
|---|---|---|
| EP | 2 402 339 | 1/2012 |
| EP | 2 402 340 | 1/2012 |
| EP | 2 402 343 | 1/2012 |
| EP | 2 402 344 | 1/2012 |
| EP | 2 402 345 | 1/2012 |
| WO | 95/31451 | 11/1995 |
| WO | 98/52937 | 11/1998 |
| WO | 98/52940 | 11/1998 |
| WO | 00/31063 | 6/2000 |
| WO | 00/39116 | 7/2000 |
| WO | 01/30154 | 5/2001 |
| WO | 02/057265 | 7/2002 |
| WO | 03/049542 | 6/2003 |
| WO | 03/095455 | 11/2003 |
| WO | 2004/029043 | 4/2004 |
| WO | 2009/076440 | 6/2009 |
| WO | WO 2010/070060 * | 6/2010 |

OTHER PUBLICATIONS

Gudmundsson et al. "Pyrazolopyrimidines and Pyrazolotriazines With Potent Activity Against Herpesvirus" Bioorg. Med.Chem. Lett. (2009) vol. 19, pp. 5689-5692.

* cited by examiner

HETEROCYCLYLPYRI (MI) DINYLPYRAZOLE AS FUNGICIDALS

CROSS REFERENCE TO RELATED APPLICATIONS

This application is a §371 National Stage Application of PCT/EP2012/069561, filed Oct. 4, 2012, which claims priority to EP 11184137.5, filed Oct. 6, 2011.

BACKGROUND

1. Field of the Invention

The invention relates to novel Heterocyclylpyri(mi)dinylpyrazole and their agrochemically active salts, to their use and to methods and compositions for controlling phytopathogenic harmful fungi in and/or on plants or in and/or on seed of plants and for reducing mycotoxins in plants and parts of the plants, to processes for preparing such compounds and compositions and treated seed and also to their use for controlling phytopathogenic harmful fungi in agriculture, horticulture, forestry, in animal husbandry, in the protection of materials, in the domestic and hygiene field and for the reduction of mycotoxins in plants and parts of the plants.

2. Description of Related Art

It is already known that certain Arylpyrazoles can be employed as fungicidal crop protection agents (see WO 2009/076440, WO 2003/49542, WO 2001/30154, EP-A 2 402 337, EP-A 2 402 338, EP-A 2 402 339, EP-A 2 402 340, EP-A 2 402 343, EP-A 2 402 344 and EP-A 2 40 2345). However, the fungicidal activity of these compounds is, in particular at low application rates, not always sufficient.

Since the ecological and economic demands made on modern crop protection agents are increasing constantly, for example with respect to activity spectrum, toxicity, selectivity, application rate, formation of residues and favourable manufacture, and there can furthermore be problems, for example, with resistance, there is a constant need to develop novel crop protection agents, in particular fungicides which, at least in some areas, have advantages over the known fungicides.

Surprisingly, it has now been found that the present Heterocyclylpyri(mi)dinylpyrazole solve at least in some aspects the problems mentioned above and are suitable for use as crop protection agents, in particular as fungicides.

Some Arylazoles are already known as pharmaceutically active compounds (see for example WO 1998/52937, EP-A 1 553 096, WO 2004/29043, WO 1998/52940, WO 2000/31063, WO 1995/31451, WO 2002/57265 and WO 2000/39116, *Bioorg. Med. Chem. Lett.* 2004, 14, 19, 4945-4948), but not their surprising fungicidal activity.

SUMMARY

The invention provides compounds of the formula (I),

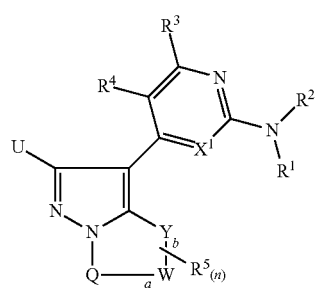

in which the symbols have the following meanings:
U represents structures of the general formula

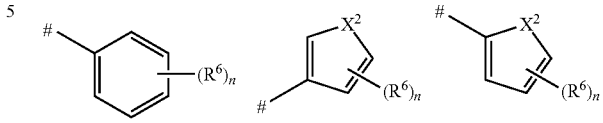

$X^1$ represents C—H or N, $X^2$ represents S or O,

Y represents O, S or N with N being optionally substituted by $R^5$,

W represents C, N each of which is optionally substituted by identical or different substituents from the group consisting of $R^5$ or represents O if Y equals N, a,b represent a single or double bond
with the proviso that "a" and "b" represent a single bond if W equals O, "a" represents a single bond if Q equals C═C or C—Si and "b" represents a single bond if Y equals O or S, n is 0, 1, 2, 3 or 4, Q represents C, C—C, C═C, C—Si or C—C—C, each of which is optionally mono or polysubstituted by identical or different substituents from the group consisting of $R^5$, $R^1$ represents H, $C(O)OR^7$, $C(O)SR^7$, $C(S)OR^7$, $C(O)R^7$, $C(S)R^7$, $C(O)NR^7R^8$, $C(S)NR^7R^8$, $C(O)C(O)R7$, $C(=NR^9)R^{10}$, $C(=NR^9)OR^{10}$, $C(=NR^9)NR^9R^{10}$, $SO(=NR^9)R^{10}$, $SO_2NR^7R^8$, $SO_2R^7$ or represents $C_1$-$C_6$-alkyl, $C_3$-$C_8$-cycloalkyl, $C_2$-$C_6$-alkenyl, $C_2$-$C_8$-alkynyl, $C_6$-$C_{14}$-aryl, $C_2$-$C_9$-heterocyclyl, $C_2$-$C_9$-heteroaryl, each of which is optionally mono- or polysubstituted by identical or different substituents from the group consisting of $R^{11}$, $R^2$ represents H, cyano, formyl, $OR^7$, $SR^7$, $C(O)OR^7$, $C(O)SR^7$, $C(S)OR^7$, $C(O)R^7$, $C(S)R^7$ or represents $C_1$-$C_6$-alkyl, $C_3$-$C_8$-cycloalkyl, $C_2$-$C_6$-alkenyl, $C_2$-$C_8$-alkynyl, $C_6$-$C_{14}$-aryl, $C_2$-$C_9$-heterocyclyl, $C_2$-$C_9$-heteroaryl, each of which is optionally mono- or polysubstituted by identical or different substituents from the group consisting of $R^{11}$, with the proviso that $R^1$ is not H, $C_1$-$C_6$-alkyl, $C_3$-$C_8$-cycloalkyl, $C_1$-$C_6$-haloalkyl, $C_3$-$C_8$-halocycloalkyl, $C_1$-$C_4$-alkoxy-C1-$C_6$-alkyl or amino-$C_1$-$C_6$-alkyl if $R^2$ is H, $C_1$-$C_6$-alkyl, $C_3$-$C_8$-cycloalkyl, $C_1$-C6-haloalkyl, $C_3$-$C_8$-halocycloalkyl, $C_1$-$C_4$-alkoxy-$C_1$-$C_6$-alkyl or amino-$C_1$-$C_6$-alkyl and vice-versa, $R^3$ and $R^4$ represent independently of each other H, F, Cl, Br, I, cyano, nitro, OH, SH or represent $C_1$-$C_6$-alkyl, $C_3$-$C_6$-cycloalkyl, $C_2$-$C_6$-alkenyl, $C_2$-$C_6$-alkinyl, $C_6$-$C_{14}$-aryl, $C_1$-$C_4$-alkoxy, O—($C_6$-$C_{14}$-aryl), S—($C_1$-$C_4$-alkyl), S(O)—($C_1$-$C_6$-alkyl), C(O)—($C_1$-$C_6$-alkyl), $C_3$-$C_8$-trialkylsilyl, heteroaryl, heterocyclyl, each of which is optionally mono- or polysubstituted by identical or different substituents from the group consisting of $R^{11}$ or form together with the carbon atoms, which they are attached to, an optionally mono- or multi identical or different by halogen, oxygen, cyano or $C_1$-$C_4$-alkyl, $C_1$-$C_4$-alkoxy, $C_1$-$C_6$-haloalkyl, $C_1$-$C_4$-haloalkoxy, $C_3$-$C_6$-cycloalkyl substituted cycle with 5 to 8 ring atoms, whereas the cycle consists of carbon atoms but may also contain 1 to 4 heteroatoms selected from oxygen, sulphur or $NR^{14}$, $R^5$ represents as substituent for C: H, Cyano, Halogen, OH, =O, $C_1$-$C_6$-alkyl, $C_2$-$C_6$-alkenyl, $C_2$-$C_6$-alkinyl, $C_1$-$C_6$-alkoxy, $C_3$-$C_6$-cycloalkyl, $C_3$-$C_8$-allenyl, $C_3$-$C_8$-trialkylsilyl, $C_4$-$C_8$-cycloalkenyl, $C_1$-$C_6$-alkoxy-$C_1$-$C_6$-alkyl, acyloxy-$C_1$-$C_6$-alkyl, heteroaryl-$C_1$-$C_6$-alkyl, aryl-$C_1$-$C_6$-alkyl, $C_1$-$C_6$-alkylthio-$C_1$-$C_6$-alkyl, $C_1$-$C_4$-alkyl-C(O)—$C_1$-$C_6$-alkyl, $C_3$-$C_6$-cycloalkyl-C(O)—$C_1$-$C_4$-alkyl, heterocyclyl-C(O)—$C_1$-$C_4$-alkyl, $C_1$-$C_4$-alkyl-C(O)O—$C_1$-$C_6$-alkyl, $C_3$-$C_6$-cycloalkyl-C(O)O—$C_1$-$C_4$-alkyl, heterocyclyl-C(O)O—$C_1$-$C_4$-alkyl, heterocyclyl-$C_1$-$C_6$-alkyl, $C_6$-$C_{10}$-aryl, heterocyclyl, heteroaryl, each of which is optionally mono- or polysubstituted by identical or different substituents from the group consisting of OH, F, Cl, Br, I, cyano, NH—C(O)$R^9$, $NR^9R^{10}$, C(O)$R^9$, C(O)O$R^9$, C(O)$NR^9R^{10}$, $SO_2R^9$, OC(O)$R^9$ or represents C(O)$NR^9R^{10}$, C(O)$R^9$, C(O)O$R^9$, $S(O)_2R^9$, C(S)$NR^9R^{10}$, C(S)$R^9$, $S(O)_2NR^9R^{10}$, =N(O$R^9$)

and represents as substituent for N: H, OH, $C_1$-$C_6$-alkyl, $C_2$-$C_6$-alkenyl-$C_1$-$C_6$-alkyl, $C_2$-$C_6$-alkinyl-$C_1$-$C_6$-alkyl, $C_1$-$C_6$-alkoxy, $C_3$-$C_6$-cycloalkyl, $C_1$-$C_6$-alkoxy-$C_1$-$C_6$-alkyl, acyloxy-$C_1$-$C_6$-alkyl, heteroaryl-$C_1$-$C_6$-alkyl, aryl-$C_1$-$C_6$-alkyl, $C_1$-$C_6$-alkylthio-$C_1$-$C_6$-alkyl, $C_1$-$C_4$-alkyl-C(O)—$C_1$-$C_6$-alkyl, $C_3$-$C_6$-cycloalkyl-C(O)—$C_1$-$C_4$-alkyl, heterocyclyl-C(O)—$C_1$-$C_4$-alkyl, $C_1$-$C_4$-alkyl-C(O)O—$C_1$-$C_6$-alkyl, $C_3$-$C_6$-cycloalkyl-C(O)O—$C_1$-$C_4$-alkyl, heterocyclyl-C(O)O—$C_1$-$C_4$-alkyl, heterocyclyl-$C_1$-$C_6$-alkyl, $C_6$-$C_{10}$-aryl, heterocyclyl, heteroaryl, each of which is optionally mono- or polysubstituted by identical or different substituents from the group consisting of OH, F, Cl, Br, I, cyano, NH—C(O)$R^9$, $NR^9R^{10}$, C(O)$R^9$, C(O)O$R^9$, C(O)$NR^9R^{10}$, $SO_2R^9$, OC(O)$R^9$ or represents C(O)$NR^9R^{10}$, C(O)$R^9$, C(O)O$R^9$, $S(O)_2R^9$, C(S)$NR^9R^{10}$, C(S)$R^9$, $S(O)_2NR^9R^{10}$, $R^6$ represents H, cyano, halogen or represents $C_1$-$C_6$-alkyl, $C_3$-$C_6$-cycloalkyl, heterocyclyl, $C_2$-$C_8$-alkenyl, $C_2$-$C_8$-alkinyl, $C_1$-$C_8$-alkoxy, $C_2$-$C_8$-alkynyloxy, $C_1$-$C_8$-alkylthio, $C_3$-$C_8$-trialkylsilyl, each of which is optionally mono- or polysubstituted by identical or different substituents from the group consisting of OH, F, Cl, cyano, $R^7$ and $R^8$ represent H, C(S)$R^{12}$, C(O)$R^{12}$, $SO_2R^{12}$, C(O)O$R^{12}$, O$R^{12}$ or C(O)$NR^{12}R^{13}$ or represent $C_1$-$C_6$-alkyl, $C_2$-$C_6$-alkenyl, $C_2$-$C_6$-alkinyl, $C_3$-$C_8$-cycloalkyl, $C_3$-$C_8$-cycloalkenyl, having a two to eight atoms long bridge containing C and O atoms in which two O atoms never follow one another, $C_6$-$C_{14}$-aryl, benzyl, phenethyl, indanyl, aryloxyalkyl, heteroaryloxyalkyl, heterocyclyl or heteroaryl, each of which is optionally mono- or polysubstituted by identical or different substituents from the group consisting of F, Cl, Br, OH, =O, cyano, nitro, $C_1$-$C_6$-alkyl, $C_3$-$C_8$-cycloalkyl, $C_1$-$C_6$-halogenalkyl, O—C(O)$R^9$, O—P(O)(O$R^9$)$_2$, O—B(O$R^9$)$_2$ or O—($C_1$-$C_4$-alkyl), O—($C_3$-$C_8$-cycloalkyl), S—($C_1$-$C_4$-alkyl), SO—($C_1$-$C_4$-alkyl), $SO_2$—($C_1$-$C_4$-alkyl), piperidin, $C_1$-$C_6$-alkylsulfinyl, ($C_1$-$C_6$-alkyl ideneamino)oxy, aryl, heteroaryl, heterocyclyl, alkoxyalkyloxy, NHC(O)H, C(O)$R^9$, C(O)O$R^9$ which is optionally mono- or polysubstituted by identical or different substituents from the group consisting of F, Cl, Br, OH, cyano, $C_1$-$C_6$-alkyl, $R^9$ and $R^{10}$ represent $C_1$-$C_6$-alkyl, $C_3$-$C_6$-cycloalkyl, $C_2$-$C_6$-alkenyl, $C_2$-$C_6$-alkinyl, aryl, benzyl, phenethyl, each of which is optionally mono- or polysubstituted by identical or different substituents from the group consisting of F, Cl, Br, I, OH, carbonyl, cyano or represent H, $R^{11}$ represents OH, F, Cl, Br, I, cyano, =O, NH—C(O)$R^9$, $NR^9R^{10}$, C(O)$R^9$, C(O)O$R^9$, C(O)$NR^9R^{10}$, $SO_2R^9$, OC(O)$R^9$ or represents $C_1$-$C_6$-alkyl, $C_2$-$C_6$-alkenyl, $C_2$-$C_6$-alkinyl, $C_3$-$C_8$-cycloalkyl, $C_1$-$C_4$-alkoxy, $C_1$-$C_4$-alkylthio, O—($C_3$-$C_8$-cycloalkyl), S—($C_3$-$C_8$-cycloalkyl), $C_6$-$C_{14}$-aryl, O—($C_6$-$C_{14}$-aryl), S—($C_6$-$C_{14}$-aryl), heterocyclyl or heteroaryl, each of which is optionally mono- or polysubstituted by identical or different substituents from the group consisting of F, Cl, Br, I, OH, carbonyl, cyano, $C_1$-$C_6$-alkyl or $C_1$-$C_4$-alkoxy, $R^{12}$ and $R^{13}$ represent H or represents $C_1$-$C_6$-alkyl, $C_3$-$C_6$-cycloalkyl, $C_2$-$C_6$-alkenyl, $C_2$-$C_6$-alkenyl, $C_3$-$C_8$-cycloalkyl, $C_6$-$C_{14}$-aryl, heterocyclyl or heteroaryl, each of which is optionally mono- or polysubstituted by identical or different substituents from the group consisting of F, Cl, Br, I, OH, carbonyl, cyano, $C_1$-$C_6$-alkyl or $C_1$-$C_4$-alkoxy, $R^{14}$ represents H, $C_1$-$C_6$-alkyl, $C_3$-$C_6$-cycloalkyl, $C_2$-$C_6$-alkenyl, $C_2$-$C_6$-alkenyl, C(S)$R^{15}$, C(O)$R^{15}$, $SO_2R^{15}$, C(O)O$R^{15}$, $R^{15}$ represent H or represents $C_1$-$C_6$-alkyl, $C_3$-$C_6$-cycloalkyl, $C_2$-$C_6$-alkenyl, $C_2$-$C_6$-alkenyl, $C_3$-$C_8$-cycloalkyl, $C_6$-$C_{14}$-aryl, benzyl, phenethyl, phenoxymethyl, heterocyclyl or heteroaryl, each of which is optionally mono- or polysubstituted by identical or different substituents from the group consisting of F, Cl, Br, I, OH, carbonyl, cyano, methyl, ethyl, n-propyl, iso-propyl, n-butyl, iso-butyl, sec-butyl, tert-butyl, n-pentyl, cyclopropyl, or methoxy, ethoxy, n-propoxy, iso-propoxy, n-butoxy, tert-butoxy, methylsulfanyl, nitro, trifluormethyl, difluoromethyl, C(O)$R^{12}$, C(O)O$R^{12}$, C(O)$NR^{12}R^{13}$, $SO_2R^{12}$, OC(O)$R^{12}$ and also agrochemically active salts thereof.

The invention also provides the use of the compounds of the formula (I) as fungicides.

DETAILED DESCRIPTION OF A PREFERRED EMBODIMENT

Heterocyclylpyri(mi)dinylpyrazole of the formula (I) according to the invention and also their agrochemically active salts are highly suitable for controlling phytopathogenic harmful fungi and for the reduction of mycotoxins. The compounds according to the invention mentioned above have in particular strong fungicidal activity and can be used both in crop protection, in the domestic and hygiene field, in the protection of materials and for the reduction of mycotoxins in plants and parts of the plants.

The compounds of the formula (I) can be present both in pure form and as mixtures of various possible isomeric forms, in particular of stereoisomers, such as E and Z, threo and erythro, and also optical isomers, such as R and S isomers or atropisomers, and, if appropriate, also of tautomers. What is claimed are both the E and the Z isomers, and the threo and erythro, and also the optical isomers, mixtures of these isomers, and also the possible tautomeric forms.

Preference is given to compounds of the formula (I) in which one or more of the symbols have one of the meanings below:

U represents structures of the general formula

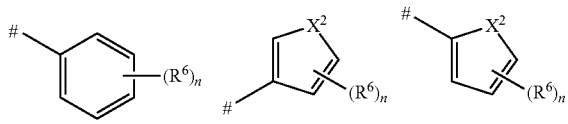

$X^1$ represents C—H,
$X^2$ represents S or O,
Y represents O or N with N being optionally substituted by $R^5$,
W represents C, N each of which is optionally substituted by identical or different substituents from the group consisting of $R^5$
or represents O if Y equals N,
a,b represent a single or double bond
  with the provisio that "a" and "b" represent a single bond if W equals O, "a" represents a single bond if Q equals C=C or C—Si and "b" represents a single bond if Y equals O,
n is 0, 1, 2, 3 or 4,
Q represents C, C—C, C=C, C—Si or C—C—C, each of which is optionally mono or polysubstituted by identical or different substituents from the group consisting of $R^5$,
$R^1$ represents H, C(O)O$R^7$, C(O)S$R^7$, C(S)O$R^7$, C(O)$R^7$, C(S)$R^7$, C(O)C(O)R7, C(O)N$R^7R^8$, C(S)N$R^7R^8$, C(=N$R^9$)$R^{10}$, C(=N$R^9$)O$R^{10}$, C(=N$R^9$)N$R^9R^{10}$, SO(=N$R^9$)$R^{10}$, SO$_2$N$R^7R^8$, SO$_2R^7$
or represents methyl, ethyl, n-propyl, iso-propyl, n-butyl, iso-butyl, sec-butyl, tert-butyl, n-pentyl, cyclopropyl, cyclobutyl, cyclopentyl, cyclohexyl, —CH$_2$CH=CH$_2$, —C≡CH, —C≡CCH$_3$, —CH$_2$C≡CH, $C_6$-$C_{14}$-aryl, $C_2$-$C_9$-heterocyclyl, $C_2$-$C_9$-heteroaryl, each of which is optionally mono- or polysubstituted by identical or different substituents from the group consisting of $R^{11}$,
$R^2$ represents H, C(O)O$R^7$, C(O)S$R^7$, C(S)O$R^7$, C(O)$R^7$, C(S)$R^7$
or represents $C_1$-$C_6$-alkyl, $C_3$-$C_8$-cycloalkyl, $C_2$-$C_6$-alkenyl, $C_2$-$C_8$-alkynyl, $C_6$-$C_{14}$-aryl, $C_2$-$C_9$-heterocyclyl, $C_2$-$C_9$-heteroaryl, each of which is optionally mono- or polysubstituted by identical or different substituents from the group consisting of $R^{11}$,
with the provisio that $R^1$ is not H, $C_1$-$C_6$-alkyl, $C_3$-$C_8$-cycloalkyl, $C_1$-$C_6$-haloalkyl, $C_3$-$C_8$-halocycloalkyl, $C_1$-$C_4$-alkoxy-C1-$C_6$-alkyl or amino-$C_1$-$C_6$-alkyl if $R^2$ is H, $C_1$-$C_6$-alkyl, $C_3$-$C_8$-cycloalkyl, $C_1$-C6-haloalkyl, $C_3$-$C_8$-halocycloalkyl, $C_1$-$C_4$-alkoxy-$C_1$-$C_6$-alkyl or amino-$C_1$-$C_6$-alkyl and vice-versa,
$R^3$ and $R^4$ represent independently of each other H, F, Cl, Br, I, cyano
or represents methyl, ethyl, cyclopropyl, —CH=CH$_2$, —CH$_2$CH=CH$_2$, —CH$_2$C≡CH, —C≡CH, phenyl, methoxy, each of which is optionally mono- or polysubstituted by identical or different substituents from the group consisting of $R^{11}$,
$R^5$ represents as substituent for C: H, Cyano, Halogen, OH, =O, methyl, ethyl, n-propyl, iso-propyl, n-butyl, iso-butyl, sec-butyl, tert-butyl, n-pentyl, cyclopropyl, cyclobutyl, cyclopentyl, cyclohexyl, —CH$_2$CH=CH$_2$, —C≡CH, —C≡CCH$_3$, —CH$_2$C≡CH, methoxy, ethoxy, n-propoxy, iso-propoxy, n-butoxy, tert-butoxy, —O—CH$_2$C≡CH, each of which is optionally mono- or polysubstituted by identical or different substituents from the group consisting of OH, F, Cl, cyano
or represents C(O)N$R^9R^{10}$, C(O)$R^9$, C(O)O$R^9$, S(O)$_2R^9$, C(S)N$R^9R^{10}$, C(S)$R^9$, S(O)$_2$N$R^9R^{10}$, =N(O$R^9$)
and represents as substituent for N: H, methyl, ethyl, n-propyl, iso-propyl, n-butyl, iso-butyl, sec-butyl, tert-butyl, n-pentyl, cyclopropyl, cyclobutyl, cyclopentyl, cyclohexyl, —CH$_2$CH=CH$_2$, —C≡CH, —C≡CCH$_3$, —CH$_2$C≡CH, each of which is optionally mono- or polysubstituted by identical or different substituents from the group consisting of OH, F, Cl, cyano
or represents C(O)N$R^9R^{10}$, C(O)$R^9$, C(O)O$R^9$, S(O)$_2R^9$, C(S)N$R^9R^{10}$, C(S)$R^9$, S(O)$_2$N$R^9R^{10}$,
$R^6$ represents H, Cl, F, Cyano
or represents methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH$_2$, —CH$_2$CH=CH$_2$, —CH$_2$C≡CH, —C≡CH, methoxy, ethoxy, n-propoxy, iso-propoxy, n-butoxy, tert-butoxy, methylthio, ethylthio, n-propylthio, iso-propylthio, tertbutylthio, n-butylthio, sec-butylthio, iso-butylthio, each of which is optionally mono- or polysubstituted by identical or different substituents from the group consisting of $R^{11}$,
$R^7$ and $R^8$ represent H, C(S)$R^{12}$, C(O)$R^{12}$, SO$_2R^{12}$, C(O)O$R^{12}$, O$R^{12}$ or C(O)N$R^{12}R^{13}$
or represent methyl, ethyl, n-propyl, iso-propyl, n-butyl, iso-butyl, sec-butyl, tert-butyl, n-pentyl, cyclopropyl, cyclopropylmethyl, cyclobutyl, cyclopentyl, cyclohexyl, cyclopentenyl, cyclohexenyl, —CH=CH$_2$, —CH$_2$CH=CH$_2$, —CH$_2$C≡CH, —C≡CH, phenyl, naphthalenyl, benzyl, phenethyl, phenoxymethyl, pyridinyl, pyrazinyl, pyrimidinyl, furanyl, thienyl, thietanyl, oxetanyl, pyrazolyl, imidazolyl, tetrahydrofuranyl, tetrahydropyranyl, morpholinyl, pyrrolidinyl, piperidinyl, indanyl, dithiolanyl, dioxanyl, dioxolanyl, tetrahydrothiopyranyl, oxazolyl, isoxazolyl triazolyl each of which is optionally mono- or polysubstituted by identical or different substituents from the group consisting of F, Cl, Br, OH, =O, cyano, methyl, ethyl, n-propyl, iso-propyl, n-butyl, iso-butyl, sec-butyl, tert-butyl, n-pentyl, cyclopropyl, cyclobutyl, cyclopentyl, or methoxy, ethoxy, n-propoxy, iso-propoxy, n-butoxy, tert-butoxy, methylsulfanyl, methylsulfinyl, nitro, trifluormethyl, difluoromethyl, acetyl, methoxycarbonyl, ethoxycarbonyl, O—C(O)$R^9$, ($C_1$-$C_6$-alkyl ideneamino)oxy, aryl, heteroaryl, heterocyclyl, $C_1$-$C_3$-alkoxyethoxy, NHC(O)H
or cyclopropyl, cyclobutyl, cyclopentyl, cyclohexyl bridged by a two to eight atom containing chain,
$R^9$ and $R^{10}$ represent methyl, ethyl, n-propyl, iso-propyl, n-butyl, iso-butyl, sec-butyl, tert-butyl, n-pentyl, cyclopropyl, cyclobutyl, cyclopentyl, cyclohexyl, —CH=CH$_2$, —CH$_2$CH=CH$_2$, —CH$_2$C≡CH, —C≡CH, phenyl, benzyl, phenethyl each of which is optionally mono- or polysubstituted by identical or different substituents from the group consisting of F, Cl, Br, I, OH, carbonyl, cyano
or represent H,
$R^{11}$ represents OH, =O, F, Cl, Br, I, cyano, NH—C(O)$R^9$, N$R^9R^{10}$, C(O)$R^9$, C(O)O$R^9$, C(O)N$R^9R^{10}$, SO$_2R^9$, OC(O)$R^9$
or represents methyl, ethyl, n-propyl, iso-propyl, n-butyl, iso-butyl, sec-butyl, tert-butyl, n-pentyl, cyclopropyl, cyclobutyl, cyclopentyl, cyclohexyl, —CH=CH$_2$, —CH$_2$CH=CH$_2$, —CH$_2$C≡CH, —C≡CH, phenyl, methoxy, ethoxy, tetrahydrofuranyl, 3-tetrahydrofuranyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-Isoxazolin-4-yl, 4-Isoxazolin-4-yl, 2-Isoxazolin-5-yl, 3-Isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2-piperidinyl, 3-piperidinyl, 4-piperidinyl, 2-piperazinyl, furan-2-yl, furan-3-yl, thiophen-2-yl, thiophen-3-yl, isoxazol-3-yl, isoxazol-4-yl, isoxazol-5-yl, 1H-pyrrol-1-yl, 1H-pyrrol-2-yl, 1H-pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, Imidazol-1-yl, Imidazol-2-yl, Imidazol-4-yl, Pyridin-2-yl, Pyridin-3-yl, pyridin-4-yl, pyridazin-3-yl, pyridazin-4-yl, pyrimidin-2-yl, pyrimidin-4-yl, pyrimidin-5-yl, pyrazin-2-yl, each of which is optionally mono- or polysubstituted by identical or different substituents from the group consisting of F, Cl, Br, I, OH, carbonyl, cyano, methyl, ethyl, methoxy, $R^{12}$ and $R^{13}$ resent H or represents methyl, ethyl, n-propyl, iso-propyl, n-butyl, iso-butyl, sec-butyl, tert-butyl, n-pentyl, cyclopropyl, cyclobutyl, cyclopentyl, cyclohexyl, —CH=CH$_2$, —CH$_2$CH=CH$_2$, —CH$_2$C≡CH, —C≡CH, phenyl, each of which is optionally mono- or polysubstituted by identical or different substituents from the group consisting of F, Cl, Br, I, OH, carbonyl, cyano, methyl, ethyl, n-propyl, iso-propyl, n-butyl, iso-butyl, sec-butyl, tert-butyl, n-pentyl or methoxy, ethoxy, n-propoxy, iso-propoxy, n-butoxy, tert-butoxy, and also agrochemically active salts thereof.

Particular preference is given to compounds of the formula (I) in which one or more of the symbols have one of the meanings below:

U represents structures of the general formula $X^1$ represents C—H,
$X^2$ represents S or O,
Y represents O or N with N being optionally substituted by $R^5$,
W represents C, N each of which is optionally substituted by identical or different substituents from the group consisting of $R^5$
or represents O if Y equals N,
a,b represent a single or double bond
  with the provisio that "a" and "b" represent a single bond if W equals O, "a" represents a single bond if Q equals C=C or C—Si and "b" represents a single bond if Y equals O,
n is 0, 1, 2, 3 or 4
Q represents C, C—C, C—Si or C=C each of which is optionally mono or polysubstituted by identical or different substituents from the group consisting of $R^5$,
$R^1$ represents formamido, acetyl, n-propionyl, isobutyryl, 2-methylbutanoyl, 3-methylbutanoyl, 3,3-dimethylbutanoyl, methoxyacetyl, (2-methoxyethoxy)acetyl, 3,3,3-trifluoropropanoyl, cyanoacetyl, lactoyl, 2-hydroxy-2-methylpropanoyl, (methylsulfanyl)acetyl, 2-(4-chlorophenoxy)propanoyl, phenylacetyl, 2-phenylpropanoyl, 2-(4-fluorophenyl)propanoyl, 2-(3-fluorophenyl)propanoyl, 3-phenylpropanoyl, 3-(4-chlorophenyl)propanoyl, 2-(2-fluorophenyl)propanoyl, cyclopentylacetyl, cyclopropylacetyl, cyclopropylcarbonyl, (2-methylcyclopropyl)carbonyl, (1-chlorocyclopropyl)carbonyl, cyclobutylcarbonyl, 2,3-dihydro-1H-inden-2-ylcarbonyl, (2-phenylcyclopropyl)carbonyl, methacryloyl, 3-methylbut-2-enoyl, 4-methylpent-3-enoyl, benzoyl, 4-fluorobenzoyl, 3-thienylcarbonyl, 2-thienylcarbonyl, tetrahydrofuran-2-ylcarbonyl, tetrahydrofuran-3-ylcarbonyl, tetrahydro-2H-pyran-4-ylcarbonyl, tetrahydro-2H-pyran-3-ylcarbonyl, methoxycarbonyl, ethoxycarbonyl, isopropoxycarbonyl, tert-butoxycarbonyl, difluoroacetyl, trifluoroacetyl or $R^1$ represents 1-cyclopropyl-cyclopropylcarbonyl, cyclopentylcarbonyl, bicyclo[2.2.1]heptane-2-carbonyl, bicyclo[4.1.0]heptane-7-carbonyl, 2-propylpentanoyl, 1,3-dithiolan-2-ylcarbonyl, (2,2,3,3-tetramethylcyclopropyl)carbonyl, cyclohex-1-en-1-ylacetyl, (5-methyl-1,2-oxazol-3-yl)carbonyl, 3-(1H-1,2,3-triazol-1-yl)propanoyl, 2-[(isopropylideneamino)oxy]propanoyl, (3,5-dimethyl-1,2-oxazol-4-yl)carbonyl, 5-oxohexanoyl, (1-methylcyclopropyl)carbonyl, [(isopropylideneamino)oxy]acetyl, 1H-pyrazol-1-ylacetyl, tetrahydro-2H-pyran-3-ylacetyl, (1-methylcyclopentyl)carbonyl, (5-methyl-1,3-dioxan-5-yl)carbonyl, (1-cyanocyclopropyl)carbonyl, tetrahydro-2H-thiopyran-4-ylcarbonyl, 1,1'-bi(cyclopropyl)-1-ylcarbonyl, (3S)-3-methylpentanoyl, (3R)-3-methylpentanoyl, 3-fluoro-2-(fluoromethyl)-2-methylpropanoyl, (4-oxocyclohexyl)carbonyl, cyclopent-3-en-1-ylcarbonyl, 2-methyl-3-furoyl, 2,4-dimethylhexanoyl, (2-chloro-2-fluorocyclopropyl)carbonyl, 2-fluoro-2-methylpropanoyl, (5-fluoropyridin-3-yl)carbonyl, 2-fluoropropanoyl, (3-oxocyclopentyl)carbonyl, (1,5-dimethyl-1H-pyrazol-4-yl)carbonyl optionally substituted with OH, F, Cl, CN, O—$C_1$-$C_6$-alkyl, $C_1$-$C_6$-alkyl, $C_2$-$C_6$-alkenyl, $C_2$-$C_6$-alkinyl, $C_1$-$C_6$-haloalkyl, $C_2$-$C_6$-haloalkenyl, $C_1$-$C_6$—S-alkyl, $R^2$ represents H, Methyl, methylsulfanyl, methoxymethyl, difluoromethyl, 2-hydroxypropan-2-yl, hydroxymethyl, 2-hydroxyethyl, 2-cyanoethyl, Ethyl, n-propyl, methoxy, ethoxy, acetyl, n-propionyl, isobutyryl, cyclopropylacetyl, cyclopropylcarbonyl, difluoroacetyl, trifluoroacetyl, methoxycarbonyl, ethoxycarbonyl, isopropoxycarbonyl, propoxycarbonyl, sec-butoxycarbonyl optionally substituted with OH, F, Cl, CN, O—$C_1$-$C_6$-alkyl, $C_1$-$C_6$-alkyl, $C_2$-$C_6$-alkenyl, $C_2$-$C_6$-alkinyl, $C_1$-$C_6$-haloalkyl, $C_2$-$C_6$-haloalkenyl, $C_1$-$C_6$—S-alkyl, $R^3$ represents H, F, Cl, Methyl,
$R^4$ represents H, F, Cl, Methyl,
$R^5$ represents as substituent for C: H, Cyano, F, OH, =O, methyl, ethyl, n-propyl, iso-propyl, n-butyl, iso-butyl, sec-butyl, tert-butyl, cyclopropyl, each of which is optionally mono- or polysubstituted by identical or different substituents from the group consisting of OH, F, Cl, cyano
and represents as substituent for N: H, methyl, ethyl, n-propyl, iso-propyl, cyclopropyl, each of which is optionally mono- or polysubstituted by identical or different substituents from the group consisting of OH, F, Cl, cyano
or represents acetyl, propionyl, isobutyryl, methoxycarbonyl, ethoxycarbonyl, methylcarbamoyl, dimethylcarbamoyl, diethylcarbamoyl, methylsulfonyl, ethylsulfonyl $R^6$ represents H, Cl, F, methyl, ethyl, cyano, difluoromethyl, trifluoromethyl, and also agrochemically active salts thereof.

Very particular preference is given to compounds of the formula (I) in which one or more of the symbols have one of the meanings below:

U represents structures of the general formula

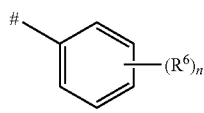

$X^1$ represents C—H,
Y represents O,
W represents C which is optionally substituted by identical or different substituents from the group consisting of $R^5$,
a and b represent a single bond,
n is 0, 1 or 2,
Q represents C or C—C, each of which is optionally mono or polysubstituted by identical or different substituents from the group consisting of $R^5$,
$R^1$ represents acetyl, n-propionyl, isobutyryl, 2-methylbutanoyl, 3-methylbutanoyl, lactoyl, phenylacetyl, cyclopropylacetyl, cyclopropylcarbonyl, 1-cyclopropyl-cyclopropylcarbonyl, cyclobutylcarbonyl, cyclopentylcarbonyl, bicyclo[2.2.1]heptane-2-carbonyl, bicyclo[4.1.0]heptane-7-carbonyl, (2-methylcyclopropyl)carbonyl, cyclobutylcarbonyl, tetrahydrofuran-3-ylcarbonyl, 3,3,3-trifluoropropanoyl, tetrahydro-2H-pyran-4-ylcarbonyl, 3-phenylpropanoyl, 2-phenylpropanoyl, 1,3-dithiolan-2-ylcarbonyl, 5-oxohexanoyl, (1-methylcyclopropyl)carbonyl, (4-oxocyclohexyl)carbonyl, 2-fluoro-2-methylpropanoyl, 2-fluoropropanoyl,
$R^2$ represents H, acetyl, n-propionyl, isobutyryl, cyclopropylacetyl, cyclopropylcarbonyl, methoxycarbonyl, ethoxycarbonyl, isopropoxycarbonyl, propoxycarbonyl, sec-butoxycarbonyl,
$R^3$ represents H,
$R^4$ represents H, F,
$R^5$ represents H, Cyano, F, OH, =O, methyl, ethyl, n-propyl, Cyclopropyl, Haloalkyl, Cyanoalkyl,
$R^6$ represents H, F
and also agrochemically active salts thereof.

Very particular preference is furthermore given to compounds of the formula (I) in which
$X^1$ represents CH,
where the other substituents have one or more of the meanings mentioned above
and to the agrochemically active salts thereof.

Very particular preference is furthermore given to compounds of the formula (I) in which
$R^1$ represents $C(O)R^7$, $C(O)OR^7$,
where the other substituents have one or more of the meanings mentioned above,
and to the agrochemically active salts thereof.

Very particular preference is furthermore given to compounds of the formula (I) in which
Y represents O
where the other substituents have one or more of the meanings mentioned above,
and to the agrochemically active salts thereof.

Very particular preference is furthermore given to compounds of the formula (I) in which
$R^2$ represents H, acetyl, n-propionyl, isobutyryl, cyclopropylacetyl, cyclopropylcarbonyl, cyclobutylcarbonyl, methoxycarbonyl, ethoxycarbonyl, isopropoxycarbonyl, propoxycarbonyl, sec-butoxycarbonyl
where the other substituents have one or more of the meanings mentioned above,
and to the agrochemically active salts thereof.

Very particular preference is furthermore given to compounds of the formula (I) in which
$R^3$ and $R^4$ represent H,
where the other substituents have one or more of the meanings mentioned above,
and to the agrochemically active salts thereof.

Very particular preference is furthermore given to compounds of the formula (I) in which
$R^6$ represents H, F, Cl, Methyl
where the other substituents have one or more of the meanings mentioned above,
and to the agrochemically active salts thereof.

Very particular preference is furthermore given to compounds of the formula (I) in which
W represents nitrogen
where the other substituents have one or more of the meanings mentioned above,
and to the agrochemically active salts thereof.

The radical definitions given above can be combined with one another as desired. Moreover, individual definitions may not apply.

Depending on the nature of the substituents defined above, the compounds of the formula (I) have acidic or basic properties and can form salts, if appropriate also inner salts, or adducts with inorganic or organic acids or with bases or with metal ions. If the compounds of the formula (I) carry amino, alkylamino or other groups which induce basic properties, these compounds can be reacted with acids to give salts, or they are directly obtained as salts in the synthesis. If the compounds of the formula (I) carries hydroxyl, carboxyl or other groups which induce acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having $(C_1-C_4)$-alkyl groups, mono-, di- and trialkanolamines of $(C_1-C_4)$-alkanols, choline and also chlorocholine.

The salts obtainable in this manner also have fungicidal properties.

Examples of inorganic acids are hydrohalic acids, such as hydrogen fluoride, hydrogen chloride, hydrogen bromide and hydrogen iodide, sulphuric acid, phosphoric acid and nitric acid, and acidic salts, such as $NaHSO_4$ and $KHSO_4$. Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulphonic acids (sulphonic acids having straight-chain or branched alkyl radicals of 1 to 20 carbon atoms), arylsulphonic acids or aryldisulphonic acids (aromatic radicals, such as phenyl and naphthyl, which carry one or two sulphonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphonic acid radicals), where the alkyl and aryl radicals may carry further substituents, for example p-toluenesulphonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminium, tin and lead, and also of the first to eighth transition group, in particular chromium, manganese, iron, cobalt, nickel, copper, zinc and others. Particular preference is given to the metal ions of the elements of the fourth period. Here, the metals can be present in various valencies that they can assume.

Optionally substituted groups may be mono- or polysubstituted, where in the case of polysubstitution the substituents may be identical or different.

In the definitions of the symbols given in the formulae above, collective terms were used which are generally representative for the following substituents:

halogen: fluorine, chlorine, bromine and iodine;

aryl: an unsubstituted or optionally substituted 6- to 14-membered partially or fully unsaturated mono-, bi- or tricyclic ring system having up to 3 ring members selected from the groups $C(=O)$, $(C=S)$, where at least one of the rings of the ring system is fully unsaturated, such as, for example (but not limited thereto) benzene, naphthalene, tetrahydronaphthalene, anthracene, indane, phenanthrene, azulene;

alkyl: saturated, straight-chain or branched hydrocarbon radicals having 1 to 8 carbon atoms, for example (but not limited thereto) $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

alkenyl: unsaturated, straight-chain or branched hydrocarbon radicals having 2 to 8 carbon atoms and a double bond in any position, for example (but not limited thereto) $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups having 2 to 8 carbon atoms and a triple bond in any position, for example (but not limited thereto) $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

alkoxy: saturated, straight-chain or branched alkoxy radicals having 1 to 8 carbon atoms, for example (but not limited thereto) $C_1$-$C_6$-alkoxy, such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

alkylthio: saturated, straight-chain or branched alkylthio radicals having 1 to 8 carbon atoms, for example (but not limited thereto) $C_1$-$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

alkoxycarbonyl: an alkoxy group having 1 to 6 carbon atoms (as mentioned above) which is attached to the skeleton via a carbonyl group (—CO—);

alkylsulphanyl: saturated, straight-chain or branched alkylsulphanyl radicals having 1 to 6 carbon atoms, for example (but not limited thereto) $C_1$-$C_6$-alkylsulphanyl, such as methylsulphanyl, ethylsulphanyl, propylsulphanyl, 1-methylethylsulphanyl, butylsulphanyl, 1-methylpropylsulphanyl, 2-methylpropylsulphanyl, 1,1-dimethylethylsulphanyl, pentylsulphanyl, 1-methylbutylsulphanyl, 2-methylbutylsulphanyl, 3-methylbutylsulphanyl, 2,2-dimethylpropylsulphanyl, 1-ethylpropylsulphanyl, hexylsulphanyl, 1,1-dimethylpropylsulphanyl, 1,2-dimethylpropylsulphanyl, 1-methylpentylsulphanyl, 2-methylpentylsulphanyl, 3-methylpentylsulphanyl, 4-methylpentylsulphanyl, 1,1-dimethylbutylsulphanyl, 1,2-dimethylbutylsulphanyl, 1,3-dimethylbutylsulphanyl, 2,2-dimethylbutylsulphanyl, 2,3-dimethylbutylsulphanyl, 3,3-dimethylbutylsulphanyl, 1-ethylbutylsulphanyl, 2-ethylbutylsulphanyl, 1,1,2-trimethylpropylsulphanyl, 1,2,2-trimethylpropylsulphanyl, 1-ethyl-1-methylpropylsulphanyl and 1-ethyl-2-methylpropylsulphanyl;

alkylsulphinyl: saturated, straight-chain or branched alkylsulphinyl radicals having 1 to 6 carbon atoms, for example (but not limited thereto) $C_1$-$C_6$-alkylsulphinyl, such as methylsulphinyl, ethylsulphinyl, propylsulphinyl, 1-methylethyl sulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentyl sulphinyl, 3-methylpentylsulphinyl, 4-methylpentylsulphinyl, 1,1-dimethylbutylsulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutylsulphinyl, 2-ethylbutylsulphinyl, 1,1,2-trimethylpropylsulphinyl, 1,2,2-trimethylpropylsulphinyl, 1-ethyl-1-methylpropylsulphinyl and 1-ethyl-2-methylpropylsulphinyl;

alkylsulphonyl: saturated, straight-chain or branched alkylsulphonyl radicals having 1 to 6 carbon atoms, for example (but not limited thereto) $C_1$-$C_6$-alkylsulphonyl, such as methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentylsulphonyl, 2-methylpentylsulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl;

cycloalkyl: monocyclic, saturated hydrocarbon groups having 3 to 10 carbon ring members, for example (but not limited thereto) cyclopropyl, cyclopentyl and cyclohexyl;

haloalkyl: straight-chain or branched alkyl groups having 1 to 8 carbon atoms (as mentioned above), where in these groups some or all of the hydrogen atoms may be replaced by halogen atoms as mentioned above, for example (but not limited thereto) $C_1$-$C_3$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl;

haloalkoxy: straight-chain or branched alkoxy groups having 1 to 8 carbon atoms (as mentioned above), where in these groups some or all of the hydrogen atoms may be replaced by halogen atoms as mentioned above, for example (but not limited thereto) $C_1$-$C_3$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy;

haloalkylthio: straight-chain or branched alkylthio groups having 1 to 8 carbon atoms (as mentioned above), where in these groups some or all of the hydrogen atoms may be replaced by halogen atoms as mentioned above, for example (but not limited thereto) $C_1$-$C_3$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio;

heteroaryl: a 5 or 6-membered completely unsaturated monocyclic ring system which contains one to four heteroatoms from the group consisting of oxygen, nitrogen and sulphur; if the ring contains a plurality of oxygen atoms, these are not directly adjacent;

5-membered heteroaryl which contains one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example (but not limited thereto) 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

5-membered heteroaryl which is attached via nitrogen and contains one to four nitrogen atoms, or benzo-fused 5-membered heteroaryl which is attached via nitrogen and contains one to three nitrogen atoms: 5-membered heteroaryl groups which, in addition to carbon atoms, may contain one to four nitrogen atoms and one to three nitrogen atoms, respectively, as ring members and in which two adjacent carbon ring members or a nitrogen and an adjacent carbon ring member may be bridged by a buta-1,3-dien-1,4-diyl group in which one or two carbon atoms may be replaced by nitrogen atoms, where these rings are attached to the skeleton via one of the nitrogen ring members, for example (but not limited thereto) 1-pyrrolyl, 1-pyrazolyl, 1,2,4-triazol-1-yl, 1-imidazolyl, 1,2,3-triazol-1-yl, 1,3,4-triazol-1-yl;

6-membered heteroaryl which contains one to four nitrogen atoms: 6-membered heteroaryl groups which, in addition to carbon atoms, may contain one to three or one to four nitrogen atoms as ring members, for example (but not limited thereto) 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 5-membered heteroaryl which contains one to three nitrogen atoms or one nitrogen atom and one oxygen or sulphur atom: for example (but not limited thereto) 1H-indol-1-yl, 1H-indol-2-yl, 1H-indol-3-yl, 1H-indol-4-yl, 1H-indol-5-yl, 1H-indol-6-yl, 1H-indol-7-yl, 1H-benzimidazol-1-yl, 1H-benzimidazol-2-yl, 1H-benzimidazol-4-yl, benzimidazol-5-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl and 1,3-benzoxazol-2-yl, benzo-fused 6-membered heteroaryl which contains one to three nitrogen atoms: for example (but not limited thereto) quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, and isoquinolin-8-yl;

heterocyclyl: a three- to fifteen-membered saturated or partially unsaturated heterocycle which contains one to four heteroatoms from the group consisting of oxygen, nitrogen and sulphur: mono-, bi- or tricyclic heterocycles which contain, in addition to carbon ring members, one to three nitrogen atoms and/or one oxygen or sulphur atom or one or two oxygen and/or sulphur atoms; if the ring contains a plurality of oxygen atoms, these are not directly adjacent; such as, for example (but not limited thereto), oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

Not included are combinations which contradict natural laws and which the person skilled in the art would therefore have excluded based on his expert knowledge. Excluded are, for example, ring structures having three or more adjacent oxygen atoms.

The present invention furthermore relates to a process for preparing Heterocyclylpyri(mi)dinylpyrazole of the formula [I] according to the invention.

EXPLANATION OF THE PROCESSES AND INTERMEDIATES

The Heterocyclylpyri(mi)dinylpyrazole according to the invention of the formula [I] can be prepared in different ways. Below, the possible processes are firstly shown schematically and then described in detail. Unless otherwise indicated, the residues stated have the meanings given below the schemes.

The Heterocyclylpyri(mi)dinylpyrazole according to the invention of the formula [I] can be produced by process A according to the following scheme.

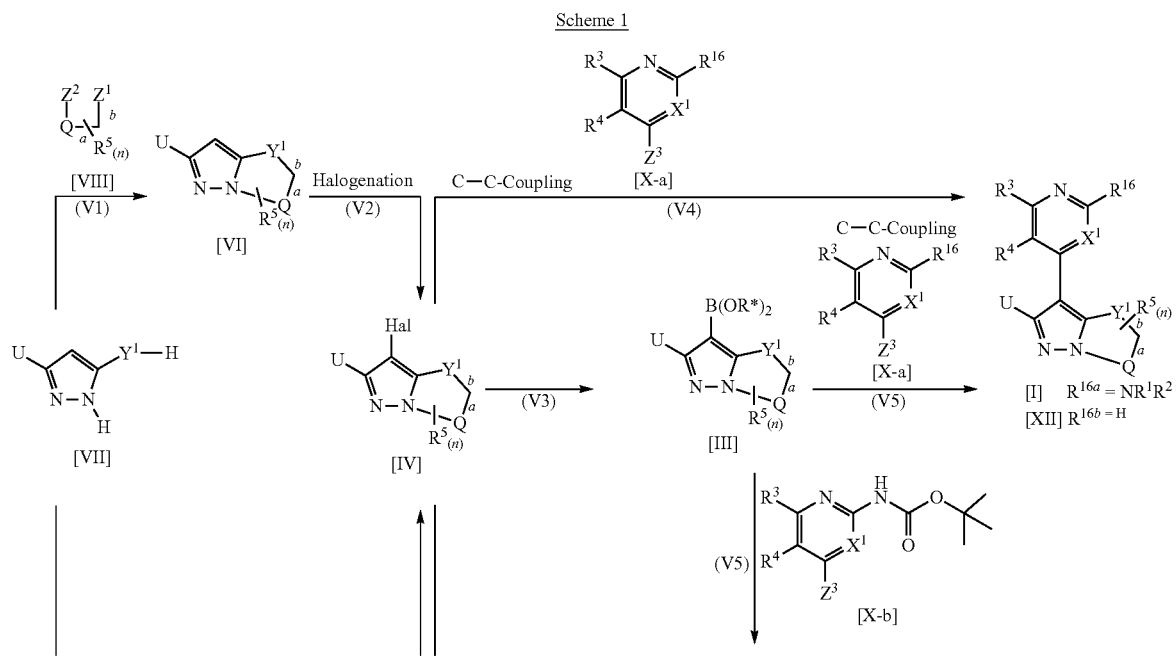

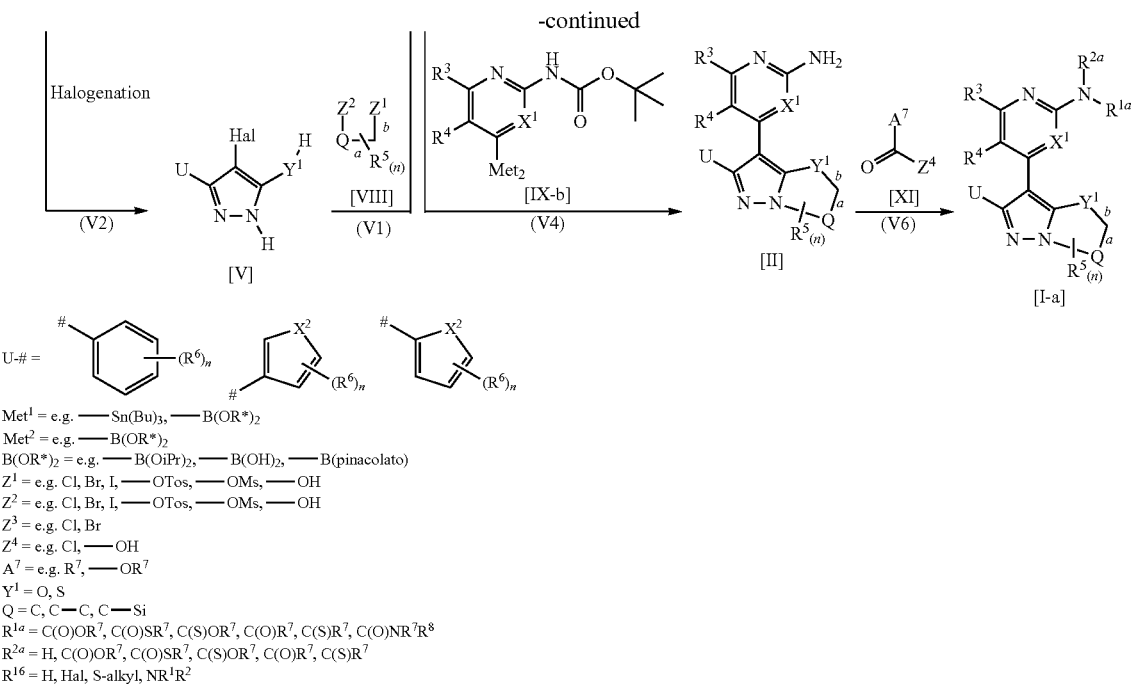
Met[1] = e.g. —Sn(Bu)$_3$, —B(OR*)$_2$
Met[2] = e.g. —B(OR*)$_2$
B(OR*)$_2$ = e.g. —B(OiPr)$_2$, —B(OH)$_2$, —B(pinacolato)
Z[1] = e.g. Cl, Br, I, —OTos, —OMs, —OH
Z[2] = e.g. Cl, Br, I, —OTos, —OMs, —OH
Z[3] = e.g. Cl, Br
Z[4] = e.g. Cl, —OH
A[7] = e.g. R[7], —OR[7]
Y[1] = O, S
Q = C, C—C, C—Si
R$^{1a}$ = C(O)OR[7], C(O)SR[7], C(S)OR[7], C(O)R[7], C(S)R[7], C(O)NR[7]R[8]
R$^{2a}$ = H, C(O)OR[7], C(O)SR[7], C(S)OR[7], C(O)R[7], C(S)R[7]
R$^{16}$ = H, Hal, S-alkyl, NR[1]R[2]
In addition, the intermediates of the formula [VII] and [VII-a] can be prepared by process B (Scheme 2)
Scheme 2
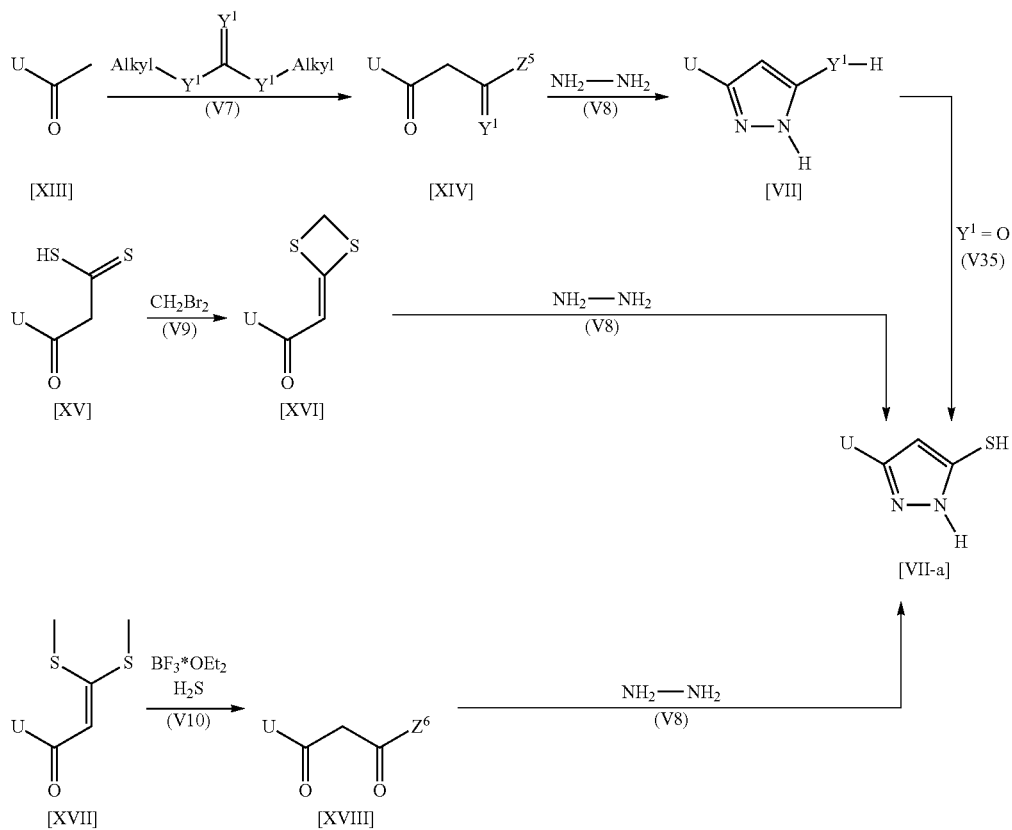

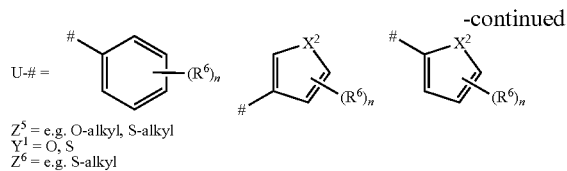
$Z^5$ = e.g. O-alkyl, S-alkyl
$Y^1$ = O, S
$Z^6$ = e.g. S-alkyl
In addition, the Heterocyclylpyri(mi)dinylpyrazole 10 according to the invention of the formula [I-b] to [I-f] can also be prepared by process C (Scheme 3)
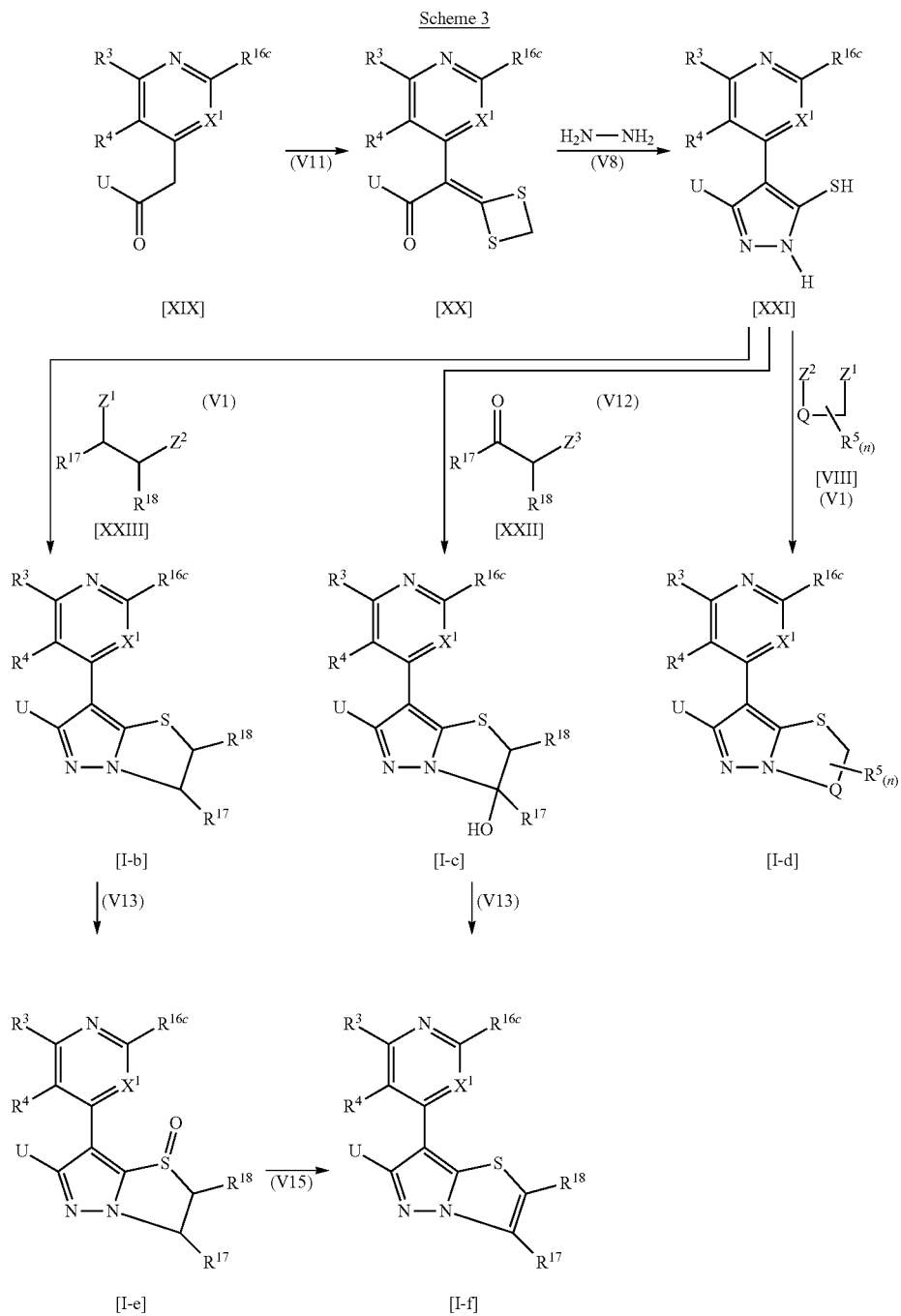

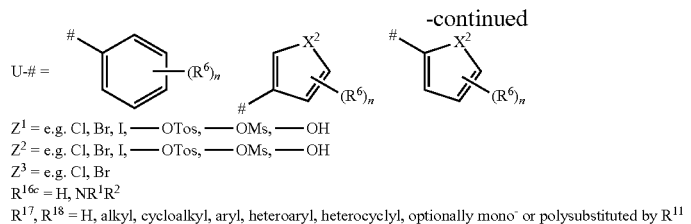

$Z^1$ = e.g. Cl, Br, I, —OTos, —OMs, —OH
$Z^2$ = e.g. Cl, Br, I, —OTos, —OMs, —OH
$Z^3$ = e.g. Cl, Br
$R^{16c}$ = H, $NR^1R^2$
$R^{17}$, $R^{18}$ = H, alkyl, cycloalkyl, aryl, heteroaryl, heterocyclyl, optionally mono- or polysubstituted by $R^{11}$ In addition, the Heterocyclylpyri(mi)dinylpyrazole according to the invention of the formula [I-g] and the intermediates of the general formula [II] can also be produced by process D (Scheme 4)

Scheme 4

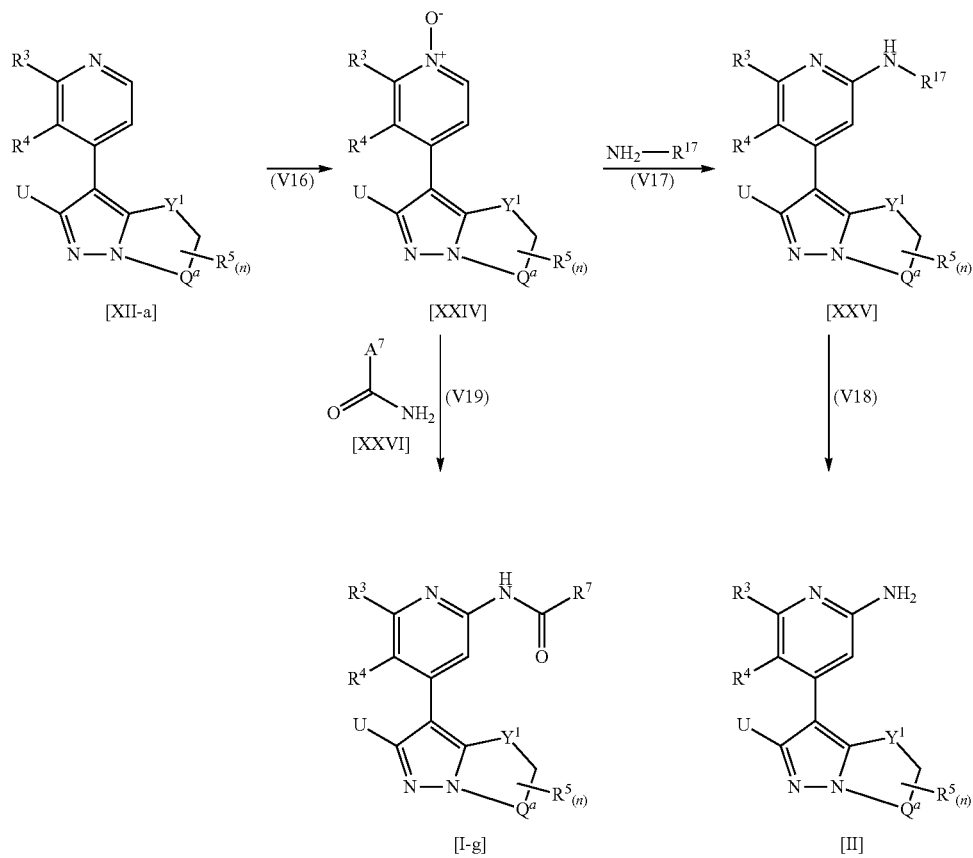

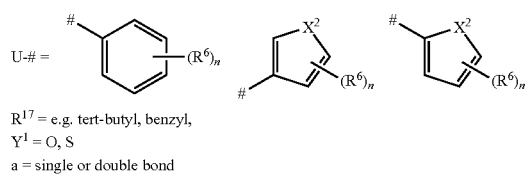

$R^{17}$ = e.g. tert-butyl, benzyl,
$Y^1$ = O, S
a = single or double bond

In addition, the Heterocyclylpyri(mi)dinylpyrazole according to the invention of the formula [I-h] can also be produced by process E (Scheme 5)

In addition, the intermediates of the formula [VI] can be prepared by process F (Scheme 6)

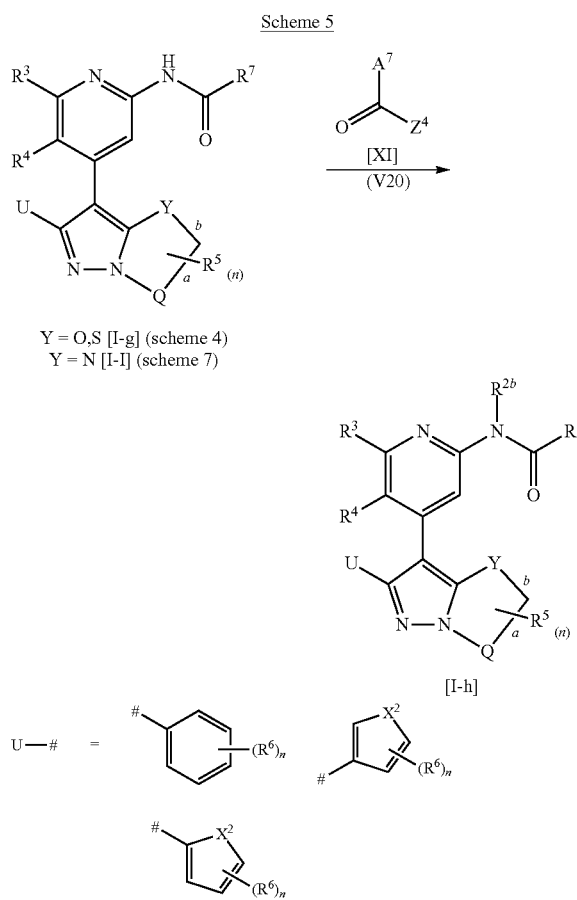

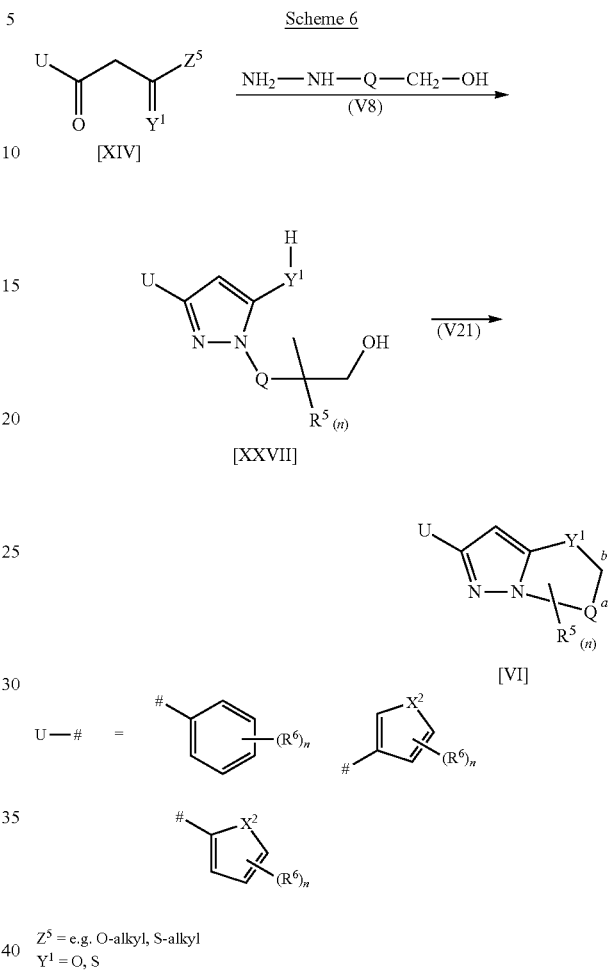

$R^{2b}$ = C(O)OR$^{7*}$, C(O)SR$^{7*}$, C(S)OR$^{7*}$, C(O)R$^{7*}$, C(S)R$^{7*}$ (whereas R$^{7*}$ can be identical or different to R$^7$)
$Y^1$ = O, S, N
a, b = single or double bond $Z^5$ = e.g. O-alkyl, S-alkyl
$Y^1$ = O, S In addition, the Heterocyclylpyri(mi)dinylpyrazole according to the invention of the formula [I] can also be prepared by process G (Scheme 7).

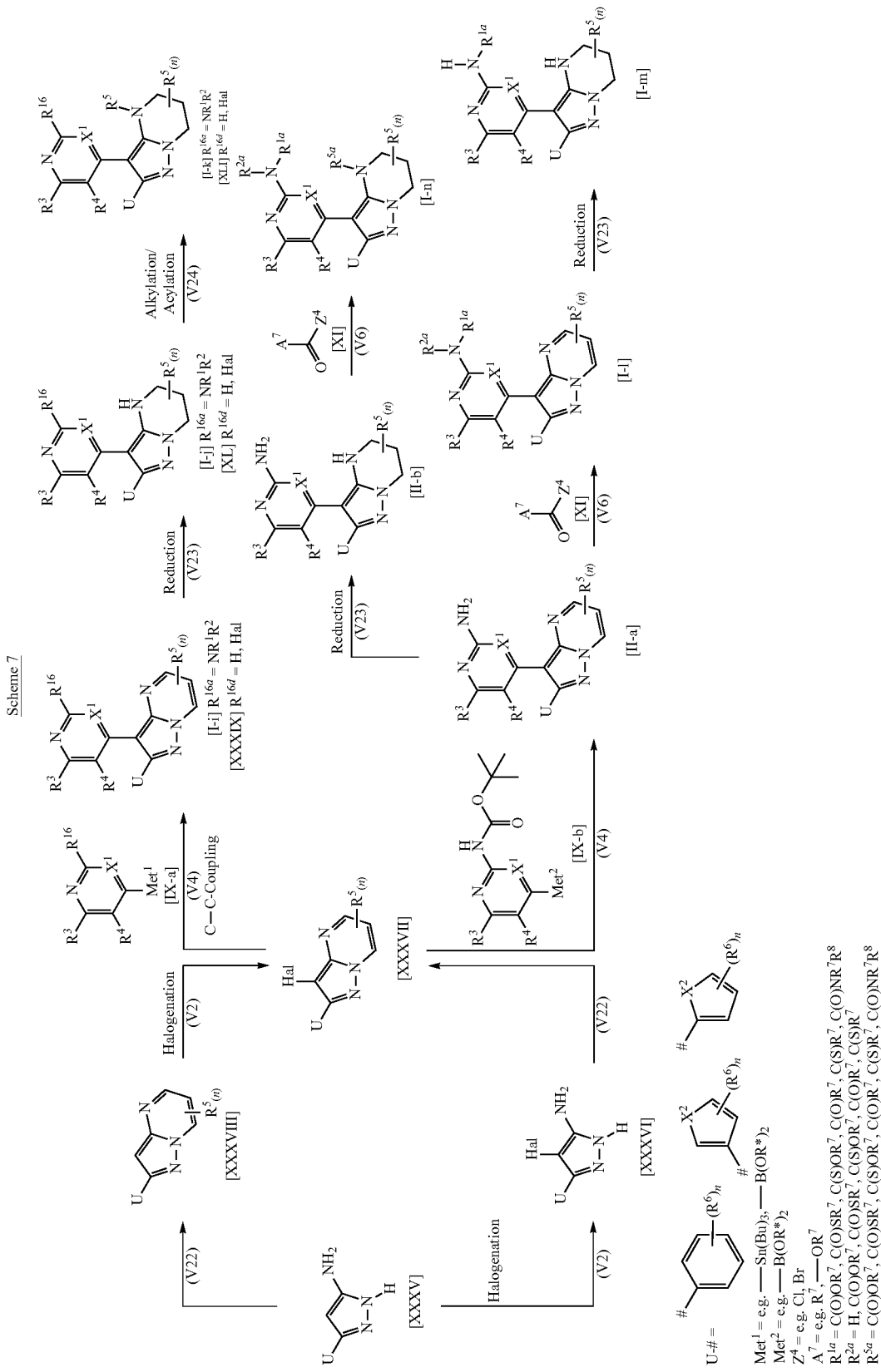

In addition, the Heterocyclylpyri(mi)dinylpyrazole according to the invention of the formula [I-o] to [I-s] can also be prepared by process H (Scheme 8).
Scheme 8
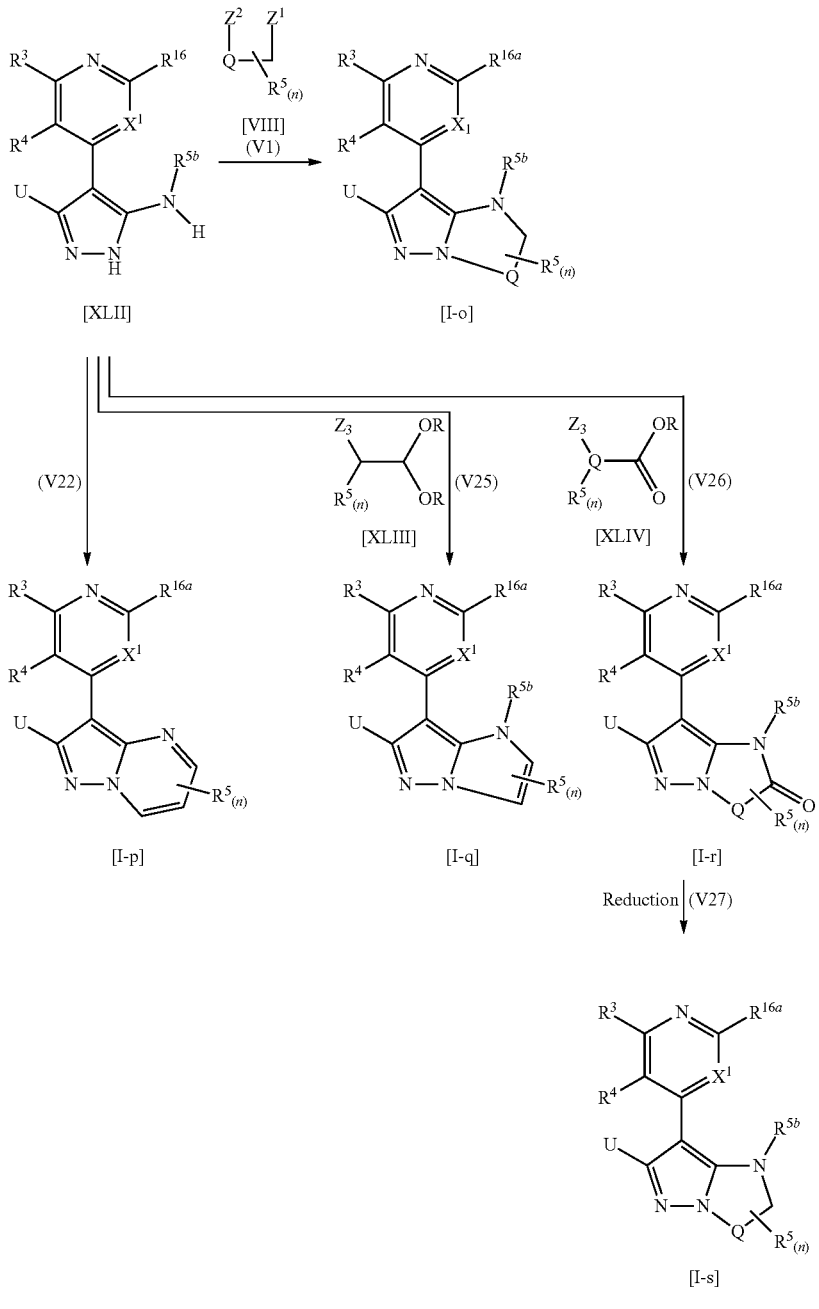
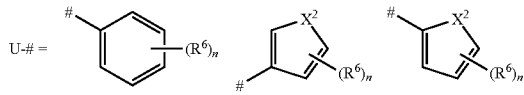
$Z^1$ = e.g. Cl, Br, I, ——OTos, ——OMs, ——OH
$Z^2$ = e.g. Cl, Br, I, ——OTos, ——OMs, ——OH
$Z^3$ = e.g. Cl, Br
$R^{16}$ = H, Hal, S-alkyl, $NR^1R^2$
$R^{16a}$ = $NR^1R^2$ In addition, the intermediates of the general formula [XLII] can also be produced by process I (Scheme 9)
Scheme 9
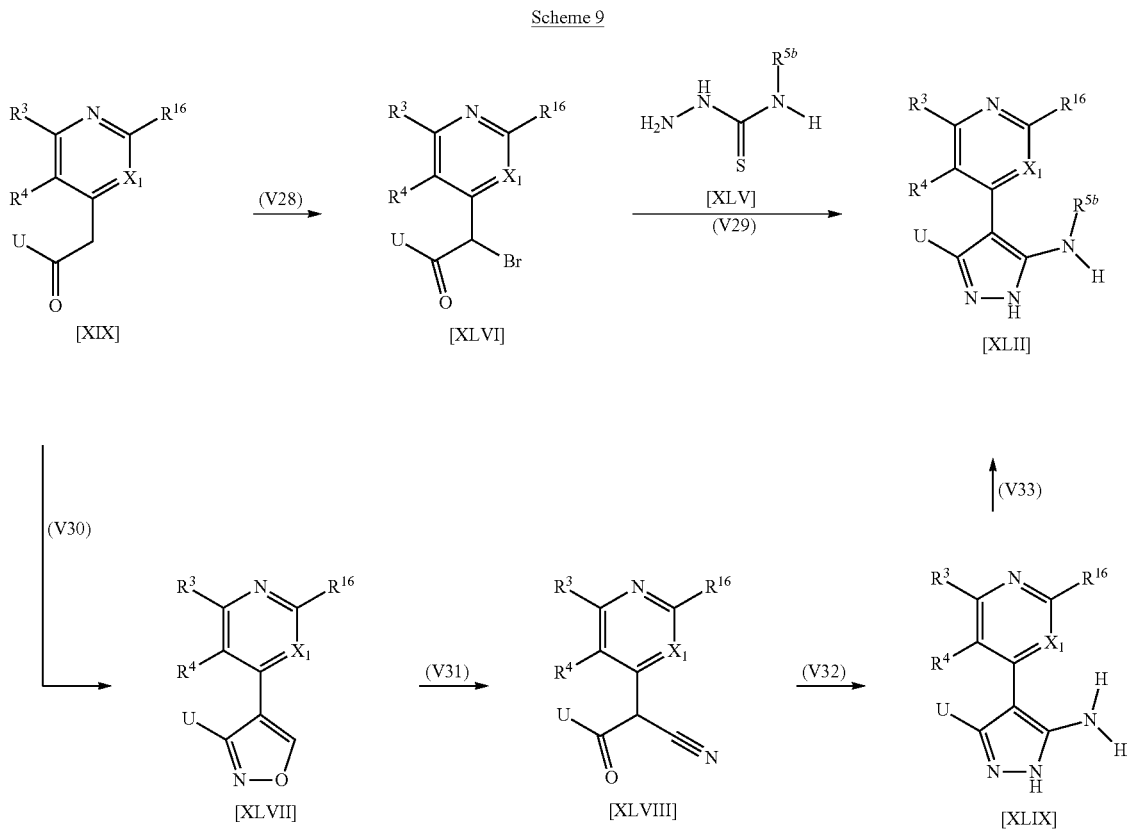
In addition, the Heterocyclylpyri(mi)dinylpyrazole according to the invention of the formula [I-u] and the intermediate of the general formula [L] can also be prepared by process J (Scheme 10)
Scheme 10
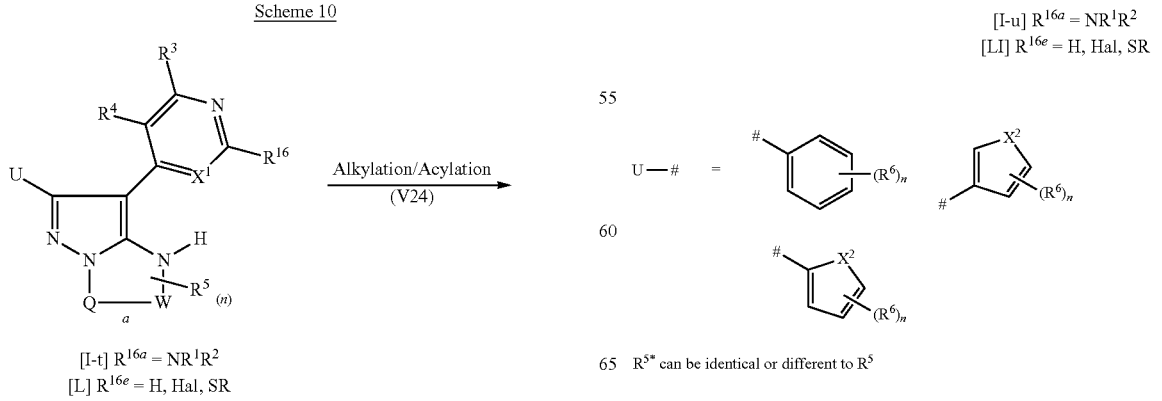
-continued
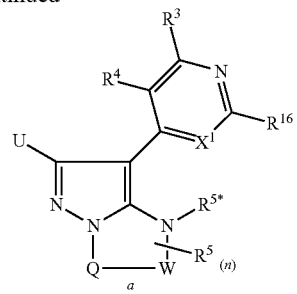
R⁵* can be identical or different to R⁵

In addition, the Heterocyclylpyri(mi)dinylpyrazole according to the invention of the formula [I-v] can also be prepared by process K (Scheme 11).

Scheme 11

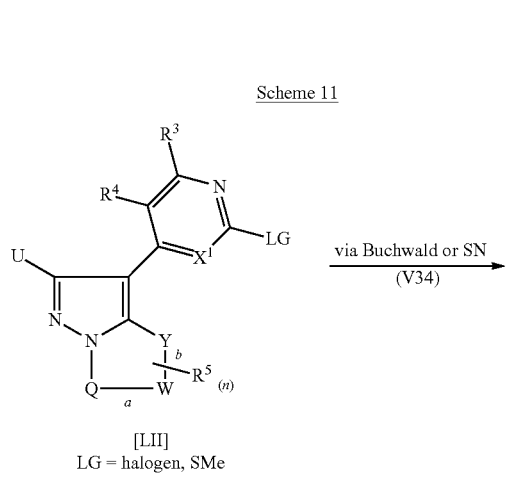

[LII]
LG = halogen, SMe

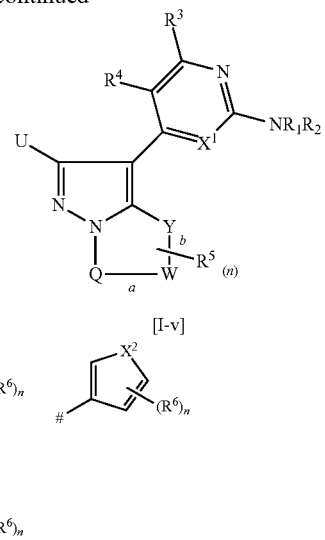

[I-v]

In addition, the intermediates of the general formula [IV] can also be prepared by process L (Scheme 12).

Scheme 12

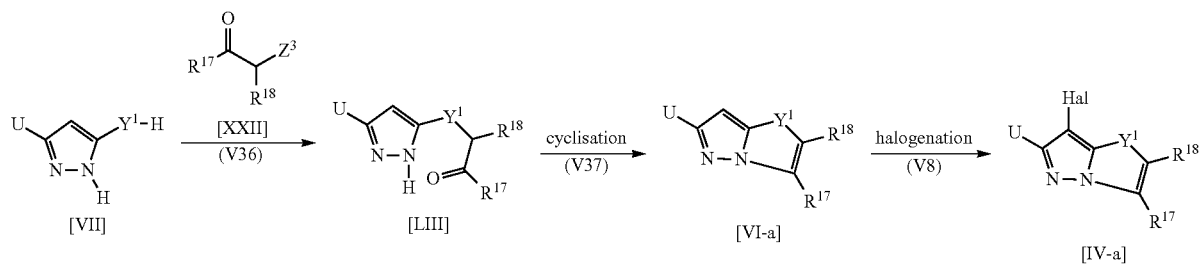

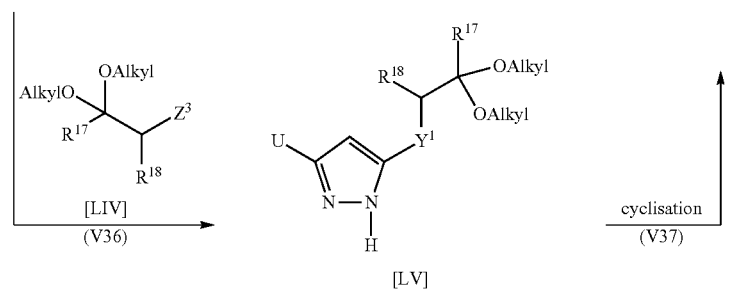

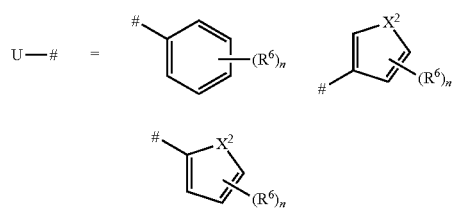

$Y^1$ = O, S
$Z^3$ = e.g. Cl, Br
$R^{17}$, $R^{18}$ = H, alkyl, cycloalkyl, aryl, heteroaryl, heterocyclyl, optionally mono- or polysubstituted by $R^{11}$

Compounds of the formula [II]

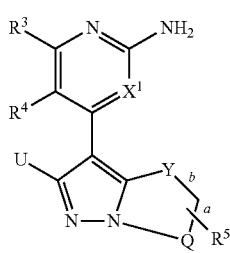

[II]

wherein the symbols Y, Q, $X^1$, $R^3$, $R^4$ and $R^5$ have the aforesaid general, preferred, particularly preferred and very particularly preferred meanings, and salts thereof, are novel.

For example the compounds of formula [II] listed in the following table are novel:

| No. | Name | U | $R^5$ | $X^1$ | Y | Q | b | LogP (pH 2.3)[1] | $[M+H]^+$ Peak[2] |
|---|---|---|---|---|---|---|---|---|---|
| [II-1] | 4-(2-phenyl-6,7-dihydro-5H-pyrazolo[5,1-b][1,3]oxazin-3-yl)pyridin-2-amine | Phenyl | H | CH | O | $CH_2$—$CH_2$— | single | 0.87 | 293.1 |
| [II-2] | 4-[2-(4-fluorophenyl)-6,7-dihydro-5H-pyrazolo[5,1-b][1,3]oxazin-3-yl]pyridin-2-amine | 4-Fluorophenyl | H | CH | O | $CH_2$—$CH_2$— | single | 0.95 | 311.1 |
| [II-3] | 4-[2-(2,4-difluorophenyl)-6,7-dihydro-5H-pyrazolo[5,1-b][1,3]oxazin-3-yl]pyridin-2-amine | 2,4-Difluorophenyl | H | CH | O | $CH_2$—$CH_2$— | single | 1.01 | 329.1 |
| [II-a-1] | 4-(2-phenylpyrazolo[1,5-a]pyrimidin-3-yl)pyridin-2-amine | Phenyl | H | CH | N | CH=CH | double | 0.98 | 288.0 |
| [II-b-1] | 4-(2-Phenyl-4,5,6,7-tetrahydropyrazolo[1,5-a]pyrimidin-3-yl)pyridin-2-amine | Phenyl | H | CH | N | $CH_2$—$CH_2$ | single | 1.05 | 292.2 |
| [II-4] | 4-[7-(4-fluorophenyl)-3,3-dimethyl-3,4-dihydro-2H-pyrazolo[5,1-b][1,3,5]oxazasilin-8-yl]pyridin-2-amine | 4-Fluorophenyl | Me | CH | O | $CH_2$—$Si(CH_3)_2$— | single | 1.66 | 355.0 |
| [II-12] | 4-[3,3-dimethyl-7-(2-thienyl)-3,4-dihydro-2H-pyrazolo[5,1-b][1,3,5]oxazasilin-8-yl]pyridin-2-amine | 2-Thienyl | Me | CH | O | $CH_2$—$Si(CH_3)_2$— | single | 1.55 | 343.2 |

$R^3, R^4$=H
"a" is a single bond

Compounds of the formula [IV], [IV-a] and [XXXVII]

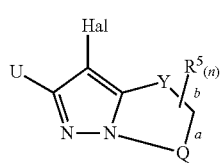

[IV]

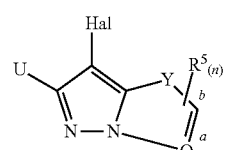

[IV-a]

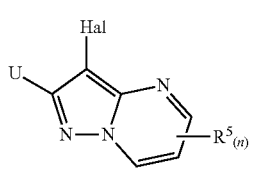

[XXXVII]

wherein the symbols Y, Q, $R^5$ have the aforesaid general, preferred, particularly preferred and very particularly preferred meanings, and salts thereof, are novel.

For example the compounds of formula [IV] and [XXX-VII] listed in the following table are novel:

| No. | Name | U | Hal | R5 | Y | Q | a | b | LogP (pH 2.3)[1] | [M + H]+ Peak[2] |
|---|---|---|---|---|---|---|---|---|---|---|
| [IV-1] | 3-bromo-2-phenyl-6,7-dihydro-5H-pyrazolo[5,1-b][1,3]oxazine | Phenyl | Br | H | O | —CH$_2$—CH$_2$— | single | single | 2.66 | 281.0 |
| [IV-2] | 3-bromo-2-(4-fluorophenyl)-6,7-dihydro-5H-pyrazolo[5,1-b][1,3]oxazine | 4-Fluorophenyl | Br | H | O | —CH$_2$—CH$_2$— | single | single | 2.86 | 299.0 |
| [IV-3] | 3-bromo-2-(2,4-difluorophenyl)-6,7-dihydro-5H-pyrazolo[5,1-b][1,3]oxazine | 2,4-Difluorophenyl | Br | H | O | —CH$_2$—CH$_2$— | single | single | 2.70 | 317.0 |
| [IV-4] | 7-bromo-6-(4-fluorophenyl)-2,3-dihydropyrazolo[5,1-b][1,3]oxazole | 4-Fluorophenyl | Br | H | O | —CH$_2$— | single | single | 2.69 | 285.0 |
| [IV-5] | 8-bromo-7-(4-fluorophenyl)-3,3-dimethyl-3,4-dihydro-2H-pyrazolo[5,1-b][1,3,5]oxazasiline | 4-Fluorophenyl | Br | Me | O | —CH$_2$—SiMe$_2$— | single | single | 3.83 | 341.0 |
| [IV-6] | 3-bromo-2-(4-fluorophenyl)-7-methyl-6,7-dihydro-5H-pyrazolo[5,1-b][1,3]oxazine | 4-Fluorophenyl | Br | Me | O | —CH(Me)—CH$_2$— | single | single | 3.36 | 312.9 |
| [IV-7] | 3-bromo-6,6-difluoro-2-(4-fluorophenyl)-6,7-dihydro-5H-pyrazolo[5,1-b][1,3]oxazine | 4-Fluorophenyl | Br | F | O | —CH$_2$—CF$_2$— | single | single | 3.30 | 333.0 |
| [IV-8] | 7-bromo-6-(4-fluorophenyl)-2,3-dimethyl-2,3-dihydropyrazolo[5,1-b][1,3]oxazole | 4-Fluorophenyl | Br | Me | O | —CH(Me)— | single | single | 3.39 & 3.46 | 312.9 |
| [IV-9a] | rac-trans-3-bromo-2-(4-fluorophenyl)-5,7-dimethyl-6,7-dihydro-5H-pyrazolo[5,1-b][1,3]oxazine | 4-Fluorophenyl | Br | Me | O | —CH(Me)— | single | single | 3.91 | 324.9 |
| [IV-9b] | Rac-cis-3-bromo-2-(4-fluorophenyl)-5,7-dimethyl-6,7-dihydro-5H-pyrazolo[5,1-b][1,3]oxazine | 4-Fluorophenyl | Br | Me | O | —CH(Me)— | single | single | 3.68 | 324.9 |
| [IV-10] | 3-bromo-2-(4-fluorophenyl)-6,6-dimethyl-6,7-dihydro-5H-pyrazolo[5,1-b][1,3]oxazine | 4-Fluorophenyl | Br | Me | O | —CH$_2$—CMe$_2$— | single | single | 3.63 | 325.0 |
| [IV-11] | 3-bromo-2-(4-fluorophenyl)-6-methyl-6,7-dihydro-5H-pyrazolo[5,1-b][1,3]oxazine-6-carbonitrile | 4-Fluorophenyl | Br | CN | O | —CH$_2$—C(CN)Me— | single | single | 2.94 | 336.1 |
| [IV-12] | 8-bromo-3,3-dimethyl-7-(2-thienyl)-3,4-dihydro-2H-pyrazolo[5,1-b][1,3,5]oxazasiline | 2-Thienyl | Br | Me | O | —CH$_2$—CMe$_2$— | single | single | 3.58 | 329.0 |
| [IV-a-1] | 7-bromo-6-(4-fluorophenyl)-3-methylpyrazolo[5,1-b][1,3]oxazole | 4-Fluorophenyl | Br | Me | O | —C(Me)=CH— | double | single | 3.56 | 295.0 |
| [IV-a-2] | 7-bromo-3-ethyl-6-(4-fluorophenyl)pyrazolo[5,1-b][1,3]oxazole | 4-Fluorophenyl | Br | Et | O | —C(Et)=CH— | double | single | 4.18 | 311.0 |
| [IV-a-3] | 7-bromo-6-(4-fluorophenyl)pyrazolo[5,1-b][1,3]oxazole | 4-Fluorophenyl | Br | H | O | —CH=CH— | double | single | 3.07 | 282.9 |
| [IV-a-4] | 7-bromo-6-phenylpyrazolo[5,1-b][1,3]oxazole | Phenyl | Br | H | O | —CH=CH— | double | single | 2.91 | 263.0 |
| [XXXVII-1] | 3-bromo-2-phenylpyrazolo[1,5-a]pyrimidine | Phenyl | Br | H | N | —CH=CH— | single | double | 2.63 | 274.0 |

| No. | Name | U | Hal | R5 | Y | Q | a | b | LogP (pH 2.3)[1] | [M + H]+ Peak[2] |
|---|---|---|---|---|---|---|---|---|---|---|
| [XXXVII-2] | 3-Bromo-2-(4-fluorophenyl)pyrazolo[1,5-a]pyrimidine | 4-Fluorophenyl | Br | H | N | —CH=CH— | single | double | 2.80 | 292.0 |

Compounds of the formula [VI] and [VI-a]

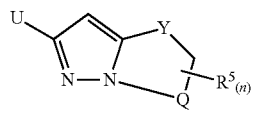

[VI]

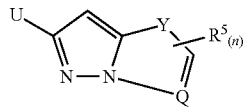

[VI-a]

wherein the symbols Y, Q, R⁵ have the aforesaid general, preferred, particularly preferred and very particularly preferred meanings, and salts thereof, are novel.

For example the compounds of formula [VI] listed in the following table are novel:

| No. | Name | U | Y | Q | R⁵ | LogP (pH 2.3)[1] | [M + H]+ Peak[2] |
|---|---|---|---|---|---|---|---|
| [VI-1] | 2-phenyl-6,7-dihydro-5H-pyrazolo[5,1-b][1,3]oxazine | Phenyl | O | CH₂—CH₂— | H | 2.04 | 201.1 |
| [VI-2] | 2-(4-fluorophenyl)-6,7-dihydro-5H-pyrazolo[5,1-b][1,3]oxazine | 4-Fluorophenyl | O | CH₂—CH₂— | H | 2.18 | 219.2 |
| [VI-3] | 2-(2,4-difluorophenyl)-6,7-dihydro-5H-pyrazolo[5,1-b][1,3]oxazine | 2,4-Difluorophenyl | O | CH₂—CH₂— | H | 2.38 | 237.1 |
| [VI-4] | 2-(4-fluorophenyl)-7-methyl-6,7-dihydro-5H-pyrazolo[5,1-b][1,3]oxazine | 4-Fluorophenyl | O | —CH(Me)—CH₂— | Me | 2.65 | 233.1 |
| [VI-5] | 7-(4-fluorophenyl)-3,3-dimethyl-3,4-dihydro-2H-pyrazolo[5,1-b][1,3,5]oxazasiline | 4-Fluorophenyl | O | —CH₂—SiMe₂— | Me | 3.11 | 363.1 |
| [VI-6] | 6-(4-fluorophenyl)-2,3-dihydropyrazolo[5,1-b][1,3]thiazole | 4-Fluorophenyl | S | —CH₂— | H | 2.53 | 221.0 |
| [VI-7] | 6,6-difluoro-2-(4-fluorophenyl)-6,7-dihydro-5H-pyrazolo[5,1-b][1,3]oxazine | 4-Fluorophenyl | O | —CH₂—CF₂— | F | — | 255.09 |
| [VI-8] | 6-(4-fluorophenyl)-2,3-dimethyl-2,3-dihydropyrazolo[5,1-b][1,3]oxazole | 4-Fluorophenyl | O | —CH(Me)— | Me | — | 233.01 |
| [VI-9] | 2-(4-fluorophenyl)-5,7-dimethyl-6,7-dihydro-5H-pyrazolo[5,1-b][1,3]oxazine | 4-Fluorophenyl | O | —CH(Me)—CH₂— | Me | — | 244.7 |
| [VI-10] | 2-(4-fluorophenyl)-6,6-dimethyl-6,7-dihydro-5H-pyrazolo[5,1-b][1,3]oxazine | 4-Fluorophenyl | O | —CH₂—C(Me)₂— | Me | 2.96 | 247.1 |
| [VI-11] | 2-(4-fluorophenyl)-6-methyl-6,7-dihydro-5H-pyrazolo[5,1-b][1,3]oxazine-6-carbonitrile | 4-Fluorophenyl | O | —CH₂—C(CN)Me— | CN | 2.39 | 258.1 |
| [VI-a-1] | 6-(4-fluorophenyl)-3-methylpyrazolo[5,1-b][1,3]oxazole | 4-Fluorophenyl | O | —C(Me)=CH— | Me | — | 217.2 |
| [VI-a-2] | 3-ethyl-6-(4-fluorophenyl)pyrazolo[5,1-b][1,3]oxazole | 4-Fluorophenyl | O | —C(Et)=CH— | Et | — | 231.0 |
| [VI-a-3] | 6-(4-fluorophenyl)pyrazolo[5,1-b][1,3]oxazole | 4-Fluorophenyl | O | —CH=CH— | H | — | 203.0 |
| [VI-a-4] | 6-phenylpyrazolo[5,1-b][1,3]oxazole | Phenyl | O | —CH=CH— | H | — | 185.0 |

[1] In the determination of the logP values, the methods described below were used.
[2] The mass stated is the peak of the isotope pattern of the [M + H]+ ion with the highest intensity; if the [M − H]− ion was detected, the mass value is marked with a 2.

A compound with the general formula [VII] is halogenated

The production of the compounds with the general formula [I] by process A can be effected as follows: and a compound of the formula [V] is obtained. This is converted to a compound of the type [IV] by reaction with substrates of the type [VIII]. Alternatively, a compound with the general formula [VII] is converted into a compound of the type [VI] by reaction with substrates of the type [VIII]. Compounds of the formula [VI] can be halogenated whereas compounds of the type [IV] are obtained. The compounds of the general formula [IV] can be reacted with substrates of the formula [IX-a] in a C—C coupling, whereby compounds of the formula [I] or compounds of the formula [XII] are obtained (Scheme 1).

Alternatively, the pyrazole compounds of the general formula [IV] can be converted into compounds of the type [III] by reaction with a boronic acid ester. These can be converted into compounds of the formula [I] by reaction with a substrate of the formula [X-a] in a C—C coupling reaction (Scheme 1).

Alternatively, compounds of the type [IV] can be converted into compounds of the formula [II] by reaction with a substrate of the formula [IX-b] in a C—C coupling reaction and subsequent deprotection. These compounds are likewise converted into the compounds of the type [I-a] by reaction with substrates of the formula [XI].

Furthermore, compounds of the type [III] can be converted into compounds of the formula [II] by reaction with a substrate of the formula [X-b] in a C—C coupling reaction and subsequent deprotection (scheme 1).

The synthesis of the intermediates with the general formula [VII] and [VII-a] by process B can be effected as follows:

Compounds of the general formula [XIII] and converted into structures of the formula [XIV] by known methods. The 1,3-diketo compounds or Thioketoesters of the structure [XIV] can be converted with hydrazine into structures of the formula [VII]. Alternatively, structures of the formula [XV] can be converted into Dithietans of the formula [XVI]. By the reaction of compounds of the structure [XVI] with hydrazine the mercaptopyrazoles of the structure [VII-a] are obtained. (scheme 2).

Furthermore, structures of the general formula [VII-a] can be obtained from thioketoesters of the general formula [XVIII] by reaction with hydrazines. The Intermediates of the general formula [XVIII] can be formed by Lewis acid cleavage of dithioketals of the general formula [XVII] (scheme 2).

The production of the compounds with the general formula [I-b] to [I-f] by process C can be effected as follows:

A compound with the general formula [XIX] is transformed to a dithioketal of the general formula [XX] by the reaction with carbon disulfide in the presence of a dihalomethane derivative. The latter is condensed with hydrazine to give a pyrazole derivative of formula [XXI].

Furthermore, a substrate of the formula [XXI] is reacted with a vicinal di-halo derivative of the general formula [XXIII] to form compounds of formula [I-b] whereby mixtures of pyrazole regioisomers can be formed. These can be separated into the individual regioisomers by common processes e.g. chromatographic processes. Compounds of the formula [I-b] can be oxidised to the corresponding sulfoxides of formula [1-e] which may undergo Pummerer rearrangement following elimination, furnishing respectively a compound of formula [1-f]. (scheme 3)

Alternatively, a substrate of the formula [XXI] can be reacted with an alpha-haloketo derivative [XXII] to furnish compounds of the formula [1-c]. The latter can then be dehydrated to yield compounds of the formula [1-f].

Furthermore, compounds of the general formula [XXI] can be reacted with a suitable terminal alkyl dihalide of formula [VIII] to form a compound of formula [I-d], wherein Q is $(CH_2)_n$ and n is as defined above. (scheme 3)

The synthesis of compounds of the formula [I-g] and intermediates with the general formula [II] by process D can be effected as follows:

A pyridine compound of the formula [XII-a] is converted into the N-oxide of the formula [XXIV]. The reaction of the latter with a suitable electrophilic species such as tosyl anhydride in the presence or followed by treatment with a suitable nucleophile such as a primary amine ($NH_2R^{17}$) amine yields a compound of formula [XXV]. Furthermore, the aminopyridine of the formula [XXV] (in which $R^{17}$ represents a cleavable protecting group such as tert butyl or benzyl) can be converted into the free aminopyridine of the formula [II] by treatment with acid or under reductive conditions.

Alternatively, a compound of the formula [XXIV] can be converted into the acylaminopyridine of formula [I-g] by reaction of the N-oxide with an acylisocyanate, in-situ generated from the carboxamide [XXVI] and oxalyl chloride. (scheme 4)

The synthesis of compounds of the formula [I-h] by process D can be effected by the reaction of compounds of the formula [1-g] with acid halides or carbamoyl halides of the formula [XI]. (scheme 5)

The synthesis of intermediates of the formula [VI] by process F can be effected as follows:

Compounds of the formula [XIV] are reacted with hydroxyalkyl hydrazines to yield pyrazoles of the general formula [XXVII]. The latter are converted into the intermediates of the formula [VI] by in-situ conversion of the hydroxy group into a leaving group and cyclisation (scheme 6)

The production of the compounds with the general formula [I-i] to [I-n] by process G can be effected as follows:

A compound with the general formula [XXXV] is halogenated and a compound of the formula [XXXVI] is obtained. This is converted to a compound of the type [XXXVII] by reaction with a substituted 1,1,3,3-tetraalkoxypropane or propan-1,3-dione. Alternatively, a compound with the general formula [XXXV] is converted into a compound of the type [XXXVIII] by reaction with a substituted 1,1,3,3-tetraalkoxypropane or propan-1,3-dione. Compounds of the formula [XXXVIII] can be halogenated whereas compounds of the type [XXXVII] are obtained. The compounds of the general formula [XXXVII] can be reacted with substrates of the formula [IX-a] in a C—C coupling, whereby compounds of the formula [I-i] or compounds of the formula [XXXIX] are obtained. Reduction of these compounds affords the corresponding tetrahydropyrazolopyrimidine of the formula [I-j] and [XL]. These compounds are converted respectively to compounds of the type [I-k] and [XLI] by alkylation, acylation or reaction with sulfonyl chloride, carbamoyl chloride or isocyanate (Scheme 7).

Alternatively, compounds of the type [XXXVII] can be converted into compounds of the formula [II-a] by reaction with a substrate of the formula [IX-b] in a C—C coupling reaction and subsequent deprotection. These compounds are likewise converted into the compounds of the type [I-l] by reaction with substrates of the formula [XI]. Further reduction of this compound affords the tetrahydropyrazolopyrimidine of the formula [I-m] (Scheme 7).

Furthermore, compounds of the type [II-a] can be converted into compounds of the formula [II-b] by reduction. These compounds are then converted into compounds of the type [I-n] by reaction with substrates of the formula [XI] (Scheme 7).

The production of the compounds with the general formula [I-o] to [I-s] by process H can be effected as follows:

A compound of formula [XLII] is reacted with a vicinal di-halo derivative of the general formula [VIII] to form compounds of formula [I-o] whereby mixtures of pyrazole regioisomers can be formed. These can be separated into the individual regioisomers by common processes e.g. chromatographic processes (Scheme 8).

Alternatively, a substrate of the formula [XLII] can be reacted with a 1,1,3,3-tetraalkoxypropane or propan-1,3-dione derivative to furnish compounds of the formula [1-p].

In addition, a substrate of the formula [XLII] can be reacted with an alpha-haloketal derivative of the formula [XLIII] and further cyclised after deprotection of the aldehyde or ketone to yield compounds of the formula [1-q].

Furthermore, compounds of the general formula [XLII] can be reacted with a suitable haloester of formula [XLIV] to form a compound of formula [I-r]. The latter can then be reduced to yield compounds of the formula [1-s] (Scheme 8).

The production of intermediates with the general formula [XLII] by process I can be effected as follows:

A compound with the general formula [XIX] is halogenated and a compound of the formula [XLVI] is obtained. The latter is condensed with a substrate of the formula [XLV] to give a pyrazole derivative of formula [XLII] (Scheme 8).

Alternatively, a compound with the general formula [XIX] is converted to an isoxazole derivative of formula [XLVII] by the reaction with dimethylformamide dimethylacetal and subsequent condensation with hydroxylamine. The latter is converted to the alpha-cyanoketone which is then condensed with hydrazine to give a pyrazole derivative of formula [XLVIII]. The latter can be alkylated by a reductive amination to afford the pyrazole of general formula [XLII] (Scheme 9).

The production of the compounds with the general formula [I-u] by process J can be effected as follows:

A compound with the general formula [I-t] with Y=NH can be subjected to alkylation, acylation or reaction with sulfonyl chloride, carbamoyl chloride or isocyanate to afford compounds of the type [I-u] where Y=N—$R^5$ (Scheme 10).

Likewise a compound with the general formula [L] can be converted into a compounds of the type [LI] (Scheme 10).

The compound of formula [LII] where LG is a leaving group can be submitted to nucleophilic substitution or Buchwald coupling to give the amino derivative of formula [I-v] (Scheme 11).

The production of intermediates with the general formula [IV] by process L can be effected as follows (Scheme 12):

A compound with the general formula [VII] with $Y^1$=O,S can be alkylated with compounds of the general formula [XXII] and [LIV] to afford compounds of the general formula [LIII] and [LV]. These compound can undergo cyclisation to yield compounds of the general formula [VI-a]. Halogenation by methods as described in scheme 1 result in intermediates of the general formula [IV-a].

Step (V1)

One possibility for the synthesis of compounds of the formula [VI] is shown in Scheme 1.

Compounds of the formula [VI] can be synthesized analogously to procedures described in the literature (*Tetrahedron* 1998, 54, 9393-9400 and *J. Org. Chem.* 2004, 69 (21), 7058-7065), by reaction of compounds of the type [VII] with a substrate of the general formula [VIII] (wherein $Z^1$ and $Z^2$ represent leaving groups, such as for example Cl, Br, I, —OTos, —OMs or the like), if necessary in the presence of a solvent and an acid scavenger/base.

Likewise, these synthesis methods can also be used for the conversion of the halogenated pyrazoles of the formula [V] into compounds of the formula [IV].

Moreover, these synthesis methods can also be used for the conversion of the mercaptopyrazoles of the formula [XXI] into compounds of the formula [I-d] and [I-b].

Likewise, these synthesis methods can also be used for the conversion of the aminopyrazoles of the formula [XLII] into compounds of the formula [I-o] as shown in scheme 8

Compounds of the type [VII], can be produced e.g. by known literature methods (EP1119567, J. Chem. Res. Miniprint; 1996, 3, 785-794 and EP1206474) from commercial β-ketoesters or ketothioesters by reaction with hydrazine hydrate.

The compounds of the formula [VIII] and [XXIII] required for the reaction are commercially available or can be produced by literature methods (R. C. Larock, *Comprehensive Organic Transformations*, 2nd Edition, 1999, Wiley-VCH, p. 690 ff. and literature cited therein)

One method for the production of suitable compounds of the formula [VIII] and [XXIII] is for example the reaction of alcohols with methanesulphonyl chloride and triethylamine (*Org. Lett.* 2008, 10, 4425-4428) or by Appel reaction with triphenylphosphine and $CCl_4$ (e.g. described in *Tetrahedron* 2008, 64, 7247-7251).

Depending on the chemical structure of the substrates of the general formula [VIII] and [XXIII], certain preferred combinations in the selection of a suitable solvent and a suitable base can be found.

In the case of an alkylation reaction with substrates of the formula [VIII] and [XXIII] all usual solvents inert under the reaction conditions, such as for example cyclic and acyclic ethers (e.g. diethyl ether, tetrahydrofuran, dioxan), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), nitriles (e.g. acetonitrile), carboxylic acid esters (e.g. ethyl acetate), amides (e.g. N,N-dimethylformamide, N,N-dimethylacetamide), dimethyl sulphoxide or 1,3-dimethyl-2-imidazolinone, can be used or the reaction can be effected in mixtures of two or more of these solvents.

The preferred solvents are dimethylformamide and acetonitrile.

Bases which can be used for this reaction are for example lithium hexamethyldisilazide (LiHMDS), potassium carbonate, caesium carbonate and sodium hydride. The preferred base is sodium hydride. As a rule at least 1 equivalent of base is used.

The reaction is normally effected at temperatures of 0° C.-100° C. and preferably at 20° C.-30° C., but it can also be effected at the reflux temperature of the reaction mixture. The reaction time varies depending on the scale of the reaction and the reaction temperature, but generally lies between a few minutes and 48 hours.

After completion of the reaction, the compounds [VI], [IV], [I-d] or [I-b] are separated from the reaction mixture by one of the usual separation techniques. Depending on the nature of the substrate of the formula [VIII] and [XXIII] used and the reaction conditions, the compounds of the formula [VI] and [IV], can be obtained as pure regioisomers or as a mixture of both possible regioisomers (wherein the group Q is attached to the 4-C atom of the pyrazole rather than the nitrogen atom). In the event that mixtures of regioisomers are obtained, these can be purified by physical methods (such as for example crystallization or chromatography methods) or can optionally also be used in the next step without prior purification.

Step (V2)

One possibility for the synthesis of compounds of the formula [V] is shown in Scheme 1.

The halogenated pyrazoles of the formula [V] can be produced by literature methods. One method for the production of suitable halogenated pyrazoles is for example the bromination of corresponding pyrazoles [VII] (e.g. described in *Heterocycles* 1984, 22, 11, 2523-2527 and WO 2010/68242) by reaction with bromine in halogenated solvents (dichloromethane or chloroform). The reaction can be performed at temperatures between room temperature and refluxing temperature of the solvent.

In analogy, intermediates of the formula [VI] can be converted into compounds of the formula [IV].

Moreover, these synthesis methods can also be used for the conversion of the pyrazoles of the formula [XXXV] into compounds of the formula [XXXVI] as shown in scheme 7.

Likewise, these synthesis methods can also be used for the conversion of the pyrazolopyrimidines of the formula [XXXVIII] into compounds of the formula [XXXVII] as shown in scheme 7.

Step (V3)

One possibility for the synthesis of compounds of the formula [III] is shown in Scheme 1.

Compounds of the formula [III] can be produced by described methods e.g. via reaction of the halopyrazoles [IV] with boronic acid esters such as for example bispinacolatodiboron (4,4,4',4',5,5,5',5'-octamethyl-2,2'-bi-1,3,2-dioxaborolane) in the presence of a catalyst such as for example 1,1'-bis(diphenyl-phosphino)ferrocene-palladium(II) dichloride in the presence of a base and a suitable solvent (see U.S. Pat. No. 0,018,156 A, WO 2007/024843 or EP-A 1 382 603).

As the solvent, all common solvents inert under the reaction conditions, such as for example sulphoxides (e.g. dimethyl sulphoxide), cyclic ethers (e.g. dioxan) and amides (e.g. N,N-dimethylformamide) can be used and the reaction can be effected in mixtures of two or more of these solvents. The preferred solvents are dimethyl sulphoxide and dioxan.

The reaction will normally be effected at temperatures of 80° C.-120° C., and the preferred reaction temperature is about 85° C.-90° C. The reaction time varies depending on the scale of the reaction and the reaction temperature, but generally lies between one hour and 16 hours.

Other synthetic methods described in the literature can likewise be used for the production of the compounds of the formula [III]. For example compounds of the formula [III] can be produced by metallation of the halogenated pyrazoles [IV] with bases such as for example n-butyllithium and reaction with boronic acid esters such as for example trimethyl borate and subsequent reaction of the pyrazoleboronic acid obtained with pinacol (see e.g. *J. Het. Chem.* 2004, 41, 931-940 or EP-A 1 382 603 and WO 2007/16392).

Step (V4)

A possibility for the synthesis of compounds of the formula [I] and [XII] is shown in Scheme 1.

Compounds of the formula can be produced for example by coupling of the halogenated pyrazoles [IV] with metallated heterocycles of the formula [IX-a] (wherein Met¹ stands for a borate ester or boronic acid such as for example B(OiPr)₃, B(OH)₂) in the presence of a catalyst, a base, if necessary a ligand and a suitable solvent at suitable temperatures by known literature procedures (*Top. Curr. Chem.* 2002, 219, 11; *Organomet. Chem.* 1999, 28, 147 and literature cited therein, 2005, 7, 21, 4753-4756). (Scheme 1)

In analogy, the synthesis of the pyrazoles [II] from the compounds of the type [IV] described in Scheme 1 can be effected with this process.

Compounds of the formula [I] can also be produced for example by coupling of the halopyrazoles [IV] with metallated heterocycles of the formula [IX-a] (wherein Met¹ stands for a tin-compound such as for example Sn(n-Bu)₃) in the presence of a catalyst, if necessary an inorganic or organic halide salt, if necessary a ligand and a suitable solvent at suitable temperatures by known literature procedures (see *Synthesis* 1992, 803-815).

Compounds of the formula [IX-a1] (wherein X¹ stands for C—H) are commercially available or can be produced by literature procedures. One method for the production of suitable haloheterocycles [IX-a1] is the reaction of haloheterocycles of the formula [XXVIII] with bispinacolatodiboron in the presence of a catalyst (such as for example Pd(OAc)₂ or PdCl₂(dppf)), if necessary a ligand (such as for example 1,3-bis(2,6-diisopropylphenyl)-4,5-dihydroimidazolium chloride), a base (such as for example potassium acetate or sodium acetate) and a solvent (such as for example tetrahydrofuran or dimethyl sulphoxide) by methods described in the literature (*Bioorg. Med. Chem. Lett.* 2006, 16, 5, 1277-1281 and WO 2011/042389) (Scheme 12).

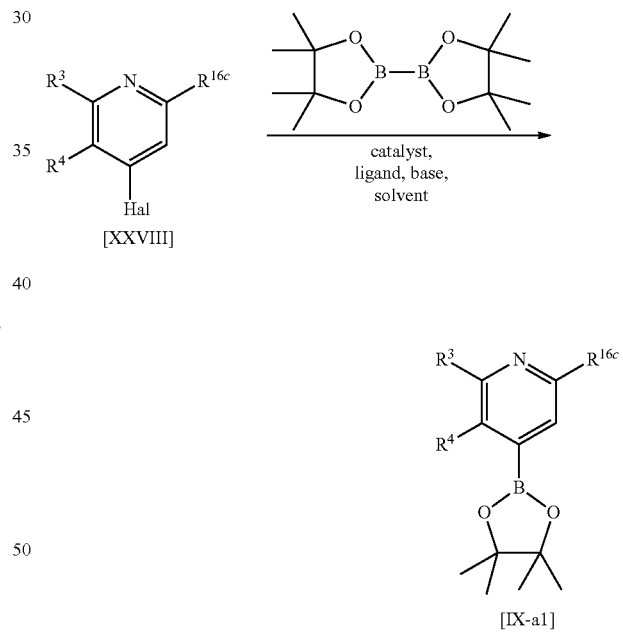

Hal = Br, Cl, I
R$^{16c}$ = NR$^1$R$^2$, H

Alternatively, compounds of the formula [IX-a1] (wherein X¹ stands for C—H) can also be prepared by other known literature methods. One method for the production of suitable heterocycles [IX-a1] is the metallation of the halopyridine [XXVIII] with a base (such as for example n-butyllithium) in a solvent (such as for example diethyl ether or tetrahydrofuran) and subsequent reaction with a boronic acid ester (such as for example B(i-PrO)₃ or B(OMe)₃) and pinacol by known literature methods (*Synthesis* 2004, 4, 469-483 and literature described therein) (Scheme 13).

Scheme 13

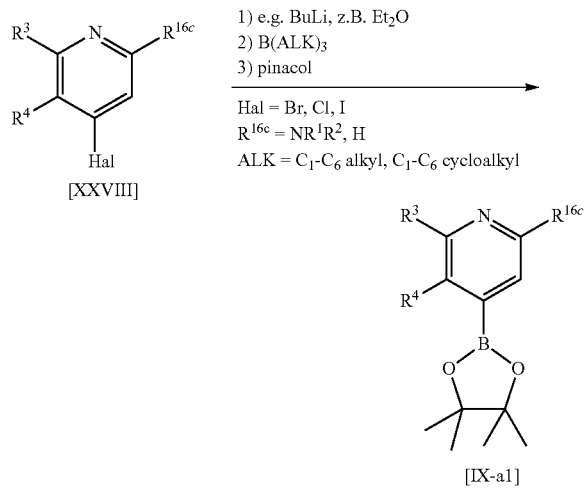

1) e.g. BuLi, z.B. Et$_2$O
2) B(ALK)$_3$
3) pinacol

Hal = Br, Cl, I
R$^{16c}$ = NR$^1$R$^2$, H
ALK = C$_1$-C$_6$ alkyl, C$_1$-C$_6$ cycloalkyl In analogy, compounds of the type [IX-b] can be synthesized according to literature described methods (WO 2011/042389) by reaction of the respective haloheterocycle precursor (replacement of Met$^2$ by Cl, Br, I in [IX-b]) with bispinacolatodiboron in the presence of a catalyst.

Compounds of the formula [IX-a2] (wherein X$^1$ stands for N) are commercially available or can be produced by literature procedures. One method for the production of suitable haloheterocycles [IX-a2] is the reaction of haloheterocycles of the formula [XXIX] with hexaalkylditin compounds (such as for example 1,1,1,2,2,2-hexabutylditin) in the presence of a catalyst (such as for example bis(triphenylphosphine)palladium(II) acetate), if necessary a fluoride ion source (such as for example tetrabutylammonium fluoride) and a solvent (such as for example tetrahydrofuran or diethyl ether) by methods described in the literature (WO 2003/095455 or WO 2007/104538) (Scheme 14).

Scheme 14

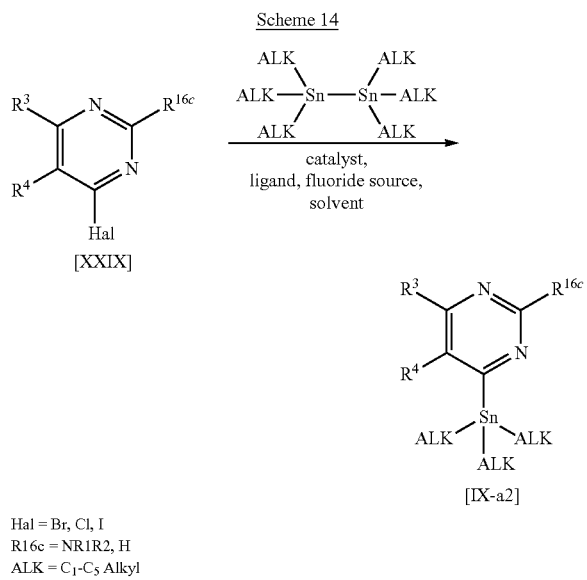

Hal = Br, Cl, I
R16c = NR1R2, H
ALK = C$_1$-C$_5$ Alkyl

Alternatively, compounds of the formula [IX-a2] (wherein X$^1$ stands for N) can also be prepared by other known literature methods. One method for the production of suitable haloheterocycles [IX-a2] is the metallation of the halopyridine [XXIX] using a metallation reagent (an alkyllithium compound such as for example n-butyllithium or a Grignard reagent such as for example isopropylmagnesium chloride) in a solvent (such as for example diethyl ether or tetrahydrofuran) and subsequent reaction with a trialkyltin halogen compound (such as for example Bu$_3$SnCl) by known literature methods (WO 2008/008747 or Tetrahedron 1994, 275-284 and literature described therein) (Scheme 15).

Scheme 15

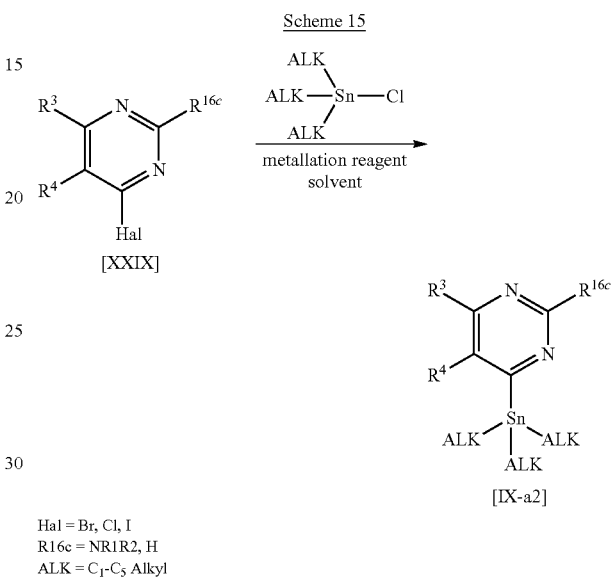

Hal = Br, Cl, I
R16c = NR1R2, H
ALK = C$_1$-C$_5$ Alkyl

Compounds of the formula [XXVIII] and [XXIX] are commercially available or can be prepared for example by acylation of corresponding amine (in the case R$^{16}$=—NH$_2$) by known literature methods (e.g. J. Org. Chem. 2004, 69, 543-548). Another method for the preparation of the compounds of the type [XXVIII] and [XXIX] consists in the halogenation of the corresponding hydroxyheterocycles analogously to the halogenation methods stated for the synthesis of the compounds [X-a1] and [X-b2].

In the coupling of the halopyrazoles [IV] with metallated heterocycles of the formula [IX-a] (wherein Met stands for a borate ester or boronic acid such as for example B(OiPr)$_3$ or B(OH)$_2$), the selection of solvent, base, temperature, catalysts and added ligands if necessary can vary depending on the borate ester substrate used and comprises the possible variations described under step (V5) for the C—C coupling of compound of the formula [III] with substrates of the formula [X-a].

In the coupling of the halopyrazoles [IV] with metallated heterocycles of the formula [IX-a] (wherein Met$^1$ stands for an alkyltin bearing group such as for example Sn(Bu)$_3$), the selection of a catalyst, if necessary an inorganic or organic halide salt, if necessary a ligand and a suitable solvent at suitable temperatures can vary depending on the alkyltin substrate used.

As the solvent for the reaction of compounds of the formula [IX-a], all usual solvents inert under the reaction conditions, such as for example cyclic and acyclic ethers (diethyl ether, dimethoxymethane, diethylene glycol dimethyl ether, tetrahydrofuran, dioxan, diisopropyl ether, tert-butyl methyl ether), aromatic hydrocarbons (e.g. benzene, toluene, xylene), amides (e.g. dimethylformamide, dimethylacetamide, N-methylpyrrolidone) and sulphoxides (e.g. dimethyl sulphoxide) can be used or the reaction can be performed in mixtures of two or more of these solvents. The preferred solvent is dimethylformamide.

Halide salts for the reaction of compounds of the formula [IX-a] which are preferably used in the process according to the invention are for example copper halides (e.g. CuBr or CuI), caesium halides (CsF) and tetraalkylammonium halides (TBAF).

The halide salts are preferably used in the process according to the invention in a proportion of 1 to 400 mol. %, based on the organic tin compound. However, mixtures of the halide salts can also be used in proportions of 1-400 mol. %. The addition of a mixture of copper iodide and caesium fluoride in proportions of 1-200 mol. % is particularly preferable.

As catalysts for the reaction of compounds of the formula [IX-a] with halogenated pyrazoles of the formula [IV] the same catalysts can be used as are described below for the production of the compounds of the formula [I], by reaction of the compounds of the formula [III] and [X-a] described for step V5.

The quantity of catalyst, based on the heteroaromatics [IX-a] bearing the leaving group $Met^1$, is preferably 0.001 to 0.5 mol. % and particularly preferably 0.01 to 0.2 mol. %.

The catalyst can contain phosphorus-containing or arsenic-containing ligands or phosphorus-containing or arsenic-containing ligands can be added separately to the reaction mixture. As phosphorus-containing ligands, preferably tri-n-alkylphosphanes, triarylphosphanes, dialkylarylphosphanes, alkyldiarylphosphanes and/or heteroarylphosphanes, such as tripyridylphosphane and trifurylphosphane, wherein the three substituents on the phosphorus can be the same or different, can be chiral or achiral and wherein one or more substituents can link the phosphorus groups of several phosphanes, wherein one part of this linkage can also be a metal atom, are suitable. Particularly preferable are phosphanes such as triphenylphosphane, tri-tert-butylphosphane and tricyclohexyl-phosphane. As arsenic-containing ligands, for example tri-n-alkylarsanes and triarylarsanes, wherein the three substituents on the arsenic can be the same or different, are suitable.

The total concentration of ligands, based on the heteroaromatics [IX-a] bearing the leaving group $Met^1$, is preferably up to 1 mol. %, particularly preferably 0.01 to 0.5 mol. %.

To effect the process according to the invention, advantageously the educts, the solvent, the base, the halide salt, the catalyst and if necessary the ligand are thoroughly mixed and reacted preferably at a temperature of 0° C.-200° C., particularly preferably at 60-150° C. The reaction time varies depending on the scale of the reaction and the reaction temperature, but generally lies between a few minutes and 48 hours. Other than as a one-pot reaction, the reaction can also be run such that the various reactants are metered in a controlled manner in the course of the reaction, whereby different metering variants are possible.

The processes according to the invention are in general performed under normal pressure. However it is also possible to operate under increased or reduced pressure. The reaction is in general performed using a blanket gas such as for example argon or nitrogen.

The molar reactant ratio of the halopyrazole [IV] to the organotin compound [IX-a2] is preferably 0.9 to 2.

After completion of the reaction, the catalyst arising as a solid is removed by filtration, the crude product freed from the solvent or solvents and then purified by methods known to those skilled in the art and appropriate for the particular product, e.g. by recrystallization, distillation, sublimation, zone melting, melt crystallization or chromatography.

Likewise, these synthesis methods can also be used for the conversion of the halopyrazolopyrimidines of the formula [XXXVII] into compounds of the formula [I-i] and [XXXIX] as shown in scheme 7.

Moreover, these synthesis methods can also be used for the conversion of the halopyrazolopyrimidines of the formula [XXXVII] into compounds of the formula [II-a] as shown in scheme 7.

Step (V5)

One possibility for the synthesis of compounds of the formula [I] and for the synthesis of compounds of the formula [XII] is shown in Scheme 1.

Compounds of the formula [I] can be produced for example by coupling of the pyrazoleboronic acids [III] with heterocycles of the formula [X-a] (wherein $Z^2$ represents a leaving group such as for example Cl or Br) in the presence of a catalyst, a base and a suitable solvent at suitable temperatures by known literature procedures (*Top. Curr. Chem.* 2002, 219, 11; *Organomet. Chem.* 1999, 28, 147 and literature cited therein).

In a similar manner, compounds of the formula [XII] can be produced by coupling of the pyrazoleboronic acids [III] with heterocycles of the formula [X-a].

Compounds of the formula [X-a] (wherein $X^1$ stands for C—H) are commercially available or can be produced by literature procedures (Scheme 16). One method for the production of suitable haloheterocycles [X-a1] is the reaction of the pyridine N-oxides with halogenating agents (e.g. $PCl_3$, $POCl_3$, $SOCl_2$ or methanesulphonyl chloride) (see *Bioorg. Med. Chem. Lett.* 2007, 17, 7, 1934-1937).

Scheme 16

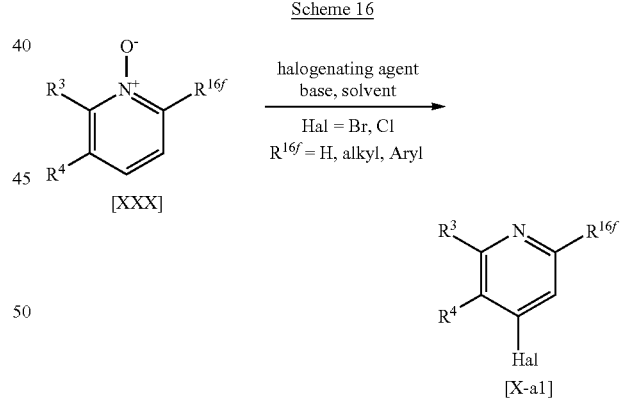

The pyridine N-oxides [XXX] are known or can be produced by oxidation of the corresponding pyridines (e.g. with $H_2O_2$, $H_2O_2$+methyltrioxorhenium, m-chloroperoxybenzoic acid, dimethyl-dioxirane or $H_2O_2$+manganese tetrakis(2,6-dichlorophenyl)porphyrin) by procedures described in the literature (*ARKIVOC* 2001 (i) 242-268 and references contained therein).

A further method for the production of suitable haloheterocycles [X-a1] is the reaction of the 4-hydroxypyridine compounds [XXXI] with halogenating agents (e.g. $PCl_3$, $POCl_3$) by known literature procedures (*Pol. J. Chem.* 1981, 55, 4, 925-929) (Scheme 17).

Scheme 17

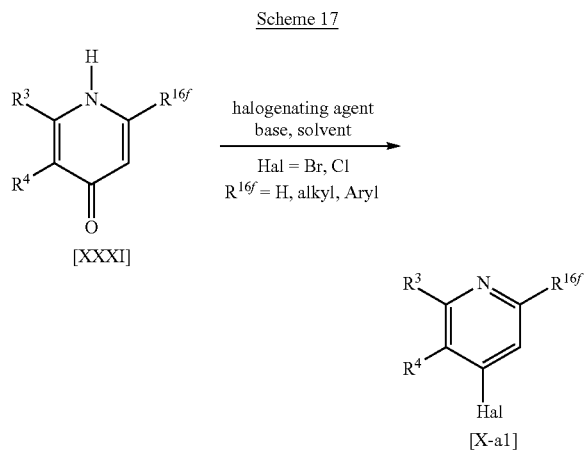

The hydroxypyridines [XXXI] are known.

Alternatively, compounds of the formula [X-a] (wherein $X^1$ stands for C—H) are commercially available or can be produced by literature methods (Scheme 18). One method for the production of suitable haloheterocycles [X-a-2] is the reaction of aminoheterocycles of the formula [XXXII] with acid chlorides in the presence of a base and a solvent (*Synth. Commun.* 1997, 27, 5, 861-870).

Scheme 18

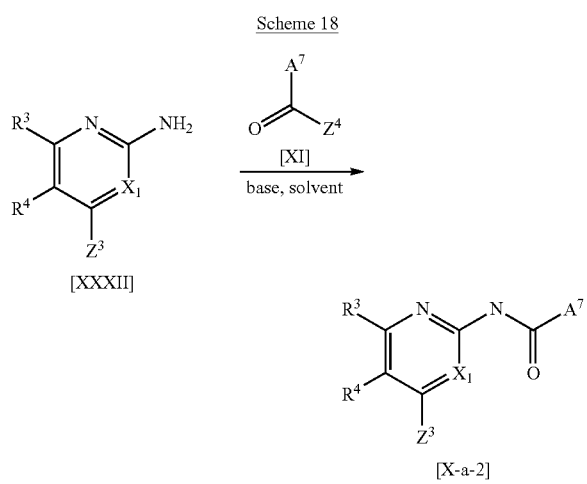

The aminoheterocycles [XXXII] (wherein $X^1$ stands for C—H) are known or can be produced by removal of the N—BOC protective group from compounds of the formula [X-b-1] by procedures described in the literature (*Aust. J. Chem.* 1982, 35, 10, 2025-2034 and references contained therein).

The aminoheterocycles [XXXII] (wherein $X^1$ stands for N) are known or can be produced by halogenation of the hydroxy compounds ($Z^3$=—OH) by procedures described in the literature (e.g. after *J. Med. Chem.* 2006, 49, 14, 4409-4424).

Compounds of the formula [X-b] (wherein $X^1$ stands for C—H) are commercially available or can be produced by literature methods (Scheme 19). One method for the production of suitable N-Boc-haloheterocycles [X-b-1] is the reaction of suitable acids (e.g. 4-bromo-picolinic acid) [XXXIII] with diphenylphosphoryl azide and tert-butanol (*Aust. J. Chem.* 1982, 35, 2025-2034, *J. Med. Chem.* 1992, 35, 15, 2761-2768 or U.S. Pat. No. 5,112,837 A).

Scheme 19

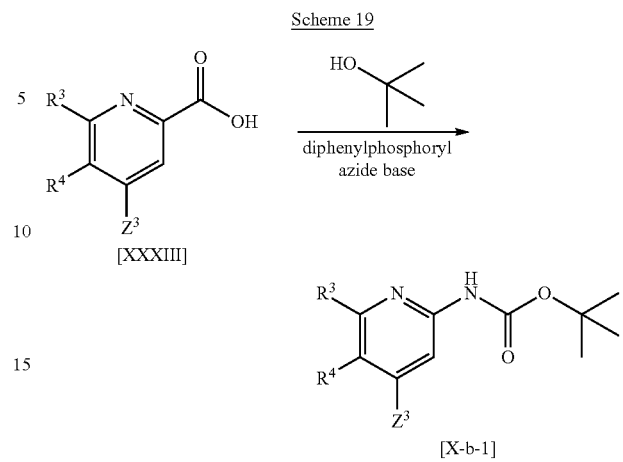

The carboxylic acids [XXXIII] are known or can be produced from commercially available precursors by procedures described in the literature (see e.g. EP-A 1 650 194), for example from the commercially available pyridine-2-carboxylic acid by reaction with thionyl chloride in dimethylformamide. Alternatively, compounds of the general formula [XXXIII] can also be produced by oxidation of commercially available 4-halo-2-methyl-pyridine derivatives by known literature procedures (*Aust. J. Chem.* 1982, 35, 2025-2034).

Compounds of the formula [X-b] (wherein $X^1$ stands for N) are commercially available or can be produced by literature methods (Scheme 20). One method for the production of suitable N-Boc-haloheterocycles [X-b-2] is the chlorination of the hydroxy compounds (e.g. (4-hydroxy-pyrimidin-2-yl) carbamate) with phosphorus oxychloride (*Chem. Pharm. Bull.* 2003, 51, 8, 975-977).

Scheme 20

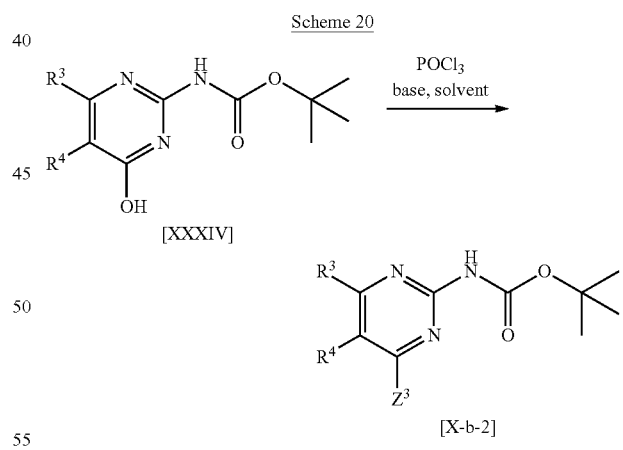

The hydroxy compounds [XXXIV] are known or can be produced from commercially available precursors by procedures described in the literature (*Chem. Pharm. Bull.* 2003, 51, 8, 975-977).

As the solvent for the synthesis of compounds of the formula [I] and [XII] all usual solvents inert under the reaction conditions, such as for example alcohols (e.g. methanol, ethanol, 1-propanol, 2-propanol, ethylene glycol, 1-butanol, 2-butanol, tert-butanol), cyclic and acyclic ethers (diethyl ether, dimethoxymethane, diethylene glycol dimethyl ether, tetrahydrofuran, dioxan, diisopropyl ether, tert-butyl methyl ether), aromatic hydrocarbons (e.g. benzene, toluene, xylene), hydrocarbons (e.g. hexane, iso-hexane, heptane, cyclohexane), ketones (e.g. acetone, ethyl methyl ketone, iso-butyl methyl ketone), nitriles (e.g. acetonitrile, propionitrile, butyronitrile) and amides (e.g. dimethyl-formamide, dimethylacetamide, N-methylpyrrolidone) and water can be used or the reaction can be effected in mixtures of two or more of these solvents. The preferred solvent is dioxan.

Bases which are preferably used in the process according to the invention are alkali and alkaline earth metal hydroxides, alkali and alkaline earth metal carbonates, alkali metal hydrogen carbonates, alkali and alkaline earth metal acetates, alkali and alkaline earth metal alcoholates, and primary, secondary and tertiary amines. Preferred bases are alkali metal carbonates such as for example caesium carbonate, sodium carbonate and potassium carbonate.

In the process according to the invention, the base is preferably used in a proportion of 100 to 1000 mol. %, based on the aromatic boronic acid. The preferred proportion is 600 to 800 mol. %.

As catalysts, for example palladium metal, palladium compounds and/or nickel compounds can be used. The catalysts can also be applied onto a solid carrier, such as activated charcoal or aluminium oxide. Palladium catalysts wherein the palladium is present in the oxidation state (0) or (II), such as tetrakis(triphenylphosphine)-palladium, bis(triphenylphosphine)palladium dichloride, bis(diphenyl-phosphino)ferrocenepalladium dichloride, palladium ketonates, palladium acetylacetonates (such as for example palladium bisacetylacetonate), nitrilepalladium halides (such as for example bis-(benzonitrile)palladium dichloride, bis(acetonitrile)-palladium dichloride), palladium halides ($PdCl_2$, $Na_2PdCl_4$, $Na_2PdCl_6$), allylpalladium halides, palladium biscarboxylates (such as for example palladium-II acetate) and tetrachloropalladic acid are preferred. Particularly preferred catalysts are tetrakis(triphenylphosphine)-palladium, bis(triphenylphosphine)-palladium dichloride and bis-(diphenylphosphino)ferrocenepalladium dichloride. The palladium compound can also be generated in situ, such as for example palladium(II) acetate from palladium(II) chloride and sodium acetate.

The quantity of catalyst, based on the heteroaromatics [X-a] and [X-b] bearing the leaving group $Z^2$, is preferably 0.001 to 0.5 mol. % and particularly preferably 0.01 to 0.2 mol. %.

The catalyst can contain phosphorus-containing ligands or phosphorus-containing ligands can be added separately to the reaction mixture. Preferably suitable as phosphorus-containing ligands are tri-n-alkylphosphanes, triarylphosphanes, dialkylarylphosphanes, alkyldiarylphosphanes and/or heteroarylphosphanes, such as tripyridylphosphane and trifurylphosphane, wherein the three substituents on the phosphorus can be the same or different and wherein one or more substituents can link the phosphorus groups of several phosphanes, wherein one part of this linkage can also be a metal atom. Particularly preferable are phosphanes such as triphenylphosphane, tri-tert-butylphosphane and tricyclohexylphosphane.

The total concentration of phosphorus-containing ligands, based on the heteroaromatics [X-a] and [X-b] bearing the leaving group $Z^3$ is preferably up to 1 mol. %, particularly preferably 0.01 to 0.5 mol. %.

To effect the process according to the invention, expediently the educts, the solvent, the base, the catalyst and if appropriate the ligand are thoroughly mixed and reacted preferably at a temperature of 0° C.-200° C., particularly preferably at 100-170° C. The reaction time varies depending on the scale of the reaction and the reaction temperature, but generally lies between a few minutes and 48 hours. Other than as a one-pot reaction, the reaction can also be run such that the various reactants are metered in a controlled way in the course of the reaction, different metering variants being possible.

The molar reactant ratio of the heteroaromatic [X-a] and [X-b] to the organoboron compound [III] is preferably 0.9 to 1.5.

The processes according to the invention are generally performed under normal pressure. It is however also possible to operate under increased or reduced pressure. The reaction is generally performed with the use of a blanket gas such as for example argon or nitrogen. After completion of the reaction, the catalyst arising as a solid is removed by filtration, the crude product freed from the solvent or solvents and then purified by methods known to those skilled in the art and appropriate for the particular product, e.g. by recrystallization, distillation, sublimation, zone melting, melt crystallization or chromatography.

Step (V6)

One possibility for the synthesis of compounds of the formula [I-a] is shown in Scheme 1.

A compound with the general formula [I-a] can be synthesized, analogously to procedures described in the literature (see e.g. WO 2004/052880 and e.g. T. W. Greene, P. G. M. Wuts, *Protective Groups in Organic Synthesis*, 1999, John Wiley & Sons, Inc.), by a coupling reaction of a compound with the corresponding general formula [II] with a substrate of the general formula [XI] (with $Z^4$ e.g. =Cl, Br, F or —OH) if necessary in the presence of an acid scavenger/base wherein the definitions of the residues $R^3$, $R^4$, $R^6$, Y, Q and $X^1$ in the above schemes correspond to the aforesaid definitions.

Acid halides [XI] ($Z^4$=Cl) or the corresponding carboxylic acids [XI] ($Z^4$=OH) are commercially available or preparable by processes described in the literature. In addition, a substrate with the general formula [XI], with $Z^4$=Cl, can be prepared from the corresponding acid ($Z^4$=OH) by chlorination using known literature processes (R. C. Larock, *Comprehensive Organic Transformations*, 2nd Edition, 1999, Wiley-VCH, page 1929 ff. and literature cited therein).

As the solvent, all usual solvents inert under the reaction conditions, such as for example cyclic and acyclic ethers (e.g. diethyl ether, tetrahydrofuran, dioxan), aromatic hydro-carbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene) and nitriles (e.g. acetonitrile) can be used or the reaction can be effected in mixtures of two or more of these solvents. The preferred solvents are tetrahydrofuran and dichloromethane.

At least one equivalent of an acid scavenger/a base (e.g. Hünig base, triethylamine or commercially available polymeric acid scavengers) relative to the starting material of the general formula [II] is used. If the starting material is a salt, at least two equivalents of the acid scavenger are needed.

The reaction is normally effected at temperatures of 0° C.-100° C. and preferably at 20° C.-30° C., but it can also be effected at the reflux temperature of the reaction mixture. The reaction time varies depending on the scale of the reaction and the reaction temperature, but generally lies between a few minutes and 48 hours.

To effect the process (V6) according to the invention for the production of the compounds of the formula [I-a] in general 0.2 to 2 mol, preferably 0.5 to 0.9 mol, of amino derivative of the formula [II] is used per mol of the carboxylic acid halide of the formula [XI]. The workup is effected by evaporation of the volatile components under vacuum and treatment of the crude material with ammoniacal methanol solution (7 molar).

After completion of the reaction, the compounds [I-a] are separated from the reaction mixture by one of the usual separation techniques. If necessary, the compounds are purified by recrystallization, distillation or chromatography.

Alternatively, a compound of the formula [I-a] can also by synthesized from the corresponding compound of the formula [II] with a substrate of the formula [XI] with $Z^4$=—OH in the presence of a coupling reagent analogously to procedures described in the literature (e.g. *Tetrahedron* 2005, 61, 10827-10852, and references cited therein).

Suitable coupling reagents are for example peptide coupling reagents (for example, N-(3-dimethyl-aminopropyl)-N'-ethyl-carbodiimide mixed with 4-dimethylamino-pyridine, N-(3-dimethylamino-propyl)-N'-ethyl-carbodiimide mixed with 1-hydroxy-benzotriazole, bromo-tripyrrolidino-phosphonium hexafluorophosphate, O-(7-azabenzotriazol-1-yl)-N,N,N',N'-tetramethyluronium hexafluorophosphate, etc.).

If necessary, a base, such as for example triethylamine or Hünig base can be used in the reaction.

As the solvent, all usual solvents inert under the reaction conditions, such as for example alcohols (e.g. methanol, ethanol, propanol), cyclic and acyclic ethers (e.g. diethyl ether, tetrahydrofuran, dioxan), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), nitriles (e.g. acetonitrile) and amides (e.g. N,N-dimethylformamide, N,N-dimethylacetamide) can be used or the reaction can be performed in mixtures of two or more of these solvents. The preferred solvent is dichloromethane.

The reaction is normally performed at temperatures of 0° C.-100° C. and preferably at 0° C.-30° C., but it can also be performed at the reflux temperature of the reaction mixture. The reaction time varies depending on the scale of the reaction and the reaction temperature, but generally lies between a few minutes and 48 hours.

After completion of the reaction, the compounds [I-a] are separated from the reaction mixture by one of the usual separation techniques. If necessary, the compounds are purified by recrystallization, distillation or chromatography.

Likewise, these synthesis methods can also be used for the conversion of the pyrazolopyrimidines of the formula [II-a] into compounds of the formula [I-l] as shown in scheme 7.

Moreover, these synthesis methods can also be used for the conversion of the substrates of the formula [I-j] and [XL] into compounds of the formula [I-k] and [XLI] respectively, as shown in scheme 7.

Step (V7)

One possibility for the synthesis of compounds of the formula [XIV] is shown in Scheme 2.

Compounds of the general formula [XIV] (where $Z^5$ stands for Oalkyl and Y stands for Oxygen) may be obtained, according to known literature methods (U.S. Pat. No. 3,950,381 and U.S. Pat. No. 4,613,610) by reacting a compound of general formula [XIII] with a carbonic acid dialkylester such as diethylcarbonate in the presence of a base (e.g. sodium hydride or potassium tert. butanolate). A solvent is used optionally. Typical solvents include alcohols (e.g. ethanol), ethers (e.g. THF), amides (DMF or NMP) and aromatic hydrocarbons (e.g. toluene, benzene), or mixtures of the respective solvents can be applied. The reaction temperature can be varied from room temperature to the boiling point of the reaction mixture. The reaction time varies depending on the scale of the reaction and the reaction temperature, but is generally between a couple of minutes and 48 hours.

In an analogous manner, the β-oxodithioesters of the general formula [XIV] (where $Z^5$ stands for Salkyl and Y stands for Sulfur) can be obtained, according to known literature methods (*Tetrahedron Letters* 2007, 48, 8376-8378) by condensation of the ketone [XIII] with (S,S)-dimethyl trithiocarbonate.

After the reaction has ended, compounds [XIV] are removed from the reaction mixture using one of the customary separation techniques. If required, the compounds are purified by recrystallisation, distillation or chromatography, or they can, if appropriate, also be used for the next step without prior purification.

Compounds of the general formula [XIII] are commercially available or can be synthetised according to known synthesis methods (Jerry March *Advanced Organic Chemistry*, $4^{th}$ edition Wiley, 1991, page 539ff and ref therein).

Step (V8)

One possibility for the synthesis of compounds of the formula [VII] is shown in Scheme 2.

Compounds of the general formula [VII] may be obtained, according to known literature methods (EP1119567, *Heterocyclic Communications* 2006, 12, 3-4, 225-228 and *J. Chem. Res*. Miniprint, 1996, 3, 785-794), by reacting a compound of general formula [XIV] with hydrazine or a hydrated form thereof. Inert solvent such as cyclic or acyclic ethers (e.g. diethyl ether, tetrahydrofuran, dioxane), alcohols (e.g. methanol or ethanol) can be used. The reaction can be carried out in mixtures of two or more of these solvents. A base e.g. triethylamine may be used if desired. The reaction temperature can be varied from 10° C. to 50° C. but room temperature is preferred. The reaction time varies depending on the scale of the reaction and the reaction temperature, but is generally between a couple of minutes and 48 hours. The reaction can be performed in a microwave apparatus (e.g. CEM Explorer) at elevated temperature, which may shorten the reaction time. After the reaction has ended, compounds [VII] are removed from the reaction mixture using one of the customary separation techniques. If required, the compounds are purified by recrystallisation, distillation or chromatography.

In an analogous manner can compounds of the general formula [XXVII] be obtained by reaction of the ketoester or ketothioester [XIV] with hydroxyhydrazines, according to known literature methods (*Tetrahedron* 1998, 54, 32, 9393-9400).

The same procedure can be used for the synthesis of compounds of the general formula [VII-a] starting either from [XVI] or from [XVIII], as well as for the conversion of dithietan compounds of the general formula [XX] into compound of the formula [XXI] (scheme 3), according to literature described methods (U.S. Pat. No. 6,342,608 and WO2010/070060).

Step (V9)

One possibility for the synthesis of dithietan compounds of the formula [XVI] is shown in Scheme 2.

Compounds of the general formula [XVI] may be obtained, according to known literature methods (*Chem. Ber.* 1985, 118, 7, 2852-2857), by reacting a dithioacid of general formula [XV] with dibromomethane or diodomethane in a solvent (e.g. ethanol) and in the presence of a base (potassium hydroxide). The required dithioacids [XV] can be obtained by reaction of Methylketones [XIII] with carbon disulfide in the presence of a base: sodium hydride or potassium tert. butoxide) and an inert solvent (e.g. dimethylformamide or benzene), according to known literature procedures (WO2009/135944 and *Tetrahedron Lett.* 1993, 34, 23, 3703-3706).

Step (V10)

One possibility for the synthesis of compounds of the formula [XVIII] is shown in Scheme 2.

The dithioesters [XVIII] can be prepared by treating dithioketals [XVII] with a Lewis acid for example BF3*etherate in the presence of hydrogen sulfide e.g. as described in *Synthetic Communications* 1999, 29, 5, 791-798.

Compounds of the general formula [XVII] can be synthetised according to known synthesis methods (e.g. in *Synlett* 2008, 15, 2331-2333 and *Tetrahedron* 2010, 66, 15, 2843-2854) by treatment of the methylketones [XIII] with carbon disulfide and methyl iodide in the presence of a base (e.g. potassium tert butoxide or sodium methanolate) and a solvent. (e.g. dimethylformamide, benzene or tetrahydrofurane or mixture thereof).

Step (V11)

One possibility for the synthesis of compounds of the formula [XX] is shown in Scheme 3.

Compounds of the general formula [XX] can be synthetised according to known synthesis methods (e.g. WO2010/070060 and U.S. Pat. No. 6,342,608) by treatment of the ketones [XIX] with carbon disulfide and dibromomethane in the presence of a base (e.g. potassium carbonate or potassium tert butoxide) and an inert solvent (dimethylsulfoxide or tetrahydrofurane).

Step (V12)

One possibility for the synthesis of compounds of the formula [I-c] is shown in Scheme 3.

Compounds of formula [I-c] can be prepared by treating the mercaptopyrazole of formula [XXI] with a halogenketone [XXII] under conditions used in state of the art methodology (e.g. in WO2010/070060) using a suitable solvent (e.g. tetrahydrofuran, 1,4-dioxane, 1,2-dimethoxyethane, methanol, ethanol, isopropanol, acetonitrile, N,N-dimethylformamide, N,N-dimethylacetamide, dimethylsulfoxide and the like), at temperatures ranging from 20° C. to reflux and for a time ranging from 30 minutes to about 48 hours.

Step (V13)

One possibility for the synthesis of compounds of the formula [I-e] is shown in Scheme 3.

Compounds of the formula [I-e] can be obtained by oxidation of the mercaptopyrazoles [I-b] by known literature procedures (WO2010/070060 and U.S. Pat. No. 6,103,667) using a suitable oxidant (e.g. m-chloroperbenzoic acid, sodium metaperiodate on silica gel or hydrogen peroxide) and solvent (e.g. dichloromethane, 1,2-dichloro-ethane).

Step (V14)

One possibility for the synthesis of compounds of the formula [I-f] is shown in Scheme 3.

A compound of the formula [I-c] is dehydrated using conditions described in the literature (WO2010/070060 and R. C. Larock, *Comprehensive Organic Transformations,* 2nd Edition, 1999, Wiley-VCH, page 291 ff. and literature cited therein) and a compound of the formula [I-f] is obtained. For example, the elimination can be effected by the transformation of the hydroxy group into a leaving group using an activating reagent (e.g. trifluoroacetic anhydride, methanesulfonyl chloride, phosphooxychloride) and a base (e.g. pyridine, triethylamine, diisopropylethylamine).

Step (V15)

One possibility for the synthesis of compounds of the formula [I-f] is shown in Scheme 3.

A sulfoxide of the formula [I-e] may undergo Pummerer rearrangement following elimination, furnishing respectively a compound of the formula [I-f], by using literature described methods (*Tetrahedron: Asymmetry* 2005, 16, 651-655 or *Chem. Pharm. Bull.* 1990, 38, 5, 1258-1265).

Step (V16)

One possibility for the synthesis of compounds of the formula [XXIV-a] is shown in Scheme 4.

A compound of the formula [XII-a] is oxidised into a compound of the formula [XXIV] by treatment with an oxidant (e.g. hydrogen peroxide, m-chloroperbenzoic acid) in a suitable solvent (e.g. dichloromethane, acetone, acetic acid, tetrahydrofuran) according to known literature methods (U.S. Pat. No. 6,423,713). The reaction can be performed at temperatures ranging from 0° C. to reflux and for a time from 30 min to about 48 hours.

Step (V17)

One possibility for the synthesis of compounds of the formula [XXV] is shown in Scheme 4.

The N-oxide compounds of formula [XXIV] are converted into aminopyridines of formula [XXV] by treatment with a suitable electrophilic species (such as phosphorous oxychloride, tosyl anhydride, bromo-tris(1-pyrrolidinyl)phosphonium hexafluorophosphate) in the presence of or followed by the treatment with a suitable nucleophile $R^{17}$—$NH_2$ (e.g. tert-butylamine, allylamine, benzylamine) according to known literature methods (*Org. Lett.* 2010, 12, 22, 5254-5257 or WO 2010/10154). A suitable base can optionally be used (e.g. diisopropylethylamine or triethylamine).

Alternatively, the intermediates from the activation (e.g. by $POCl_3$) such as [XXVIII] can be isolated and reacted with nucleophilic amines $R^{17}$—$NH_2$ in a separate reaction to compounds of the formula [XXV], as described by literature methods (EP1402900 and US2010/168185). (scheme 15)

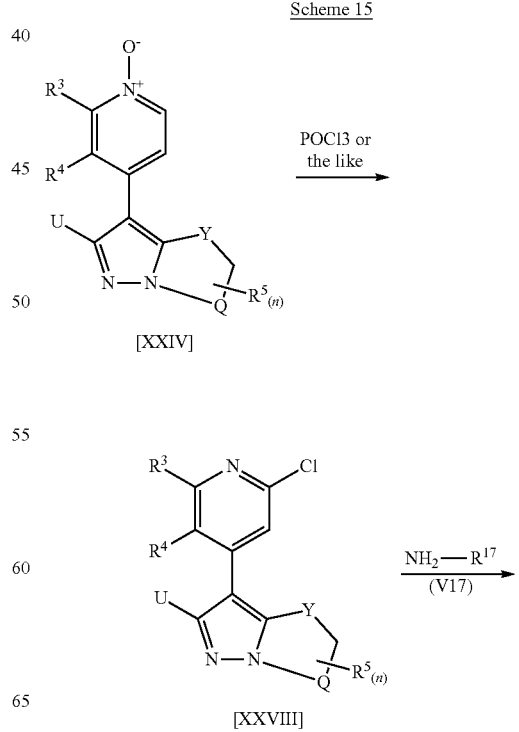

Scheme 15

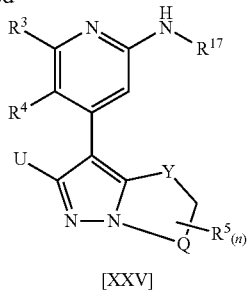

[XXV]

Step (V18)

A compound of formula [XXV], in which $R^{17}$ represents a suitable protecting group, can be transformed into a compound of the general formula [II] according to literature described methods (WO2010/10154 or US2010/168185) for instance by treatment with acids (trifluoroacetic acid, hydrobromic acid, hydrochloric acid). Alternatively the cleavage can be performed under reductive conditions (e.g. with ammonium formate using a catalysts as described in EP1787991 or with ethanol-water using Wilkinson Catalyst Rh(PPh$_3$)$_3$Cl (as described in US2005/245530).

Step (V19)

An N-oxide of formula [XXIV] can be converted into a compound of formula [I-g] by using an activating reagent (such as oxalyl chloride) in the presence of a carboxamide [XXVI] as described in the literature (*Org. Lett.* 2006, 8, 9, 1929-1932).

Step (V20)

Compounds of the general formula [I-h] in which $R^{2b}$ stands for C(O)OR$^{7*}$, C(O)SR$^{7*}$, C(S)OR$^{7*}$, C(O)R$^{7*}$ or C(S)R$^{7*}$ (symmetrically or unsymmetrically bisacylated aminopyridines) can be produced directly by the aforesaid method (V6) from compounds of the general formula [I-g] (monoacylated aminopyridines), by reaction with acid halides of the formula [XI] ($Z^4$=e.g. Cl, F).

Step (V21)

Compounds of the formula [VI-b] can moreover be synthesized analogously to procedures described in the literature (Mitsunobu, O. *Synthesis* 1981, 1-28 and *Bioorg. Med. Chem.* 2004, 12 1357-1366), e.g. by cyclisation of hydroxy compounds of the type [XXVII] in the presence of a phosphane (e.g. triphenylphosphane) and an azodicarboxylate (e.g. diethyl azodicarboxylate) and a solvent (e.g. THF). Alternatively, this cyclisation can also be affected by treatment of the hydroxypyrazole compound under dehydratisation conditions (e.g. heating in the presence of phosphoric acid as described in *Bioorg. Med. Chem.* 2004, 12 1357-1366) or by activation (e.g. using Toluolsulfonyl chloride and a base as described in *Tetrahedron Lett.* 2011, 52, 16, 1949-1951).

Step (V22)

One possibility for the synthesis of compounds of the formula [XXXVIII] is shown in Scheme 7.

Compounds of the general formula [XXXVIII] may be obtained, according to known literature methods by reacting a compound of general formula [XXXV] with a substituted 1,1,3,3-tetraalkoxypropane (EP531901, WO2006128692) or a substituted propan-1,3-dione (WO201125951). The reaction is usually carried out in a solvent such as acetic acid. The reaction temperature can be varied from room temperature to the boiling point of the reaction mixture, but it is usually in the range 90-110° C. The reaction time varies depending on the scale of the reaction and the reaction temperature, but is generally between 1 and 48 hours.

Compounds of the type [XXXV], required for the reaction are commercially available or can be produced by literature methods (WO200568473) from 3-oxo-3-arylpropanenitrile by reaction with hydrazine.

Likewise, these synthesis methods can also be used for the conversion of the halogenated pyrazoles of the formula [XXXVI] into compounds of the formula [XXXVII].

Moreover, these synthesis methods can also be used for the conversion of the trisubstituted pyrazoles of the formula [XLII] into compounds of the formula [I-p] as shown in scheme 8.

After the reaction has ended, compounds [XXXVIII], [XXXVII] and [I-p] are removed from the reaction mixture using one of the customary separation techniques. If required, the compounds are purified by recrystallisation, distillation or chromatography, or they can, if appropriate, also be used for the next step without prior purification.

Step (V23)

One possibility for the synthesis of compounds of the formula [I-j] is shown in Scheme 7.

Compounds of the formula [I-j] can be obtained by reduction of the pyrazolopyrimidine of general formula by known literature procedures (WO200638734, EP531901, Bioorganic and Medicinal Chemistry, 2010, 18, 8501). Reduction is carried out in a conventional manner, including chemical reduction and catalytic reduction.

Suitable reducing agents to be used in chemical reduction are hydrides (e.g. sodium borohydride, lithium borohydride, diborane, sodium cyanoborohydride, lithium aluminium hydride) or a combination of a metal (e.g. tin, zinc, iron) or metallic compound (e.g. chromium acetate) and an organic or inorganic acid (e.g. acetic acid, formic acid, hydrochloric acid, trifluoroacetic acid).

Suitable catalyst to be used in catalytic reduction are conventional ones such as palladium catalysts (e.g. palladium on carbon, palladium oxide, palladium black), nickel catalysts (e.g. Raney Nickel), platinum catalysts (e.g. platinum oxide) and the likes.

The reaction is usually carried out in a solvent such as alcohol (e.g. ethanol, methanol), tetrahydrofurane, N,N-dimethylformamide, a mixture thereof or any other solvent that does not adversely affect the reaction.

The reaction temperature can be varied from room temperature to the boiling point of the reaction mixture, but it is usually in the range 20-60° C. The reaction time varies depending on the scale of the reaction and the reaction temperature, but is generally between 1 and 48 hours.

Likewise, these synthesis methods can also be used for the conversion of the pyrazolopyrimidines of the formula [XXXIX] into compounds of the formula [XL].

Moreover, these synthesis methods can also be used for the conversion of the pyrazolopyrimidines of the formula [II-a] into compounds of the formula [II-b].

Alternatively, these synthesis methods can also be used for the conversion of the pyrazolopyrimidines of the formula [I-l] into compounds of the formula [I-m].

After the reaction has ended, compounds [I-j], [XL], [II-b] and [I-m] are removed from the reaction mixture using one of the customary separation techniques. If required, the compounds are purified by recrystallisation, distillation or chromatography, or they can, if appropriate, also be used for the next step without prior purification.

Step (V24)

One possibility for the synthesis of compounds of the formula [I-k] is shown in Scheme 7.

Compounds of the general formula [I-k] may be obtained by alkylation, acylation or by reaction with sulfonyl chloride, carbamoyl chloride, isocyanate of compounds of general formula [I-j].

The alkylation can be performed with an alkylating agent of formula $R^5$-$LG^1$ (where $LG^1$ is a leaving group such as halogen, triflate, mesylate) in the presence of a base. Suitable for use as solvents are all customary solvents which are inert under the reaction conditions, such as cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), amides (e.g. N,N-dimethylformamide) and nitriles e.g. acetonitrile) or the reaction can be carried out in mixtures of two or more of these solvents. The preferred solvents are N,N-dimethylformamide and acetonitrile.

At least one equivalent of base (e.g. cesium carbonate or sodium hydride) is employed, based on the starting material of the general formula [I-j].

The reaction temperature can be varied from room temperature to the boiling point of the reaction mixture. The reaction time varies depending on the scale of the reaction and the reaction temperature, but is generally between a couple of minutes and 48 hours.

The acylation is performed in the presence of an acylating agent such as $R^9C(O)Cl$ in the presence of an acid scavenger/base.

Suitable for use as solvents are all customary solvents which are inert under the reaction conditions, such as, for example, cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene) and nitriles (e.g. acetonitrile), or the reaction can be carried out in mixtures of two or more of these solvents. The preferred solvents are tetrahydrofuran and dichloromethane.

At least one equivalent of an acid scavenger/a base (e.g. Hünig base, triethylamine or commercially available polymeric acid scavengers) is employed, based on the starting material of the general formula [I-j]. If the starting material is a salt, at least two equivalents of the acid scavenger are required.

The reaction is usually carried out at temperatures of 0° C.-100° C. and preferably at 20° C.-30° C., but it can also be carried out at the reflux temperature of the reaction mixture. The reaction time varies depending on the scale of the reaction and the reaction temperature, but is generally between a couple of minutes and 48 hours.

Alternatively the compound of general formula [I-j] can be subjected to a reactant of general formula LG-C(O)$NR^9R^{10}$, LG-C(O)$OR^9$, LG-S(O)$_2R^9$, LG-S(O)$_2NR^9R^{10}$, $R^9$N=C=O or $R^9$N=C=S, where LG is a leaving group, in similar conditions as described above for the acetylation reaction to provide the compound of general formula [I-k].

If $R^5$ contains a carbonyl function, it can be subjected to thionation in the presence of a thionating agent like for example sulphur (S), sulfhydric acid ($H_2S$), sodium sulfide ($Na_2S$), sodium hydrosulfide (NaHS), boron trisulfide ($B_2S_3$), bis(diethylaluminium)sulfide (($AlEt_2)_2S$), ammonium sulfide (($NH_4)_2S$), phosphorous pentasulfide ($P_2S_5$), Lawesson's reagent (2,4-bis(4-methoxyphenyl)-1,2,3,4-dithiadiphosphetane 2,4-disulfide) or a polymer-supported thionating reagent such as described in J. Chem. Soc. Perkin 1, (2001), 358.

Likewise, these synthesis methods can also be used for the conversion of the bicyclic pyrazoles of the formula [XL] into compounds of the formula [XLI].

Moreover, these synthesis methods can also be used for the conversion of the bicyclic pyrazoles of the formula [I-t] into compounds of the formula [I-u] as shown in scheme 10.

Alternatively, these synthesis methods can also be used for the conversion of the bicyclic pyrazoles of the formula [L] into compounds of the formula [LI] as shown in scheme 10.

After the reaction has ended, compounds [I-k], [I-u], [XLI] and [LI] are removed from the reaction mixture using one of the customary separation techniques. If required, the compounds are purified by recrystallisation, distillation or chromatography, or they can, if appropriate, also be used for the next step without prior purification.

Step (V25)

One possibility for the synthesis of compounds of the formula [I-q] is shown in Scheme 8.

Compounds of the general formula [I-q] may be obtained, according to known literature methods (e.g. as described in U.S. Pat. No. 5,232,939, WO2007129195) by alkylation of a compound of general formula [XLII] with a compound of formula [XLIII] in which $Z^3$ is a leaving group (e.g. chlorine, bromine, tosylate or mesylate) and subsequent cyclisation mediated by the deprotection of the ketone or aldehyde.

The alkylation is effected in the presence of a base, the nature of which is not critical. examples of suitable bases include hydrides (e.g. sodium hydride), carbonates (e.g. cesium, potassium or sodium carbonate) and organic bases (e.g. triethylamine).

Suitable for use as solvents are all customary solvents which are inert under the reaction conditions, such as, for example, aromatic hydrocarbons (e.g. toluene, xylene), halogenated hydrocarbons (e.g. dichloromethane, chloroform), amides (e.g. N,N-dimethylformamide) and nitriles (e.g. acetonitrile), or the reaction can be carried out in mixtures of two or more of these solvents.

The reaction temperature can be varied from room temperature to the boiling point of the reaction mixture, but it is usually in the range 20-80° C. The reaction time varies depending on the scale of the reaction and the reaction temperature, but is generally between 1 and 48 hours.

After the reaction has ended, the intermediate aminopyrazole is removed from the reaction mixture using one of the customary separation techniques. If required, the compound is purified by recrystallisation, distillation or chromatography, or they can, if appropriate, also be used for the next step without prior purification.

Compound of formula [XLIII] in which $Z^3$ is a leaving group are commercially available or can be produced by literature methods for example by reaction of a alkylvinylether with a brominating agent and an alcohol (as described in Tetrahedron Letters, 1972, 4055; U.S. Pat. No. 2,433,890).

The subsequent ring closure reaction may be effected by adding at least a catalytic amount of a suitable acid like for example an organic sulfonic acid (e.g. p-toluenesulfonic acid) or a mineral acid (e.g. hydrochloric acid or sulfuric acid), but is generally performed with hydrochloric acid in dioxane. The amount of acid may vary widely from a catalytic amount up to a large excess.

Suitable for use as solvents are all customary solvents which are inert under the reaction conditions, such as, for example, aromatic hydrocarbons (e.g. toluene, xylene), alcohols (e.g. ethanol, methanol), ethers (e.g. dioxane, tetrahydrofurane) or the reaction can be carried out in mixtures of two or more of these solvents.

The reaction temperature can be varied from room temperature to the boiling point of the reaction mixture. The reaction time varies depending on the scale of the reaction and the reaction temperature, but is generally between 1 and 48 hours.

After the reaction has ended, compounds [I-q] are removed from the reaction mixture using one of the customary separation techniques. If required, the compounds are purified by recrystallisation, distillation or chromatography, or they can, if appropriate, also be used for the next step without prior purification.

Compounds of the type [XLII], required for the reaction can be prepared for example from ketone [XIX] as described in scheme 9.

Step (V26)

One possibility for the synthesis of compounds of the formula [I-r] is shown in Scheme 8.

Compounds of the general formula [I-r] may be obtained, according to known literature methods (e.g. as described in WO2002072576, WO2007129195) by alkylation of a compound of general formula [XLII] with a compound of formula [XLIV] in which $Z^3$ is a leaving group (e.g. chlorine, bromine, tosylate or mesylate) and subsequent cyclisation.

The alkylation is effected in the presence of a base, the nature of which is not critical. Examples of suitable bases include hydrides (e.g. sodium hydride), carbonates (e.g. cesium, potassium or sodium carbonate) and organic bases (e.g. triethylamine).

Suitable for use as solvents are all customary solvents which are inert under the reaction conditions, such as, for example, aromatic hydrocarbons (e.g. toluene, xylene), halogenated hydrocarbons (e.g. dichloromethane, chloroform), amides (e.g. N,N-dimethylformamide) and nitriles (e.g. acetonitrile), or the reaction can be carried out in mixtures of two or more of these solvents.

The reaction temperature can be varied from room temperature to the boiling point of the reaction mixture, but it is usually in the range 20-80° C. The reaction time varies depending on the scale of the reaction and the reaction temperature, but is generally between 1 and 48 hours.

After the reaction has ended, the intermediate aminopyrazole is removed from the reaction mixture using one of the customary separation techniques. If required, the compound is purified by recrystallisation, distillation or chromatography, or they can, if appropriate, also be used for the next step without prior purification.

Compound of formula [XLIV] in which $Z^3$ is a leaving group are commercially available or can be produced by literature methods, for example by esterification of the corresponding carboxylic acid (as described in European Journal of Organic Chemistry, 1999, 11, 2909).

The subsequent ring closure reaction may be effected using a base like for example sodium ethylate in ethanol (as describes in EP531901).

Alternatively, the cyclisation can be performed by using a coupling agent (like for example 2-(1H-7-Azabenzotriazol-1-yl)-1,1,3,3-tetramethyl uronium hexafluorophosphate) in the presence of a base (such as for example Hünig base) in a solvent (such as for example N,N-dimethylformamide) on the aminoacid obtained by saponification of the ester intermediate as described in WO2007129195.

After the reaction has ended, compounds [I-r] are removed from the reaction mixture using one of the customary separation techniques. If required, the compounds are purified by recrystallisation, distillation or chromatography, or they can, if appropriate, also be used for the next step without prior purification.

Step (V27)

One possibility for the synthesis of compounds of the formula [I-r] is shown in Scheme 8.

Compounds of the formula [I-s] can be obtained by reduction of the substrates of general formula [I-r] by known literature procedures (U.S. Pat. No. 5,356,897, U.S. Pat. No. 5,173,485, Journal of Organic Chemistry, 1984, 49, 1964).

Suitable reducing agents to be used in chemical reduction are for example hydrides (e.g. sodium borohydride, lithium borohydride, diborane, sodium cyanoborohydride, lithium aluminium hydride).

The reaction is usually carried out in a solvent such as alcohol (e.g. ethanol, methanol), tetrahydrofurane, diethylether, a mixture thereof or any other solvent that does not adversely affect the reaction.

The reaction temperature can be varied from room temperature to the boiling point of the reaction mixture. The reaction time varies depending on the scale of the reaction and the reaction temperature, but is generally between 1 and 48 hours.

After the reaction has ended, compounds [I-r] are removed from the reaction mixture using one of the customary separation techniques. If required, the compounds are purified by recrystallisation, distillation or chromatography, or they can, if appropriate, also be used for the next step without prior purification.

Step (V28)

One possibility for the synthesis of compounds of the formula [XLVI] is shown in Scheme 9.

The bromoketones of the formula [XLVI] can be produced by literature methods. One method is for example the bromination of corresponding ketones [XIX] (e.g. described in EP1140916, WO20066137658, WO2005105814) by reaction with a brominating agent (like bromine or N-bromosuccinimide) in acetic acid, halogenated solvents (dichloromethane or chloroform) or N,N-dimethylformamide. The reaction can be performed at temperatures between room temperature and refluxing temperature of the solvent.

Step (V29)

One possibility for the synthesis of compounds of the formula [XLII] is shown in Scheme 9.

The aminopyrazole of the formula [XLII] can be obtained (e.g. as described in WO200638734, WO200726950, Tetrahedron, 2009, 65, 3292) by reaction of haloketone of the formula [XLVI] with a thiosemicarbazide of the formula [XLV] in a solvent such as ethanol followed by treatment of the intermediate 2,3-dihydro-6H-1,3,4-thiazine by for example aqueous hydrobromic acid. The reaction can be performed at temperatures between room temperature and refluxing temperature of the solvent. The reaction time varies depending on the scale of the reaction and the reaction temperature, but is generally between 1 and 48 hours.

Compounds of the type [XLV], required for the reaction are commercially available or can be produced by literature methods (Can. J. Chem., 1968, 45, 1865; Chem. Ber., 1894, 27, 623) from isothiocyanates and hydrazine.

Step (V30)

One possibility for the synthesis of compounds of the formula [XLVII] is shown in Scheme 9.

Compounds of the general formula [XLVII] can be prepared according to known procedure (EP531901, WO2007129195) for example using compounds of general formula [XIX] and react it with N,N-dimethylformamide dimethyl acetal and subsequently with hydroxylamine.

Step (V31)

One possibility for the synthesis of compounds of the formula [XLVIII] is shown in Scheme 9.

Compounds of the general formula [XLVIII] can be prepared according to known procedure (EP531901) for example by subjecting isoxazoles of general formula [XLVII] to cleavage of O—N bond. This reaction can be carried out by using a base like for example sodium hydroxyde 1M in water.

Step (V32)

One possibility for the synthesis of compounds of the formula [XXXV-a] is shown in Scheme 9.

Compounds of the general formula [XLIX] can be prepared according to known procedure (EP531901) for example by subjecting alpha-cyanoketone of general formula [XLVIII] to halogenation reaction followed by a cyclisation of the halointermediate using hydrazine hydrate.

The halogenation is carried out using a conventional halogenating agent such as halogen (e.g. chlorine, bromine), phosphorus trihalide (e.g. phosphorus trichloride, phosphorus tribromide), phosphorus pentahalide (e.g. phosphorus pentachloride), thionyl halide (e.g. thionyl chloride), oxalyl halide (e.g. oxalyl chloride) and the like. The reaction can be carried out in a solvent such as dichloromethane, tetrahydrofurane or any other solvent that does not adversely affect the reaction. The reaction temperature can be varied from room temperature to the boiling point of the reaction mixture. The reaction time varies depending on the scale of the reaction and the reaction temperature, but is generally between 1 and 48 hours.

After evaporation of the solvent, the intermediate is then condensed with hydrazine hydrate. The reaction can be carried out in a solvent such as ethanol or any other solvent that does not adversely affect the reaction. The reaction temperature can be varied from room temperature to the boiling point of the reaction mixture. The reaction time varies depending on the scale of the reaction and the reaction temperature, but is generally between 1 and 48 hours.

After the reaction has ended, compounds [XLIX] are removed from the reaction mixture using one of the customary separation techniques. If required, the compounds are purified by recrystallisation, distillation or chromatography, or they can, if appropriate, also be used for the next step without prior purification.

Step (V33)

One possibility for the synthesis of compounds of the formula [XLII] is shown in Scheme 9.

Compounds of the general formula [XLII] where $R^5$=alkyl can be prepared for example by reductive amination (e.g. as described in WO2010127975, WO2006127595) with a suitable aldehyde or ketone. The reaction is carried out using a suitable reducing agent such as sodium cyanoborohydride in a solvent such as methanol or dichloromethane. An acid like for example acetic acid can be added if necessary. The reaction temperature can be varied from room temperature to the boiling point of the reaction mixture. The reaction time varies depending on the scale of the reaction and the reaction temperature, but is generally between 1 and 48 hours.

After the reaction has ended, compounds [XLII] are removed from the reaction mixture using one of the customary separation techniques. If required, the compounds are purified by recrystallisation, distillation or chromatography, or they can, if appropriate, also be used for the next step without prior purification.

Step (V34)

One possibility for the synthesis of compounds of the formula [I-v] is shown in Scheme 11.

Compounds of formula [I-v] can be prepared from [LII], where LG represents a leaving group by Buchwald amination or amidation reaction (Scheme 11). The reaction can be performed in the presence of a primary amide or amine, of a palladium (II) catalyst such as palladium diacetate, a ligand such as Xantphos, a base such as potassium or cesium carbonate in an aprotic solvent such as dioxane or THF under thermal or microwave conditions (see Org. Lett. 2001, 3 (21) 3417).

The reaction is usually carried out at temperatures of 20° C.-140° C. and preferably at 60° C.-100° C. The reaction time varies depending on the scale of the reaction and the reaction temperature, but is generally between a couple of minutes and 48 hours. After the reaction has ended, the compounds [I-v] are removed from the reaction mixture using one of the customary separation techniques. If required, the compounds are purified by recrystallisation, distillation or chromatography.

Compounds of formula [I-v] may also be prepared by nucleophilic substitution which means by direct treatment of compounds of formula [LII], where LG represents a leaving group such as chlorine with an amine of general formula $HNR^1R^2$ under thermal or microwave conditions, if appropriate in the presence of a solvent and if appropriate in the presence of a base.

Suitable for use as solvents are all customary solvents which are inert under the reaction conditions, such as cyclic and acyclic ethers (e.g. diethyl ether, tetrahydrofuran, dioxane), aromatic hydrocarbons (e.g. benzene, toluene, xylene), halogenated hydrocarbons (e.g. dichloromethane, chloroform, carbon tetrachloride), halogenated aromatic hydrocarbons (e.g. chlorobenzene, dichlorobenzene), amides (e.g. N,N-dimethylformamide) and nitriles (e.g. acetonitrile), or the reaction can be carried out in mixtures of two or more of these solvents. Preferably the reaction can be performed without solvent.

The reaction is usually carried out at temperatures of 20° C.-160° C. and preferably at 140° C. in the microwave oven. The reaction time varies depending on the scale of the reaction and the reaction temperature, but is generally between a couple of minutes and 48 hours.

After the reaction has ended, compound [I-v] is removed from the reaction mixture using one of the customary separation techniques. If required, the compounds are purified by recrystallisation, distillation or chromatography.

For compounds where X1=N and LG=SMe, it may be necessary to generate the sulfone using an oxidating agent like for example meta-chloroperbenzoic acid in a solvent like for example dichloromethane (see Tetrahedron Letters, 2009, 50, 1377-1380) to facilitate the nucleophilic substitution.

For compounds where X1=CH and LG=Cl, it may be necessary to generate the N-oxide using an oxidating agent like for example meta-chloroperbenzoic acid in a solvent like for example dichloromethane (as described in WO 07/143,597) to facilitate the nucleophilic substitution. Compound of the general formula [I-v] would then be obtained after reduction of the N-oxide using a reducing agent like for example $PCl_3$ (see Chemical & Pharmaceutical Bulletin, 1996, 44, 103-14).

Step (V35)

One possibility for the synthesis of compounds of the formula [VII-a] is shown in Scheme 2.

Compounds of the formula [VII-a] can be prepared from hydroxypyrazoles of the formula [VII] (where $Y^1$ stands for oxygen) by sulfurisation according to known literature procedures (US2011/184188 and *Bioorganic & Medicinal*

*Chemistry Letters,* 2009, 19, 462-468) e.g. by reaction of the hydroxypyrazole with 2,4-bis(4-methoxyphenyl)-1,3-dithia-2,4-diphosphetane-2,4-disulfide (Lawson reagent). The reaction is typically carried out in a solvent (e.g. toluene, benzene) at increased temperatures (e.g. 60° C. to reflux of the solvent).
Step (V36)

One possibility for the synthesis of compounds of the formula [LIII] is shown in Scheme 12.

Compounds of formula [LIII] can be prepared by treating the mercaptopyrazole of formula [VII] with a halogenketone [XXII] under conditions used in state of the art methodology (e.g. EP1206474) using a suitable solvent (e.g. tetrahydrofuran, 1,4-dioxane, 1,2-dimethoxyethane, methanol, ethanol, isopropanol, acetonitrile, N,N-dimethylformamide, N,N-dimethylacetamide, dimethylsulfoxide and the like) and a base (e.g. potassium carbonate and the like), at temperatures ranging from 20° C. to reflux and for a time ranging from 30 minutes to about 48 hours.

Likewise, this synthesis methods can also be used for the conversion of the pyrazoles of the formula [VII] into compounds of the formula [LV].
Step (V37)

One possibility for the synthesis of compounds of the formula [VI-a] is shown in Scheme 12. Compounds of the formula [VI-a] can be prepared from pyrazoles of the formula [LIII] (where $Y^1$ stands for O, S) by cyclisation according to known literature procedures (e.g. EP1206474). The reaction is typically carried out in a solvent (e.g. toluene, benzene) at increased temperatures (e.g. 60° C. to reflux of the solvent) in the presence of an activating reagent (e.g. acetic acid, p-toluenesulfonic acid).

Likewise, this synthesis methods can also be used for the synthesis of the intermediates of the formula [VI-a] from compounds of the formula [LV].

In the field of veterinary medicine the compounds according to the invention are suitable, with favourable warm blood toxicity, for controlling parasitic protozoa which occur in animal breeding and animal husbandry in livestock, breeding, zoo, laboratory, experimental and domestic animals. They are active against all or specific stages of development of the protozoa.

Agricultural livestock are, for example mammals, such as, sheep, goats, horses, donkeys, camels, buffaloes, rabbits, and in particular cattle and pigs; or poultry such as turkeys, ducks, geese, and in particular chickens, and as the case may be insects such as bees.

Domestic animals are for example mammals, such as hamsters, guinea pigs, rats, mice or in particular dogs, cats; or cage birds.

According to a preferred embodiment mammals the compounds according to the invention are administered to birds.

According to another preferred embodiment the compounds according to the invention are administered to birds.

By controlling the parasitic protozoa it is intended to reduce or prevent illness, cases of deaths and performance reductions (in the case of meat, milk, wool, hides, eggs, honey and the like), so that more economical and simpler animal keeping is made possible by the use of the active compounds according to the invention.

The term "controlling" as used herein with regard to the animal health field, means that the active compounds are effective in reducing the incidence of the respective parasite in an animal infected with such parasites to innocuous levels. More specifically, "controlling", as used herein, means that the active compound is effective in killing the respective parasite, inhibiting its growth, or inhibiting its proliferation.

In the veterinary field and in animal keeping, the administration of the active compounds according to the invention is carried out in the known manner directly or enterally, parenterally, dermally or nasally in the form of suitable preparations. Enteral administration of the active compounds takes place, for example, orally in the form of powders, suppositories, tablets, capsules, pastes, drinks, granules, drenches, boli, medicated feed or drinking water. Dermal administration takes place, for example, in the form of dipping, spraying, bathing, washing, pouring on and spotting on, and dusting. Parenteral administration takes place, for example, in the form of injection (intramuscular, subcutaneous, intravenous, intraperitoneal) or by means of implants. Administration can be carried out prophylactically or therapeutically.

The following parasitic protozoa may be mentioned by way of example and by way of preference—but without any limitation:

Mastigophora (Flagellata), such as, for example, Trypanosomatidae, for example, *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica*, such as, for example, Trichomonadidae, for example, *Giardia lamblia, G. canis.*

Sarcomastigophora (Rhizopoda), such as Entamoebidae, for example, *Entamoeba histolytica*, Hartmanellidae, for example, *Acanthamoeba* sp., *Harmanella* sp.

Apicomplexa (Sporozoa), such as Eimeridae, for example, *Eimeria acervulina, E. adenoides, E. alabahmensis, E. anatis, E. anserina, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. zuernii, Globidium* spec., *Isospora belli, I. canis, I. felis, I. ohioensis, I. rivolta, I.* spec., *I. suis, Cystisospora* spec., *Cryptosporidium* spec., in particular *C. parvum*; such as Toxoplasmadidae, for example, *Toxoplasma gondii, Hammondia heydornii, Neospora caninum, Besnoitia besnoitii*; such as Sarcocystidae, for example, *Sarcocystis bovicanis, S. bovihominis, S. ovicanis, S. ovifelis, S. neurona, S.* spec., *S. suihominis*, such as Leucozoidae, for example, *Leucozytozoon simondi*, such as Plasmodiidae, for example, *Plasmodium berghei, P. falciparum, P. malariae, P. ovale, P. vivax, P.* spec., such as Piroplasmea, for example, *Babesia argentina, B. bovis, B. canis, B.* spec., *Theileria parva, Theileria* spec., such as Adeleina, for example, *Hepatozoon canis, H.* spec.

A further subject of the invention relates to the nonmedicinal use of the Heterocyclylpyri(mi)dinylpyrazole according to the invention or mixtures thereof for the control of undesired microorganisms and for the reduction of mycotoxins in plants and plant parts.

A further subject of the invention relates to an agent for the control of undesired microorganisms and for the reduction of mycotoxins in plants and plant parts, comprising at least one Heterocyclylpyri(mi)dinylpyrazole according to the present invention.

In addition, the invention relates to a method for the control of undesired microorganisms and for the reduction of mycotoxins in plants and plant parts, characterized in that the Heterocyclylpyri(mi)dinylpyrazoles according to the invention are applied onto the microorganisms and/or in their habitat.

The substances according to the invention have potent microbicidal activity and can be employed for controlling unwanted microorganisms, such as fungi and bacteria, in crop protection and in the protection of materials.

The present invention furthermore relates to a crop protection composition for controlling unwanted microorganisms, in particular unwanted fungi, which comprises the active compounds according to the invention. These are preferably fungicidal compositions which comprise agriculturally suitable auxiliaries, solvents, carriers, surfactants or extenders.

Moreover, the invention relates to a method for controlling unwanted microorganisms, characterized in that the active compounds according to the invention are applied to the phytopathogenic fungi and/or their habitat.

According to the invention, a carrier is a natural or synthetic organic or inorganic substance with which the active compounds are mixed or bonded for better applicability, in particular for application to plants or plant parts or seed. The carrier, which may be solid or liquid, is generally inert and should be suitable for use in agriculture.

Suitable solid or liquid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral and vegetable oils and derivatives of these. Mixtures of such carriers may also be used. Suitable solid carriers for granules are: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Suitable liquefied gaseous extenders or carriers are liquids which are gaseous at ambient temperature and under atmospheric pressure, for example aerosol propellants, such as halogenated hydrocarbons, and also butane, propane, nitrogen and carbon dioxide.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

The compositions according to the invention may comprise additional further components, such as, for example, surfactants. Suitable surfactants are emulsifiers and/or foam formers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolyzates, lignosulphite waste liquors and methylcellulose. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers.

In general, the active compounds can be combined with any solid or liquid additive customarily used for formulation purposes.

The compositions and formulations according to the invention generally comprise between 0.05 and 99% by weight, 0.01 and 98% by weight, preferably between 0.1 and 95% by weight, particularly preferably between 0.5 and 90% of active compound, very particularly preferably between 10 and 70% by weight.

The active compounds or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be prepared in a manner known per se, for example by mixing the active compounds with at least one customary extender, solvent or diluent, emulsifier, dispersant, and/or binder or fixative, wetting agent, water repellent, if appropriate desiccants and UV stabilizers and, if appropriate, dyes and pigments, defoamers, preservatives, secondary thickeners, adhesives, gibberellins and also further processing auxiliaries.

The compositions according to the invention include not only formulations which are already ready for use and can be applied with a suitable apparatus to the plant or the seed, but also commercial concentrates which have to be diluted with water prior to use.

The active compounds according to the invention can be present as such or in their (commercial) formulations and in the use forms prepared from these formulations as a mixture with other (known) active compounds, such as insecticides, attractants, sterilants, bactericides, acaricides, nematicides, fungicides, growth regulators, herbicides, fertilizers, safeners and/or semiochemicals.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. It is furthermore possible to apply the active compounds by the ultra-low volume method or to inject the active compound preparation or the active compound itself into the soil.

The invention furthermore includes a method for treating seed.

The invention furthermore relates to seed which has been treated in accordance with one of the methods described in the previous paragraph. The seeds according to the invention are used in methods for the protection of seed from undesirable microorganisms. In these methods, seed treated with at least one active compound according to the invention is employed.

The active compounds or compositions according to the invention are also suitable for treating seed. A large part of the damage to crop plants caused by harmful organisms is triggered by the infection of the seed during storage or after sowing both during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of phytopathogenic fungi by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with, or at least reduce considerably, the additional application of crop protection agents after sowing or after emergence of the plants. It is furthermore desirable to optimize the amount of active compound employed in such a way as to provide optimum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore also relates to a method for the protection of seed and germinating plants, from attack by phytopathogenic fungi, by treating the seed with a composition according to the invention. The invention also relates to the use of the compositions according to the invention for treating seed for protecting the seed and the germinating plant against phytopathogenic fungi. Furthermore, the invention relates to seed treated with a composition according to the invention for protection against phytopathogenic fungi.

The control of phytopathogenic fungi which damage plants post-emergence is carried out primarily by treating the soil and the above-ground parts of plants with crop protection agents. Owing to the concerns regarding a possible impact of the crop protection agents on the environment and the health of humans and animals, there are efforts to reduce the amount of active compounds applied.

One of the advantages of the present invention is that the particular systemic properties of the active compounds and compositions according to the invention mean that treatment of the seed with these active compounds and compositions not only protects the seed itself, but also the resulting plants after emergence, from phytopathogenic fungi. In this manner, the immediate treatment of the crop at the time of sowing or shortly thereafter can be dispensed with.

It is also considered to be advantageous that the active compounds or compositions according to the invention can be used in particular also for transgenic seed where the plant growing from this seed is capable of expressing a protein which acts against pests. By treating such seed with the active compounds or compositions according to the invention, even by the expression of the, for example, insecticidal protein, certain pests may be controlled. Surprisingly, a further synergistic effect may be observed here, which additionally increases the effectiveness of the protection against attack by pests.

The compositions according to the invention are suitable for protecting seed of any plant variety which is employed in agriculture, in the greenhouse, in forests or in horticulture and viticulture. In particular, this takes the form of seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cacao, sugar cane, tobacco, vegetables (such as tomato, cucumbers, onions and lettuce), turf and ornamentals (see also hereinbelow). The treatment of the seed of cereals (such as wheat, barley, rye, triticale and oats), maize and rice is of particular importance.

As also described further below, the treatment of transgenic seed with the active compounds or compositions according to the invention is of particular importance. This refers to the seed of plants containing at least one heterologous gene which allows the expression of a polypeptide or protein having insecticidal properties. The heterologous gene in transgenic seed can originate, for example, from microorganisms of the species *Bacillus*, *Rhizobium*, *Pseudomonas*, *Serratia*, *Trichoderma*, *Clavibacter*, *Glomus* or *Gliocladium*. Preferably, this heterologous gene is from *Bacillus* sp., the gene product having activity against the European corn borer and/or the Western corn rootworm. Particularly preferably, the heterologous gene originates from *Bacillus thuringiensis*.

Within the context of the present invention, the composition according to the invention is applied to the seed either alone or in a suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged.

This must be borne in mind in particular in the case of active compounds which can have phytotoxic effects at certain application rates.

The compositions according to the invention can be applied directly, i.e. without containing any other components and undiluted. In general, it is preferred to apply the compositions to the seed in the form of a suitable formulation. Suitable formulations and methods for treating seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compounds which can be used in accordance with the invention can be converted into the customary seed-dressing formulations, such as solutions, emulsions, suspensions, powders, foams, slurries or other coating compositions for seed, and also ULV formulations.

These formulations are prepared in a known manner, by mixing the active compounds with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. In this context, not only pigments, which are sparingly soluble in water, but also dyes, which are soluble in water, may be used. Examples which may be mentioned are the colorants known by the names Rhodamin B, C.I. Pigment Red 112 and C.I. Solvent Red 1.

Suitable wetting agents which may be present in the seed-dressing formulations which can be used in accordance with the invention are all substances which promote wetting and which are conventionally used for the formulation of agrochemical active compounds. Preference is given to using alkylnaphthalenesulphonates, such as diisopropyl- or diisobutylnaphthalenesulphonates.

Suitable dispersants and/or emulsifiers which may be present in the seed-dressing formulations which can be used in accordance with the invention are all nonionic, anionic and cationic dispersants conventionally used for the formulation of agrochemical active compounds. Preference is given to using nonionic or anionic dispersants or mixtures of nonionic or anionic dispersants. Suitable nonionic dispersants which may be mentioned are, in particular, ethylene oxide/propylene oxide block polymers, alkylphenol polyglycol ethers and tristryrylphenol polyglycol ether, and their phosphated or sulphated derivatives. Suitable anionic dispersants are, in particular, lignosulphonates, polyacrylic acid salts and arylsulphonate/formaldehyde condensates.

Antifoams which may be present in the seed-dressing formulations which can be used in accordance with the invention are all foam-inhibiting substances conventionally used for the formulation of agrochemical active compounds. Silicone antifoams and magnesium stearate can preferably be used.

Preservatives which may be present in the seed-dressing formulations which can be used in accordance with the invention are all substances which can be employed for such purposes in agrochemical compositions. Dichlorophene and benzyl alcohol hemiformal may be mentioned by way of example.

Secondary thickeners which may be present in the seed-dressing formulations which can be used in accordance with the invention are all substances which can be employed for such purposes in agrochemical compositions. Cellulose derivatives, acrylic acid derivatives, xanthan, modified clays and finely divided silica are preferred.

Adhesives which may be present in the seed-dressing formulations which can be used in accordance with the invention are all customary binders which can be employed in seed-dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel" [Chemistry of crop protection agents and pesticides], vol. 2, Springer Verlag, 1970, p. 401-412).

The seed-dressing formulations which can be used in accordance with the invention can be employed for the treatment of a wide range of seed, including the seed of transgenic plants, either directly or after previously having been diluted with water. In this context, additional synergistic effects may also occur in cooperation with the substances formed by expression.

All mixers which can conventionally be employed for the seed-dressing operation are suitable for treating seed with the seed-dressing formulations which can be used in accordance with the invention or with the preparations prepared therefrom by addition of water. Specifically, a procedure is followed during the seed-dressing operation in which the seed is placed into a mixer, the specific desired amount of seed-dressing formulations, either as such or after previously having been diluted with water, is added, and everything is mixed until the formulation is distributed uniformly on the seed. If appropriate, this is followed by a drying process.

The active compounds or compositions according to the invention have a potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

The fungicidal compositions according to the invention can be used for the curative or protective control of phytopathogenic fungi. Accordingly, the invention also relates to curative and protective methods for controlling phytopathogenic fungi using the active compounds or compositions according to the invention, which are applied to the seed, the plant or plant parts, the fruit or the soil in which the plants grow.

The compositions according to the invention for controlling phytopathogenic fungi in crop protection comprise an effective, but non-phytotoxic amount of the active compounds according to the invention. "Effective, but non-phytotoxic amount" means an amount of the composition according to the invention which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on a plurality of factors, for example on the fungus to be controlled, the plant, the climatic conditions and the ingredients of the compositions according to the invention.

The fact that the active compounds are well tolerated by plants at the concentrations required for controlling plant diseases permits the treatment of above-ground parts of plants, of propagation stock and seeds, and of the soil.

All plants and plant parts can be treated in accordance with the invention. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. Parts of plants also include harvested plants and vegetative and generative propagation material, for example seedlings, tubers, rhizomes, cuttings and seeds.

The active compounds according to the invention are suitable for the protection of plants and plant organs, for increasing the harvest yields, for improving the quality of the harvested crop, while being well tolerated by plants, having favourable toxicity to warm-blooded species and being environmentally friendly. They may be preferably employed as crop protection agents. They are active against normally sensitive and resistant species and also against all or some stages of development.

The following plants may be mentioned as plants which can be treated according to the invention: cotton, flax, grapevine, fruit, vegetables, such as Rosaceae sp. (for example pome fruits such as apples and pears, but also stone fruits such as apricots, cherries, almonds and peaches, and soft fruits such as strawberries), Ribesioidae sp., Juglandaceae sp., Betulaceae sp., Anacardiaceae sp., Fagaceae sp., Moraceae sp., Oleaceae sp., Actimidaceae sp., Lauraceae sp., Musaceae sp. (for example banana plants and banana plantations), Rubiaceae sp. (for example coffee), Theaceae sp., Sterculiceae sp., Rutaceae sp. (for example lemons, oranges and grapefruit); Solanaceae sp. (for example tomatoes), Liliaceae sp., Asteraceae sp. (for example lettuce), Umbelliferae sp., Cruciferae sp., Chenopodiaceae sp., Cucurbitaceae sp. (for example cucumber), Alliaceae sp. (for example leeks, onions), Papilionaceae sp. (for example peas); major crop plants such as Gramineae sp. (for example maize, turf, cereals such as wheat, rye, rice, barley, oats, millet and triticale), Poaceae sp. (for example sugar cane), Asteraceae sp. (for example sunflower), Brassicaceae sp. (for example white cabbage, red cabbage, broccoli, cauliflower, Brussels sprouts, pak choi, kohlrabi, small radishes, and also oilseed rape, mustard, horseradish and cress), Fabacae sp. (for example beans, peanuts), Papilionaceae sp. (for example soya beans), Solanaceae sp. (for example potatoes), Chenopodiaceae sp. (for example sugar beet, fodder beet, Swiss chard, beetroot); useful plants and ornamental plants in gardens and forests; and in each case genetically modified types of these plants.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above. Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene that is located in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. Possible are thus, for example, the following effects which exceed the effects which were actually to be expected: reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products.

At certain application rates, the active compounds according to the invention may also have a strengthening effect on plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, also those substances or combinations of substances which are capable of stimulating the defence system of plants in such a way that, when subsequently inoculated with unwanted phytopathogenic fungi, the treated plants display a substantial degree of resistance to these unwanted phytopathogenic fungi. Thus, the substances according to the invention can be employed for protecting plants against attack by the abovementioned pathogens within a certain period of time after the treatment. The period within which protection is brought about generally extends from 1 to 10 days, preferably 1 to 7 days, after the treatment of the plants with the active compounds.

Plants and plant varieties which are preferably treated according to the invention include all plants which have genetic material which imparts particularly advantageous, useful traits to these plants (whether obtained by breeding and/or biotechnological means).

Plants and plant varieties which are also preferably treated according to the invention are resistant against one or more biotic stress factors, i.e. said plants have a better defence against animal and microbial pests, such as against nematodes, insects, mites, phytopathogenic fungi, bacteria, viruses and/or viroids.

Plants and plant varieties which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which may also be treated according to the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid effect, which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant varieties (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the abovementioned genes.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species for example). Plants expressing an exogenous phosphinothricin acetyltransferase have been described.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme prephenate dehydrogenase in addition to a gene encoding an HPPD-tolerant enzyme.

Further herbicide-resistant plants are plants that have been made tolerant to acetolactate synthase (ALS) inhibitors. Known ALS inhibitors include, for example, sulphonylurea, imidazolinone, triazolopyrimidines, pyrimidinyl oxy(thio)benzoates, and/or sulphonylaminocarbonyltriazolinone herbicides. Different mutations in the ALS enzyme (also known as acetohydroxy acid synthase, AHAS) are known to confer tolerance to different herbicides and groups of herbicides. The production of sulphonylurea-tolerant plants and imidazolinone-tolerant plants has been described in the international publication WO 1996/033270. Further sulphonylureaand imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins listed online at: http://www.lifesci.sussex.ac.uk/Home/Neil_Crickmore/Bt/, or insecticidal portions thereof, for example proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR 604;

5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, e.g. proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins;

7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose)polymerase (PARP) gene in the plant cells or plants;

b. plants which contain a stress tolerance-enhancing transgene capable of reducing the expression and/or the activity of the PARG-encoding genes of the plants or plant cells;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant varieties (obtained by plant biotechnology methods such as genetic engineering) which may also be treated according to the invention show altered quantity, quality and/or storage stability of the harvested product and/or altered properties of specific ingredients of the harvested product such as, for example:

1) Transgenic plants which synthesize a modified starch which is altered with respect to its chemophysical traits, in particular the amylose content or the amylose/amylopectin ratio, the degree of branching, the average chain length, the distribution of the side chains, the viscosity behaviour, the gel resistance, the grain size and/or grain morphology of the starch in comparison to the synthesized starch in wild-type plant cells or plants, such that this modified starch is better suited for certain applications.

2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.

3) Transgenic plants which produce hyaluronan.

Plants or plant varieties (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:

a) plants, such as cotton plants, which contain an altered form of cellulose synthase genes;

b) plants, such as cotton plants, which contain an altered form of rsw2 or rsw3 homologous nucleic acids;

c) plants, such as cotton plants, with an increased expression of sucrose phosphate synthase;

d) plants, such as cotton plants, with an increased expression of sucrose synthase;

e) plants, such as cotton plants, wherein the timing of the plasmodesmatal gating at the basis of the fibre cell is altered, for example through downregulation of fibre-selective β-1,3-glucanase;

f) plants, such as cotton plants, which have fibres with altered reactivity, for example through the expression of the N-acetylglucosaminetransferase gene including nodC and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, which produce oil having a high oleic acid content;

b) plants, such as oilseed rape plants, which produce oil having a low linolenic acid content;

c) plants, such as oilseed rape plants, which produce oil having a low level of saturated fatty acids.

Particularly useful transgenic plants which may be treated according to the invention are plants which comprise one or more genes which encode one or more toxins and are the transgenic plants available under the following trade names: YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are available under the following trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize) Herbicide-resistant plants (plants bred in a conventional manner for herbicide tolerance) which may be mentioned include the varieties sold under the name Clearfield® (for example maize)

Particularly useful transgenic plants which may be treated according to the invention are plants containing transformation events, or a combination of transformation events, and that are listed for example in the databases for various national or regional regulatory agencies (see for example http://gmoinfo.jrc.ec.europa.eu/).

Moreover, in the protection of materials, the active compounds or compositions according to the invention can be employed for protecting industrial materials against attack and destruction by unwanted microorganisms, such as, for example, fungi and insects.

Furthermore, the compounds according to the invention can be used alone or in combinations with other active compounds as antifouling compositions.

Industrial materials in the present context are understood as meaning non-living materials which have been prepared for use in industry. For example, industrial materials which are intended to be protected by active compounds according to the invention from microbial change or destruction can be adhesives, sizes, paper, wallpaper, and board, textiles, carpets, leather, wood, paints and plastic articles, cooling lubricants and other materials which can be infected with, or destroyed by, microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood. The active compounds or compositions according to the invention may prevent disadvantageous effects, such as rotting, decay, discoloration, decoloration or formation of mould. Moreover, the compounds according to the invention can be employed for protecting objects which come into contact with saltwater or brackish water, in particular hulls, screens, nets, buildings, moorings and signalling systems, against fouling.

The method according to the invention for controlling unwanted fungi can also be employed for protecting storage goods. Here, storage goods are to be understood as meaning natural substances of vegetable or animal origin or processed products thereof of natural origin, for which long-term protection is desired. Storage goods of vegetable origin, such as, for example, plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The active compounds according to the invention may prevent disadvantageous effects, such as rotting, decay, discoloration, decolouration or formation of mould.

Some pathogens of fungal diseases which can be treated according to the invention may be mentioned by way of example, but not by way of limitation:

diseases caused by powdery mildew pathogens, such as, for example, *Blumeria* species, such as, for example, *Blumeria graminis*; *Podosphaera* species, such as, for example, *Podosphaera leucotricha*; *Sphaerotheca* species, such as, for example, *Sphaerotheca fuliginea*; *Uncinula* species, such as, for example, *Uncinula necator*;

diseases caused by rust disease pathogens, such as, for example, *Gymnosporangium* species, such as, for example, *Gymnosporangium sabinae*; *Hemileia* species, such as, for example, *Hemileia vastatrix*; *Phakopsora* species, such as, for example, *Phakopsora pachyrhizi* and *Phakopsora meibomiae*; *Puccinia* species, such as, for example, *Puccinia recondita, Puccinia graminis, Puccinia striiformis* or *Puccinia triticina*; *Uromyces* species, such as, for example, *Uromyces appendiculatus*;

diseases caused by pathogens from the group of the Oomycetes, such as, for example, *Albugo* species, such as, for example, *Albugo candida*; *Bremia* species, such as, for example, *Bremia lactucae*; *Peronospora* species, such as, for example, *Peronospora pisi* or *P. brassicae*; *Phytophthora* species, such as, for example, *Phytophthora infestans*; *Plasmopara* species, such as, for example, *Plasmopara viticola*; *Pseudoperonospora* species, such as, for example, *Pseudoperonospora humuli* or *Pseudoperonospora cubensis*; *Pythium* species, such as, for example, *Pythium ultimum*;

leaf blotch diseases and leaf wilt diseases caused, for example, by *Alternaria* species, such as, for example, *Alternaria solani*; *Cercospora* species, such as, for example, *Cercospora beticola*; *Cladiosporium* species, such as, for example, *Cladiosporium cucumerinum*; *Cochliobolus* species, such as, for example, *Cochliobolus sativus* (conidia form: *Drechslera*, syn: *Helminthosporium*) or *Cochliobolus miyabeanus*; *Colletotrichum* species, such as, for example,

*Colletotrichum lindemuthanium; Cycloconium* species, such as, for example, *Cycloconium oleaginum; Diaporthe* species, such as, for example, *Diaporthe citri; Elsinoe* species, such as, for example, *Elsinoe fawcettii; Gloeosporium* species, such as, for example, *Gloeosporium laeticolor; Glomerella* species, such as, for example, *Glomerella cingulata; Guignardia* species, such as, for example, *Guignardia bidwelli; Leptosphaeria* species, such as, for example, *Leptosphaeria maculans* or *Leptosphaeria nodorum; Magnaporthe* species, such as, for example, *Magnaporthe grisea; Mycosphaerella* species, such as, for example, *Mycosphaerella graminicola, Mycosphaerella arachidicola* or *Mycosphaerella fijiensis; Phaeosphaeria* species, such as, for example, *Phaeosphaeria nodorum; Pyrenophora* species, such as, for example, *Pyrenophora teres* or *Pyrenophora tritici repentis; Ramularia* species, such as, for example, *Ramularia collo-cygni* or *Ramularia areola; Rhynchosporium* species, such as, for example, *Rhynchosporium secalis; Septoria* species, such as, for example, *Septoria apii* or *Septoria lycopersici; Typhula* species, such as, for example, *Typhula incarnata; Venturia* species, such as, for example, *Venturia inaequalis;* root and stem diseases caused, for example, by *Corticium* species, such as, for example, *Corticium graminearum; Fusarium* species, such as, for example, *Fusarium oxysporum; Gaeumannomyces* species, such as, for example, *Gaeumannomyces graminis; Plasmodiophora* species, such as, for example, *Plasmodiophora brassicae; Rhizoctonia* species, such as, for example, *Rhizoctonia solani; Sarocladium* species, such as, for example, *Sarocladium oryzae; Sclerotium* species, such as, for example, *Sclerotium oryzae; Tapesia* species, such as, for example, *Tapesia acuformis; Thielaviopsis* species, such as, for example, *Thielaviopsis basicola;* ear and panicle diseases (including corn cobs) caused, for example, by *Alternaria* species, such as, for example, *Alternaria* spp.; *Aspergillus* species, such as, for example, *Aspergillus flavus; Cladosporium* species, such as, for example, *Cladosporium cladosporioides; Claviceps* species, such as, for example, *Claviceps purpurea; Fusarium* species, such as, for example, *Fusarium culmorum; Gibberella* species, such as, for example, *Gibberella zeae; Monographella* species, such as, for example, *Monographella nivalis;* diseases caused by smut fungi, such as, for example, *Sphacelotheca* species, such as, for example, *Sphacelotheca reiliana; Tilletia* species, such as, for example, *Tilletia caries, T. controversa; Urocystis* species, such as, for example, *Urocystis occulta; Ustilago* species, such as, for example, *Ustilago nuda, U. nuda tritici;* fruit rot caused, for example, by *Aspergillus* species, such as, for example, *Aspergillus flavus; Botrytis* species, such as, for example, *Botrytis cinerea; Penicillium* species, such as, for example, *Penicillium expansum* and *Penicillium purpurogenum; Sclerotinia* species, such as, for example, *Sclerotinia sclerotiorum; Verticilium* species, such as, for example, *Verticilium alboatrum;* seed- and soil-borne rot and wilt diseases, and also diseases of seedlings, caused, for example, by *Alternaria* species, such as, for example, *Alternaria brassicicola; Aphanomyces* species, such as, for example, *Aphanomyces euteiches; Ascochyta* species, such as, for example, *Ascochyta lentis; Aspergillus* species, such as, for example, *Aspergillus flavus; Cladosporium* species, such as, for example, *Cladosporium herbarum; Cochliobolus* species, such as, for example, *Cochliobolus sativus* (conidia form: *Drechslera, Bipolaris* Syn: *Helminthosporium); Colletotrichum* species, such as, for example, *Colletotrichum coccodes; Fusarium* species, such as, for example, *Fusarium culmorum; Gibberella* species, such as, for example, *Gibberella zeae; Macrophomina* species, such as, for example, *Macrophomina phaseolina; Microdochium* species, such as, for example, *Microdochium nivale; Monographella* species, such as, for example, *Monographella nivalis; Penicillium* species, such as, for example, *Penicillium expansum; Phoma* species, such as, for example, *Phoma lingam; Phomopsis* species, such as, for example, *Phomopsis sojae; Phytophthora* species, such as, for example, *Phytophthora cactorum; Pyrenophora* species, such as, for example, *Pyrenophora graminea; Pyricularia* species, such as, for example, *Pyricularia oryzae; Pythium* species, such as, for example, *Pythium ultimum; Rhizoctonia* species, such as, for example, *Rhizoctonia solani; Rhizopus* species, such as, for example, *Rhizopus oryzae; Sclerotium* species, such as, for example, *Sclerotium rolfsii; Septoria* species, such as, for example, *Septoria nodorum; Typhula* species, such as, for example, *Typhula incarnata;*

*Verticillium* species, such as, for example, *Verticillium dahliae;* cancerous diseases, galls and witches' broom caused, for example, by *Nectria* species, such as, for example, *Nectria galligena;* wilt diseases caused, for example, by *Monilinia* species, such as, for example, *Monilinia laxa;* deformations of leaves, flowers and fruits caused, for example, by *Exobasidium* species, such as, for example, *Exobasidium vexans; Taphrina* species, such as, for example, *Taphrina deformans;* degenerative diseases of woody plants caused, for example, by *Esca* species, such as, for example, *Phaeomoniella chlamydospora, Phaeoacremonium aleophilum* or *Fomitiporia mediterranea; Ganoderma* species, such as, for example, *Ganoderma boninense;* diseases of flowers and seeds caused, for example, by *Botrytis* species, such as, for example, *Botrytis cinerea;* diseases of plant tubers caused, for example, by *Rhizoctonia* species, such as, for example, *Rhizoctonia solani; Helminthosporium* species, such as, for example, *Helminthosporium solani;* diseases caused by bacterial pathogens, such as, for example, *Xanthomonas* species, such as, for example, *Xanthomonas campestris* pv. *oryzae; Pseudomonas* species, such as, for example, *Pseudomonas syringae* pv. *lachrymans; Erwinia* species, such as, for example, *Erwinia amylovora.*

Preference is given to controlling the following diseases of soya beans:

Fungal diseases on leaves, stems, pods and seeds caused, for example, by alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), *mycoleptodiscus* root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Microorganisms capable of degrading or changing the industrial materials which may be mentioned are, for example, bacteria, fungi, yeasts, algae and slime organisms. The active compounds according to the invention preferably act against fungi, in particular moulds, wood-discoloring and wood-destroying fungi (Basidiomycetes), and against slime organisms and algae. Microorganisms of the following genera may be mentioned as examples: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Escherichia*, such as *Escherichia coli*; *Pseudomonas*, such as *Pseudomonas aeruginosa*; *Staphylococcus*, such as *Staphylococcus aureus*.

In addition, the active compounds according to the invention also have very good antimycotic activity. They have a very broad antimycotic activity spectrum, in particular against dermatophytes and yeasts, moulds and diphasic fungi (for example against *Candida* species, such as *Candida albicans, Candida glabrata*), and *Epidermophyton floccosum*, *Aspergillus* species, such as *Aspergillus niger* and *Aspergillus fumigatus*, *Trichophyton* species, such as *Trichophyton mentagrophytes*, *Microsporon* species such as *Microsporon canis* and *audouinii*. The list of these fungi by no means limits the mycotic spectrum covered, but is only for illustration.

Accordingly, the active compounds according to the invention can be used both in medical and in non-medical applications.

When using the active compounds according to the invention as fungicides, the application rates can be varied within a relatively wide range, depending on the kind of application. The application rate of the active compounds according to the invention is when treating plant parts, for example leaves: from 0.1 to 10 000 g/ha, preferably from 10 to 1000 g/ha, particularly preferably from 50 to 300 g/ha (when the application is carried out by watering or dripping, it is even possible to reduce the application rate, especially when inert substrates such as rock wool or perlite are used);

when treating seed: from 2 to 200 g per 100 kg of seed, preferably from 3 to 150 g per 100 kg of seed, particularly preferably from 2.5 to 25 g per 100 kg of seed, very particularly preferably from 2.5 to 12.5 g per 100 kg of seed;

when treating the soil: from 0.1 to 10 000 g/ha, preferably from 1 to 5000 g/ha.

The doses herein indicated are given as illustrative examples of the method according to the invention. A person skilled in the art will know how to adapt the application doses, notably according to the nature of the plant or crop to be treated.

The combination according to the invention can be used in order to protect plants within a certain time range after the treatment against pests and/or phytopathogenic fungi and/or microorganisms. The time range, in which protection is effected, spans in general 1 to 28 days, preferably 1 to 14 days, more preferably 1 to 10 days, even more preferably 1 to 7 days after the treatment of the plants with the combinations or up to 200 days after the treatment of plant propagation material.

Furthermore combinations and compositions according to the invention may also be used to reduce the contents of mycotoxins in plants and the harvested plant material and therefore in foods and animal feed stuff made therefrom. Especially but not exclusively the following mycotoxins can be specified: Deoxynivalenole (DON), Nivalenole, 15-Ac-DON, 3-Ac-DON, T2-und HT2-Toxins, Fumonisines, Zearalenone Moniliformine, Fusarine, Diaceotoxyscirpenole (DAS), Beauvericine, Enniatine, Fusaroproliferine, Fusarenole, Ochratoxins, Patuline, Ergotalkaloides und Aflatoxines, which are caused for example by the following fungal diseases: *Fusarium* spec., like *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudo graminearum, F. sambucinum, F. scirpi, F. semitectum, F. solani, F. sporotrichoides, F. langsethiae, F. subglutinans, F. tricinctum, F. verticillioides* and others but also by *Aspergillus* spec., *Penicillium* spec., *Claviceps purpurea, Stachybotrys* spec. and others.

Die erfindungsgemäßen Wirkstoffe eignen sich auch auf dem Veterinärsektor bei günstiger Warmblütertoxizität zur Bekämpfung von parasitischen Protozoen, die in der Tierhaltung und Tierzucht bei Nutz-, Zucht-, Zoo-, Labor-, Versuchs- und Hobbytieren vorkommen Sie sind dabei gegen alle oder ein-zelne Entwicklungsstadien der Schädlinge wirksam.

Landwirtschaftliche Nutz-oder Zuchttiere sind z.B. Säugetiere wie Schafe, Ziegen, Pferde, Esel, Kamele, Büffel, Kaninchen sowie insbesondere Rinder und Schweine oder Vögel wie Puten, Enten, Gänse und insbesondere Hühner oder gegebenenfalls auch Insekten, wie z. B. Bienen.

Haustiere sind z.B. Säugetiere wie Hamster, Meerschweinchen, Ratten, Mäuse sowie insbeonsdere Hunde und Katzen oder auch Stubenvögel.

Eine bevorzugte Ausführungsform ist die Anwendung bei Vögeln. Eine weitere bevorzugte Ausführungsform ist die Anwendung bei Säugetieren.

Durch die Anwendung sollen Krankheiten, Todesfälle und Leistungsminderungen (z. B. bei Fleisch, Milch, Wolle, Häuten, Eiern, Honig usw.) verhindert oder vermindert werden, so dass durch den Einsatz der erfindungsgemäßen Wirkstoffe eine wirtschaftlichere und einfachere Tierhaltung möglich ist.

Die Anwendung der erfindungsgemäßen Wirkstoffe erfolgt im Veterinärsektor und bei der Tierhaltung in an sich bekannter Weise direkt oder in Form von geeigneten Zubereitungen enteral, parenteral, dermal, nasal. Die enterale Anwendung der Wirkstoffe geschieht z.B. oral in Form von Pulver, Zäpfchen, Tabletten, Kapseln, Pasten, Tränken, Granulaten, Drenchen, Boli, medikiertem Futter oder Trinkwasser. Die dermale Anwendung geschieht z.B. in Form des Tauchens (Dippen), Sprühens (Sprayen), Badens, Waschens, Aufgießens (pour-on and spot-on) und des Einpuderns. Die parenterale Anwendung geschieht z.B. in Form der Injektion (intramuskulär, subcutan, intravenös, intraperitoneal) oder durch Implantate. Die Anwendung kann sowohl prophylaktisch als auch therapeutisch erfolgen. Zu den parasitischen Protozoen zählen:

Mastigophora (Flagellata) wie z.B. Trypanosomatidae z.B. *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica,* wie z.B. Trichomonadidae z.B. *Giardia lamblia, G. canis.* Sarcomastigophora (Rhizopoda) wie Entamoebidae z.B. *Entamoeba histolytica,* Hartmanellidae z.B. *Acanthamoeba* sp., *Harmanella* sp.

Apicomplexa (Sporozoa) wie Eimeridae z.B. *Eimeria acervulina, E. adenoides, E. alabahmensis, E. anatis, E. anserina, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E. faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. zuernii, Globidium* spec., *Isospora belli, I. canis, I. felis, I. ohioensis, I. rivolta, I. spec., I. suis, Cystisospora* spec., *Cryptosporidium* spec., insbesondere *C. parvum,* wie Toxoplasmadidae z.B. *Toxoplasma gondii, Hammondia heydornii, Neospora caninum, Besnoitia besnoitii,* wie Sarcocystidae z.B. *Sarcocystis bovicanis, S. bovihominis, S. ovicanis, S. ovifelis, S. neurona, S. spec., S. suihominis* wie Leucozoidae z.B. *Leucozytozoon simondi,* wie Plasmodiidae z.B. *Plasmodium berghei, P. falciparum, P. malariae, P. ovale, P. vivax, P.* spec., wie Piroplasmea z.B. *Babesia argentina, B. bovis, B. canis, B.* spec., *Theileria parva, Theileria* spec., wie Adeleina z.B. *Hepatozoon canis, H. spec.*

The preparation of the active substances according to the invention of the formula [I] follows from the following examples. However, the invention is not restricted to these examples.

Production of Intermediates of the Formula [XIV] by Route (V7)

Ethyl 3-(4-fluorophenyl)-3-oxopropanoate [XIV-1]

To a mixture of 4-fluoroacetophenone (20.0 g, 0.145 mol), ethanol (1 mL) and diethylcarbonate (100 mL) is added sodium hydride (60%, 12.0 g, 0.29 mol) at 0° C. portionwise over a period of 30 min. Afterwards the reaction mixture is allowed to warm to room temperature and stirred for 3 h. Thereafter, the reaction is quenched with aqueous 10% HCl and extracted with ethyl acetate (2×100 mL). The ethyl acetate layer is dried over anhydrous sodium sulphate, filtered and concentrated under reduced pressure. The crude material is purified by column chromatography using silica gel (230-400 mesh) in ethyl acetate and hexane (1:99 to 5:95) as eluent and 25 g (83%) of ethyl 3-(4-fluorophenyl)-3-oxopropanoate are obtained as light yellow liquid.

$^1$H-NMR (300 MHz, CDCl$_3$): δ=7.96-8.01 (m, 1H), 7.10-7.19 (m, 2H), 5.30 (s, 1H), 4.23 (q, 2H), 1.26 (t, 3H) ppm
MS (ESI): 209.1 ([M−H]$^+$)

Production of Intermediates of the Formula [VII] by Route (V8)

3-(4-fluorophenyl)-1H-pyrazol-5-ol [VII-2]

A mixture of methyl 3-(4-fluorophenyl)-3-oxopropanoate (10.0 g, 0.051 mol) and hydrazine hydrate (1.1 eq, 2.8 g, 0.056 mol) in 20 mL glacial acetic acid is heated 3 h under reflux. The resulting suspension is cooled down and 10 mL diethyl ether is added. The precipitate is filtered off, dried in vacuo and 9 g (100%) of 3-(4-fluorophenyl)-1H-pyrazol-5-ol are obtained as white solid.

$^1$H-NMR (400 MHz, d$_6$-DMSO): δ=7.65-7.60 (m, 2H), 7.21-7.15 (m, 2H), 5.89 (s, 1H), 2.50 (s, 1H, br) ppm
log P (pH 2.7): 1.11
MS (ESI): 179.1 ([M+H]$^+$)

The following compounds are prepared in analogous manner:

3-(2,4-difluorophenyl)-1H-pyrazol-5-ol [VII-3]

$^1$H-NMR (400 MHz, d$_6$-DMSO): δ=12.0 (s, 1H, br), 7.84-7.80 (m, 1H), 7.36-7.32 (m, 1H), 7.20-7.16 (m, 1H), 5.81 (s, 1H) ppm
log P (pH 2.7): 1.25
MS (ESI): 197.1 ([M+H]$^+$)

Production of Intermediates of the Formula [VI] by Route (V1)

2-phenyl-6,7-dihydro-5H-pyrazolo[5,1-b][1,3]oxazine [VI-1]

A mixture of 3-phenyl-1H-pyrazol-5-ol (8.80 g, 0.055 mol), 1-bromo-3-chloropropane (9.5 g, 1.1 eq, 0.06 mol) and potassium carbonate (30.3 g, 4 eq, 0.22 mol) in acetonitrile (120 mL) is heated for 5.5 h under reflux. Thereafter the volatiles are evaporated and the residue is treated with 50 mL ethyl acetate. The residual solid is washed 2× with ethyl acetate and the combined organic phases are evaporated. The obtained crude product is triturated with methyl tert butylether and 6.4 g (53%) of 2-phenyl-6,7-dihydro-5H-pyrazolo[5,1-b][1,3]oxazine are obtained as solid.

$^1$H-NMR (400 MHz, CD$_3$CN): δ=7.73-7.71 (m, 1H), 7.39-7.35 (m, 1H), 7.30-7.26 (m, 1H), 5.83 (s, 1H), 4.28 (t, 2H), 4.12 (t, 2H), 2.23 (m, 2H) ppm
log P (pH 2.7): 2.04
MS (ESI): 201.1 ([M+H]$^+$)

The following compounds are prepared in analogous manner:

2-(4-fluorophenyl)-6,7-dihydro-5H-pyrazolo[5,1-b][1,3]oxazine [VI-2]

$^1$H-NMR (400 MHz, CD$_3$CN): δ=7.75-7.70 (m, 2H), 7.14-7.08 (m, 2H), 5.80 (s, 1H), 4.28 (t, 2H), 4.11 (t, 2H), 2.24 (m, 2H) ppm
log P (pH 2.7): 2.18
MS (ESI): 219.2 ([M+H]$^+$)

2-(2,4-difluorophenyl)-6,7-dihydro-5H-pyrazolo[5,1-b][1,3]oxazine [VI-3]

$^1$H-NMR (400 MHz, CD$_3$CN): δ=7.95-7.89 (m, 1H), 7.01-6.96 (m, 2H), 5.86 (d, 1H), 4.29 (t, 2H), 4.14 (t, 2H), 2.24 (m, 2H) ppm
log P (pH 2.7): 2.38
MS (ESI): 237.1 ([M+H]$^+$)

2-(4-fluorophenyl)-7-methyl-6,7-dihydro-5H-pyrazolo[5,1-b][1,3]oxazine [VI-4]

$^1$H-NMR (400 MHz, d6-DMSO): δ=7.80-7.72 (m, 2H), 7.23-7.15 (m, 2H), 5.94 (s, 1H), 4.40-4.20 (m, 3H), 2.37-2.27 (m, 1H), 1.98-1.87 (m, 1H), 1.50 (d, 3H) ppm
Log P (pH 2.7): 2.65
MS (ESI): 233.1 ([M+H]$^+$)

7-(4-fluorophenyl)-3,3-dimethyl-3,4-dihydro-2H-pyrazolo[5,1-b][1,3,5]oxazasiline [VI-5]

A mixture of 3-(4-fluorophenyl)-1H-pyrazol-5-ol (1 g, 5.6 mmol), bis(chloromethyl)(dimethyl)-silane (1 g, 1.1 eq, 6.1 mmol), potassium iodide (93 mg, 0.1 eq., 0.56 mmol) and potassium carbonate (3.1 g, 4 eq, 22 mmol) in 30 mL of a 1:1 mixture of acetonitrile and dimethylformamide is heated for 10 h at 40° C. The crude mixture is then filtered over a sintered glass, washed by dichloromethane and the filtrate is concentrated to yield 2.9 g of a dark brown oil. The crude material is purified by column chromatography using silica gel with ethyl acetate and heptane (35:65) as eluent to give 1.095 g (74%) of 7-(4-fluorophenyl)-3,3-dimethyl-3,4-dihydro-2H-pyrazolo[5,1-b][1,3,5]oxazasiline as a yellow solid.

$^1$H-NMR (400 MHz, CDCl$_3$): δ=7.70 (m, 2H), 7.05 (m, 2H), 5.80 (s, 1H), 3.98 (s, 2H), 3.72 (s, 2H), 0.38 (s, 6H) ppm
log P (pH 2.7): 3.11
MS (ESI): 263.1 ([M+H]$^+$)

6-(4-fluorophenyl)-2,3-dihydropyrazolo[5,1-b][1,3]thiazole [VI-6]

Step 1: Production of Intermediates of the Formula [VII] by Route (V35)

A mixture of 9.8 g (55 mmol) of 3-(4-fluorophenyl)-1H-pyrazol-5-ol and 48.9 g (220 mmol) of phosphorus pentasulphide in 250 ml of xylene is heated with stirring at about 130° C. overnight. The mixture is then allowed to cool to room temperature, and water is added. The phases are separated and the aqueous phase is extracted with ethyl acetate. The combined organic phases are dried over sodium sulphate and concentrated under reduced pressure. The residue is dissolved in dichloromethane and filtrated by using silica gel with ethyl acetate and cyclohexane (1:1). The filtrate is concentrated under reduced pressure. It gives 4.5 g of a solid containing 3-(4-fluorophenyl)-1H-pyrazole-5-thiol [VII-a-1] which was used for step 2 without further purification.

Step 2: Production of Intermediates of the Formula [VI] by Route (V1)

A mixture of the solid obtained in step 1 (2.72 g), tetra-n-butylammoniumbromide (1.35 g, 0.0042 mol), and aqueous sodium hydroxide solution (28 mL, 50%) in toluene (280 mL) is stirred for 2 h at room temperature. Thereafter, 1,2-dibromoethane (3.95 g, 0.021 mol) is added and the mixture is stirred for 16 h at 20° C. Then the mixture is treated with 100 mL ethyl acetate and 100 mL water. The organic phase are separated, dried with sodium sulfate and evaporated. The crude material is purified by column chromatography using silica gel with ethyl acetate and cyclohexane as eluent and 0.44 g of 6-(4-fluorophenyl)-2,3-dihydropyrazolo[5,1-b][1,3]thiazole are obtained.

$^1$H-NMR (400 MHz, d$_6$-DMSO): δ=7.80-7.75 (m, 2H), 7.22 (t, 2H), 6.54 (s, 1H), 4.35 (t, 2H), 3.89 (t, 2H) ppm
log P (pH 2.7): 2.53
MS (ESI): 221.0 ([M+H]$^+$)

6,6-difluoro-2-(4-fluorophenyl)-6,7-dihydro-5H-pyrazolo[5,1-b][1,3]oxazine [V-7]

To a solution of 3-(4-fluorophenyl)-1H-pyrazol-5-ol (4 g, 22.47 mmol) in DMF (30 mL) was added K$_2$CO$_3$ (12.4 g, 89.88 mmol) and 2,2-difluoropropane-1,3-diyl dimethanesulfonate (9 g, 33.7 mmol) at room temperature and then stirred for 16 h at 60° C. The progress of the reaction was monitored by TLC. Thereafter, the reaction mixture was diluted with cold water and extracted with diethyl ether. The organic layer was dried over anhydrous sodium sulphate and concentrated to get the crude product. Purification by column chromatography over silica gel (eluent 5-10% ethyl acetate in petrol ether) yielded 6,6-difluoro-2-(4-fluorophenyl)-6,7-dihydro-5H-pyrazolo[5,1-b][1,3]oxazine (3.2 g, 56%) as an off-white solid.

$^1$H-NMR (400 MHz, d$_6$-DMSO): δ=7.83-7.80 (m, 2H), 7.25-7.20 (m, 2H), 6.21 (s, 1H), 4.72 (t, 2H), 4.62 (t, 2H) ppm

Synthesis of 2,2-difluoropropane-1,3-diyl dimethanesulfonate

To a solution of 5 g (44.6 mmol) 2,2-difluoropropane-1,3-diol (prepared as described in *J. Med. Chem.* 1994, 37, 1857-1864) in DCM (50 mL) was added triethylamine (18.6 mL, 133.83 mmol) and methane sulphonyl chloride (6.9 mL, 89.22 mmol) at 0° C. and stirred for 1 h at 0° C. Thereafter the reaction mixture was quenched with water and extracted with DCM. The organic layer was dried over anhydrous sodium sulphate and concentrated to afford 2,2-difluoropropane-1,3-diyl dimethanesulfonate (9 g, 84%) which was used immediately in the next step.

$^1$H-NMR (400 MHz, CDCl$_3$): δ=4.43 (t, 4H), 3.05 (s, 6H) ppm

6-(4-fluorophenyl)-2,3-dimethyl-2,3-dihydropyrazolo[5,1-b][1,3]oxazole [VI-8]

To a solution of 3-(4-fluorophenyl)-1H-pyrazol-5-ol (3 g, 16.8 mmol) in DMF (15 mL) was added K$_2$CO$_3$ (9.3 g, 67.4 mmol) and butane-2,3-diyl dimethanesulfonate (4.8 g, 18.5 mmol) (prepared as described in US2010/41748) at room temperature and then stirred for 16 h at 60° C. Thereafter, the reaction mixture was diluted with cold water and extracted with ethyl acetate. The organic layer was dried over anhydrous sodium sulphate and concentrated to get the crude product. Purification by column chromatography over silica gel (eluent 5-10% ethyl acetate in petrol ether) yielded 6-(4-fluorophenyl)-2,3-dimethyl-2,3-dihydropyrazolo[5,1-b][1,3]oxazole (2.8 g, 71%) as yellow oil and a mixture of diastereoisomers.

$^1$H-NMR (400 MHz, CDCl$_3$): δ=7.95 (s, 1H), 7.80-7.75 (m, 2H), 7.23-7.18 (m, 2H), 5.50-5.45 (m, 1H, major isomer), 5.00-4.95 (m, 1H, minor isomer), 4.65-4.60 (m, 1H, major isomer), 4.25-4.18 (m, 1H, minor isomer), 1.54 (d, 3H, minor isomer), 1.48 (d, 3H, minor isomer), 1.44 (d, 3H, major isomer), 1.28 (d, 3H, major isomer) ppm In an analogous manner the following compound [VI-9] was prepared from pentane-2,4-diyl dimethanesulfonate (*Tetrahedron;* 2010, 66; 6977-6989) as mixture of diastereoisomers:

2-(4-fluorophenyl)-5,7-dimethyl-6,7-dihydro-5H-pyrazolo[5,1-b][1,3]oxazine [VI-9]

$^1$H-NMR (400 MHz, DMSO-d6): δ=7.78-7.70 (m, 2H), 7.25-7.18 (m, 2H), 5.93 (s, 1H, isomer 1), 5.90 (s, 1H, isomer 2), 4.60-4.50 (m, 1H, isomer 1), 4.45-4.35 (m, 1H, both isomers), 4.30-4.23 (m, 1H, isomer 2), 2.35-2.30 (m, 1H), 2.15-2.10 (m, 1H), 2.03-1.95 (m, 1H), 1.75-1.65 (m, 1H), 1.50 (m, 6H, both isomers), 1.38 (m, 6H, both isomers) ppm

2-(4-fluorophenyl)-6,6-dimethyl-6,7-dihydro-5H-pyrazolo[5,1-b][1,3]oxazine [VI-10]

In a 20 mL microwave vial, 3-(4-fluorophenyl)-1H-pyrazol-5-ol (1.5 g, 8.4 mmol), 1,3-dichloro-2,2-dimethylpropane (1.3 g, 1.1 eq, 9.2 mmol) and potassium iodide (140 mg, 0.1 eq., 0.56 mmol) are dissolved in 12 mL of N-methylpyrrolidine. Sodium hydride (60% dispersion in mineral oil, 670 mg, 2 eq., 16.8 mmol) is added and the mixture is stirred a few minutes at room temperature. The vial is then sealed and heated for 2 h at 180° C. in the microwave apparatus (Biotage—Initiator). The reaction mixture is diluted by 50 mL of slightly acidic water and reextracted by ethyl acetate (2×50 mL). The combined organic phases are washed by a saturated aqueous solution of lithium chloride, dried over magnesium sulfate and concentrated to yield 2.79 g of an orange solid. The crude material is purified by column chromatography using silica gel with ethyl acetate and heptane (50:50) as eluent to give 1.25 g (60% yield) of 2-(4-fluorophenyl)-6,6-dimethyl-6,7-dihydro-5H-pyrazolo[5,1-b][1,3]oxazine as a yellow solid.

$^1$H-NMR (400 MHz, CDCl$_3$): δ=7.56 (m, 2H), 7.10 (m, 2H), 5.82 (s, 1H), 3.94 (s, 2H), 3.92 (s, 2H), 1.20 (s, 6H) ppm log P (pH 2.7): 2.96

MS (ESI): 247.1 ([M+H]$^+$)

In an analogous manner the following compound [VI-11] was prepared 2-(4-fluorophenyl)-6-methyl-6,7-dihydro-5H-pyrazolo[5,1-b][1,3]oxazine-6-carbonitrile [VI-11]

1H-NMR (400 MHz, CDCl$_3$): δ=7.69 (m, 2H), 7.08 (t, 2H), 5.88 (s, 1H), 4.53 (d, 1H), 4.40 (d, 1H), 4.04 (m, 2H), 1.60 (s, 3H) ppm log P (pH 2.7): 2.39

MS (ESI): 258.1 ([M+H]$^+$)

Production of Intermediates of the Formula [VI-a] by Route (V37)

6-(4-fluorophenyl)-3-methylpyrazolo[5,1-b][1,3]oxazole [VI-a-1]

Step-1: Preparation of 1-{[3-(4-fluorophenyl)-1H-pyrazol-5-yl]oxy}acetone

To a solution of 3-(4-fluorophenyl)-1H-pyrazol-5-ol (5 g, 28 mmol) in DMF (50 ml), potassium carbonate (7.7 g, 56 mmol) was added and the mixture was stirred for 30 min at 30° C. Thereafter, 2-oxopropyl methanesulfonate (4.7 g 30 mmol) was added drop wise and the reaction mixture was heated at 60° C. for 16 h. After completion, the crude was diluted with ethyl acetate (200 ml) and washed with water (3×500 ml). The organic layer was washed with brine, dried over sodium sulphate and evaporated under reduced pressure to get the crude which was then purified by column chromatography with silica gel (100-200 mesh) eluted with 10-25% ethyl acetate in hexane as eluent to get compound 1-{[3-(4-fluorophenyl)-1H-pyrazol-5-yl]oxy}acetone (2.5 g, yield 38%). MS (ESI): 231.0 ([M+H]$^+$)

Step-2: Preparation of 6-(4-fluorophenyl)-3-methylpyrazolo[5,1-b][1,3]oxazole

To a stirred solution of 1-{[3-(4-fluorophenyl)-1H-pyrazol-5-yl]oxy}acetone (0.25 g, 1.0 mmol) in toluene, equipped with dean stark apparatus, acetic acid (2 ml) and p-TsOH (25 mg, cat.) was charged at RT and the reaction mass was refluxed at 130° C. for 16 h. After completion, the reaction was diluted with EtOAc (50 ml) and washed with brine. The organic layer dried over sodium sulphate and concentrated under reduced pressure to get the crude which was then purified by column chromatography 100-200 mesh) eluted with 5-10% ethyl acetate in hexane as eluent to get compound 6-(4-fluorophenyl)-3-methylpyrazolo[5,1-b][1,3]oxazole (0.1 g, yield 43%).

MS (ESI): 217.2 ([M+H]$^+$) The following compounds were prepared in analogous manner: 3-ethyl-6-(4-fluorophenyl)pyrazolo[5,1-b][1,3]oxazole [VI-a-2]

MS (ESI): 231.0 ([M+H]$^+$)

6-(4-fluorophenyl)pyrazolo[5,1-b][1,3]oxazole [VI-a-3]

MS (ESI): 203.0 ([M+H]$^+$)

6-phenylpyrazolo[5,1-b][1,3]oxazole [VI-a-4]

MS (ESI): 185.0 ([M+H]$^+$)

Production of Intermediates of the Formula [IV] by Route (V2)

3-bromo-2-phenyl-6,7-dihydro-5H-pyrazolo[5,1-b][1,3]oxazine [IV-1]

To a solution of 2-phenyl-6,7-dihydro-5H-pyrazolo[5,1-b][1,3]oxazine (6.3 g, 0.031 mol) in 60 mL chloroform is added a solution of bromine (1 eq, 5.03 g, 0.031 mol) in 40 mL chloroform over a period of 25 min at room temperature. The resulting suspension is stirred for 4 h at room temperature. Thereafter the reaction mixture is treated with aqueous sodium thiosulfate, the phases are separated and the organic phase is washed with water and dried over sodium sulfate. The volatiles are evaporated and the crude product is purified by filtration over silica using a 1:1 mixture of ethyl acetate/cyclohexane as eluent. After evaporation of the solvent 7.0 g (90%) of 3-bromo-2-phenyl-6,7-dihydro-5H-pyrazolo[5,1-b][1,3]oxazine are obtained as solid.

$^1$H-NMR (400 MHz, d$_6$-DMSO): δ=7.79-7.76 (m, 1H), 7.46-7.42 (m, 1H), 7.39-7.34 (m, 1H), 4.40 (t, 2H), 4.14 (t, 2H), 2.24 (m, 2H) ppm log P (pH 2.7): 2.66

MS (ESI): 281.0 ([M+H]$^+$)

The following compounds are prepared in analogous manner:

3-bromo-2-(4-fluorophenyl)-6,7-dihydro-5H-pyrazolo[5,1-b][1,3]oxazine [IV-2]

$^1$H-NMR (400 MHz, CD$_3$CN): δ=7.88-7.83 (m, 2H), 7.20-7.14 (m, 2H), 4.38 (t, 2H), 4.12 (t, 2H), 2.27 (m, 2H) ppm log P (pH 2.7): 2.86

MS (ESI): 299.0 ([M+H]$^+$)

3-bromo-2-(2,4-difluorophenyl)-6,7-dihydro-5H-pyrazolo[5,1-b][1,3]oxazine [IV-3]

$^1$H-NMR (400 MHz, d$_6$-DMSO): δ=7.53-7.47 (m, 1H), 7.39-7.34 (m, 1H), 7.20-7.15 (m, 1H), 4.41 (t, 2H), 4.15 (t, 2H), 2.25 (m, 2H) ppm log P (pH 2.7): 2.70

MS (ESI): 317.0 ([M+H]$^+$)

7-bromo-6-(4-fluorophenyl)-2,3-dihydropyrazolo[5,1-b][1,3]oxazole [IV-4]

$^1$H-NMR (400 MHz, CD$_3$CN): δ=7.86-7.81 (m, 2H), 7.20-7.14 (m, 2H), 5.12 (t, 2H), 4.35 (t, 2H) ppm log P (pH 2.7): 2.69

MS (ESI): 285.0 ([M+H]$^+$)

3-bromo-2-(4-fluorophenyl)-7-methyl-6,7-dihydro-5H-pyrazolo[5,1-b][1,3]oxazine [IV-6]

$^1$H-NMR (400 MHz, d6-DMSO): δ=7.85-7.78 (m, 2H), 7.32-7.25 (m, 2H), 4.50-4.45 (m, 1H), 4.39-4.32 (m, 2H), 2.40-2.32 (m, 1H), 2.04-1.97 (m, 1H), 1.50 (d, 3H) ppm
Log P (pH 2.7): 3.36
MS (ESI): 312.9 ([M+H]$^+$)

3-bromo-6,6-difluoro-2-(4-fluorophenyl)-6,7-dihydro-5H-pyrazolo[5,1-b][1,3]oxazine [IV-7]

$^1$H-NMR (400 MHz, CD$_3$CN): δ=7.88-7.83 (m, 2H), 7.22-7.16 (m, 2H), 4.62-4.51 (m, 4H) ppm
Log P (pH 2.7): 3.30
MS (ESI): 333.0 ([M+H]$^+$)

7-bromo-6-(4-fluorophenyl)-2,3-dimethyl-2,3-dihydropyrazolo[5,1-b][1,3]oxazole [IV-8]

$^1$H-NMR (400 MHz, CD$_3$CN): δ=7.85-7.81 (m, 2H), 7.19-7.14 (m, 2H), 5.55-5.50 (m, 1H, major isomer), 5.05-4.95 (m, 1H, minor isomer), 4.70-4.65 (m, 1H, major isomer), 4.25-4.20 (m, 1H, minor isomer), 1.60 (d, 3H, minor isomer), 1.51 (d, 3H, minor isomer), 1.50 (d, 3H, major isomer), 1.32 (d, 3H, major isomer) ppm
Log P (pH 2.7): 3.39 (major isomer) and 3.46 (minor isomer)
MS (ESI): 312.9 ([M+H]$^+$)

rac-trans-3-bromo-2-(4-fluorophenyl)-5,7-dimethyl-6,7-dihydro-5H-pyrazolo[5,1-b][1,3]oxazine [IV-9a]

$^1$H-NMR (400 MHz, CD$_3$CN): δ=7.89-7.84 (m, 2H), 7.20-7.14 (m, 2H), 4.50-4.42 (m, 1H), 4.30-4.22 (m, 1H), 2.34-2.29 (ddd, 1H), 1.83-1.74 (ddd, 1H), 1.53 (d, 3H), 1.45 (d, 3H) ppm
Log P (pH 2.7): 3.91
MS (ESI): 324.9 ([M+H]$^+$)

rac-cis-3-bromo-2-(4-fluorophenyl)-5,7-dimethyl-6,7-dihydro-5H-pyrazolo[5,1-b][1,3]oxazine [IV-9b]

$^1$H-NMR (400 MHz, CD$_3$CN): δ=7.89-7.83 (m, 2H), 7.20-7.14 (m, 2H), 4.64-4.60 (m, 1H), 4.41-4.37 (m, 1H), 2.23-2.13 (ddd, 1H), 2.05-2.00 (m, 1H), 1.51 (d, 3H), 1.45 (d, 3H) ppm
Log P (pH 2.7): 3.68
MS (ESI): 324.9 ([M+H]$^+$)

8-bromo-7-(4-fluorophenyl)-3,3-dimethyl-3,4-dihydro-2H-pyrazolo[5,1-b][1,3,5]oxazasiline [IV-5]

To a solution of 7-(4-fluorophenyl)-3,3-dimethyl-3,4-dihydro-2H-pyrazolo[5,1-b][1,3,5]oxazasiline (0.5 g, 1.9 mmol) in 25 mL dichloromethane is added by portion N-bromosuccinimide (1 eq, 0.34 g, 1.9 mmol) at 0° C. The reaction mixture is then stirred for 18 h at room temperature. Thereafter the reaction mixture is washed by 25 mL of a saturated solution of sodium bicarbonate, dried over magnesium sulfate and concentrated to yield 779 mg of a brown oil. The crude material is purified by column chromatography using silica gel with ethyl acetate and heptane (30:70) as eluent to give 616 mg (94%) of 8-bromo-7-(4-fluorophenyl)-3,3-dimethyl-3,4-dihydro-2H-pyrazolo[5,1-b][1,3,5]-oxazasiline as a light brown oil.

$^1$H-NMR (400 MHz, CDCl$_3$): δ=7.85 (m, 2H), 7.10 (m, 2H), 4.10 (s, 2H), 3.72 (s, 2H), 0.38 (s, 6H) ppm
log P (pH 2.7): 3.83
MS (ESI): 341.0 ([M+H]$^+$)

In analogous manner the following compound was prepared

3-bromo-2-(4-fluorophenyl)-6,6-dimethyl-6,7-dihydro-5H-pyrazolo[5,1-b][1,3]oxazine [IV-10]

$^1$H-NMR (400 MHz, CDCl$_3$): δ=7.91 (m, 2H), 7.15 (m, 2H), 4.07 (s, 2H), 3.95 (s, 2H), 1.21 (s, 6H) ppm
log P (pH 2.7): 3.63
MS (ESI): 325.0 ([M+H]$^+$)

3-bromo-2-(4-fluorophenyl)-6-methyl-6,7-dihydro-5H-pyrazolo[5,1-b][1,3]oxazine-6-carbonitrile [IV-11]

$^1$H-NMR (400 MHz, CDCl$_3$): δ=7.85 (m, 2H), 7.11 (t, 2H), 4.54 (m, 2H), 4.09 (m, 2H), 1.62 (s, 3H) ppm
log P (pH 2.7): 2.94
MS (ESI): 336.1 ([M+H]$^+$)

8-bromo-3,3-dimethyl-7-(2-thienyl)-3,4-dihydro-2H-pyrazolo[5,1-b][1,3,5]oxazasiline [IV-12]

$^1$H-NMR (400 MHz, CDCl$_3$): δ=7.73 (s, 1H), 7.30 (m, 1H), 7.10 (m, 1H), 4.11 (s, 2H), 3.73 (s, 2H), 0.38 (s, 6H) ppm
log P (pH 2.7): 3.58
MS (ESI): 329.0 ([M+H]$^+$)

7-bromo-6-(4-fluorophenyl)-3-methylpyrazolo[5,1-b][1,3]oxazole [IV-a-1]

$^1$H-NMR (400 MHz, CD$_3$CN): δ=7.92-7.88 (m, 2H), 7.49 (s, 1H), 7.25-7.19 (m, 2H), 2.37 (s, 3H) ppm
log P (pH 2.7): 3.56
MS (ESI): 295.0 ([M+H]$^+$)

7-bromo-3-ethyl-6-(4-fluorophenyl)pyrazolo[5,1-b][1,3]oxazole [IV-a-2]

$^1$H-NMR (400 MHz, CD$_3$CN): δ=7.92-7.88 (m, 2H), 7.48 (s, 1H), 7.25-7.19 (m, 2H), 2.89-2.78 (q, 2H), 1.24 (t, 3H) ppm
log P (pH 2.7): 4.18
MS (ESI): 311.0 ([M+H]$^+$)

7-bromo-6-(4-fluorophenyl)pyrazolo[5,1-b][1,3]oxazole [IV-a-3]

$^1$H-NMR (400 MHz, CD$_3$CN): δ=7.92-7.88 (m, 2H), 7.85 (d, 1H), 7.71 (d, 1H), 7.28-7.19 (m, 2H) ppm
log P (pH 2.7): 3.07
MS (ESI): 282.9 ([M+H]$^+$)

7-bromo-6-phenylpyrazolo[5,1-b][1,3]oxazole [IV-a-4]

$^1$H-NMR (400 MHz, CD$_3$CN): δ=7.89-7.86 (m, 3H), 7.71 (d, 1H), 7.50-7.40 (m, 3H) ppm
log P (pH 2.7): 2.91
MS (ESI): 263.0 ([M+H]$^+$)

Production of Intermediates of the Formula [III] by Route (V3)

2-(4-fluorophenyl)-7-methyl-3-(4,4,5,5-tetramethyl-1,3,2-dioxaborolan-2-yl)-6,7-dihydro-5H-pyrazolo[5,1-b][1,3]oxazine [III-1]

To a solution of 3-bromo-2-(4-fluorophenyl)-7-methyl-6,7-dihydro-5H-pyrazolo[5,1-b][1,3]oxazine (1.5 g, 4.82 mmol, 1 eq) in THF (40 ml) is added a solution of n-Buli (3.314 ml, 1.6 M, 5.30 mmol, 1.1 eq) dropwise at −78° C. After 20 min of stirring, a solution of 1.23 g of 2-isopropyl-4,4,5,5-tetramethyl-1,3,2-dioxaborolane (7.23 mmol, 1.1 eq) in THF is added dropwise and the reaction mixture is stirred for 2 hours at −78° C. Then the reaction mixture is quenched by the addition of an aqueous solution of $NH_4Cl$ and is extracted with EtOAc. The combined organic phases are washed with water and brine, dried over $Na_2SO_4$ and concentrated in vacuo. The crude is purified by silica gel chromatography (eluent cyclohexane/ethyl acetate). 760 mg (42%) of 2-(4-fluorophenyl)-7-methyl-3-(4,4,5,5-tetramethyl-1,3,2-dioxaborolan-2-yl)-6,7-dihydro-5H-pyrazolo[5,1-b][1,3]oxazine are obtained.

$^1$H-NMR (400 MHz, d6-DMSO): δ=7.77-7.67 (m, 2H), 7.20-7.10 (m, 2H), 4.45-4.25 (m, 3H), 2.47-2.27 (m, 1H), 1.98-1.86 (m, 1H), 1.48 (d, 3H), 1.02 (s, 12H) ppm
Log P (pH 2.7): 3.50
MS (ESI): 359.1 ([M+H]+)

Production of Intermediates of the Formula [II] by Route (V4)

4-(2-phenyl-6,7-dihydro-5H-pyrazolo[5,1-b][1,3]oxazin-3-yl)pyridin-2-amine [II-1]

3-bromo-2-phenyl-6,7-dihydro-5H-pyrazolo[5,1-b][1,3]oxazine (700 mg, 2.25 mmol) and tert-butyl [4-(4,4,5,5-tetramethyl-1,3,2-dioxaborolan-2-yl)pyridin-2-yl]carbamate (792 mg, 2.47 mmol, 1.1 eq) are dissolved in 10 mL 1,4-dioxan. To this mixture Bis(tricyclohexylphosphine)palladium(II)-dichloride (166 mg, 0.22 mmol, 0.1 eq) and 5.4 mL sodium carbonate solution (2 molar) are added. The reaction mixture is flushed with argon for 5 mins and then sealed. Next the mixture is heated for 12 mins at 150° C. in the microwave (Biotage). The procedure is repeated 7× using the same scale and all crude reaction mixtures are combined thereafter. After cooling, insoluble components are filtered off over Celite and the residue washed with 1,4-dioxan. The organic phase is evaporated and the crude product purified by column chromatography over silica gel using dichloromethane/methanole as eluent. After evaporation of the solvents 2.10 g (41%) of 4-(2-phenyl-6,7-dihydro-5H-pyrazolo[5,1-b][1,3]oxazin-3-yl)pyridin-2-amine are obtained as a colourless solid.

$^1$H-NMR (400 MHz, d$_6$-DMSO): δ=7.72 (d, 1H), 7.40-7.25 (m, 5H), 6.36 (s, 1H), 6.18-6.15 (dd, 1H), 5.76 (s, 2H), 4.38 (t, 2H), 4.16 (t, 2H), 2.25 (m, 2H) ppm
log P (pH 2.7): 0.87
MS (ESI): 293.1 ([M+H]$^+$)

The following compounds were prepared in analogous manner:

4-[2-(4-fluorophenyl)-6,7-dihydro-5H-pyrazolo[5,1-b][1,3]oxazin-3-yl]pyridin-2-amine [II-2]

$^1$H-NMR (400 MHz, CD$_3$CN): δ=7.81-7.79 (dd, 1H), 7.46-7.41 (m, 2H), 7.12-7.06 (m, 2H), 6.42 (d, 1H), 6.37 (s, 1H), 4.72 (s, 2H), 4.38 (t, 2H), 4.16 (t, 2H), 2.28 (m, 2H) ppm
log P (pH 2.7): 0.95
MS (ESI): 311.1 ([M+H]$^+$)

4-[2-(2,4-difluorophenyl)-6,7-dihydro-5H-pyrazolo[5,1-b][1,3]oxazin-3-yl]pyridin-2-amine [II-3]

$^1$H-NMR (400 MHz, CD$_3$CN): δ=7.75-7.74 (dd, 1H), 7.47-7.41 (m, 1H), 7.07-7.04 (m, 1H), 7.03-6.95 (m, 1H), 6.42 (d, 1H), 6.33 (s, 1H), 4.78 (s, 2H), 4.42 (t, 2H), 4.17 (t, 2H), 2.29 (m, 2H) ppm
log P (pH 2.7): 1.01
MS (ESI): 329.1 ([M+H]$^+$)

Production of Compounds of the Formula [I] by Route (V4)

N-{4-[6-(4-fluorophenyl)-2,3-dihydropyrazolo[5,1-b][1,3]oxazol-7-yl]pyridin-2-yl}cyclopropanecarboxamide

Example No 3

115 mg (0.40 mmol) of N-[4-(4,4,5,5-tetramethyl-1,3,2-dioxaborolan-2-yl)pyridin-2-yl]cyclopropanecarboxamide and 124 mg (1.1 eq 0.44 mmol) of 7-bromo-6-(4-fluorophenyl)-2,3-dihydropyrazolo[5,1-b][1,3]oxazole are dissolved in 2 mL 1,4-dioxan. To this are added 30 mg of bis(tricyclohexylphosphine)-palladium(II)dichloride (0.04 mmol, 0.1 eq) and 2 mL sodium carbonate solution (2M in H$_2$O). The reaction mixture is flushed for 5 mins with argon and then sealed. Next the mixture is heated for 12 mins at 120° C. in the microwave (CEM Explorer). After cooling, insoluble components are filtered off and the salt residue washed with 1,4-dioxan. The organic phase is evaporated and the crude product purified by silica gel chromatography (eluent cyclohexane/ethyl acetate). 90 mg (61%) of N-{4-[6-(4-fluorophenyl)-2,3-dihydropyrazolo[5,1-b][1,3]oxazol-7-yl]pyridin-2-yl}cyclopropanecarboxamide are obtained as a colourless solid.

$^1$H-NMR (400 MHz, CD$_3$CN): δ=8.80 (s, 1H), 8.10 (d, 1H), 8.04-8.02 (dd, 1H), 7.49-7.44 (m, 2H), 7.14-7.08 (m, 2H), 6.75-6.73 (d, 1H), 5.18 (t, 2H), 4.34 (t, 2H), 1.78-1.72 (m, 1H), 0.89-0.85 (m, 2H), 0.85-0.82 (m, 2H) ppm
log P (pH 2.7): 1.48
MS (ESI): 365.2 ([M+H]$^+$)

Production of Compounds of the Formula by Route (V5)

N-{4-[2-(4-fluorophenyl)-7-methyl-6,7-dihydro-5H-pyrazolo[5,1-b][1,3]oxazin-3-yl]pyridin-2-yl}propanamide

Example No 63

150 mg of 2-(4-fluorophenyl)-7-methyl-3-(4,4,5,5-tetramethyl-1,3,2-dioxaborolan-2-yl)-6,7-dihydro-5H-pyrazolo[5,1-b][1,3]oxazine (0.419 mmol, 1.1 eq.) and 87 mg of N-(4-bromopyridin-2-yl)propanamide (0.381 mmol, 1 eq.) are dissolved in 1.5 ml of 1,4-dioxane. To this solution are added 22 mg of bis(tricyclohexylphosphine)-palladium(II)dichloride (0.03 mmol, 0.08 eq) and a aqueous solution of Na$_2$CO$_3$ (5 eq, 0.952 ml). The reaction mixture is flushed for 5 mins with argon and then sealed. Next the mixture is heated for 15 mins at 120° C. in the microwave (CEM Explorer). After cooling, the reaction mixture is diluted with EtOAc and washed with water. The combined organic phase are dried over Na$_2$SO$_4$ and concentrated in vacuo. The crude product is purified by silica gel chromatography (eluent cyclohexane/ethyl acetate). 34 mg (21%) of N-{4-[2-(4-fluorophenyl)-7-methyl-6,7-dihydro-5H-pyrazolo[5,1-b][1,3]oxazin-3-yl]pyridin-2-yl}propanamide are obtained.

$^1$H-NMR (400 MHz, d$_6$-DMSO): δ=10.29 (s, 1H), 8.12-8.06 (m, 2H), 7.45-7.37 (m, 2H), 7.24-7.16 (m, 2H), 6.70 (dd, 1H), 4.54-4.45 (m, 1H), 4.45-4.32 (m, 2H), 2.47-2.30 (m, 3H), 2.10-1.97 (m, 1H), 1.54 (d, 3H), 1.03 (t, 3H) ppm Log P (pH 2.7): 1.61

MS (ESI): 381.2 ([M+H]$^+$)

Production of Compounds of the Formula [I-a] by Route (V6) from Carboxylic Acid Halides N-{4-[2-(4-fluorophenyl)-6,7-dihydro-5H-pyrazolo[5,1-b][1,3]oxazin-3-yl]pyridin-2-yl}cyclo-propan-ecarboxamide Example No 4

93 mg (0.3 mmol) of 4-[2-(4-fluorophenyl)-6,7-dihydro-5H-pyrazolo[5,1-b][1,3]oxazin-3-yl]pyridin-2-amine and 46 mg (0.36 mmol, 1.2 eq) of Huenigs base are dissolved in 2 mL tetrahydrofuran. To this are added 63 mg of cyclopropanecarbonyl chloride (0.6 mmol, 2 eq) and the reaction mixture is stirred for 16 hrs at room temperature. Next, the volatile components are removed under vacuum and the crude material treated with 3 mL NH$_3$ in methanol (7 molar). The mixture is stirred for 16 hrs at room temperature and then evaporated. The crude product is purified by preparative HPLC (Phenomenex AMA Gemini C18; 110 A; 10 μm 100×30 mm, gradient: 0-2.0 mins 80% water, 20% acetonitrile, 2.0-12.0 mins linear gradient up to 25% water, 75% acetonitrile, 12.0-16.0 mins 5% water, 95% acetonitrile, modifier 15% NH$_4$OH in H$_2$O, addition of the modifier at 1.0 mL/min throughout the separation). 38.2 mg (33%) of N-{4-[2-(4-fluorophenyl)-6,7-dihydro-5H-pyrazolo[5,1-b][1,3]oxazin-3-yl]pyridin-2-yl}cyclo-propanecarboxamide are obtained as a colourless solid.

$^1$H-NMR (400 MHz, d$_6$-DMSO): δ=10.64 (s, 1H), 8.10 (d, 1H), 8.05 (s, 1H), 7.41-7.35 (m, 2H), 7.21-7.16 (m, 2H), 6.70-6.68 (d, 1H), 4.40 (t, 2H), 4.17 (t, 2H), 2.29-2.24 (m, 2H), 1.99-1.93 (m, 1H), 0.76-0.75 (m, 4H) ppm log P (pH 2.7): 1.39

MS (ESI): 379.3 ([M+H]$^+$)

Production of Compounds of the Formula [I-a] by Route (V6) from Carboxylic Acids 2-fluoro-N-{4-[2-(4-fluorophenyl)-6,7-dihydro-5H-pyrazolo[5,1-b][1,3]oxazin-3-yl]pyridin-2-yl}propanamide Example No 113

To a solution of 73 mg (2 eq, 0.8 mmol) 2-fluoropropanoic acid in 2 mL dichloromethane are added 81 mg (1.2 eq, 0.48 mmol) 6-chloro-hydroxybenzotriazole, 153 mg (2 eq, 0.8 mmol) N-(3-dimethylaminopropyl)-N'-ethyl-carbodiimide hydrochloride and 129 mg (2.5 eq, 1 mmol) N-ethyl-diisopropylamine. After stirring for 20 min at room temperature 133 mg (1.0 eq, 0.40 mmol) 4-[2-(4-fluorophenyl)-6,7-dihydro-5H-pyrazolo[5,1-b][1,3]oxazin-3-yl]pyridin-2-amine were added and the mixture was stirred for 12 h at room temperature. Then, the crude reaction mixture was evaporated and the material was purified by preparative HPLC (Kromasil 100 C18 16 μm; 110 A; VDS Optilab 250×32 mm; gradient: 0-3 min 75% water, 25% acetonitrile with 1% formic acid, 3-12.0 min linear gradient to 5% water, 95% acetonitrile with 1% formic acid, 12.0-17.00 min 5% water, 95% acetonitrile). After purification 65 mg (34%) 2-fluoro-N-{4-[2-(4-fluorophenyl)-6,7-dihydro-5H-pyrazolo[5,1-b][1,3]oxazin-3-yl]pyridin-2-yl}propanamide are obtained as colourless solid.

$^1$H-NMR (400 MHz, d$_6$-DMSO): δ=10.34 (s, 1H), 8.16-8.14 (d, 1H), 8.02 (s, 1H), 7.42-7.37 (m, 2H), 7.23-7.17 (m, 2H), 6.81-6.79 (dd, 1H), 5.29-5.10 (qd, 1H, CHF), 4.43 (t, 2H), 4.16 (t, 2H), 2.33-2.25 (m, 2H), 1.51-1.40 (dd, 3H) ppm log P (pH 2.7): 2.00

MS (ESI): 385.2 ([M+H]$^+$)

Production of Intermediates of the Formula [XXXVII] by Route (V22)

3-Bromo-2-phenylpyrazolo[1,5-a]pyrimidine [XXXVII-1]

To a solution of 4-bromo-3-phenyl-1H-pyrazole-5-amine (5.0 g, 0.02 mol) in acetic acid (50 mL) is added 1,1,3,3-tetramethoxypropane (4.14 g, 0.025 mol). The mixture is stirred at 110° C. for 1 h. The reaction mixture is then poured into water, basified with NH$_4$OH and extracted with dichloromethane (3×100 mL). The organic layer is dried over anhydrous magnesium sulphate, filtered and concentrated under reduced pressure. The crude material is purified by column chromatography using silica gel in dichloromethane and ethyl acetate (1:0 to 95:5) as eluent and 4.2 g (75%) of 3-bromo-2-phenylpyrazolo[1,5-a]pyrimidine are obtained as a beige solid.

$^1$H-NMR (300 MHz, DMSO): δ=9.22 (dd, 1H), 8.68 (dd, 1H), 8.04-8.02 (m, 2H), 7.59-7.52 (m, 3H), 7.20 (dd, 1H) ppm log P (pH 2.7): 2.63

MS (ESI): 274 ([M+H]$^+$)

Production of Intermediates of the Formula [XXXVIII] by Route (V22)

2-(4-Fluorophenyl)pyrazolo[1,5-a]pyrimidine [XXXVIII-1]

To a solution of 3-(4-fluorophenyl)-1H-pyrazole-5-amine (5.0 g, 0.028 mol) in acetic acid (50 mL) is added 1,1,3,3-tetramethoxypropane (5.79 g, 0.035 mol). The mixture is stirred at 110° C. for 1 h. The reaction mixture is then poured into water, basified with NH$_4$OH and extracted with dichloromethane (3×100 mL). The organic layer is dried over anhydrous magnesium sulphate, filtered and concentrated under reduced pressure. 6.8 g (79%) of 2-(4-fluorophenyl)pyrazolo[1,5-a]pyrimidine are obtained as a beige solid which is used in the next step without further purification.

$^1$H-NMR (300 MHz, DMSO): δ=9.13 (dd, 1H), 8.55 (dd, 1H), 8.09 (m, 2H), 7.34 (m, 2H), 7.24 (s, 1H), 7.05 (dd, 1H) ppm log P (pH 2.7): 2.17

MS (ESI): 214.1 ([M+H]$^+$)

Production of Intermediates of the Formula [XXXVII] by Route (V2)

3-Bromo-2-(4-fluorophenyl)pyrazolo[1,5-a]pyrimidine [XXXVII-2]

To a solution of 2-(4-fluorophenyl)pyrazolo[1,5-a]pyrimidine (5.8 g, 0.027 mol) in chloroform (60 mL) is added, at 0°

C., N-bromosuccinimide (4.8 g, 0.027 mol). The mixture is stirred at room temperature for 1 h 30. The reaction mixture is then poured into water and extracted with dichloromethane (3×100 mL). The organic layer is dried over anhydrous magnesium sulphate, filtered and concentrated under reduced pressure. The crude material is filtered through a short pad of silica. 6 g (75%) of 3-bromo-2-(4-fluorophenyl)pyrazolo[1,5-a]pyrimidine are obtained as a brown solid which is used in the next step without further purification.

$^1$H-NMR (300 MHz, DMSO): δ=9.21 (dd, 1H), 8.68 (dd, 1H), 8.07 (m, 2H), 7.42 (m, 2H), 7.20 (dd, 1H) ppm log P (pH 2.7): 2.80

MS (ESI): 292 ([M+H]$^+$)

Production of Compounds of the Formula [I-i] by Route (V4)

N-{4-[2-(4-Fluorophenyl)pyrazolo[1,5-a]pyrimidin-3-yl]pyridin-2-yl}acetamide [I-i-1]

3-Bromo-2-(4-fluorophenyl)pyrazolo[1,5-a]pyrimidine (150 mg, 0.51 mmol) and N-[4-(4,4,5,5-tetramethyl-1,3,2-dioxaborolan-2-yl)pyridin-2-yl]acetamide (148 mg, 0.56 mmol, 1.1 eq) are dissolved in 1.5 mL 1,4-dioxan. To this mixture, bis(tricyclohexylphosphine)palladium(II)-dichloride (57 mg, 0.07 mmol, 0.15 eq) and 0.83 mL sodium carbonate solution (2 molar) are added. The reaction mixture is flushed with argon for 5 mins and then sealed. Next the mixture is heated for 30 min at 150° C. in the microwave (Biotage). The reaction mixture is then poured in water and extracted with dichloromethane (3×20 mL). The organic layer is dried over anhydrous magnesium sulphate, filtered and concentrated under reduced pressure. The crude material is purified by column chromatography using silica gel in heptane and ethyl acetate (1:0 to 1:1) as eluent and 0.03 g (17%) of N-{4-[2-(4-fluorophenyl)pyrazolo[1,5-a]pyrimidin-3-yl]pyridin-2-yl}acetamide are obtained as a white solid.

$^1$H-NMR (300 MHz, DMSO): δ=10.48 (bs, 1H), 9.23 (dd, 1H), 8.69 (dd, 1H), 8.30 (s, 1H), 8.25 (d, 1H), 7.62 (m, 2H), 7.31 (m, 2H), 7.22 (dd, 1H), 7.11 (dd, 1H), 2.05 (s, 3H) ppm log P (pH 2.7): 1.47

MS (ESI): 348.1 ([M+H]$^+$)

Production of compound of the formula [I-j] by route (V23)

N-{4-[2-(4-Fluorophenyl)-4,5,6,7-tetrahydropyrazolo[1,5-a]pyrimidin-3-yl]pyridin-2-yl}acetamide [I-j-1]

To a mixture of N-{4-[2-(4-fluorophenyl)pyrazolo[1,5-a]pyrimidin-3-yl]pyridin-2-yl}acetamide (120 mg, 0.34 mmol, 1 eq) in 2 mL of ethanol is added sodium borohydride (29 mg, 0.76 mmol, 2.2 eq). The mixture is refluxed for 1 h. The mixture is then poured into water, extracted with dichloromethane (3×20 mL), dried over anhydrous magnesium sulphate, filtered and concentrated under reduced pressure. The crude material is purified by column chromatography using silica gel in heptane and ethyl acetate (1:0 to 0:1) as eluent and 30 mg (25%) of N-{4-[2-(4-fluorophenyl)-4,5,6,7-tetrahydropyrazolo[1,5-a]pyrimidin-3-yl]pyridin-2-yl}acetamide are obtained as a white solid.

log P (pH 2.7): 1.48

MS (ESI): 352.2 ([M+H]$^+$)

Production of Intermediates of the Formula [II-a] by Route (V4)

4-(2-Phenylpyrazolo[1,5-a]pyrimidin-3-yl)pyridin-2-amine [II-a-1] and tert-butyl [4-(2-phenylpyrazolo[1,5-a]pyrimidin-3-yl)pyridin-2-yl]carbamate [I-i-2]

3-Bromo-2-phenylpyrazolo[1,5-a]pyrimidine (1.0 g, 3.65 mmol) and tert-butyl [4-(4,4,5,5-tetramethyl-1,3,2-dioxaborolan-2-yl)pyridin-2-yl]carbamate (1.29 g, 4.01 mmol, 1.1 eq) are dissolved in 10 mL 1,4-dioxan. To this mixture bis(tricyclohexylphosphine)palladium(II)-dichloride (269 mg, 0.37 mmol, 0.1 eq) and 9.1 mL sodium carbonate solution (2 molar) are added. The reaction mixture is flushed with argon for 5 mins and then sealed. Next the mixture is heated for 90 min at 120° C. in the microwave (Biotage). Tert-butyl [4-(4,4,5,5-tetramethyl-1,3,2-dioxaborolan-2-yl)pyridin-2-yl]carbamate (214 mg, 1.4 mmol, 0.37 eq) and bis(tricyclohexylphosphine)palladium(II)-dichloride (269 mg, 0.37 mmol, 0.1 eq) are then added and the mixture is heated for 2 h at 120° C. The reaction mixture is then poured in water and extracted with ethyl acetate (3×50 mL). The organic layer is dried over anhydrous magnesium sulphate, filtered and concentrated under reduced pressure. The crude material is purified by column chromatography using silica gel in heptane and ethyl acetate (1:0 to 1:1) as eluent and 0.48 g (44%) of 4-(2-phenylpyrazolo[1,5-a]pyrimidin-3-yl)pyridin-2-amine are obtained as a white solid.

$^1$H-NMR (300 MHz, DMSO): δ=9.21 (dd, 1H), 8.64 (dd, 1H), 7.85 (d, 1H), 7.62-7.60 (m, 2H), 7.46-7.45 (m, 3H), 7.17 (dd, 1H), 6.70 (s, 1H), 6.43 (dd, 1H), 5.89 (bs, 2H) ppm log P (pH 2.7): 0.98

MS (ESI): 288 ([M+H]$^+$)

56 mg (4%) of tert-butyl [4-(2-phenylpyrazolo[1,5-a]pyrimidin-3-yl)pyridin-2-yl]carbamate is also isolated as a yellow solid.

$^1$H-NMR (300 MHz, DMSO): δ=9.68 (s, 1H), 9.25 (dd, 1H), 8.68 (dd, 1H), 8.17 (d, 1H), 8.06 (bs, 1H), 7.59-7.57 (m, 2H), 7.46-7.45 (m, 3H), 7.21 (dd, 1H), 7.00 (dd, 1H), 1.43 (s, 9H) ppm log P (pH 2.7): 2.32

MS (ESI): 388 ([M+H]$^+$)

Production of Intermediates of the Formula [II-b] by Route (V23)

4-(2-Phenyl-4,5,6,7-tetrahydropyrazolo[1,5-a]pyrimidin-3-yl)pyridin-2-amine [II-b-1]

To a mixture of 4-(2-phenylpyrazolo[1,5-a]pyrimidin-3-yl)pyridin-2-amine (60 mg, 0.2 mmol, 1 eq) in 3 mL of ethanol is added sodium borohydride (17 mg, 0.45 mmol, 2.2 eq). The mixture is stirred at room temperature for 2 h. The mixture is then poured into water, extracted with dichloromethane (3×50 mL), dried over anhydrous magnesium sulphate, filtered and concentrated under reduced pressure. 29 mg (47%) of 4-(2-phenyl-4,5,6,7-tetrahydropyrazolo[1,5-a]pyrimidin-3-yl)pyridin-2-amine are obtained as a white solid which is used in the next step without further purification.

log P (pH 2.7): 1.05

MS (ESI): 292.2 ([M+H]$^+$)

Production of Compounds of the Formula [I-n] by Route (V6)

N-acetyl-N-[4-(4-acetyl-2-phenyl-4,5,6,7-tetrahydropyrazolo[1,5-a]pyrimidin-3-yl)pyridin-2-yl]acetamide [I-n-1]

To a solution of 4-(2-phenyl-4,5,6,7-tetrahydropyrazolo[1,5-a]pyrimidin-3-yl)pyridin-2-amine (29 mg, 0.1 mmol, 1 eq) in 2 mL of tetrahydrofurane is added triethylamine (0.055 mL, 0.4 mmol, 4 eq) and then acetyl chloride (0.024 mL, 0.3 mmol, 3 eq). The mixture is stirred for 4 h at room temperature. Triethylamine (0.055 mL, 0.4 mmol, 4 eq) and acetyl chloride (0.024 mL, 0.3 mmol, 3 eq) are then added. The mixture is stirred overnight at room temperature and then poured into water and extracted with dichloromethane (3×50 mL). The combined organic layers are washed with a saturated solution of $NaHCO_3$, brine, dried over anhydrous magnesium sulphate, filtered and concentrated under reduced pressure. The crude material is purified by column chromatography using silica gel in heptane and ethyl acetate (1:0 to 0:1) as eluent and 4 mg (8%) of N-[4-(2-phenyl-4,5,6,7-tetrahydropyrazolo[1,5-a]pyrimidin-3-yl)pyridin-2-yl]acetamide are obtained as a light brown oil.

log P (pH 2.7): 1.72
MS (ESI): 418.3 ([M+H]$^+$)

Production of compounds of the formula [I-l] by route (V23)

N-Acetyl-N-[4-(2-phenylpyrazolo[1,5-a]pyrimidin-3-yl)pyridin-2-yl]acetamide [I-l-1] and N-[4-(2-phenylpyrazolo[1,5-a]pyrimidin-3-yl)pyridin-2-yl]acetamide [I-l-2]

To a solution of 4-(2-phenylpyrazolo[1,5-a]pyrimidin-3-yl)pyridin-2-amine (420 mg, 1.46 mmol, 1 eq) in 20 mL of tetrahydrofurane is added triethylamine (0.82 mL, 5.85 mmol, 4 eq) and then acetyl chloride (234 mg, 2.92 mmol, 2 eq). The mixture is stirred overnight at room temperature and then poured into water and extracted with dichloromethane (3×50 mL). The combined organic layers are washed with a saturated solution of $NaHCO_3$, brine, dried over anhydrous magnesium sulphate, filtered and concentrated under reduced pressure. The crude material is purified by column chromatography using silica gel in heptane and ethyl acetate (1:0 to 0:1) as eluent and 0.23 g (37%) of N-acetyl-N-[4-(2-phenylpyrazolo[1,5-a]pyrimidin-3-yl)pyridin-2-yl]acetamide are obtained as a yellow solid.

$^1$H-NMR (300 MHz, DMSO): δ=9.29 (dd, 1H), 8.75 (dd, 1H), 8.57 (d, 1H), 7.68 (dd, 1H), 7.61-7.59 (m, 2H), 7.49-7.46 (m, 4H), 7.26 (dd, 1H), 2.16 (s, 6H) ppm
log P (pH 2.7): 2.13
MS (ESI): 372 ([M+H]$^+$)

23 mg (4%) of N-[4-(2-phenylpyrazolo[1,5-a]pyrimidin-3-yl)pyridin-2-yl]acetamide is also purified as a yellow solid.

$^1$H-NMR (300 MHz, CDCl$_3$): δ=8.75 (dd, 1H), 8.63-8.60 (m, 2H), 8.26 (bs, 1H), 8.18 (d, 1H), 7.65-7.61 (m, 2H), 7.46-7.40 (m, 3H), 7.13 (dd, 1H), 6.94 (dd, 1H), 2.20 (s, 3H) ppm
log P (pH 2.7): 1.41
MS (ESI): 330 ([M+H]$^+$)

Production of Compounds of the Formula [I-m] by Route (V23)

N-acetyl-N-[4-(4-acetyl-2-phenyl-4,5,6,7-tetrahydropyrazolo[1,5-a]pyrimidin-3-yl)pyridin-2-yl]acetamide [I-m-1]

To a mixture of N-acetyl-N-[4-(2-phenylpyrazolo[1,5-a]pyrimidin-3-yl)pyridin-2-yl]acetamide (158 mg, 0.43 mmol, 1 eq) in 3 mL of ethanol is added sodium borohydride (35 mg, 0.94 mmol, 2.2 eq). The mixture is refluxed for 1 h. The mixture is then poured into water, extracted with dichloromethane (3×50 mL), dried over anhydrous magnesium sulphate, filtered and concentrated under reduced pressure. The crude material is purified by column chromatography using silica gel in heptane and ethyl acetate (1:0 to 0:1) as eluent and 66 mg (46%) of N-acetyl-N-[4-(4-acetyl-2-phenyl-4,5,6,7-tetrahydropyrazolo[1,5-a]pyrimidin-3-yl)pyridin-2-yl]acetamide are obtained as a white solid.

$^1$H-NMR (300 MHz, CDCl$_3$): δ=8.23 (bs, 1H), 8.07 (bs, 1H), 8.00 (d, 1H), 7.47-7.45 (m, 2H), 7.32 (m, 3H), 6.64 (m, 1H), 4.75 (bs, 1H), 4.21 (t, 2H), 3.42 (bs, 2H), 2.20 (m, 3H), 1.63 (s, 3H) ppm
log P (pH 2.7): 1.13
MS (ESI): 334 ([M+H]$^+$)

The compounds of the formula [I] named in the following Tables I and II are also obtained by the aforesaid methods.

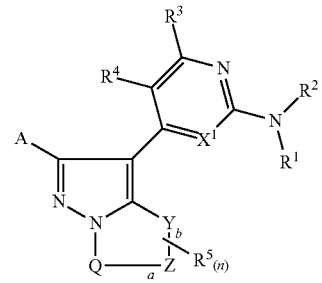

[I] In which $X^1$ stands for CH and the other residues are defined as described in the following table 1

TABLE 1

| Exa. | A | $R^5_{(n)}$ | $R^1$ | $R^2$ | $R^3$ | $R^4$ |
|---|---|---|---|---|---|---|
| 1 | 4-fluorophenyl | $CH_2CH_2O$ | acetyl | H | H | H |
| 2 | 4-fluorophenyl | $CH_2CH_2CH_2O$ | acetyl | H | H | H |
| 3 | 4-fluorophenyl | $CH_2CH_2O$ | cyclopropylcarbonyl | H | H | H |
| 4 | 4-fluorophenyl | $CH_2CH_2CH_2O$ | cyclopropylcarbonyl | H | H | H |
| 5 | 4-fluorophenyl | $CH_2CH_2CH_2O$ | propanoyl | H | H | H |
| 6 | phenyl | $CH_2CH_2CH_2O$ | propanoyl | H | H | H |

TABLE 1-continued

—Q—Z—Y—
     R⁵₍ₙ₎

| Exa. | A | (Z-Y with R⁵) | R¹ | R² | R³ | R⁴ |
|---|---|---|---|---|---|---|
| 7 | phenyl | CH₂CH₂CH₂O | cyclopropylcarbonyl | H | H | H |
| 8 | phenyl | CH₂CH₂CH₂O | 2-methylpropanoyl | H | H | H |
| 9 | phenyl | CH₂CH₂CH₂O | ethoxycarbonyl | H | H | H |
| 10 | phenyl | CH₂CH₂CH₂O | 2-methylbutanoyl | H | H | H |
| 11 | phenyl | CH₂CH₂CH₂O | 3-methylbutanoyl | H | H | H |
| 12 | phenyl | CH₂CH₂CH₂O | lactoyl | H | H | H |
| 13 | phenyl | CH₂CH₂CH₂O | cyclopropylacetyl | H | H | H |
| 14 | phenyl | CH₂CH₂CH₂O | tetrahydro-2H-pyran-4-ylcarbonyl | H | H | H |
| 15 | phenyl | CH₂CH₂CH₂O | 3-phenylpropanoyl | H | H | H |
| 16 | phenyl | CH₂CH₂CH₂O | (methylsulfanyl)acetyl | H | H | H |
| 17 | phenyl | CH₂CH₂CH₂O | 3,3,3-trifluoropropanoyl | H | H | H |
| 18 | phenyl | CH₂CH₂CH₂O | 2-(4-fluorophenyl)propanoyl | H | H | H |
| 19 | phenyl | CH₂CH₂CH₂O | 4-methylpent-3-enoyl | H | H | H |
| 20 | phenyl | CH₂CH₂CH₂O | 3,3-dimethylbutanoyl | H | H | H |
| 21 | phenyl | CH₂CH₂CH₂O | (1-chlorocyclopropyl)carbonyl | H | H | H |
| 22 | 4-fluorophenyl | CH₂CH₂CH₂O | 2-methylpropanoyl | H | H | H |
| 23 | 4-fluorophenyl | CH₂CH₂CH₂O | ethoxycarbonyl | H | H | H |
| 24 | 4-fluorophenyl | CH₂CH₂CH₂O | 2-methylbutanoyl | H | H | H |
| 25 | 4-fluorophenyl | CH₂CH₂CH₂O | 3-methylbutanoyl | H | H | H |
| 26 | 4-fluorophenyl | CH₂CH₂CH₂O | lactoyl | H | H | H |
| 27 | 4-fluorophenyl | CH₂CH₂CH₂O | cyclopropylacetyl | H | H | H |
| 28 | 4-fluorophenyl | CH₂CH₂CH₂O | tetrahydro-2H-pyran-4-ylcarbonyl | H | H | H |
| 29 | 4-fluorophenyl | CH₂CH₂CH₂O | 3-phenylpropanoyl | H | H | H |
| 30 | 4-fluorophenyl | CH₂CH₂CH₂O | (methylsulfanyl)acetyl | H | H | H |
| 31 | 4-fluorophenyl | CH₂CH₂CH₂O | 3,3,3-trifluoropropanoyl | H | H | H |
| 32 | 4-fluorophenyl | CH₂CH₂CH₂O | 2-(4-fluorophenyl)propanoyl | H | H | H |
| 33 | 4-fluorophenyl | CH₂CH₂CH₂O | 4-methylpent-3-enoyl | H | H | H |
| 34 | 4-fluorophenyl | CH₂CH₂CH₂O | 3,3-dimethylbutanoyl | H | H | H |
| 35 | 2,4-difluorophenyl | CH₂CH₂CH₂O | propanoyl | H | H | H |
| 36 | 2,4-difluorophenyl | CH₂CH₂CH₂O | cyclopropylcarbonyl | H | H | H |
| 37 | 2,4-difluorophenyl | CH₂CH₂CH₂O | 2-methylpropanoyl | H | H | H |
| 38 | 2,4-difluorophenyl | CH₂CH₂CH₂O | ethoxycarbonyl | H | H | H |
| 39 | 2,4-difluorophenyl | CH₂CH₂CH₂O | 2-methylbutanoyl | H | H | H |
| 40 | 2,4-difluorophenyl | CH₂CH₂CH₂O | 3-methylbutanoyl | H | H | H |
| 41 | 2,4-difluorophenyl | CH₂CH₂CH₂O | lactoyl | H | H | H |
| 42 | 2,4-difluorophenyl | CH₂CH₂CH₂O | cyclopropylacetyl | H | H | H |
| 43 | 2,4-difluorophenyl | CH₂CH₂CH₂O | tetrahydro-2H-pyran-4-ylcarbonyl | H | H | H |
| 44 | 2,4-difluorophenyl | CH₂CH₂CH₂O | 3-phenylpropanoyl | H | H | H |
| 45 | 2,4-difluorophenyl | CH₂CH₂CH₂O | (methylsulfanyl)acetyl | H | H | H |
| 46 | 2,4-difluorophenyl | CH₂CH₂CH₂O | 3,3,3-trifluoropropanoyl | H | H | H |
| 47 | 2,4-difluorophenyl | CH₂CH₂CH₂O | 2-(4-fluorophenyl)propanoyl | H | H | H |
| 48 | 2,4-difluorophenyl | CH₂CH₂CH₂O | 4-methylpent-3-enoyl | H | H | H |
| 49 | 2,4-difluorophenyl | CH₂CH₂CH₂O | 3,3-dimethylbutanoyl | H | H | H |
| 50 | 2,4-difluorophenyl | CH₂CH₂CH₂O | (1-chlorocyclopropyl)carbonyl | H | H | H |
| 51 | phenyl | CH=CH—CH=N | acetyl | H | H | H |
| 52 | 4-fluorophenyl | CH₂CH₂CH₂O | propanoyl | acetyl | H | H |
| 53 | 4-fluorophenyl | CH₂CH₂CH₂O | propanoyl | propanoyl | H | H |
| 54 | 4-fluorophenyl | CH₂CH₂CH₂O | cyclopropylcarbonyl | propanoyl | H | H |
| 55 | phenyl | CH₂CH₂CH₂NH | acetyl | H | H | H |
| 56 | phenyl | CH=CH—CH=N | acetyl | acetyl | H | H |
| 57 | 4-fluorophenyl | CH₂CH₂CH₂O | ethoxycarbonyl | propanoyl | H | H |
| 58 | phenyl | CH₂CH₂CH₂N(CH₃CO) | acetyl | acetyl | H | H |
| 59 | 4-fluorophenyl | CH₂CH₂CH₂NH | acetyl | H | H | H |
| 60 | 4-fluorophenyl | CH=CH—CH=N | acetyl | H | H | H |
| 61 | 4-fluorophenyl | CH₂Si(Me)₂CH₂O | acetyl | H | H | H |
| 62 | 4-fluorophenyl | CH(Me)CH₂CH₂O | 2-methylpropanoyl | H | H | H |
| 63 | 4-fluorophenyl | CH(Me)CH₂CH₂O | propanoyl | H | H | H |
| 64 | 4-fluorophenyl | CH₂CH₂CH₂O | bicyclo[2.2.1]hept-2-ylcarbonyl | H | H | H |
| 65 | 4-fluorophenyl | CH₂CH₂CH₂O | bicyclo[4.1.0]hept-7-ylcarbonyl | H | H | H |
| 66 | 4-fluorophenyl | CH₂CH₂CH₂O | piperidin-1-ylacetyl | H | H | H |
| 67 | 4-fluorophenyl | CH₂CH₂CH₂O | 2-propylpentanoyl | H | H | H |
| 68 | 4-fluorophenyl | CH₂CH₂CH₂O | 2-methyl-2-(methylsulfinyl)propanoyl | H | H | H |
| 69 | 4-fluorophenyl | CH₂CH₂CH₂O | 1,3-dithiolan-2-ylcarbonyl | H | H | H |
| 70 | 4-fluorophenyl | CH₂CH₂CH₂O | oxo(piperidin-1-yl)acetyl | H | H | H |
| 71 | 4-fluorophenyl | CH₂CH₂CH₂O | 2,6-difluorobenzoyl | H | H | H |
| 72 | 4-fluorophenyl | CH(Me)CH₂CH(Me)O | propanoyl | H | H | H |
| 73 | 4-fluorophenyl | CH(Me)CH₂CH(Me)O | propanoyl | H | H | H |
| 74 | 4-fluorophenyl | CH₂C(F)₂CH₂O | propanoyl | H | H | H |
| 75 | 4-fluorophenyl | CH(Me)CH(Me)O | propanoyl | H | H | H |
| 76 | 4-fluorophenyl | CH₂Si(Me)₂CH₂O | 2-methylpropanoyl | H | H | H |
| 77 | 4-fluorophenyl | CH₂Si(Me)₂CH₂O | propanoyl | H | H | H |
| 78 | phenyl | CH₂CH₂CH₂N(COEt) | propanoyl | H | H | H |

TABLE 1-continued

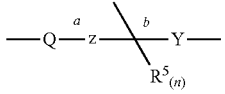

| Exa. | A | Z | R¹ | R² | R³ | R⁴ |
|---|---|---|---|---|---|---|
| 79 | 4-fluorophenyl | CH=CH—CH=N | propanoyl | H | H | H |
| 80 | 4-fluorophenyl | CH$_2$CH$_2$CH$_2$NH | propanoyl | H | H | H |
| 81 | 4-fluorophenyl | CH$_2$Si(Me)$_2$CH$_2$O | cyclopropylcarbonyl | H | H | H |
| 82 | thiophen-2-yl | CH$_2$Si(Me)$_2$CH$_2$O | propanoyl | H | H | H |
| 83 | 4-fluorophenyl | CH=CH—CH=N | acetyl | acetyl | H | H |
| 84 | 4-fluorophenyl | CH=CH—CH=N | cyclopropylcarbonyl | Cyclopropyl-carbonyl | H | H |
| 85 | thiophen-2-yl | CH$_2$Si(Me)$_2$CH$_2$O | acetyl | H | H | H |
| 86 | thiophen-2-yl | CH$_2$Si(Me)$_2$CH$_2$O | isobutyryl | H | H | H |
| 87 | thiophen-2-yl | CH$_2$Si(Me)$_2$CH$_2$O | cyclopropylcarbonyl | H | H | H |
| 88 | 4-fluorophenyl | CH=CH—CH=N | cyclopropylcarbonyl | H | H | H |
| 89 | thiophen-2-yl | CH$_2$Si(Me)$_2$CH$_2$O | H | H | H | H |
| 90 | 4-fluorophenyl | CH$_2$CH$_2$CH$_2$N(COEt) | propanoyl | acetyl | H | H |
| 91 | 4-fluorophenyl | CH$_2$CH$_2$CH$_2$N(COEt) | propanoyl | H | H | H |
| 92 | phenyl | CH$_2$CH$_2$CH$_2$NH | isobutyryl | 2-methylpropanoyl | H | H |
| 93 | 4-fluorophenyl | CH$_2$CH$_2$CH$_2$N(COEt) | propanoyl | CH$_3$ | H | H |
| 94 | 4-fluorophenyl | CH$_2$CH$_2$CH$_2$N(CH$_3$CO) | acetyl | H | H | H |
| 95 | 2,4-difluorophenyl | CH$_2$CH$_2$CH$_2$O | propanoyl | propanoyl | H | H |
| 96 | thiophen-3-yl | CH$_2$Si(Me)$_2$CH$_2$O | acetyl | H | H | H |
| 97 | 4-fluorophenyl | CH$_2$CH$_2$CH$_2$N(Et) | benzyl | H | H | H |
| 98 | 4-fluorophenyl | CH$_2$CH$_2$CH$_2$O | (1-methylcyclopropyl)carbonyl | H | H | H |
| 99 | 4-fluorophenyl | CH$_2$CH$_2$CH$_2$O | 5-oxohexanoyl | H | H | H |
| 100 | thiophen-3-yl | CH$_2$Si(Me)$_2$CH$_2$O | propanoyl | H | H | H |
| 101 | thiophen-3-yl | CH$_2$Si(Me)$_2$CH$_2$O | isobutyryl | H | H | H |
| 102 | thiophen-3-yl | CH$_2$Si(Me)$_2$CH$_2$O | cyclopropylcarbonyl | H | H | H |
| 103 | 4-fluorophenyl | C(CH$_3$)=CH—O | propanoyl | H | H | H |
| 104 | 4-fluorophenyl | C(C$_2$H$_5$)=CH—O | propanoyl | H | H | H |
| 105 | 4-fluorophenyl | CH=CH—O | propanoyl | H | H | H |
| 106 | phenyl | CH=CH—O | propanoyl | H | H | H |
| 107 | 4-fluorophenyl | CH$_2$C(Me)(CN)CH$_2$O | 2-methylpropanoyl | H | H | H |
| 108 | 4-fluorophenyl | CH$_2$C(Me)$_2$CH$_2$O | cyclopropylcarbonyl | H | H | H |
| 109 | 4-fluorophenyl | CH$_2$C(Me)$_2$CH$_2$O | acetyl | H | H | H |
| 110 | 4-fluorophenyl | CH$_2$C(Me)$_2$CH$_2$O | propanoyl | H | H | H |
| 111 | 4-fluorophenyl | CH$_2$C(Me)$_2$CH$_2$O | isobutyryl | H | H | H |
| 112 | 4-fluorophenyl | CH$_2$CH$_2$CH$_2$O | (3-oxocyclopentyl)carbonyl | H | H | H |
| 113 | 4-fluorophenyl | CH$_2$CH$_2$CH$_2$O | 2-fluoropropanoyl | H | H | H |
| 114 | 4-fluorophenyl | CH$_2$CH$_2$CH$_2$O | (5-fluoropyridin-3-yl)carbonyl | H | H | H |
| 115 | 4-fluorophenyl | CH$_2$CH$_2$CH$_2$O | 2-fluoro-2-methylpropanoyl | H | H | H |
| 116 | 4-fluorophenyl | CH$_2$CH$_2$CH$_2$O | (2-chloro-2-fluorocyclopropyl)carbonyl | H | H | H |
| 117 | 4-fluorophenyl | CH$_2$CH$_2$CH$_2$O | (1-methylcyclopentyl)carbonyl | H | H | H |
| 118 | 4-fluorophenyl | CH$_2$CH$_2$CH$_2$O | (5-methyl-1,3-dioxan-5-yl)carbonyl | H | H | H |
| 119 | 4-fluorophenyl | CH$_2$CH$_2$CH$_2$O | (3-ethyloxetan-3-yl)carbonyl | H | H | H |
| 120 | 4-fluorophenyl | CH$_2$CH$_2$CH$_2$O | (1-cyanocyclopropyl)carbonyl | H | H | H |
| 121 | 4-fluorophenyl | CH$_2$CH$_2$CH$_2$O | (1-methylcyclohex-3-en-1-yl)carbonyl | H | H | H |
| 122 | 4-fluorophenyl | CH$_2$CH$_2$CH$_2$O | [(isopropylideneamino)oxy]acetyl | H | H | H |
| 123 | 4-fluorophenyl | CH$_2$CH$_2$CH$_2$O | 1H-pyrazol-1-ylacetyl | H | H | H |
| 124 | 4-fluorophenyl | CH$_2$CH$_2$CH$_2$O | tetrahydro-2H-pyran-3-ylacetyl | H | H | H |
| 125 | 4-fluorophenyl | CH$_2$CH$_2$CH$_2$O | cyclopent-3-en-1-ylcarbonyl | H | H | H |
| 126 | 4-fluorophenyl | CH$_2$CH$_2$CH$_2$O | 2-methyl-3-furoyl | H | H | H |
| 127 | 4-fluorophenyl | CH$_2$CH$_2$CH$_2$O | 2,4-dimethylhexanoyl | H | H | H |
| 128 | 4-fluorophenyl | CH$_2$CH$_2$CH$_2$O | tetrahydro-2H-thiopyran-4-ylcarbonyl | H | H | H |
| 129 | 4-fluorophenyl | CH$_2$CH$_2$CH$_2$O | 1,1'-bi(cyclopropyl)-1-ylcarbonyl | H | H | H |
| 130 | 4-fluorophenyl | CH$_2$CH$_2$CH$_2$O | (5-fluoro-2-thienyl)carbonyl | H | H | H |
| 131 | 4-fluorophenyl | CH$_2$CH$_2$CH$_2$O | 3-methylpentanoyl | H | H | H |
| 132 | 4-fluorophenyl | CH$_2$CH$_2$CH$_2$O | 3-fluoro-2-(fluoromethyl)-2-methylpropanoyl | H | H | H |
| 133 | 4-fluorophenyl | CH$_2$CH$_2$CH$_2$O | 3-(1H-1,2,3-triazol-1-yl)propanoyl | H | H | H |
| 134 | 4-fluorophenyl | CH$_2$CH$_2$CH$_2$O | (5-methyl-1,2-oxazol-3-yl)carbonyl | H | H | H |
| 135 | 4-fluorophenyl | CH$_2$CH$_2$CH$_2$O | (3,5-dimethyl-1,2-oxazol-4-yl)carbonyl | H | H | H |
| 136 | 4-fluorophenyl | CH$_2$CH$_2$CH$_2$O | 2-[(isopropylideneamino)oxy]propanoyl | H | H | H |

TABLE 1-continued $$-Q\overset{a}{-}Z\overset{b}{-}\underset{R^5_{(n)}}{\diagdown}Y-$$

| Exa. | A | Z | R¹ | R² | R³ | R⁴ |
|---|---|---|---|---|---|---|
| 137 | 4-fluorophenyl | CH₂CH₂CH₂O | 1H-1,2,4-triazol-1-ylacetyl | H | H | H |
| 138 | 4-fluorophenyl | CH₂CH₂CH₂O | N-formylvalyl | H | H | H |
| 139 | 4-fluorophenyl | CH₂CH₂CH₂O | cyclohex-1-en-1-ylacetyl | H | H | H |
| 140 | 4-fluorophenyl | CH₂CH₂CH₂O | (2,2,3,3-tetramethylcyclopropyl)carbonyl | H | H | H |

TABLE 2

NMR and Mass spectroscopic/logP data of compounds of the type [I]

| No. | Name | NMR | LogP$_A$ | $[M+H]_A^{+1}$ | Method² |
|---|---|---|---|---|---|
| 1 | N-{4-[6-(4-fluorophenyl)-2,3-dihydropyrazolo[5,1-b][1,3]oxazol-7-yl]pyridin-2-yl}acetamide | 1H-NMR (400 MHz, d3-CD3CN): δ = 8.60 (s, 1H), 8.09-8.06 (m, 2H), 7.52-7.48 (m, 2H), 7.18-7.13 (m, 2H), 6.83-6.82 (dd, 1H), 5.22 (t, 2H), 4.37 (t, 2H), 2.09 (s, 3H) ppm | 1.19 | 339.2 | B |
| 2 | N-{4-[2-(4-fluorophenyl)-6,7-dihydro-5H-pyrazolo[5,1-b][1,3]oxazin-3-yl]pyridin-2-yl}acetamide | 1H-NMR (400 MHz, d3-CD3CN): δ = 8.58 (s, 1H), 8.09-8.06 (m, 2H), 7.48-7.44 (m, 2H), 7.13-7.09 (m, 2H), 6.89-6.87 (dd, 1H), 4.42 (t, 2H), 4.20 (t, 2H), 2.36-2.30 (m, 2H), 2.09 (s, 3H) ppm | 1.22 | 353.2 | B |
| 3 | N-{4-[6-(4-fluorophenyl)-2,3-dihydropyrazolo[5,1-b][1,3]oxazol-7-yl]pyridin-2-yl}cyclopropanecarboxamide | 1H-NMR (400 MHz, d3-CD3CN): δ = 8.84 (s, 1H), 8.12 (s, 1H), 8.05 (d, 1H), 7.52-7.48 (m, 2H), 7.17-7.12 (m, 2H), 6.78-6.77 (dd, 1H), 5.21 (t, 2H), 4.37 (t, 2H), 1.81-1.75 (m, 1H), 0.91-0.83 (m, 4H) ppm | 1.48 | 365.1 | B |
| 4 | N-{4-[2-(4-fluorophenyl)-6,7-dihydro-5H-pyrazolo[5,1-b][1,3]oxazin-3-yl]pyridin-2-yl}cyclopropanecarboxamide | 1H-NMR (400 MHz, d6-DMSO): δ = 10.65 (s, 1H), 8.09 (d, 1H), 8.05 (s, 1H), 7.41-7.36 (m, 2H), 7.22-7.16 (m, 2H), 6.70-6.69 (dd, 1H), 4.40 (t, 2H), 4.17 (t, 2H), 2.34-2.24 (m, 2H), 1.99-1.94 (m, 1H), 0.78 (d, 4H) ppm | 1.47 | 379.3 | B |
| 5 | N-{4-[2-(4-fluorophenyl)-6,7-dihydro-5H-pyrazolo[5,1-b][1,3]oxazin-3-yl]pyridin-2-yl}propanamide | 1H-NMR (400 MHz, d6-DMSO): δ = 10.28 (s, 1H), 8.10-8.07 (m, 2H), 7.42-7.37 (m, 2H), 7.22-7.16 (m, 2H), 6.71-6.70 (dd, 1H), 4.42 (t, 2H), 4.18 (t, 2H), 2.37-2.25 (m, 4H), 1.02 (t, 3H) ppm | 1.46 | 367.1 | A |
| 6 | N-[4-(2-phenyl-6,7-dihydro-5H-pyrazolo[5,1-b][1,3]oxazin-3-yl)pyridin-2-yl]propanamide | 1H-NMR (400 MHz, d6-DMSO): δ = 10.28 (s, 1H), 8.10 (s, 1H), 8.07 (d, 1H), 7.37-7.32 (m, 5H), 6.68-6.66 (dd, 1H), 4.41 (t, 2H), 4.18 (t, 2H), 2.37-2.32 (q, 2H), 2.28 (m, 2H), 1.03 (t, 3H) ppm | 1.16 | 349.3 | B |
| 7 | N-[4-(2-phenyl-6,7-dihydro-5H-pyrazolo[5,1-b][1,3]oxazin-3-yl)pyridin-2-yl]cyclopropanecarboxamide | 1H-NMR (400 MHz, d6-DMSO): δ = 10.65 (s, 1H), 8.09-8.07 (m, 2H), 7.36-7.31 (m, 5H), 6.67-6.65 (dd, 1H), 4.40 (t, 2H), 4.18 (t, 2H), 2.28-2.26 (m, 2H), 1.97-1.94 (m, 1H), 0.77 (d, 4H) ppm | 1.25 | 361.3 | B |
| 8 | 2-methyl-N-[4-(2-phenyl-6,7-dihydro-5H-pyrazolo[5,1-b][1,3]oxazin-3-yl)pyridin-2-yl]propanamide | 1H-NMR (400 MHz, d6-DMSO): δ = 10.28 (s, 1H), 8.13 (s, 1H), 8.07 (d, 1H), 7.37-7.32 (m, 5H), 6.65-6.64 (dd, 1H), 4.42 (t, 2H), 4.18 (t, 2H), 2.75-2.68 (m, 1H), 2.33-2.26 (m, 2H), 1.05 (d, 6H) ppm | 1.39 | 363.3 | B |
| 9 | ethyl [4-(2-phenyl-6,7-dihydro-5H-pyrazolo[5,1-b][1,3]oxazin-3-yl)pyridin-2-yl]carbamate | 1H-NMR (400 MHz, d6-DMSO): δ = 9.91 (s, 1H), 8.04 (d, 1H), 7.80 (s, 1H), 7.37-7.34 (m, 5H), 6.68-6.66 (dd, 1H), 4.42 (t, 2H), 4.18 (t, 2H), 4.10-4.05 (q, 2H), 1.19 (t, 3H) ppm | 1.51 | 365.3 | B |
| 10 | 2-methyl-N-[4-(2-phenyl-6,7-dihydro-5H-pyrazolo[5,1-b][1,3]oxazin-3-yl)pyridin-2-yl]butanamide | 1H-NMR (400 MHz, d6-DMSO): δ = 10.28 (s, 1H), 8.13 (s, 1H), 8.07 (d, 1H), 7.38-7.32 (m, 5H), 6.68-6.60 (dd, 1H), 4.42 (t, 2H), 4.18 (t, 2H), 2.32-2.25 (m, 3H), 1.59-1.50 (m, 1H), 1.38-1.31 (m, 1H), 1.04 (d, 3H), 0.82 (t, 3H) ppm | 1.63 | 377.3 | B |
| 11 | 3-methyl-N-[4-(2-phenyl-6,7-dihydro-5H-pyrazolo[5,1-b][1,3]oxazin-3-yl)pyridin-2-yl]butanamide | 1H-NMR (400 MHz, d6-DMSO): δ = 10.27 (s, 1H), 8.08-8.07 (m, 2H), 7.38-7.32 (m, 5H), 6.71-6.69 (dd, 1H), 4.42 (t, 2H), 4.18 (t, 2H), 2.32-2.25 (m, 2H), 2.21 (d, 2H), 2.05-1.98 (m, 1H), 0.89 (d, 3H) ppm | 1.66 | 377.3 | B |
| 12 | (2S)-2-hydroxy-N-[4-(2-phenyl-6,7-dihydro-5H-pyrazolo[5,1-b][1,3]oxazin-3-yl)pyridin-2-yl]propanamide | 1H-NMR (400 MHz, d6-DMSO): δ = 9.48 (s, 1H), 8.12 (s, 1H), 8.10 (d, 1H), 7.38-7.34 (m, 5H), 6.74-6.72 (dd, 1H), 5.88 (d, 1H), 4.42 (t, 2H), 4.20-4.13 (m, 3H), 2.32-2.25 (m, 2H), 1.28 (d, 3H) ppm | 1.2 | 365.3 | B |
| 13 | 2-cyclopropyl-N-[4-(2-phenyl-6,7-dihydro-5H-pyrazolo-[5,1-b][1,3]oxazin-3-yl)pyridin-2-yl]acetamide | 1H-NMR (400 MHz, d6-DMSO): δ = 10.22 (s, 1H), 8.12 (s, 1H), 8.07 (d, 1H), 7.38-7.33 (m, 5H), 6.68-6.66 (dd, 1H), 4.42 (t, 2H), 4.18 (t, 2H), 2.32-2.25 (m, 2H), 2.23 (d, 2H), 1.04-0.98 (m, 1H), 0.47-0.44 (m, 2H), 0.18-0.14 (m, 2H) ppm | 1.54 | 375.3 | B |
| 14 | N-[4-(2-phenyl-6,7-dihydro-5H-pyrazolo[5,1-b][1,3]oxazin-3-yl)pyridin-2-yl]tetrahydro-2H-pyran-4-carboxamide | 1H-NMR (400 MHz, d6-DMSO): δ = 10.32 (s, 1H), 8.12 (s, 1H), 8.07 (d, 1H), 7.37-7.33 (m, 5H), 6.66-6.65 (dd, 1H), 4.42 (t, 2H), 4.18 (t, 2H), 3.89-3.86 (m, 2H), 3.29-3.25 (m, 2H), 2.75-2.66 (m, 1H), 2.32-2.25 (m, 2H), 1.70-1.55 (m, 4H) ppm | 1.22 | 405.4 | B |
| 15 | 3-phenyl-N-[4-(2-phenyl-6,7-dihydro-5H-pyrazolo[5,1-b][1,3]oxazin-3-yl)pyridin-2-yl]propanamide | 1H-NMR (400 MHz, d6-DMSO): δ = 10.35 (s, 1H), 8.10 (s, 1H), 8.08 (d, 1H), 7.37-7.33 (m, 5H), 7.29-7.16 (m, 5H), 6.70-6.68 (dd, 1H), 4.42 (t, 2H), 4.18 (t, 2H), 2.85 (t, 2H), 2.67 (t, 2H), 2.33-2.27 (m, 2H) ppm | 2.04 | 425.4 | B |
| 16 | 2-(methylsulfanyl)-N-[4-(2-phenyl-6,7-dihydro-5H-pyrazolo[5,1-b][1,3]oxazin-3-yl)pyridin-2-yl]acetamide | 1H-NMR (400 MHz, d6-DMSO): δ = 10.40 (s, 1H), 8.10 (d, 1H), 8.07 (s, 1H), 7.37-7.33 (m, 5H), 6.75-6.73 (dd, 1H), 4.42 (t, 2H), 4.18 (t, 2H), 3.28 (s, 2H), 2.33-2.27 (m, 2H), 2.11 (s, 3H) ppm | 1.54 | 381.3 | B |
| 17 | 3,3,3-trifluoro-N-[4-(2-phenyl-6,7-dihydro-5H-pyrazolo[5,1-b][1,3]oxazin-3-yl)pyridin-2-yl]propanamide | 1H-NMR (400 MHz, d6-DMSO): δ = 10.72 (s, 1H), 8.11 (d, 1H), 8.07 (s, 1H), 7.37-7.33 (m, 5H), 6.75-6.73 (dd, 1H), 4.43 (t, 2H), 4.18 (t, 2H), 3.62-3.53 (q, 2H), 2.33-2.27 (m, 2H) ppm | 1.98 | 403.3 | B |

TABLE 2-continued

NMR and Mass spectroscopic/logP data of compounds of the type [I]

| No. | Name | NMR | LogP$_A$ | [M + H]$_A$ [+1] | Method [2] |
|---|---|---|---|---|---|
| 18 | 2-(4-fluorophenyl)-N-[4-(2-phenyl-6,7-dihydro-5H-pyrazolo[5,1-b][1,3]oxazin-3-yl)pyridin-2-yl]propanamide | 1H-NMR (400 MHz, d6-DMSO): δ = 10.52 (s, 1H), 8.08 (s, 1H), 6.67-6.65 (dd, 1H), 4.41 (t, 2H), 4.17 (t, 2H), 4.00-3.88 (m, 1H), 2.33-2.26 (m, 2H), 1.36 (d, 3H) ppm | 2.27 | 443.4 | B |
| 19 | 4-methyl-N-[4-(2-phenyl-6,7-dihydro-5H-pyrazolo[5,1-b][1,3]oxazin-3-yl)pyridin-2-yl]pent-3-enamide | 1H-NMR (400 MHz, d6-DMSO): δ = 10.28 (s, 1H), 8.08 (m, 2H), 7.37-7.33 (m, 5H), 6.68-6.67 (dd, 1H), 5.28 (t, 1H), 4.41 (t, 2H), 4.18 (t, 2H), 3.09 (d, 2H), 2.33-2.25 (m, 2H), 1.69 (s, 3H), 1.62 (s, 3H) ppm | 1.91 | 389.4 | B |
| 20 | 3,3-dimethyl-N-[4-(2-phenyl-6,7-dihydro-5H-pyrazolo[5,1-b][1,3]oxazin-3-yl)pyridin-2-yl]butanamide | 1H-NMR (400 MHz, d6-DMSO): δ = 10.18 (s, 1H), 8.09 (d, 1H), 8.06 (s, 1H), 7.37-7.32 (m, 5H), 6.74-6.72 (dd, 1H), 4.42 (t, 2H), 4.18 (t, 2H), 2.33-2.27 (m, 2H), 2.21 (s, 2H), 0.97 (s, 9H) ppm | 1.88 | 391.4 | B |
| 21 | 1-chloro-N-[4-(2-phenyl-6,7-dihydro-5H-pyrazolo[5,1-b][1,3]oxazin-3-yl)pyridin-2-yl]cyclopropanecarboxamide | 1H-NMR (400 MHz, d6-DMSO): δ = 9.64 (s, 1H), 8.14 (d, 1H), 7.96 (s, 1H), 7.37-7.32 (m, 5H), 6.79-6.78 (dd, 1H), 4.42 (t, 2H), 4.18 (t, 2H), 2.33-2.25 (m, 2H), 1.59-1.57 (m, 2H), 1.41-1.39 (m, 2H) ppm | 2.62 | 395.3 | B |
| 22 | N-{4-[2-(4-fluorophenyl)-6,7-dihydro-5H-pyrazolo[5,1-b][1,3]oxazin-3-yl]pyridin-2-yl}-2-methylpropanamide | 1H-NMR (400 MHz, d6-DMSO): δ = 10.28 (s, 1H), 8.10-8.08 (m, 2H), 7.41-7.37 (m, 2H), 7.22-7.17 (m, 2H), 6.69-6.67 (dd, 1H), 4.42 (t, 2H), 4.18 (t, 2H), 2.74-2.67 (m, 1H), 2.33-2.25 (m, 2H), 1.05 (d, 6H) ppm | 1.54 | 381.3 | B |
| 23 | ethyl {4-[2-(4-fluorophenyl)-6,7-dihydro-5H-pyrazolo[5,1-b][1,3]oxazin-3-yl]pyridin-2-yl}carbamate | 1H-NMR (400 MHz, d6-DMSO): δ = 9.91 (s, 1H), 8.06 (d, 1H), 7.76 (s, 1H), 7.41-7.37 (m, 2H), 7.22-7.17 (m, 2H), 6.70-6.69 (dd, 1H), 4.42 (t, 2H), 4.18 (t, 2H), 4.10-4.05 (q, 2H), 1.19 (t, 3H) ppm | 1.66 | 383.3 | B |
| 24 | N-{4-[2-(4-fluorophenyl)-6,7-dihydro-5H-pyrazolo[5,1-b][1,3]oxazin-3-yl]pyridin-2-yl}-2-methylbutanamide | 1H-NMR (400 MHz, d6-DMSO): δ = 10.28 (s, 1H), 8.10 (s, 1H), 8.09 (d, 1H), 7.41-7.37 (m, 2H), 7.21-7.15 (m, 2H), 6.72-6.70 (dd, 1H), 4.43 (t, 2H), 4.18 (t, 2H), 2.33-2.25 (m, 3H), 1.59-1.52 (m, 1H), 1.38-1.31 (m, 1H), 1.04 (d, 3H), 0.82 (t, 3H) ppm | 1.82 | 395.4 | B |
| 25 | N-{4-[2-(4-fluorophenyl)-6,7-dihydro-5H-pyrazolo[5,1-b][1,3]oxazin-3-yl]pyridin-2-yl}-3-methylbutanamide | 1H-NMR (400 MHz, d6-DMSO): δ = 10.26 (s, 1H), 8.11 (d, 1H), 8.04 (s, 1H), 7.41-7.37 (m, 2H), 7.20-7.16 (m, 2H), 6.77-6.74 (dd, 1H), 4.42 (t, 2H), 4.18 (t, 2H), 2.33-2.25 (m, 2H), 2.20 (d, 2H), 2.05-1.99 (m, 1H), 0.88 (d, 3H) ppm | 1.82 | 395.3 | B |
| 26 | (2S)-N-{4-[2-(4-fluorophenyl)-6,7-dihydro-5H-pyrazolo[5,1-b][1,3]oxazin-3-yl]pyridin-2-yl}-2-hydroxypropanamide | 1H-NMR (400 MHz, d6-DMSO): δ = 9.48 (s, 1H), 8.13 (d, 1H), 8.08 (s, 1H), 7.42-7.37 (m, 2H), 7.22-7.17 (m, 2H), 6.79-6.77 (dd, 1H), 5.88 (d, 1H), 4.43 (t, 2H), 4.20-4.13 (m, 3H), 2.32-2.25 (m, 2H), 1.27 (d, 3H) ppm | 1.31 | 383.3 | B |
| 27 | 2-cyclopropyl-N-{4-[2-(4-fluorophenyl)-6,7-dihydro-5H-pyrazolo[5,1-b][1,3]oxazin-3-yl]pyridin-2-yl}acetamide | 1H-NMR (400 MHz, d6-DMSO): δ = 10.22 (s, 1H), 8.10-8.08 (m, 2H), 7.42-7.37 (m, 2H), 7.21-7.17 (m, 2H), 6.72-6.70 (dd, 1H), 4.42 (t, 2H), 4.18 (t, 2H), 2.33-2.25 (m, 2H), 2.23 (d, 2H), 1.04-0.98 (m, 1H), 0.47-0.42 (m, 2H), 0.18-0.14 (m, 2H) ppm | 1.69 | 393.3 | B |
| 28 | N-{4-[2-(4-fluorophenyl)-6,7-dihydro-5H-pyrazolo[5,1-b][1,3]oxazin-3-yl]pyridin-2-yl}tetrahydro-2H-pyran-4-carboxamide | 1H-NMR (400 MHz, d6-DMSO): δ = 10.32 (s, 1H), 8.10-8.09 (m, 2H), 7.41-7.37 (m, 2H), 7.21-7.16 (m, 2H), 6.69-6.68 (dd, 1H), 4.42 (t, 2H), 4.18 (t, 2H), 3.89-3.86 (m, 2H), 3.31-3.25 (m, 2H), 2.74-2.67 (m, 1H), 2.32-2.25 (m, 2H), 1.70-1.55 (m, 4H) ppm | 1.37 | 423.3 | B |
| 29 | N-{4-[2-(4-fluorophenyl)-6,7-dihydro-5H-pyrazolo[5,1-b][1,3]oxazin-3-yl]pyridin-2-yl}-3-phenylpropanamide | 1H-NMR (400 MHz, d6-DMSO): δ = 10.35 (s, 1H), 8.10 (d, 1H), 8.06 (s, 1H), 7.41-7.38 (m, 2H), 7.29-7.25 (m, 2H), 7.24-7.16 (m, 5H), 6.74-6.72 (dd, 1H), 4.42 (t, 2H), 4.18 (t, 2H), 2.85 (t, 2H), 2.66 (t, 2H), 2.33-2.27 (m, 2H) ppm | 2.2 | 443.4 | B |
| 30 | N-{4-[2-(4-fluorophenyl)-6,7-dihydro-5H-pyrazolo[5,1-b][1,3]oxazin-3-yl]pyridin-2-yl}-2-(methylsulfanyl)acetamide | 1H-NMR (400 MHz, d6-DMSO): δ = 10.40 (s, 1H), 8.13-8.12 (d, 1H), 8.02 (s, 1H), 7.41-7.38 (m, 2H), 7.21-7.17 (m, 2H), 6.79-6.78 (dd, 1H), 4.42 (t, 2H), 4.18 (t, 2H), 3.28 (s, 2H), 2.33-2.27 (m, 2H), 2.11 (s, 3H) ppm | 1.72 | 399.3 | B |
| 31 | 3,3,3-trifluoro-N-{4-[2-(4-fluorophenyl)-6,7-dihydro-5H-pyrazolo[5,1-b][1,3]oxazin-3-yl]pyridin-2-yl}propanamide | 1H-NMR (400 MHz, d6-DMSO): δ = 10.72 (s, 1H), 8.14 (d, 1H), 8.03 (s, 1H), 7.41-7.37 (m, 2H), 7.21-7.17 (m, 2H), 6.79-6.78 (dd, 1H), 4.43 (t, 2H), 4.18 (t, 2H), 3.62-3.53 (q, 2H), 2.33-2.27 (m, 2H) ppm | 2.13 | 421.3 | B |
| 32 | 2-(4-fluorophenyl)-N-{4-[2-(4-fluorophenyl)-6,7-dihydro-5H-pyrazolo[5,1-b][1,3]oxazin-3-yl]pyridin-2-yl}propanamide | 1H-NMR (400 MHz, d6-DMSO): δ = 10.52 (s, 1H), 8.08 (d, 1H), 8.05 (s, 1H), 7.42-7.34 (m, 4H), 7.20-7.12 (m, 4H), 6.70-6.69 (dd, 1H), 4.41 (t, 2H), 4.17 (t, 2H), 4.00-3.96 (m, 1H), 2.36-2.27 (m, 2H), 1.35 (d, 3H) ppm | 2.48 | 461.4 | B |
| 33 | N-{4-[2-(4-fluorophenyl)-6,7-dihydro-5H-pyrazolo[5,1-b][1,3]oxazin-3-yl]pyridin-2-yl}-4-methylpent-3-enamide | 1H-NMR (400 MHz, d6-DMSO): δ =10.28 (s, 1H), 8.10 (d, 1H), 8.04 (s, 1H), 7.41-7.37 (m, 2H), 7.22-7.17 (m, 2H), 6.73-6.70 (dd, 1H), 5.28 (t, 1H), 4.42 (t, 2H), 4.18 (t, 2H), 3.08 (d, 2H), 2.33-2.25 (m, 2H), 1.70 (s, 3H), 1.62 (s, 3H) ppm | 2.07 | 407.3 | B |
| 34 | N-{4-[2-(4-fluorophenyl)-6,7-dihydro-5H-pyrazolo[5,1-b][1,3]oxazin-3-yl]pyridin-2-yl}-3,3-dimethylbutanamide | 1H-NMR (400 MHz, d6-DMSO): δ = 10.14 (s, 1H), 8.12 (d, 1H), 8.10 (s, 1H), 7.40-7.37 (m, 2H), 7.19-7.16 (m, 2H), 6.80-6.78 (dd, 1H), 4.43 (t, 2H), 4.18 (t, 2H), 2.30-2.26 (m, 2H), 2.20 (s, 2H), 0.96 (s, 9H) ppm | 2.04 | 409.4 | B |
| 35 | N-{4-[2-(2,4-difluorophenyl)-6,7-dihydro-5H-pyrazolo[5,1-b][1,3]oxazin-3-yl]pyridin-2-yl}propanamide | 1H-NMR (400 MHz, d6-DMSO): δ = 10.21 (s, 1H), 8.06 (d, 1H), 8.01 (s, 1H), 7.51-7.46 (m, 1H), 7.29-7.23 (m, 1H), 7.20-7.15 (m, 1H), 6.71-6.69 (dd, 1H), 4.47 (t, 2H), 4.19 (t, 2H), 2.35-2.27 (m, 4H), 1.01 (t, 3H) ppm | 1.34 | 385.3 | B |
| 36 | N-{4-[2-(2,4-difluorophenyl)-6,7-dihydro-5H-pyrazolo[5,1-b][1,3]oxazin-3-yl]pyridin-2-yl}cyclopropanecarboxamide | 1H-NMR (400 MHz, d6-DMSO): δ =10.58 (d, 1H), 8.06 (d, 1H), 7.99 (s, 1H), 7.51-7.45 (m, 1H), 7.28-7.23 (m, 1H), 7.19-7.14 (m, 1H), 6.69-6.68 (dd, 1H), 4.46 (t, 2H), 4.19 (t, 2H), 2.30-2.26 (m, 2H), 1.97-1.91 (m, 1H), 0.76-0.74 (m, 4H) ppm | 1.42 | 397.3 | B |

TABLE 2-continued

NMR and Mass spectroscopic/logP data of compounds of the type [I]

| No. | Name | NMR | LogP$_A$ | [M + H]$_A^{+1}$ | Method [2] |
|---|---|---|---|---|---|
| 37 | N-{4-[2-(2,4-difluorophenyl)-6,7-dihydro-5H-pyrazolo[5,1-b][1,3]oxazin-3-yl]pyridin-2-yl}-2-methylpropanamide | 1H-NMR (400 MHz, d6-DMSO): δ = 10.20 (s, 1H), 8.06-8.04 (m, 2H), 7.51-7.46 (m, 1H), 7.29-7.23 (m, 1H), 7.20-7.15 (m, 1H), 6.68-6.66 (dd, 1H), 4.47 (t, 2H), 4.20 (t, 2H), 2.72-2.65 (m, 1H), 2.33-2.27 (m, 2H), 1.03 (d, 6H) ppm | 1.6 | 399.3 | B |
| 38 | ethyl {4-[2-(2,4-difluorophenyl)-6,7-dihydro-5H-pyrazolo[5,1–b][1,3]oxazin-3-yl]pyridin-2-yl}carbamate | 1H-NMR (400 MHz, d6-DMSO):δ = 9.85 (s, 1H), 8.03 (d, 1H), 7.70 (s, 1H), 7.49-7.46 (m, 1H), 7.29-7.24 (m, 1H), 7.20-7.16 (m, 1H), 6.71-6.69 (dd, 1H), 4.47 (t, 2H), 4.19 (t, 2H), 4.08-4.03 (q, 2H), 1.19 (t, 3H) ppm | 1.72 | 401.3 | B |
| 39 | N-{4-[2-(2,4-difluorophenyl)-6,7-dihydro-5H-pyrazolo[5,1-b][1,3]oxazin-3-yl]pyridin-2-yl}-2-methylbutanamide | 1H-NMR (400 MHz, d6-DMSO): δ =10.21 (s, 1H), 8.07 (d, 1H), 8.01 (s, 1H), 7.51-7.45 (m, 1H), 7.28-7.24 (m, 1H), 7.22-7.14 (m, 1H), 6.72-6.70 (dd, 1H), 4.48 (t, 2H), 4.20 (t, 2H), 2.33-2.27 (m, 3H), 1.57-1.50 (m, 1H), 1.36-1.31 (m, 1H), 1.01 (d, 3H), 0.80 (t, 3H) ppm | 1.85 | 413.3 | B |
| 40 | N-{4-[2-(2,4-difluorophenyl)-6,7-dihydro-5H-pyrazolo[5,1-b][1,3]oxazin-3-yl]pyridin-2-yl}-3-methylbutanamide | 1H-NMR (400 MHz, d6-DMSO): δ = 10.19 (s, 1H), 8.08 (d, 1H), 7.96 (s, 1H), 7.51-7.45 (m, 1H), 7.27-7.22 (m, 1H), 7.18-7.14 (m, 1H), 6.77-6.76 (dd, 1H), 4.47 (t, 2H), 4.19 (t, 2H), 2.34-2.27 (m, 2H), 2.18 (d, 2H), 2.03-1.96 (m, 1H), 0.87 (d, 3H) ppm | 1.88 | 413.3 | B |
| 41 | (2S)-N-{4-[2-(2,4-difluorophenyl)-6,7-dihydro-5H-pyrazolo[5,1-b][1,3]oxazin-3-yl]pyridin-2-yl}-2-hydroxypropanamide | 1H-NMR (400 MHz, d6-DMSO): δ =9.40 (s, 1H), 8.09 (d, 1H), 8.01 (s, 1H), 7.53-7.47 (m, 1H), 7.30-7.24 (m, 1H), 7.20-7.15 (m, 1H), 6.79-6.77 (dd, 1H), 5.87 (d, 1H), 4.48 (t, 2H), 4.20 (t, 2H), 4.18-4.10 (m, 1H), 2.33-2.27 (m, 2H), 1.26 (d, 3H) ppm | 1.34 | 401.3 | B |
| 42 | 2-cyclopropyl-N-{4-[2-(2,4-difluorophenyl)-6,7-dihydro-5H-pyrazolo[5,1-b][1,3]-oxazin-3-yl]pyridin-2-yl}acetamide | 1H-NMR (400 MHz, d6-DMSO): δ = 10.14 (s, 1H), 8.07 (d, 1H), 8.02 (s, 1H), 7.52-7.46 (m, 1H), 7.29-7.24 (m, 1H), 7.20-7.15 (m, 1H), 6.72-6.70 (dd, 1H), 4.47 (t, 2H), 4.20 (t, 2H), 2.33-2.28 (m, 2H), 2.20 (d, 2H), 1.04-0.98 (m, 1H), 0.47-0.42 (m, 2H), 0.16-0.14 (m, 2H) ppm | 1.72 | 411.3 | B |
| 43 | N-{4-[2-(2,4-difluorophenyl)-6,7-dihydro-5H-pyrazolo[5,1-b][1,3]oxazin-3-yl]pyridin-2-yl}tetrahydro-2H-pyran-4-carboxamide | 1H-NMR (400 MHz, d6-DMSO): δ = 10.25 (s, 1H), 8.07 (d, 1H), 8.02 (s, 1H), 7.50-7.46 (m, 1H), 7.29-7.24 (m, 1H), 7.20-7.15 (m, 1H), 6.69-6.68 (dd, 1H), 4.47 (t, 2H), 4.20 (t, 2H), 3.89-3.86 (m, 2H), 3.31-3.25 (m, 2H), 2.72-2.67 (m, 1H), 2.32-2.28 (m, 2H), 1.70-1.55 (m, 4H) ppm | 1.39 | 441.4 | B |
| 44 | N-{4-[2-(2,4-difluorophenyl)-6,7-dihydro-5H-pyrazolo[5,1-b][1,3]oxazin-3-yl]pyridin-2-yl}-3-phenylpropanamide | 1H-NMR (400 MHz, d6-DMSO): δ = 10.28 (s, 1H), 8.07 (d, 1H), 8.00 (s, 1H), 7.52-7.48 (m, 1H), 7.29-7.15 (m, 7H), 6.75-6.73 (dd, 1H), 4.47 (t, 2H), 4.20 (t, 2H), 2.84 (t, 2H), 2.62 (t, 2H), 2.33-2.27 (m, 2H) ppm | 2.23 | 461.4 | B |
| 45 | N-{4-2-(2,4-difluorophenyl)-6,7-dihydro-5H-pyrazolo[5,1-b][1,3]oxazin-3-yl]pyridin-2-yl}-2-(methylsulfanyl)acetamide | 1H-NMR (400 MHz, d6-DMSO): δ =10.33 (s, 1H), 8.10 (d, 1H), 7.93 (s, 1H), 7.52-7.46 (m, 1H), 7.29-7.23 (m, 1H), 7.19-7.15 (m, 1H), 6.82-6.80 (dd, 1H), 4.47 (t, 2H), 4.20 (t, 2H), 3.25 (s, 2H), 2.33-2.27 (m, 2H), 2.10 (s, 3H) ppm | 1.75 | 417.3 | B |
| 46 | N-{4-[2-(2,4-difluorophenyl)-6,7-dihydro-5H-pyrazolo[5,1-b][1,3]oxazin-3-yl]pyridin-2-yl}-3,3,3-trifluoropropanamide | 1H-NMR (400 MHz, d6-DMSO): δ = 10.66 (s, 1H), 8.76 (d, 1H), 8.12 (s, 1H), 7.53-7.47 (m, 1H), 7.28-7.23 (m, 1H), 7.23-7.15 (m, 1H), 6.80-6.78 (dd, 1H), 4.48 (t, 2H), 4.20 (t, 2H), 3.60-3.50 (q, 2H), 2.33-2.27 (m, 2H) ppm | 2.13 | 439.3 | B |
| 47 | N-{4-[2-(2,4-difluorophenyl)-6,7-dihydro-5H-pyrazolo[5,1-b][1,3]oxazin-3-yl]pyridin-2-yl}-2-(4-fluorophenyl)propanamide | 1H-NMR (400 MHz, d6-DMSO): δ = 10.45 (s, 1H), 8.06 (d, 1H), 7.97 (s, 1H), 7.50-7.44 (m, 1H), 7.39-7.35 (m, 2H), 7.26-7.23 (m, 1H), 7.23-7.15 (m, 3H), 6.72-6.70 (dd, 1H), 4.46 (t, 2H), 4.19 (t, 2H), 3.98-3.93 (m, 1H), 2.33-2.27 (m, 2H), 1.33 (d, 3H) ppm | 2.48 | 479.3 | B |
| 48 | N-{4-[2-(2,4-difluorophenyl)-6,7-dihydro-5H-pyrazolo[5,1-b][1,3]oxazin-3-yl]pyridin-2-yl}-4-methylpent-3-enamide | 1H-NMR (400 MHz, d6-DMSO):δ = 10.20 (s, 1H), 8.07 (d, 1H), 7.98 (s, 1H), 7.50-7.47 (m, 1H), 7.28-7.20 (m, 1H), 7.20-7.15 (m, 1H), 6.72-6.70 (m, 1H), 5.26 (t, 1H), 4.47 (t, 2H), 4.19 (t, 2H), 3.06 (d, 2H), 2.33-2.25 (m, 2H), 1.69 (s, 3H), 1.61 (s, 3H) ppm | 2.1 | 425.4 | B |
| 49 | N-{4-[2-(2,4-difluorophenyl)-6,7-dihydro-5H-pyrazolo[5,1-b][1,3]oxazin-3-yl]pyridin-2-yl}-3,3-dimethylbutanamide | 1H-NMR (400 MHz, d6-DMSO): δ = 10.10 (s, 1H), 8.09 (d, 1H), 7.89 (s, 1H), 7.48-7.46 (m, 1H), 7.25-7.14 (m, 2H), 6.84-6.82 (dd, 1H), 4.47 (t, 2H), 4.20 (t, 2H), 2.33-2.29 (m, 2H), 2.17 (s, 2H), 0.95 (s, 9H) ppm | 2.1 | 427.4 | B |
| 50 | 1-chloro-N-{4-[2-(2,4-difluorophenyl)-6,7-dihydro-5H-pyrazolo[5,1-b][1,3]oxazin-3-yl]pyridin-2-yl}cyclopropanecarboxamide | 1H-NMR (400 MHz, d6-DMSO): δ = 9.57 (s, 1H), 8.14 (d, 1H), 7.87 (s, 1H), 7.52-7.46 (m, 1H), 7.30-7.25 (m, 1H), 7.20-7.15 (m, 1H), 6.84-6.82 (dd, 1H), 4.48 (t, 2H), 4.20 (t, 2H), 2.33-2.27 (m, 2H), 1.57-1.56 (m, 2H), 1.39-1.38 (m, 2H) ppm | 2.84 | 431.3 | B |
| 51 | N-[4-(2-phenylpyrazolo[1,5–a]pyrimidin-3-yl)pyridin-2-yl]acetamide | 1H-NMR (300MHz, CDCl3): δ = 8.75 (dd, 1H), 8.63-8.60 (m, 2H), 8.26 (bs, 1H), 8.18 (d, 1H), 7.65-7.61 (m, 2H), 7.46-7.40 (m, 3H), 7.13 (dd, 1H), 6.94 (dd, 1H), 2.20 (s, 3H) ppm | 1.41 | 330.0 | C |
| 52 | N-accetyl-N-{4-[2-(4-fluorophenyl)-6,7-dihydro-5H-pyrazolo[5,1-b][1,3]oxazin-3-yl]pyridin-2-yl}propanamide | 1H-NMR (400 MHz, d3-CD3CN): δ = 8.38-8.37 (d, 1H), 7.45-7.40 (m, 2H), 7.31-7.30 (dd, 1H), 7.13-7.06 (m, 3H), 4.43 (t, 2H), 4.18 (t, 2H), 2.40-2.36 (q, 2H), 2.36-2.30 (m, 2H), 2.20 (s, 3H), 1.00 (t, 3H) ppm | 2.4 | 409.2 | A |
| 53 | N-{4-[2-(4-fluorophenyl)-6,7-dihydro-5H-pyrazolo[5,1-b][1,3]oxazin-3-yl]pyridin-2-yl}-N-propionylpropanamide | 1H-NMR (400 MHz, d3-CD3CN): δ = 8.38-8.37 (d, 1H), 7.44-7.41 (m, 2H), 7.32-7.31 (dd, 1H), 7.11-7.08 (m, 2H), 7.03 (s, 1H), 4.43 (t, 2H), 4.17 (t, 2H), 2.48-2.44 (q, 4H), 2.36-2.30 (m, 2H), 1.00 (t, 6H) ppm | 2.74 | 423.2 | A |
| 54 | N-{4-[2-(4-fluorophenyl)-6,7-dihydro-5H-pyrazolo[5,1-b][1,3]oxazin-3-yl]pyridin-2-yl}-N-propionylcyclopropanecarboxamide | 1H-NMR (400 MHz, d3-CD3CN): δ = 8.38-8.37 (d, 1H), 7.44-7.41 (m, 2H), 7.31-7.30 (m, 1H), 7.12-7.06 (m, 3H), 4.43 (t, 2H), 4.17 (t, 2H), 2.59-2.55 (q, 2H), 2.33-2.30 (m, 2H), 1.75 (m, 1H), 1.05 (t, 3H), 0.95 (m, 2H), 0.81 (m, 2H) ppm | 2.77 | 435.1 | A |

TABLE 2-continued

NMR and Mass spectroscopic/logP data of compounds of the type [I]

| No. | Name | NMR | LogP$_A$ | [M + H]$_A^{+1}$ | Method [2] |
|---|---|---|---|---|---|
| 55 | N-[4-(2-phenyl-4,5,6,7-tetrahydropyrazolo[1,5-a]pyrimidin-3-yl)pyridin-2-yl]acetamide | 1H-NMR (300MHz, CDC13): δ = 8.23 (bs, 1H), 8.07 (bs, 1H), 8.00 (d, 1H), 7.47-7.45 (m, 2H), 7.32 (m, 3H), 6.64 (m, 1H), 4.75 (bs, 1H), 4.21 (t, 2H), 3.42 (bs, 2H), 2.20 (m, 3H), 1.63 (s, 3H) ppm | 1.13 | 334.0 | C |
| 56 | N-acetyl-N-[4-(2-phenylpyrazolo[1,5-a]pyrimidin-3-yl)pyridin-2-yl]acetamide | 1H-NMR (300MHz, DMSO): δ = 9.29 (dd, 1H), 8.75 (dd, 1H), 8.57 (d, 1H), 7.68 (dd, 1H), 7.61-7.59 (m, 2H), 7.49-7.46 (m, 4H), 7.26 (dd, 1H), 2.16 (s, 6H) ppm | 2.13 | 372.0 | C |
| 57 | ethyl {4-[2-(4-fluorophenyl)-6,7-dihydro-5H-pyrazolo[5,1-b][1,3]oxazin-3-yl]pyridin-2-yl}propionylcarbamate | 1H-NMR (400 MHz, d3-CD3CN): δ = 8.32-8.30 (d, 1H), 7.44-7.41 (m, 2H), 7.26-7.24 (m, 1H), 7.13-7.05 (m, 3H), 4.43-4.39 (dd, 2H), 4.17 (t, 2H), 4.05 (q, 2H), 2.98-2.86 (q, 2H), 2.33-2.30 (m, 2H), 1.30-1.25 (m, 3H), 1.15-1.05 (m, 3H) ppm | 2.64 | 439.1 | A |
| 58 | N-acetyl-N-[4-(4-acetyl-2-phenyl-4,5,6,7-tetrahydropyrazolo[1,5-a]pyrimidin-3-yl)pyridin-2-yl] acetamide | — | 1.72 | 418.3 | C |
| 59 | N-{4-[2-(4-Fluorophenyl)-4,5,6,7-tetrahydropyrazolo[1,5-a]pyrimidin-3-yl]pyridin-2-yl}acetamide | — | 1.48 | 352.2 | C |
| 60 | N-{4-[2-(4-Fluorophenyl)pyrazolo[1,5-a]pyrimidin-3-yl]pyridin-2-yl}acetamide | 1H-NMR (300MHz, DMSO): δ = 10.48 (bs, 1H), 9.23 (dd, 1H), 8.69 (dd, 1H), 8.30 (s, 1H), 8.25 (d, 1H), 7.62 (m, 2H), 7.31 (m, 2H), 7.22 (dd, 1H), 7.11 (dd, 1H), 2.05 (s, 3H) ppm | 1.47 | 348.1 | C |
| 61 | N-{4-[7-(4-fluorophenyl)-3,3-dimethyl-3,4-dihydro-2H-pyrazolo[5,1-b][1,3,5]oxazasilin-8-yl]pyridin-2-yl}acetamide | 1H-NMR (400 MHz, CDC13): δ = 8.25 (bs, 2H), 8.05 (d, 1H), 7.50 (t, 2H), 7.10 (t, 2H), 6.78 (d, 1H), 4.10 (s, 2H), 3,72 (s, 2H), 2.17 (s, 3H), 0.38 (s, 6H) ppm | 2.01 | 397.3 | C |
| 62 | N-{4-[2-(4-fluorophenyl)-7-methyl-6,7-dihydro-5H-pyrazolo[5,1-b][1,3]oxazin-3-yl]pyridin-2-yl}-2-methylpropanamide | 1H-NMR (400 MHz, d6-DMSO): δ = 10.29 (s, 1H), 8.12-8.07 (m, 2H), 7.45-7.37 (m, 2H), 7.24-7.16 (m, 2H), 6.68 (dd, 1H), 4.54-4.45 (m, 1H), 4.45-4.32(m, 2H), 2.72 (hept, 1H), 2.46-2.35 (m, 1H), 2.10-1.99 (m, 1H), 1.54 (d, 3H), 1.06 (d, 6H) ppm | 1.86 | 395.2 | A |
| 63 | N-{4-[2-(4-fluorophenyl)-7-methyl-6,7-dihydro-5H-pyrazolo[5,1-b][1,3]oxazin-3-yl]pyridin-2-yl}propanamide | 1H-NMR (400 MHz, d6-DMSO): δ = 10.29 (s, 1H), 8.12-8.06 (m, 2H), 7.45-7.37 (m, 2H), 7.24-7.16 (m, 2H), 6.70 (dd, 1H), 4.54-4.45 (m, 1H), 4.45-4.32(m, 2H), 2.47-2.30 (m, 3H), 2.10-1.97(m, 1H), 1.54 (d, 3H), 1.03 (t, 3H) ppm | 1.61 | 381.2 | A |
| 64 | N-{4-[2-(4-fluorophenyl)-6,7-dihydro-5H-pyrazolo[5,1-b][1,3]oxazin-3-yl]pyridin-2-yl}bicyclo[2.2.1]heptane-2-carboxamide | 1H-NMR (400 MHz, d6-DMSO): δ = 10.16 (s, 1H), 8.11-8.10 (d, 1H), 8.00 (s, 1H), 7.42-7.35 (m, 2H), 7.20-7.16 (m, 2H), 6.77-6.75 (dd, 1H), 4.42 (t, 2H), 4.18 (t, 2H), 2.90-2.85 (m, 1H), 2.30-2.15 (m, 4H), 1.60-1.10 (m, 6H) ppm | 3.11 | 449.2 | B |
| 65 | N-{4-[2-(4-fluorophenyl)-6,7-dihydro-5H-pyrazolo[5,1-b][1,3]oxazin-3-yl]pyridin-2-yl}bicyclo[4.1.0]heptane-7-carboxamide | 1H-NMR (400 MHz, d6-DMSO): δ = 10.40 (s, 1H), 8.10-8.08 (d, 1H), 8.02 (s, 1H), 7.40-7.35 (m, 2H), 7.21-7.15 (m, 2H), 6.69-6.67 (dd, 1H), 4.39 (t, 2H), 4.16 (t, 2H), 2.30-2.20 (m, 2H), 1.90-1.80 (m, 3H), 1.70-1.60 (m, 2H), 1.40-1.36 (m, 2H), 1.30-1.10 (m, 4H) ppm | 2.13 | 433.3 | B |
| 66 | N-{4-[2-(4-fluorophenyl)-6,7-dihydro-5H-pyrazolo[5,1-b][1,3]oxazin-3-yl]pyridin-2-yl}-2-(piperidin-1-yl)acetamide | 1H-NMR (400 MHz, d6-DMSO): δ = 10.10 (s, 1H), 8.12-8.11 (d, 1H), 8.05 (s, 1H), 7.42-7.37 (m, 2H), 7.22-7.16 (m, 2H), 6.79-6.78 (dd, 1H), 4.43 (t, 2H), 4.18 (t, 2H), 3.10 (s, 2H), 2.35-2.25 (m, 4H), 1.60-1.55 (m, 6H), 1.45-1.40 (m, 2H) ppm | 1 | 436.3 | B |
| 67 | N-{4-[2-(4-fluorophenyl)-6,7-dihydro-5H-pyrazolo[5,1-b][1,3]oxazin-3-yl]pyridin-2-yl}-2-propylpentanamide | 1H-NMR (400 MHz, d6-DMSO): δ = 10.29 (s, 1H), 8.12-8.10 (d, 1H), 8.03 (s, 1H), 7.40-7.36 (m, 2H), 7.19-7.15 (m, 2H), 6.77-6.75 (dd, 1H), 4.43 (t, 2H), 4.18 (t, 2H), 3.10 (s, 2H), 2.30-2.25 (m, 1H), 1.52-1.43 (m, 2H), 1.30-1.10 (m, 8H), 0.85 (t, 6H) ppm | 2.64 | 437.3 | B |
| 68 | N-{4-[2-(4-fluorophenyl)-6,7-dihydro-5H-pyrazolo[5,1-b][1,3]oxazin-3-yl]pyridin-2-yl}-2-methyl-2-(methylsulfinyl)propanamide | 1H-NMR (400 MHz, d6-DMSO): δ = 9.76 (s, 1H), 8.13-8.12 (d, 1H), 7.98 (s, 1H), 7.41-7.38 (m, 2H), 7.22-7.17 (m, 2H), 6.81-6.79 (dd, 1H), 4.43 (t, 2H), 4.18 (t, 2H), 2.55-2.45 (m, 3H), 2.31-2.25 (m, 2H), 1.55 (s, 3H), 1.33 (s, 3H) ppm | 1.69 | 443.2 | B |
| 69 | N-{4-[2-(4-fluorophenyl)-6,7-dihydro-5H-pyrazolo[5,1-b][1,3]oxazin-3-yl]pyridin-2-yl]-1,3-dithiolane-2-carboxamide | 1H-NMR (400 MHz, d6-DMSO): δ = 10.48 (s, 1H), 8.12-8.11 (d, 1H), 8.01 (s, 1H), 7.41-7.36 (m, 2H), 7.21-7.15 (m, 2H), 6.74-6.72 (dd, 1H), 5.23 (s, 1H), 4.42 (t, 2H), 4.18 (t, 2H), 3.45-3.30 (m, 4H), 2.31-2.25 (m, 2H) ppm | 2.1 | 443.1 | B |
| 70 | N-{4-[2-(4-fluorophenyl)-6,7-dihydro-5H-pyrazolo[5,1-b][1,3]oxazin-3-yl]pyridin-2-yl}-2-oxo-2-(piperidin-1-yl)acetamide | 1H-NMR (400 MHz, d6-DMSO): δ = 10.98 (s, 1H), 8.20-7.90 (m, 2H), 7.42-7.38 (m, 2H), 7.21-7.14 (m, 2H), 6.88-6.78 (dd, 1H), 4.44 (t, 2H), 4.18 (t, 2H), 3.50-3.40 (m, 2H), 3.05-3.00 (m, 2H), 2.31-2.25 (m, 2H), 1.70-1.60 (m, 6H) ppm | 2.23 | 450.2 | B |
| 71 | 2,6-difluoro-N-{4-[2-(4-fluorophenyl)-6,7-dihydro-5H-pyrazolo[5,1-b][1,3]oxazin-3-yl]pyridin-2-yl}benzamide | 1H-NMR (400 MHz, d6-DMSO): δ = 8.86-8.84 (d, 1H), 8.17-8.10 (m, 2H), 7.89-7.84 (m, 1H), 7.56-7.51 (m, 2H), 7.48-7.40 (m, 1H), 7.32-7.28 (m, 2H), 6.95 (t, 1H), 6.75-6.69 (dd, 1H), 4.55 (t, 2H), 4.22 (t, 2H), 2.35-2.25 (m, 2H) ppm | 2.43 | 451.1 | B |
| 72 | rel-N-{4-[(5R,7R)-2-(4-fluorophenyl)-5,7-dimethyl-6,7-dihydro-5H-pyrazolo[5,1-b][1,3]oxazin-3yl]pyridin-2-yl}propanamide | 1H-NMR (400 MHz, CD3CN): δ = 8.41 (s, 1H), 8.10 (s, 1H), 8.05-8.04 (d, 1H), 7.45-7.40 (m, 2H), 7.11-7.05 (m, 2H), 6.86-.6.84 (dd, 1H), 4.53-4.46 (m, 1H), 4.34-4.28 (m, 1H), 2.38-2.32 (m, 3H), 1.90-1.80 (m, 1H), 1.56 (d, 3H), 1.46 (d, 3H), 1.09 (t, 3H) ppm | 1.84 | 395.1 | A |
| 73 | rel-N-{4-[(5R,7S)-2-(4-fluorophenyl)-5,7-dimethyl-6,7-dihydro-5H-pyrazolo[5,1-b][1,3]oxazin-3-yl]pyridin-2-yl}propanamide | 1H-NMR (400 MHz, CD3CN): δ = 8.42 (s, 1H), 8.10 (s, 1H), 8.05-8.04 (d, 1H), 7.46-7.41 (m, 2H), 7.11-7.06 (m, 2H), 6.85-6.83 (dd, 1H), 4.68-4.63 (m, 1H), 4.46-4.42 (m, 1H), 2.38-2.33 (q, 2H), 2.27-2.21 (m, 1H), 2.08-2.03 (m, 1H), 1.55 (d, 3H), 1.45 (d, 3H), 1.10 (t, 3H) ppm | 1.74 | 395.2 | A |

TABLE 2-continued

NMR and Mass spectroscopic/logP data of compounds of the type [I]

| No. | Name | NMR | LogP$_A$ | [M + H]$_A$$^{+1}$ | Method$^2$ |
|---|---|---|---|---|---|
| 74 | N-{4-[6,6-difluoro-2-(4-fluorophenyl)-6,7-dihydro-5H-pyrazolo[5,1-b][1,3]oxazin-3-yl]pyridin-2-yl}propanamide | 1H-NMR (400 MHz, CD3CN): δ = 8.51 (s, 1H), 8.11-8.09 (m, 2H), 7.46-7.42 (m, 2H), 7.11-7.07 (m, 2H), 6.85-6.83 (dd, 1H), 4.63 (t, 2H), 4.55 (t, 2H), 2.40-2.34 (q, 2H), 1.10 (t, 3H) ppm | 1.9 | 403.1 | A |
| 75 | N-{4-[6-(4-fluorophenyl)-2,3-dimethyl-2,3-dihydropyrazolo[5,1-b][1,3]oxazol-7-yl]pyridin-2-yl}propanamide | 1H-NMR (400 MHz, CD3CN): δ = 8.77 (s, 1H), 8.05 (s, 1H), 8.02-8.01 (d, 1H), 7.49-7.46 (m, 2H), 7.15-7.10 (m, 2H), 6.82-6.80 (dd, 1H), 5.60-5.56 (m, 1H, major isomer), 5.10-5.07 (m, 1H, minor isomer), 4.70-4.66 (m, 1H, major isomer), 4.26-4.22 (m, 1H, minor isomer), 2.41-2.35 (q, 2H), 1.63 (d, 3H, minor isomer), 1.55 (d, 3H, major isomer), 1.36 (d, 3H, major isomer), 1.20 (d, 3H, minor isomer), 1.12-1.08 (m, 3H) ppm | 1.67 | 381.2 | A |
| 76 | N-{4-[7-(4-fluorophenyl)-3,3-dimethyl-3,4-dihydro-2H-pyrazolo[5,1-b][1,3,5]oxazasilin-8-yl]pyridin-2-yl}-2-methylpropanamide | 1H-NMR (250 MHz, CDC13): δ = 8.31 (s, 1H), 8.02 (d, 1H), 7.40 (m, 2H), 7.02 (t, 2H), 6.73 (m, 1H), 4.13 (s, 2H), 3.74 (s, 2H), 2.54 (m, 1H), 1.27 (d, 6H), 0.40 (s, 6H) ppm | 2.14 | 425.2 | C |
| 77 | N-{4-[7-(4-fluorophenyl)-3,3-dimethyl-3,4-dihydro-2H-pyrazolo[5,1-b][1,3,5]oxazasilin-8-yl]pyridin-2-yl}propanamide | 1H-NMR (250 MHz, CDC13): δ = 8.28 (s, 1H), 8.04(m, 1H), 7.40 (m, 2H), 7.02 (t, 2H), 6.75 (m, 1H), 4.12 (s, 2H), 3.74 (s, 2H), 2.40 (m, 2H), 1.68 (s, 2H), 1.24 (t, 3H), 0.40 (s, 6H) ppm | 2.15 | 411.3 | C |
| 78 | N-{4-[2-phenyl-4-propionyl-4,5,6,7-tetrahydropyrazolo[1,5 – a]pyrimidin-3-yl]pyridin-2-yl}propanamide | 1H-NMR (400 MHz, d6-DMSO): δ = 10.33 (s, 1H), 8.17 (d, 1H), 7.93 (s, 5H), 6.72 (d, 1H), 4.27 (t, 2H), 3.95 (m, 2H), 2.35 (m, 2H), 2.18 (m, 2H), 2.05 (m, 2H), 1.02 (m, 6H) ppm | 1.45 | 404.2 | C |
| 79 | N-{4-[2-(4-fluorophenyl)pyrazolo[1,5 – a]pyrimidin-3-yl]pyridin-2-yl}propanamide | 1H-NMR (400 MHz, d6-DMSO): δ = 10.39 (s, 1H), 9.25 (m, 1H), 8.69 (d, 1H), 8.37 (s, 1H), 8.26 (d, 1H), 7.62 (t, 2H), 7.30 (t, 2H), 7.07 (m, 1H), 2.75 (q, 2H), 1.06 (t, 3H) ppm | 1.91 | 362.1 | C |
| 80 | N-{4-[2-(4-fluorophenyl)-4,5,6,7-tetrahydropyrazolo[1,5 – a]pyrimidin-3-yl]pyridin-2-yl}propanamide | 1H-NMR (400 MHz, d6-DMSO): δ = 10.26 (s, 1H), 8.11 (d, 1H), 7.92 (s, 1H), 7.35 (t, 2H), 7.14 (t, 2H), 6.67 (t, 1H), 6.08 (s, 1H), 4.07 (m, 2H), 3.21 (s, 2H), 2.35 (m, 2H), 2.07(m, 2H), 1.03 (t, 3H) ppm | 1.35 | 366.2 | C |
| 81 | N-{4-[7-(4-fluorophenyl)-3,3-dimethyl-3,4-dihydro-2H-pyrazolo[5,1-b][1,3,5]oxazasilin-8-yl]pyridin-2-yl}cyclopropanecarboxamide | 1H-NMR (250 MHz, CDC13): δ = 8.41 (s, 1H), 8.24 (s, 1H), 8.02 (d, 1H), 7.39 (m, 2H), 7.01 (t, 2H), 6.73 (d, 1H), 4.10 (d, 2H), 3.73 (m, 2H), 1.55 (m, 1H), 1.08 (m, 2H), 0.89 (m, 2H), 0.40 (s, 6H) ppm | 2.18 | 423.3 | C |
| 82 | N-{4-[3,3-dimethyl-7-(2-thienyl)-3,4-dihydro-2H-pyrazolo[5,1-b][1,3,5]oxazasilin-8-yl]pyridin-2-yl}propanamide | — | 1.81 | 399.2 | C |
| 83 | N-acetyl-N-{4-[2-(4-fluorophenyl)pyrazolo[1,5 – a]pyrimidin-3-yl]pyridin-2-yl}acetamide | 1H-NMR (400 MHz, d6-DMSO): δ = 9.30 (m, 1H), 8.75 (m, 1H), 8.58 (d, 1H), 7.65 (m, 3H), 7.48 (s, 1H), 7.32 (m, 3H), 2.17 (s, 2H) ppm | 2.22 | 390.1 | C |
| 84 | N-(cyclopropylcarbonyl)-N-{4-[2-(4-fluorophenyl)pyrazolo[1,5 – a]pyrimidin-3-yl]pyridin-2-yl}cyclopropanecarboxamide | 1H-NMR (400 MHz, d6-DMSO): δ = 9.30 (m, 1H), 8.76 (m, 1H), 8.58 (d, 1H), 7.71 (d, 1H), 7.62 (m, 2H), 7.39 (s,1H), 7.33 (m, 3H), 1.93 (m, 2H), 0.93 (m; 8H) ppm | 2.94 | 442.2 | C |
| 85 | N-{4-[3,3-dimethyl-7-(2-thienyl)-3,4-dihydro-2H-pyrazolo[5,1-b][1,3,5]oxazasilin-8-yl]pyridin-2-yl}acetamide | — | 1.74 | 385.2 | C |
| 86 | N-{4-[3,3-dimethyl-7-(2-thienyl)-3,4-dihydro-2H-pyrazolo[5,1-b][1,3,5]oxazasilin-8-yl]pyridin-2-yl}-2-methylpropanamide | 1H-NMR (250 MHz, CDC13): δ = 8.34 (s, 1H), 8.11(d, 1H), 7.99 (s, 1H), 7.27 (m, 1H), 7.03 (m, 1H), 6.97 (m, 1H), 4.10 (s, 2H), 3.74 (s, 2H), 2.56 (m, 1H), 1.25 (s, 6H), 0.39 (s, 6H) ppm | 2.28 | 413.3 | C |
| 87 | N-{4-[3,3-dimethyl-7-(2-thienyl)-3,4-dihydro-2H-pyrazolo[5,1-b][1,3,5]oxazasilin-8-yl]pyridin-2-yl}cyclopropanecarboxamide | — | 2.08 | 411.2 | C |
| 88 | N-{4-[2-(4-fluorophenyl)pyrazolo[1,5 – a]pyrimidin-3-yl]pyridin-2-yl}cyclopropanecarboxamide | 1H-NMR (400 MHz, d6-DMSO): δ = 10.77 (s, 1H), 9.25 (d, 1H), 8.68 (t, 1H), 8.36 (s, 1H), 8.26 (d, 1H), 7.61 (t, 2H), 7.30 (t, 2H), 7.28 (m, 1H), 7.05 (m, 1H), 2.02 (m, 1H), 0.77 (d, 4H) ppm | 1.75 | 374.1 | C |
| 89 | 4-[3,3-dimethyl-7-(2-thienyl)-3,4-dihydro-2H-pyrazolo[5,1-b][1,3,5]oxazasilin-8-yl]pyridin-2-amine formic acid salt | — | 1.55 | 343.2 | C |
| 90 | N-acetyl-N-{4-[2-(4-fluorophenyl)-4-propionyl-4,5,6,7-tetrahydropyrazolo[1,5 – a]pyrimidin-3-yl]pyridin-2-yl}propanamide | 1H-NMR (250 MHz, d6-DMSO): δ = 8.46 (d, 1H), 7.33 (t, 2H), 7.19 (m, 4H), 4.27 (t, 2H), 3.96 (m, 2H), 2.20 (m, 5H), 0.96 (t, 3H), 0.76 (t, 3H) ppm | 2.39 | 464.4 | C |
| 91 | N-{4-[2-(4-fluorophenyl)-4-propionyl-4,5,6,7-tetrahydropyrazolo[1,5 – a]pyrimidin-3-yl]pyridin-2-yl}propanamide | 1H-NMR (250 MHz, CDC13): δ = 8.36 (s, 1H), 8.14 (d, 1H), 8.08 (s, 1H), 7.34 (m, 2H), 7.01 (t, 2H), 6.77 (d, 1H), 4.32 (t, 2H), 4.05 (s, 2H), 2.38 (m, 2H), 2.26 (m, 2H), 2.02 (m, 2H), 1.22 (t, 3H), 0.83 (t, 3H) ppm | 1.62 | 422.2 | C |
| 92 | N-isobutyryl-2-methyl-N-[4-(2-phenyl-4,5,6,7-tetrahydropyrazolo[1,5 – a]pyrimidin-3-yl)pyridin-2-yl]propanamide | 1H-NMR (400 MHz, d6-DMSO): δ = 8.40 (d, 1H), 7.32(m, 6H), 6.73 (s, 1H), 6.43 (s, 1H), 4.09 (t, 2H), 3.26 (bs, 2H), 2.78 (m, 2H), 2.08 (s, 2H), 1.00 (d, 12H) ppm | 3.08 | 432.3 | C |

TABLE 2-continued

NMR and Mass spectroscopic/logP data of compounds of the type [I]

| No. | Name | NMR | LogP$_A$ | [M + H]$_A^{+1}$ | Method [2] |
|---|---|---|---|---|---|
| 93 | N-{4-[2-(4-fluorophenyl)-4-propionyl-4,5,6,7-tetrahydropyrazolo[1,5-a]pyrimidin-3-yl]pyridin-2-yl}-N-methylpropanamide | 1H-NMR (400 MHz, d6-DMSO): δ = 8.39 (s, 1H), 7.34(t, 2H), 7.23 (t, 2H), 7.18 (bs, 1H), 6.99 (bs, 1H), 4.27 (t, 2H), 3.96 (bs, 2H), 3.15 (s, 3H), 2.17 (m, 2H), 2.09 (t, 2H), 0.91 (t, 3H), 0.73 (s, 3H) ppm | 2.05 | 436.2 | C |
| 94 | N-{4-[4-acetyl-2-(4-fluorophenyl)-4,5,6,7-tetrahydropyrazolo[1,5-a]pyrimidin-3-yl]pyridin-2-yl}acetamide | — | 1.26 | 394.2 | C |
| 95 | N-14-[2-(2,4-difluorophenyl)-6,7-dihydro-5H-pyrazolo[5,1-b][1,3]oxazin-3-yl]pyridin-2-yl}-N-propionylpropanamide | 1H-NMR (400 MHz, CD3CN): δ = 8.35-8.33 (d, 1H), 7.50-7.45 (m, 1H), 7.26-7.24 (dd, 1H), 7.08-7.04 (m, 1H), 6.99-6.94 (m, 2H), 4.45 (t, 2H), 4.19 (t, 2H), 2.46-2.41 (q, 4H), 2.35-2.30 (m, 2H), 1.00 (t, 6H) ppm | 2.68 | 441.1 | A |
| 96 | N-{4-[3,3-dimethyl-7-(3-thienyl)-3,4-dihydro-2H-pyrazolo[5,1-b][1,3,5]oxazasilin-8-yl]pyridin-2-yl}acetamide | — | 1.62 | 385.2 | C |
| 97 | N-benzyl-4-[4-ethyl-2-(4-fluorophenyl)-4,5,6,7-tetrahydropyrazolo[1,5-a]pyrimidin-3-yl]pyridin-2-amine | — | 1.86 | 428.2 | C |
| 98 | N-{4-[2-(4-fluorophenyl)-6,7-dihydro-5H-pyrazolo[5,1-b][1,3]oxazin-3-yl]pyridin-2-yl}-1-methylcyclopropanecarboxamide | 1H-NMR (400 MHz, d6-DMSO): δ = 9.32 (s, 1H), 8.13-8.11 (dd, 1H), 7.97 (s, 1H), 7.41-7.36 (m, 2H), 7.22-7.17 (m, 2H), 6.74-6.72 (dd, 1H), 4.42 (t, 2H), 4.17 (t, 2H), 2.30-2.25 (m, 2H), 1.39 (s, 3H), 1.08-1.06 (m, 2H), 0.64-0.62 (m, 2H) ppm | 1.79 | 393.2 | B |
| 99 | N-{4-[2-(4-fluorophenyl)-6,7-dihydro-5H-pyrazolo[5,1-b][1,3]oxazin-3-yl]pyridin-2-yl}-5-oxohexanamide | 1H-NMR (400 MHz, d6-DMSO): δ = 10.29 (s, 1H), 8.11-8.09 (dd, 1H), 8.05 (s, 1H), 7.41-7.37 (m, 2H), 7.22-7.17 (m, 2H), 6.74-6.72 (dd, 1H), 4.42 (t, 2H), 4.18 (t, 2H), 2.43 (t, 2H), 2.32 (t, 2H), 2.30-2.25 (m, 2H), 2.07 (s, 3H), 1.74-1.67 (m, 2H) ppm | 1.35 | 423.3 | B |
| 100 | N-{4-[3,3-dimethyl-7-(3-thienyl)-3,4-dihydro-2H-pyrazolo[5,1-b][1,3,5]oxazasilin-8-yl]pyridin-2-yl}propanamide | — | 1.88 | 399.1 | C |
| 101 | N-{4-[3,3-dimethyl-7-(3-thienyl)-3,4-dihydro-2H-pyrazolo-[5,1-b][1,3,5]oxazasilin-8-yl]pyridin-2-yl}-2-methylpropanamide | — | 2.11 | 413.2 | C |
| 102 | N-{4-[3,3-dimethyl-7-(3-thienyl)-3,4-dihydro-2H-pyrazolo-[5,1-b][1,3,5]oxazasilin-8-yl]pyridin-2-yl}cyclopropanecarboxamide | — | 1.97 | 411.2 | C |
| 103 | N-{4-[6-(4-fluorophenyl)-3-methylpyrazolo[5,1-b][1,3]oxazol-7-yl]pyridin-2-yl}propanamide | 1H-NMR (400 MHz, CD3CN): δ = 8.52 (s, 1H), 8.27 (s, 1H), 8.08-8.07 (d, 1H), 7.58-7.54 (m, 3H), 7.19-7.15 (m, 2H), 6.88-6.87 (dd, 1H), 2.41 (s, 3H), 2.41-2.35 (q, 2H), 1.10 (t, 3H) ppm | 1.86 | 365.1 | A |
| 104 | N-{4-[3-ethyl-6-(4-fluorophenyl)pyrazolo[5,1-b][1,3]oxazol-7-yl]pyridin-2-yl}propanamide | 1H-NMR (400 MHz, CD3CN): δ = 8.52 (s, 1H), 8.27 (s, 1H), 8.08-8.07 (d, 1H), 7.58-7.54 (m, 3H), 7.19-7.15 (m, 2H), 6.88-6.87 (dd, 1H), 2.85-2.83 (q, 2H), 2.39-2.37 (q, 2H), 1.37 (t, 3H), 1.11 (t, 3H) ppm | 2.23 | 379.1 | A |
| 105 | N-{4-[6-(4-fluorophenyl)pyrazolo[5,1-b][1,3]oxazol-7-yl]pyridin-2-yl}propanamide | 1H-NMR (400 MHz, CD3CN): δ = 8.49 (s, 1H), 8.28 (s, 1H), 8.09-8.08 (d, 1H), 7.88 (d, 1H), 7.79 (d, 1H), 7.58-7.53 (m, 2H), 7.20-7.14 (m, 2H), 6.89-6.88 (dd, 1H), 2.41-2.36 (q, 2H), 1.12 (t, 3H) ppm | 1.61 | 351.1 | A |
| 106 | N-[4-(6-phenylpyrazolo[5,1-b][1,3]oxazol-7-yl)pyridin-2-yl]propanamide | 1H-NMR (400 MHz, CD3CN): δ = 8.51 (s, 1H), 8.32 (s, 1H), 8.07-8.06 (d, 1H), 7.88 (d, 1H), 7.79 (d, 1H), 7.56-7.53 (m, 2H), 7.44-7.41 (m, 3H), 6.87-6.85 (dd, 1H), 2.41-2.36 (q, 2H), 1.12 (t, 3H) ppm | 1.46 | 333.1 | A |
| 107 | N-{4-[6-cyano-2-(4-fluorophenyl)-6-methyl-6,7-dihydro-5H-pyrazolo[5,1-b][1,3]oxazin-3-yl]pyridin-2-yl}-2-methylpropanamide | 1H-NMR (400 MHz, CDC13): δ = 8.30 (bs, 1H), 8.10 (s, 1H), 8.05 (d, 1H), 7.40 (m, 2H), 7.05 (t, 2H), 6.72 (d, 1H), 4.58 (d, 2H), 4.11 (m, 2H), 2.54 (m, 1H), 1.62 (s, 3H), 1.23 (d, 6H) ppm | 1.94 | 420.3 | C |
| 108 | N-{4-[2-(4-fluorophenyl)-6,6-dimethyl-6,7-dihydro-5H-pyrazolo[5,1-b][1,3]oxazin-3-yl]pyridin-2-yl}cyclopropanecarboxamide | 1H-NMR (300 MHz, CDC13): δ = 8.49 (s, 1H), 8.27 (s, 1H), 8.04 (s, 1H), 7.43 (bs, 2H), 7.03 (t, 2H), 6.74 (s, 1H), 4.04 (s, 2H), 3.91 (s, 2H), 1.55 (bs, 1H), 1.20 (s, 6H), 1.09 (bs, 2H), 0. 87 (bs, 2H) ppm | 2.08 | 407.3 | C |
| 109 | N-{4-[2-(4-fluorophenyl)-6,6-dimethyl-6,7-dihydro-5H-pyrazolo[5,1-b][1,3]oxazin-3-yl]pyridin-2-yl}acetamide | 1H-NMR (400 MHz, CDC13): δ = 8.34 (s, 2H), 8.08 (bs, 1H), 7.48 (m, 2H), 7.07 (m, 2H), 6.82 (bs, 1H), 4.06 (s, 2H), 3.94 (s, 2H), 2.19 (s, 3H), 1.20 (s, 6H) ppm | 1.75 | 381.3 | C |
| 110 | N-{4-[2-(4-fluorophenyl)-6,6-dimethyl-6,7-dihydro-5H-pyrazolo[5,1-b][1,3]oxazin-3-yl]pyridin-2-yl}propanamide | 1H-NMR (300 MHz, CDC13): δ = 8.32 (s, 1H), 8.11 (s, 1H), 8.03 (s, 1H), 7.44 (s, 2H), 7.04 (t, 2H), 6.76 (s, 1H), 4.05 (s, 2H), 3.92 (s, 2H), 2.40 (m, 2H), 1.21 (m, 9H) ppm | 2.00 | 395.3 | C |
| 111 | N-{4-[2-(4-fluorophenyl)-6,6-dimethyl-6,7-dihydro-5H-pyrazolo[5,1-b][1,3]oxazin-3-yl]pyridin-2-yl}-2-methylpropanamide | 1H-NMR (300 MHz, CDC13): δ = 8.34 (s, 1H), 8.01 (d, 2H), 7.44 (s, 2H), 7.04 (t, 2H), 6.74 (s, 1H), 4.06 (s, 2H), 3.92 (s, 2H), 2.54 (d, 1H), 1.21 (m, 12H) ppm | 2.23 | 409.3 | C |

TABLE 2-continued

NMR and Mass spectroscopic/logP data of compounds of the type [I]

| No. | Name | NMR | LogP$_A$ | [M + H]$_A$$^{+\,1}$ | Method$^{\,2}$ |
|---|---|---|---|---|---|
| 112 | N-{4-[2-(4-fluorophenyl)-6,7-dihydro-5H-pyrazolo[5,1-b][1,3]oxazin-3-yl]pyridin-2-yl}-3-oxocyclopentanecarboxamide | 1H-NMR (400 MHz, d6-DMSO): δ = 10.53 (s, 1H), 8.12-8.10 (d, 1H), 8.08 (s, 1H), 7.41-7.36 (m, 2H), 7.21-7.15 (m, 2H), 6.72-6.71 (dd, 1H), 4.42 (t, 2H), 4.18 (t, 2H), 2.35-2.10 (m, 8H), 2.00-1.90 (m, 1H) ppm | 1.38 | 421.3 | B |
| 113 | 2-fluoro-N-{4-[2-(4-fluorophenyl)-6,7-dihydro-5H-pyrazolo[5,1-b][1,3]oxazin-3-yl]pyridin-2-yl}propanamide | 1H-NMR (400 MHz, d6-DMSO): δ = 10.34 (s, 1H), 8.16-8.14 (d, 1H), 8.02 (s, 1H), 7.42-7.37 (m, 2H), 7.23-7.17 (m, 2H), 6.81-6.79 (dd, 1H), 5.29-5.10 (qd, 1H, CHF), 4.43 (t, 2H), 4.16 (t, 2H), 2.33-2.25 (m, 2H), 1.51-1.40 (dd, 3H) ppm | 2 | 385.2 | B |
| 114 | 5-fluoro-N-{4-[2-(4-fluorophenyl)-6,7-dihydro-5H-pyrazolo[5,1-b][1,3]oxazin-3-yl]pyridin-2-yl}nicotinamide | 1H-NMR (400 MHz, d6-DMSO): δ = 11.05 (s, 1H), 8.97 (s, 1H), 8.78 (d, 1H), 8.25-8.22 (m, 2H), 8.08 (s, 1H), 7.45-7.38 (m, 2H), 7.23-7.15 (m, 2H), 6.86-6.84 (dd, 1H), 4.44 (t, 2H), 4.19 (t, 2H), 2.33-2.26 (m, 2H) ppm | 1.96 | 434.3 | B |
| 115 | 2-fluoro-N-{4-[2-(4-fluorophenyl)-6,7-dihydro-5H-pyrazolo[5,1-b][1,3]oxazin-3-yl]pyridin-2-yl}-2-methylpropanamide | 1H-NMR (400 MHz, d6-DMSO): δ = 9.66 (s, 1H), 8.16-8.15 (d, 1H), 8.00 (s, 1H), 7.41-7.38 (m, 2H), 7.23-7.18 (m, 2H), 6.81-6.79 (dd, 1H), 4.43 (t, 2H), 4.18 (t, 2H), 2.31-2.25 (m, 2H), 1.58-1.53 (d, 3H) ppm | 2.38 | 399.2 | B |
| 116 | 2-chloro-2-fluoro-N-{4-[2-(4-fluorophenyl)-6,7-dihydro-5H-pyrazolo[5,1-b][1,3]oxazin-3-yl]pyridin-2-yl}cyclopropanecarboxamide | 1H-NMR (400 MHz, d6-DMSO): δ = 10.96 (s, 1H), 8.16-8.14 (m, 1H), 8.00 (m, 1H), 7.41-7.38 (m, 2H), 7.21-7.15 (m, 2H), 6.80-6.75 (dd, 1H), 4.42 (t, 2H), 4.16 (t, 2H), 2.95-2.88 (m, 1H), 2.31-2.25 (m, 2H), 2.20-2.00 (m, 1H), 1.90-1.75 (m, 1H) ppm | 2.13 | 431.2 | B |
| 117 | N-{4-[2-(4-fluorophenyl)-6,7-dihydro-5H-pyrazolo[5,1-b][1,3]oxazin-3-yl]pyridin-2-yl}-1-methylcyclopentanecarboxamide | 1H-NMR (400 MHz, d6-DMSO): δ = 9.68 (s, 1H), 8.11-8.10 (d, 1H), 8.02 (s, 1H), 7.41-7.37 (m, 2H), 7.21-7.16 (m, 2H), 6.72-6.66 (dd, 1H), 4.43 (t, 2H), 4.18 (t, 2H), 2.31-2.25 (m, 2H), 2.10-2.00 (m, 1H), 1.70-1.50 (m, 8H), 1.28 (s, 3H) ppm | 2.23 | 421.3 | B |
| 118 | N-{4-[2-(4-fluorophenyl)-6,7-dihydro-5H-pyrazolo[5,1-b][1,3]oxazin-3-yl]pyridin-2-yl}-5-methyl-1,3-dioxane-5-carboxamide | 1H-NMR (400 MHz, d6-DMSO): δ = 9.79 (s, 1H), 8.12-8.11 (m, 2H), 7.42-7.37 (m, 2H), 7.22-7.17 (m, 2H), 6.72-6.70 (dd, 1H), 4.92 (d, 1H), 4.72 (d, 1H), 4.44-4.41 (t, 2H), 4.22-4.18 (m, 4H), 3.66 (d, 2H), 2.31-2.25 (m, 2H), 1.06 (s, 3H) ppm | 1.86 | 439.3 | B |
| 119 | 3-ethyl-N-{4-[2-(4-fluorophenyl)-6,7-dihydro-5H-pyrazolo[5,1-b][1,3]oxazin-3-yl]pyridin-2-yl}oxetane-3-carboxamide | 1H-NMR (400 MHz, d6-DMSO): δ = 8.25 (s, 1H), 7.78-7.76 (d, 2H), 7.46-7.41 (m, 2H), 7.30-7.18 (m, 2H), 6.60 (s, 1H), 6.47-6.45 (dd, 1H), 4.49 (t, 2H), 4.16 (t, 2H), 4.15-4.05 (q, 2H), 2.33-2.28 (m, 2H), 1.54-1.45 (m, 1H), 1.38-1.29 (m, 1H), 0.76 (t, 3H) ppm | 1.56 | 423.3 | B |
| 120 | 1-cyano-N-{4-[2-(4-fluorophenyl)-6,7-dihydro-5H-pyrazolo{5,1-b][1,3]oxazin-3-yl]pyridin-2-yl}cyclopropanecarboxamide | 1H-NMR (400 MHz, d6-DMSO): δ = 10.10 (s, 1H), 8.17-8.11 (d, 1H), 7.88 (s, 1H), 7.42-7.36 (m, 2H), 7.23-7.16 (m, 2H), 6.81-6.79 (dd, 1H), 4.43 (t, 2H), 4.18 (t, 2H), 2.31-2.25 (m, 2H), 1.67-1.65 (m, 4H) ppm | 2.13 | 404.3 | B |
| 121 | N-{4-[2-(4-fluorophenyl)-6,7-dihydro-5H-pyrazolo[5,1-b][1,3]oxazin-3-yl]pyridin-2-yl}-1-methylcyclohex-3-ene-1-carboxamide | 1H-NMR (400 MHz, d6-DMSO): δ = 9.59 (s, 1H), 8.12-8.09 (d, 1H), 8.00 (s, 1H), 7.40-7.37 (m, 2H), 7.21-7.15 (m, 2H), 6.73-6.71 (dd, 1H), 5.61 (m, 2H), 4.43 (t, 2H), 4.18 (t, 2H), 2.31-2.25 (m, 2H), 2.05-1.90 (m, 5H), 1.61-1.56 (m, 1H), 1.21 (s, 3H) ppm | 2.38 | 433.3 | B |
| 122 | N-{4-[2-(4-fluorophenyl)-6,7-dihydro-5H-pyrazolo[5,1-b][1,3]oxazin-3-yl]pyridin-2-yl}-2-[(isopropylideneamino)oxy]acetamide | 1H-NMR (400 MHz, d6-DMSO): δ = 9.89 (s, 1H), 8.12-8.11 (d, 1H), 8.04 (s, 1H), 7.41-7.38 (m, 2H), 7.21-7.17 (m, 2H), 6.77-6.75 (dd, 1H), 4.55 (s, 2H), 4.43 (t, 2H), 4.18 (t, 2H), 2.31-2.25 (m, 2H), 1.88 (s, 3H), 1.81 (s, 3H) ppm | 2.13 | 424.3 | B |
| 123 | N-{4-[2-(4-fluorophenyl)-6,7-dihydro-5H-pyrazolo[5,1-b][1,3]oxazin-3-y]pyridin-2-yl}-2-(1H-pyrazol-1-yl)acetamide | 1H-NMR (400 MHz, d6-DMSO): δ = 10.61 (s, 1H), 8.14-8.12 (d, 1H), 8.03 (s, 1H), 7.75-7.74 (dd, 1H), 7.47-7.46 (dd, 1H), 7.41-7.36 (m, 2H), 7.21-7.15 (m, 2H), 6.73-6.72 (dd, 1H), 6.27 (dd, 1H), 5.07 (s, 2H), 4.40 (t, 2H), 4.16 (t, 2H), 2.35-2.25 (m, 2H), 2.53 (s, 3H), 2.50 (s, 3H) ppm | 1.63 | 419.3 | B |
| 124 | N-{4-[2-(4-fluorophenyl)-6,7-dihydro-5H-pyrazolo[5,1-b][1,3]oxazin-3-yl]pyridin-2-yl}-2-(tetrahydro-2H-pyran-3-yl)acetamide | 1H-NMR (400 MHz, d6-DMSO): δ = 10.31 (s, 1H), 8.11-8.10 (d, 1H), 8.02 (s, 1H), 7.42-7.37 (m, 2H), 7.21-7.15 (m, 2H), 6.76-6.75 (dd, 1H), 4.43 (t, 2H), 4.18 (t, 2H), 3.73-3.70 (m, 2H), 3.32-3.25 (m, 1H), 3.05-3.00 (m, 1H), 2.30-2.25 (m, 2H), 2.22-2.18 (m, 2H), 2.00-1.90 (m, 1H), 1.80-1.70 (m, 1H), 1.60-1.40 (m, 2H), 1.21-1.12 (m, 1H) ppm | 1.57 | 437.3 | B |
| 125 | N-{4-[2-(4-fluorophenyl)-6,7-dihydro-5H-pyrazolo[5,1-b][1,3]oxazin-3-yl]pyridin-2-yl}cyclopent-3-ene-1-carboxamide | 1H-NMR (400 MHz, d6-DMSO): δ = 10.35 (s, 1H), 8.10-8.09 (m, 2H), 7.42-7.37 (m, 2H), 7.22-7.16 (m, 2H), 6.71-6.69 (dd, 1H), 5.64 (s, 2H), 4.42 (t, 2H), 4.18 (t, 2H), 3.33-3.25 (m, 1H), 2.60-2.50 (m, 4H), 2.30-2.25 (m, 2H) ppm | 1.76 | 405.3 | B |
| 126 | N-{4-[2-(4-fluorophenyl)-6,7-dihydro-5H-pyrazolo[5,1-b][1,3]oxazin-3-yl]pyridin-2-yl}-2-methyl-3-furamide | 1H-NMR (400 MHz, d6-DMSO): δ = 10.14 (s, 1H), 8.18-8.16 (d, 1H), 8.08 (s, 1H), 7.55 (d, 1H), 7.43-7.40 (m, 2H), 7.22-7.17 (m' 3H), 6.81-6.80 (dd, 1H), 4.44 (t, 2H), 4.18 (t, 2H), 2.60 (s, 3H), 2.33-2.25 (m, 2H) ppm | 1.96 | 419.2 | B |
| 127 | N-{4-[2-(4-fluorophenyl)-6,7-dihydro-5H-pyrazolo[5,1-b][1,3]oxazin-3-yl]pyridin-2-yl}-2,4-dimethylhexanamide | 1H-NMR (400 MHz, d6-DMSO): δ = 10.32 (s, 1H), 8.12-8.10 (m, 2H), 8.09 (s, 1H), 7.41-7.38 (m, 2H), 7.22-7.15 (m, 2H), 6.75-6.72 (m, 1H), 4.42 (t, 2H), 4.18 (t, 2H), 2.73-2.68 (m, 1H), 2.30-2.25 (m, 2H), 1.70-1.60 (m, 2H), 1.45-1.32 (m, 1H), 1.32-1.20 (m, 2H), 1.12-1.05 (m, 1H), 1.00 (t, 3H), 0.90-0.75 (m, 6H) ppm | 2.65 | 437.3 | B |
| 128 | N-{4-[2-(4-fluorophenyl)-6,7-dihydro-5H-pyrazolo[5,1-b][1,3]oxazin-3-yl]pyridin-2-yl}tetrahydro-2H-thiopyran-4-carboxamide | 1H-NMR (400 MHz, d6-DMSO): δ = 10.28 (s, 1H), 8.09-8.07 (m, 2H), 7.43-7.36 (m, 2H), 7.21-7.16 (m, 2H), 6.69-6.68 (dd, 1H), 4.42 (t, 2H), 4.18 (t, 2H), 2.65-2.55 (m, 5H), 2.30-2.25 (m, 2H), 2.10-2.00 (m, 2H), 1.60-1.50 (m, 2H) ppm | 1.83 | 439.3 | B |

TABLE 2-continued

NMR and Mass spectroscopic/logP data of compounds of the type [I]

| No. | Name | NMR | LogP$_A$ | [M + H]$_A$$^{+\,1}$ | Method [2] |
|---|---|---|---|---|---|
| 129 | N-{4-[2-(4-fluorophenyl)-6,7-dihydro-5H-pyrazolo-[5,1-b][1,3]oxazin-3-yl]pyridin-2-yl}-1,1'-bi(cyclopropyl)-1-carboxamide | 1H-NMR (400 MHz, d6-DMSO): δ = 9.25 (s, 1H), 8.13-8.10 (d, 1H), 8.05 (s, 1H), 7.41-7.36 (m, 2H), 7.22-7.16 (m, 2H), 6.76-6.74 (dd, 1H), 4.42 (t, 2H), 4.16 (t, 2H), 2.30-2.25 (m, 2H), 1.60-1.54 (m, 1H), 0.94-0.86 (m, 2H), 0.62-0.59 (m, 4H), 0.23-0.18 (m, 2H) ppm | 2.46 | 419.3 | B |
| 130 | 5-fluoro-N-{4-[-(4-fluorophenyl)-6,7-dihydro-5H-pyrazolo[5,1-b][1,3]oxazin-3-yl]pyridin-2-yl}thiophene-2-carboxamide | 1H-NMR (400 MHz, d6-DMSO): δ = 10.86 (s, 1H), 8.20-8.19 (d, 1H), 8.06 (s, 1H), 8.02-8.00 (dd, 1H), 7.44-7.39 (m, 2H), 7.23-7.18 (m, 2H), 6.87-6.86 (dd, 1H), 6.81-6.80 (dd, 1H), 4.40 (t, 2H), 4.18 (t, 2H), 2.30-2.25 (m, 2H) ppm | 2.42 | 439.2 | B |
| 131 | (3S)-N-{4-[2-(4-fluorophenyl)-6,7-dihydro-5H-pyrazolo[5,1-b][1,3]oxazin-3-yl]pyridin-2-yl}-3-methylpentanamide | 1H-NMR (400 MHz, d6-DMSO): δ = 10.27 (s, 1H), 8.11-8.09 (d, 1H), 8.03 (s, 1H), 7.41-7.36 (m, 2H), 7.20-7.15 (m, 2H), 6.76-6.74 (dd, 1H), 4.42 (t, 2H), 4.18 (t, 2H), 2.30-2.25 (m, 2H), 2.17-2.11 (dd, 1H), 1.84-1.78 (m, 1H), 1.34-1.26 (m, 1H), 1.17-1.12 (m, 1H), 0.86-0.83 (m, 6H) ppm | 2.1 | 409.3 | B |
| 132 | 3-fluoro-2-(fluorophenyl)-N-{4-[2-(4-fluorophenyl)-6,7-dihydro-5H-pyrazolo[5,1-b][1,3]oxazin-3-yl]pyridin-2-yl}-2-methylpropanamide | 1H-NMR (400 MHz, d6-DMSO): δ = 10.21 (s, 1H), 8.15-8.14 (d, 1H), 8.03 (s, 1H), 7.42-7.37 (m, 2H), 7.22-7.16 (m, 2H), 6.75-6.74 (dd, 1H), 4.84 (d, 1H), 4.72 (d, 1H), 4.66 (d, 1H), 4.54 (d, 1H), 4.42 (t, 2H), 4.18 (t, 2H), 2.30-2.25 (m, 2H), 1.26 (s, 3H) ppm | 2.27 | 431.3 | B |
| 133 | N-{4-[2-(4-fluorophenyl)-6,7-dihydro-5H-pyrazolo[5,1-b][1,3]oxazin-3-yl]pyridin-2-yl}-3-(1H-1,2,3-triazol-1-yl)propanamide | 1H-NMR (400 MHz, d6-DMSO): δ = 10.47 (s, 1H), 8.11-8.10 (d, 1H), 8.02 (s, 1H), 8.00 (s, 1H), 7.69 (s, 1H), 7.42-7.37 (m, 2H), 7.22-7.16 (m, 2H), 6.76-6.75 (dd, 1H), 4.63 (t, 2H), 4.42 (t, 2H), 4.18 (t, 2H), 3.01 (t, 2H), 2.30-2.25 (m, 2H) ppm | 1.23 | 434.3 | B |
| 134 | N-{4-[2-(4-fluorophenyl)-6,7-dihydro-5H-pyrazolo[5,1-b][1,3]oxazin-3-yl]pyridin-2-yl}-5-methyl-1,2-oxazole-3-carboxamide | 1H-NMR (400 MHz, d6-DMSO): δ = 10.38 (s, 1H), 8.21-8.20 (d, 1H), 8.05 (s, 1H), 7.45-7.39 (m, 2H), 7.24-7.18 (m, 2H), 6.88-6.87 (dd, 1H), 6.71 (s, 1H), 4.45 (t, 2H), 4.19 (t, 2H), 2.54 (s, 3H), 2.30-2.25 (m, 2H) ppm | 2.53 | 420.3 | B |
| 135 | N-{4-[2-(4-fluorophenyl)-6,7-dihydro-5H-pyrazolo[5,1-b][1,3]oxazin-3-yl]pyridin-2-yl}-3,5-dimethyl-1,2-oxazole-4-carboxamide | 1H-NMR (400 MHz, d6-DMSO): δ = 10.42 (s, 1H), 8.16-8.15 (d, 1H), 8.08 (s, 1H), 7.45-7.40 (m, 2H), 7.23-7.18 (m, 2H), 6.81-6.79 (dd, 1H), 4.44 (t, 2H), 4.18 (t, 2H), 2.56 (s, 3H), 2.30 (s, 3H), 2.30-2.25 (m, 2H) ppm | 2.06 | 434.3 | B |
| 136 | N-{4-[2-(4-fluorophenyl)-6,7-dihydro-5H-pyrazolo[5,1-b][1,3]oxazin-3-yl]pyridin-2-yl}-2-[(isopropylideneamino)oxy]propanamide | 1H-NMR (400 MHz, d6-DMSO): δ = 9.90 (s, 1H), 8.12-8.10 (dd, 1H), 8.08 (s, 1H), 7.41-7.38 (m, 2H), 7.21-7.16 (m, 2H), 6.75-6.73 (dd, 1H), 4.70-4.65 (q, 1H), 4.43 (t, 2H), 4.18 (t, 2H), 2.30-2.25 (m, 2H), 1.88 (s, 3H), 1.79 (s, 3H), 1.33 (d, 3H) ppm | 2.34 | 438.3 | B |
| 137 | N-{4-[2-(4-fluorophenyl)-6,7-dihydro-5H-pyrazolo[5,1-b][1,3]oxazin-3-yl]pyridin-2-yl}-2-(1H-1,2,4-triazol-1-yl)acetamide | 1H-NMR (400 MHz, d6-DMSO): δ = 10.82 (s, 1H), 8.52 (s, 1H), 8.15-8.14 (dd, 1H), 8.01 (s, 1H), 7.98 (s, 1H), 7.41-7.36 (m, 2H), 7.21-7.15 (m, 2H), 6.74-6.72 (dd, 1H), 5.18 (s, 2H), 4.40 (t, 2H), 4.16 (t, 2H), 2.30-2.25 (m, 2H) ppm | 1.32 | 420.2 | B |
| 138 | N-{4-[2-(4-fluorophenyl)-6,7-dihydro-5H-pyrazolo[5,1-b][1,3]oxazin-3-yl]pyridin-2-yl}-N$^2$-formylvalinamide | 1H-NMR (400 MHz, d6-DMSO): δ = 10.47 (s, 1H), 8.27 (d, 1H), 8.15-8.14 (d, 1H), 8.05 (s, 1H), 7.98 (s, 1H), 7.42-7.37 (m, 2H), 7.21-7.15 (m, 2H), 6.82-6.79 (dd, 1H), 4.58-4.51 (m, 1H), 4.42 (t, 2H), 4.18 (t, 2H), 2.30-2.25 (m, 2H), 2.05-1.96 (m, 1H), 0.88-0.77 (m, 6H) ppm | 1.6 | 438.3 | B |
| 139 | 2-(cyclohex-1-en-1-yl)-N-{4-[2-(4-fluorophenyl)-6,7-dihydro-5H-pyrazolo[5,1-b][1,3]oxazin-3-yl]pyridin-2-yl}acetamide | 1H-NMR (400 MHz, d6-DMSO): δ = 10.25 (s, 1H), 8.12-8.10 (d, 1H), 8.01 (s, 1H), 7.41-7.36 (m, 2H), 7.21-7.15 (m, 2H), 6.76-6.74 (dd, 1H), 5.52 (s, 1H), 4.58-4.51 (m, 1H), 4.42 (t, 2H), 4.18 (t, 2H), 2.96 (s, 2H), 2.30-2.25 (m, 2H), 2.00-1.90 (m, 4H), 1.60-1.48 (m, 4H) ppm | 2.46 | 433.3 | B |
| 140 | N-{4-[2-(4-fluorophenyl)-6,7-dihydro-5H-pyrazolo[5,1-b][1,3]oxazin-3-yl]pyridin-2-yl}-2,2,3,3-tetramethylcyclopropanecarboxamide | 1H-NMR (400 MHz, d6-DMSO): δ = 10.19 (s, 1H), 8.09-8.08 (dd, 1H), 7.94 (s, 1H), 7.39-7.36 (m, 2H), 7.19-7.14 (m, 2H), 6.75-6.73 (dd, 1H), 4.42 (t, 2H), 4.17 (t, 2H), 2.30-2.25 (m, 2H), 1.18 (s, 6H), 1.14 (s, 6H) ppm | 2.27 | 435.3 | B |

[1] The stated mass is the peak of the isotope pattern of the [M + H]+ ion with the highest intensity; if the [M − H]− ion was detected,
[2] In the determination of the logP values, the methods described below were used.

Method A

Note on the determination of the log P values and mass detection: The stated log P values were determined in accordance with EEC-Directive 79/831 Annex V.A8 by HPLC (High Performance Liquid Chromatography) on a reverse phase column (C18). Agilent 1100 LC system; 50*4.6 Zorbax Eclipse Plus C18 1.8 micron; eluent A: acetonitrile (0.1% formic acid); eluent B: water (0.09% formic acid); linear gradient from 10% acetonitrile to 95% acetonitrile in 4.25 mins, then 95% acetonitrile for a further 1.25 mins; oven temperature 55° C.; flow rate: 2.0 mL/min. The mass detection was effected with an Agilend MSD system.

Method B

Note on the determination of the log P values and mass detection: The stated log P values were determined in accordance with EEC-Directive 79/831 Annex V.A8 by HPLC (High Performance Liquid Chromatography) on a reverse phase column (C18). HP1100; 50*4.6 Zorbax Eclipse Plus C18 1.8 micron; eluent A: acetonitrile (0.1% formic acid); eluent B: water (0.08% formic acid); linear gradient from 5% acetonitrile to 95% acetonitrile in 1.70 min, then 95% acetonitrile for a further 1.00 min; oven temperature 55° C.; flow rate: 2.0 mL/min. The mass detection was effected with the Micronass ZQ2000 mass detector from Waters.

Method C

Note on the determination of the log P values and mass detection: The stated log P values were determined in accordance with EEC-Directive 79/831 Annex V.A8 by UPLC (Ultra Performance Liquid Chromatography) on a reverse phase column (C18). HP1100; 50*2.1 Zorbax Eclipse Plus C18 1.8 micron; eluent A: acetonitrile (0.09% formic acid); eluent B: water (0.1% formic acid); linear gradient from 10% A to 95% A in 3.25 min; oven temperature 40° C.; flow rate: 0.8 mL/min. The mass detection was effected with the LCT Premier or SQD mass detector from Waters.

Calibration was performed with unbranched alkan-2-ones (with 3 to 16 carbon atoms), whose log P values are known (determination of the log P values on the basis of the retention times by linear interpolation between two successive alkanones).

The lambda-max values were determined on the basis of the UV spectra from 200 nm to 400 nm in the maxima of the chromatographic signals.

USE EXAMPLES

Example A

*Sphaerotheca* Test (Cucumber)/Preventive

| Solvent: | 49 parts by weight of N,N-Dimethylformamide |
|---|---|
| Emulsifier: | 1 part by weight of Alkylarylpolyglycolether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Sphaerotheca fuliginea*. Then the plants are placed in a greenhouse at approximately 23° C. and a relative atmospheric humidity of approximately 70%.

The test is evaluated 7 days after the inoculation. 0% means an efficacy which corresponds to that of the untreated control, while an efficacy of 100% means that no disease is observed.

In this test the following compounds according to the invention showed efficacy of 70% or even higher at a concentration of 500 ppm of active ingredient: 1 (75%), 2 (100%), 3 (93%), 4 (100%), 5 (95%), 6 (98%), 7 (95%), 8 (100%), 9 (95%), 10 (100%), 11 (100%), 12 (83%), 13 (70%), 14 (100%), 16 (93%), 18 (93%), 19 (90%), 20 (100%), 21 (93%), 22 (100%), 24 (98%), 25 (100%), 27 (95%), 28 (100%), 30 (98%), 31 (88%), 34 (95%), 36 (100%), 37 (100%), 39 (98%), 40 (98%), 43 (100%), 45 (95%), 49 (93%), 52 (95%), 53 (95%), 54 (100%), 55 (88%), 56 (80%), 57 (100%), 62 (100%), 63 (95%), 76 (95%), 77 (95%), 79 (80%), 80 (93%), 81 (98%), 83 (90%), 84 (88%), 88 (93%), 92 (100%).

Example B

*Uromyces* Test (Beans)/Preventive

| Solvent: | 49 parts by weight of N,N-Dimethylformamide |
|---|---|
| Emulsifier: | 1 part by weight of Alkylarylpolyglycolether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Uromyces appendiculatus*. The plants remain for 24 hours in an incubation cabinet at 22° C. and a relative atmospheric humidity of 100%. Then the plants are placed in a greenhouse at a temperature of approximately 22° C. and a relative atmospheric humidity of approximately 80%.

The test is evaluated 6-8 days after the inoculation. 0% means an efficacy which corresponds to that of the untreated control while an efficacy of 100% means that no disease is observed.

In this test the following compounds according to the invention showed efficacy of 70% or even higher at a concentration of 500 ppm of active ingredient: 2 (74%), 4 (90%), 5 (93%), 6 (89%), 7 (94%), 8 (94%), 9 (94%), 10 (94%), 11 (94%), 12 (94%), 13 (92%), 14 (94%), 15 (83%), 16 (92%), 17 (94%), 18 (94%), 19 (92%), 20 (97%), 22 (94%), 23 (94%), 24 (94%), 25 (94%), 26 (72%), 28 (94%), 29 (94%), 30 (92%), 31 (92%), 32 (92%), 33 (89%), 34 (94%), 35 (92%), 36 (92%), 37 (94%), 38 (89%), 39 (94%), 40 (94%), 41 (94%), 42 (94%), 43 (92%), 44 (94%), 45 (92%), 46 (94%), 47 (92%), 48 (86%), 49 (94%), 53 (74%), 57 (89%), 61 (84%), 62 (78%), 76 (94%), 77 (94%), 80 (78%), 81 (94%), 86 (94%), 92 (78%), 101 (75%).

Example C

*Leptosphaeria* Test (Wheat)/Preventive

| Solvent: | 49 parts by weight of N,N-Dimethylformamide |
|---|---|
| Emulsifier: | 1 part by weight of Alkylarylpolyglycolether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with a preparation of active compound at the stated rate of application. One day after this treatment, the plants are inoculated with an aqueous spore suspension of *Leptosphaeria nodorum*. The plants remain for 48 hours in an incubation cabinet at 22° C. and a relative atmospheric humidity of 100%. Then the plants are placed in a greenhouse at a temperature of approximately 22° C. and a relative atmospheric humidity of approximately 90%.

The test is evaluated 7-9 days after the inoculation. 0% means an efficacy which corresponds to that of the untreated control, while an efficacy of 100% means that no disease is observed.

In this test the following compounds according to the invention showed efficacy of 70% or even higher at a concentration of 500 ppm of active ingredient: 1 (88%), 2 (88%), 3 (88%), 4 (90%), 5 (90%), 6 (90%), 7 (90%), 8 (95%), 9 (95%), 10 (80%), 11 (100%), 12 (80%), 14 (95%), 18 (90%), 20 (95%), 21 (70%), 22 (90%), 24 (95%), 25 (95%), 26 (70%), 27 (90%), 28 (95%), 30 (70%), 34 (90%), 35 (80%), 36 (90%), 37 (70%), 42 (70%), 43 (70%), 49 (90%), 52 (80%), 53 (90%), 54 (80%), 61 (78%), 76 (75%), 77 (94%), 81 (75%), 85 (90%), 100 (80%), 101 (80%), 102 (80%).

Example D

Pyrenophora Test (Barley)/Preventive

| Solvent: | 49 parts by weight of N,N-Dimethylformamide |
| --- | --- |
| Emulsifier: | 1 part by weight of Alkylarylpolyglycolether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Pyrenophora teres*. The plants remain for 48 hours in an incubation cabinet at 22° C. and a relative atmospheric humidity of 100%. Then the plants are placed in a greenhouse at a temperature of approximately 20° C. and a relative atmospheric humidity of approximately 80%.

The test is evaluated 7-9 days after the inoculation. 0% means an efficacy which corresponds to that of the untreated control while an efficacy of 100% means that no disease is observed.

In this test the following compounds according to the invention showed efficacy of 70% or even higher at a concentration of 500 ppm of active ingredient: 1 (95%), 2 (100%), 3 (100%), 4 (100%), 5 (95%), 6 (95%), 7 (95%), 8 (95%), 9 (100%), 10 (80%), 11 (100%), 12 (100%), 13 (95%), 14 (95%), 15 (95%), 16 (95%), 17 (95%), 18 (95%), 19 (95%), 20 (95%), 21 (100%), 22 (95%), 23 (95%), 24 (95%), 25 (100%), 26 (100%), 27 (95%), 28 (95%), 29 (70%), 30 (95%), 31 (95%), 32 (90%), 33 (90%), 34 (100%), 35 (95%), 36 (95%), 37 (95%), 38 (95%), 39 (95%), 40 (95%), 41 (90%), 42 (100%), 43 (95%), 45 (90%), 46 (90%), 47 (80%), 48 (70%), 49 (95%), 52 (95%), 53 (100%), 54 (95%), 55 (90%), 56 (95%), 57 (95%), 59 (80%), 61 (95%), 62 (95%), 63 (100%), 76 (95%), 77 (95%), 79 (100%), 80 (100%), 81 (90%), 82 (95%), 83 (80%), 84 (90%), 85 (95%), 86 (90%), 88 (95%), 96 (95%), 100 (95%), 101 (100%), 102 (100%).

Example E

Puccinia Test (Wheat)/Preventive

| Solvent: | 49 parts by weight of N,N-Dimethylformamide |
| --- | --- |
| Emulsifier: | 1 part by weight of Alkylarylpolyglycolether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Puccinia recondita*. The plants remain for 48 hours in an incubation cabinet at 22° C. and a relative atmospheric humidity of 100%. Then the plants are placed in a greenhouse at a temperature of approximately 20° C. and a relative atmospheric humidity of approximately 80%.

The test is evaluated 7-9 days after the inoculation. 0% means an efficacy which corresponds to that of the untreated control while an efficacy of 100% means that no disease is observed.

In this test the following compounds according to the invention showed efficacy of 70% or even higher at a concentration of 500 ppm of active ingredient: 4 (100%), 5 (100%), 6 (100%), 7 (100%), 8 (100%), 9 (100%), 10 (100%), 11 (100%), 12 (100%), 13 (95%), 14 (100%), 15 (95%), 16 (95%), 17 (100%), 18 (95%), 19 (95%), 20 (100%), 21 (89%), 22 (100%), 23 (95%), 24 (100%), 25 (100%), 26 (100%), 27 (100%), 28 (100%), 29 (95%), 30 (100%), 31 (100%), 32 (100%), 33 (100%), 34 (100%), 35 (100%), 36 (100%), 37 (100%), 38 (90%), 39 (100%), 40 (100%), 41 (95%), 42 (95%), 43 (100%), 44 (95%), 45 (90%), 46 (100%), 47 (95%), 48 (95%), 49 (95%), 52 (95%), 53 (95%), 54 (95%), 57 (95%), 61 (75%), 62 (90%), 63 (80%), 76 (95%), 77 (100%), 81 (100%), 82 (70%), 85 (78%), 86 (95%), 92 (78%).

Example F

Pyricularia Test (Rice)/Preventive

| Solvent: | 49 parts by weight of N,N-Dimethylformamide |
| --- | --- |
| Emulsifier: | 1 part by weight of Alkylarylpolyglycolether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with a preparation of active compound at the stated rate of application. One day after this treatment, the plants are inoculated with an aqueous spore suspension of *Pyricularia oryzae*. The plants remain for 48 hours in an incubation cabinet at 24° C. and a relative atmospheric humidity of 100%. Then the plants are placed in a greenhouse at a temperature of approximately 24° C. and a relative atmospheric humidity of approximately 80%.

The test is evaluated 7 days after the inoculation. 0% means an efficacy which corresponds to that of the untreated control, while an efficacy of 100% means that no disease is observed.

In this test the following compounds according to the invention showed efficacy of 70% or even higher at a concentration of 500 ppm of active ingredient: 1 (70%), 2 (90%), 3 (95%), 4 (100%), 5 (100%), 6 (94%), 7 (94%), 8 (94%), 9 (94%), 10 (94%), 11 (94%), 12 (100%), 13 (100%), 14 (94%), 15 (94%), 16 (94%), 17 (94%), 18 (94%), 19 (94%), 20 (94%), 21 (89%), 22 (94%), 23 (94%), 24 (94%), 25 (100%), 26 (94%), 27 (100%), 28 (94%), 29 (94%), 30 (94%), 31 (94%), 32 (94%), 33 (94%), 34 (94%), 35 (94%), 36 (94%), 37 (94%), 38 (94%), 39 (94%), 40 (94%), 41 (94%), 42 (94%), 43 (94%), 44 (78%), 45 (94%), 46 (94%), 47 (89%), 48 (78%), 49 (94%), 52 (95%), 53 (90%), 54 (90%), 55 (70%), 57 (70%), 59 (70%), 61 (70%), 62 (95%), 63 (95%), 76 (90%), 77 (90%), 80 (90%), 81 (95%), 82 (70%), 84 (90%), 85 (90%), 86 (80%), 88 (90%), 96 (70%), 100 (70%), 101 (80%), 102 (70%).

Example G

Phytophthora Test (Tomatoes)/Preventive

| Solvent: | 24.5 parts by weight of acetone |
| --- | --- |
|  | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Phytophthora infestans*. The plants are then placed in an incubation cabinet at approximately 20° C. and a relative atmospheric humidity of 100%.

The test is evaluated 3 days after the inoculation. 0% means an efficacy which corresponds to that of the untreated control, while an efficacy of 100% means that no disease is observed.

In this test the following compounds according to the invention showed efficacy of 70% or even higher at a concentration of 100 ppm of active ingredient: 2 (92%), 3 (92%), 4 (94%), 5 (95%), 6 (96%), 8 (95%), 9 (95%), 10 (95%), 17 (95%), 22 (95%), 25 (93%), 28 (95%), 35 (99%), 37 (95%), 52 (95%), 53 (95%), 54 (99%), 55 (91%), 57 (95%), 61 (71%), 62 (95%), 63 (95%), 77 (100%), 79 (95%), 82 (85%), 85 (95%), 86 (98%), 104 (93%), 105 (95%).

Example H

Plasmopara Test (Grapevines)/Preventive

| Solvent: | 24.5 parts by weight of acetone |
| --- | --- |
|  | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Plasmopara viticola* and then remain for 1 day in an incubation cabinet at approximately 20° C. and a relative atmospheric humidity of 100%. The plant is subsequently placed for 4 days in a greenhouse at approximately 21° C. and a relative atmospheric humidity of approximately 90%. The plants are then misted and placed for 1 day in an incubation cabinet.

The test is evaluated 6 days after the inoculation. 0% means an efficacy which corresponds to that of the untreated control, while an efficacy of 100% means that no disease is observed.

In this test the following compounds according to the invention showed efficacy of 70% or even higher at a concentration of 100 ppm of active ingredient: 4 (100%), 5 (100%), 6 (94%), 8 (100%), 9 (94%), 10 (94%), 11 (86%), 17 (100%), 22 (100%), 25 (98%), 28 (92%), 35 (95%), 37 (100%), 52 (84%), 53 (98%), 54 (100%), 57 (90%), 61 (100%), 62 (100%), 63 (95%), 76 (100%), 77 (100%), 79 (88%), 81 (100%), 82 (100%), 85 (97%), 86 (100%), 104 (95%), 105 (100%).

Example I

Venturia Test (Apples)/Preventive

| Solvent: | 24.5 parts by weight of acetone |
| --- | --- |
|  | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous conidia suspension of the causal agent of apple scab (*Venturia inaequalis*) and then remain for 1 day in an incubation cabinet at approximately 20° C. and a relative atmospheric humidity of 100%.

The plants are then placed in a greenhouse at approximately 21° C. and a relative atmospheric humidity of approximately 90%.

The test is evaluated 10 days after the inoculation. 0% means an efficacy which corresponds to that of the untreated control, while an efficacy of 100% means that no disease is observed.

In this test the following compounds according to the invention showed efficacy of 70% or even higher at a concentration of 100 ppm of active ingredient: 4 (95%), 5 (98%), 6 (100%), 8 (98%), 9 (100%), 10 (99%), 11 (100%), 17 (100%), 22 (99%), 25 (100%), 28 (98%), 35 (100%), 37 (100%), 52 (98%), 53 (100%), 54 (95%), 55 (93%), 57 (98%), 61 (96%), 62 (100%), 63 (100%), 76 (100%), 77 (96%), 79 (96%), 81 (99%), 82 (94%), 85 (97%), 86 (100%), 104 (93%), 105 (93%).

Example J

Septoria tritici-Test (Wheat)/Preventive

| Solvent: | 49 parts by weight of N,N-dimethylacetamide |
| --- | --- |
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are sprayed with a spore suspension of *Septoria tritici*. The plants remain for 48 hours in an incubation cabinet at approximately 20° C. and a relative atmospheric humidity of approximately 100% and afterwards for 60 hours at approximately 15° C. in a translucent incubation cabinet at a relative atmospheric humidity of approximately 100%.

The plants are placed in the greenhouse at a temperature of approximately 15° C. and a relative atmospheric humidity of approximately 80%.

The test is evaluated 21 days after the inoculation. 0% means an efficacy which corresponds to that of the untreated control, while an efficacy of 100% means that no disease is observed.

In this test the following compounds according to the invention showed an efficacy of 70% or even higher at a concentration of 500 ppm of active ingredient: 4 (80%), 5 (92%), 6 (100%), 8 (80%), 9 (80%), 10 (86%), 11 (70%), 12 (100%), 13 (100%), 14 (100%), 22 (100%), 24 (100%), 25 (80%), 27 (100%), 28 (88%), 31 (100%), 34 (88%), 35 (100%), 36 (88%), 37 (88%), 43 (88%), 46 (88%), 52 (100%), 53 (75%), 54 (100%), 57 (100%), 62 (75%), 63 (94%), 76 (86%), 77 (71%), 81 (88%), 84 (88%), 85 (86%).

Example K

*Fusarium nivale* (Var. *majus*)-Test (Wheat)/Preventive

| | |
|---|---|
| Solvent: | 49 parts by weight of N,N-dimethylacetamide |
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are slightly injured by using a sandblast and afterwards they are sprayed with a conidia suspension of *Fusarium* nivale (var. *majus*).

The plants are placed in the greenhouse under a translucent incubation cabinet at a temperature of approximately 10° C. and a relative atmospheric humidity of approximately 100%.

The test is evaluated 5 days after the inoculation. 0% means an efficacy which corresponds to that of the untreated control, while an efficacy of 100% means that no disease is observed.

In this test the following compounds according to the invention showed an efficacy of 70% or even higher at a concentration of 500 ppm of active ingredient: 4 (100%), 5 (100%), 6 (100%), 8 (93%), 9 (93%), 10 (100%), 11 (100%), 12 (93%), 14 (100%), 17 (100%), 22 (100%), 24 (100%), 25 (100%), 28 (100%), 31 (100%), 34 (75%), 35 (100%), 36 (88%), 37 (100%), 43 (88%), 52 (100%), 53 (100%), 54 (100%), 57 (100%), 62 (100%), 63 (100%), 76 (100%), 77 (90%), 81 (100%), 84 (100%), 85 (100%).

Example L

*Fusarium graminearum*-Test (Barley)/preventive

| | |
|---|---|
| Solvent: | 49 parts by weight of N,N-dimethylacetamide |
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are slightly injured by using a sandblast and afterwards they are sprayed with a conidia suspension of *Fusarium graminearum*.

The plants are placed in the greenhouse under a translucent incubation cabinet at a temperature of approximately 22° C. and a relative atmospheric humidity of approximately 100%.

The test is evaluated 5 days after the inoculation. 0% means an efficacy which corresponds to that of the untreated control, while an efficacy of 100% means that no disease is observed.

In this test the following compounds according to the invention showed an efficacy of 70% or even higher at a concentration of 500 ppm of active ingredient: 4 (100%), 5 (100%), 6 (100%), 8 (100%), 9 (100%), 10 (90%), 11 (100%), 12 (86%), 13 (71%), 14 (86%), 22 (100%), 24 (90%), 25 (100%), 27 (86%), 28 (86%), 31 (86%), 34 (86%), 35 (100%), 36 (100%), 37 (100%), 43 (100%), 46 (86%), 52 (100%), 53 (100%), 54 (100%), 57 (100%), 62 (100%), 63 (88%), 76 (86%), 77 (100%), 81 (100%), 84 (83%), 85 (71%).

Example M

In Vivo Preventive Test on *Alternaria brassicae*

Leaf Spot on Radish

The active ingredients tested are prepared by homogenization in a mixture of acetone/tween/DMSO, and then diluted with water to obtain the desired active material concentration.

Radish plants ("Pernod Clair" variety), sown in starter cups on a 50/50 peat soil-pozzolana substrate and grown at 17° C., are treated at the 2-leaf stage by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Alternaria brassicae* spores (50 000 spores per ml). The spores are collected from a 15-day-old culture. The contaminated rice plants are incubated at 20° C. and at 100% relative humidity.

Grading (% of efficacy) is carried out 5 days after the contamination, in comparison with the control plants.

Under these conditions, good (at least 70%) or total protection is observed at a dose of 500 ppm with the following compounds: 103 (93%), 104 (79%), 105 (93%), 106 (79%).

Example N

In Vivo Preventive Test on *Botrytis cinerea*

Grey Mould

The active ingredients tested are prepared by homogenization in a mixture of acetone/tween/DMSO and then diluted with water to obtain the desired active material.

Gherkin plants ("Vert petit de Paris" variety), sown in starter cups on a 50/50 peat soil-pozzolana substrate and grown at 24° C., are treated at the Z11 cotyledon stage by spraying with the active ingredient prepared as described above. Plants, used as controls, are treated with the mixture of acetone/tween/DMSO/water not containing the active material.

After 24 hours, the plants are contaminated by spraying the cotyledons with an aqueous suspension of cryopreserved *Botrytis cinerea* spores (50 000 spores per ml). The spores are suspended in a nutrient solution composed of 10 g/L of PDB, 50 g/L of D-Fructose, 2 g/L of NH4NO3 and 1 g/L of KH2PO4. The contaminated gherkin plants are incubated at 17° C. and at 80% relative humidity.

Grading (% of efficacy) is carried out 4-5 days after the contamination, in comparison with the control plants.

Under these conditions, good (at least 70%) or total protection is observed at a dose of 500 ppm with the following compounds: 64 (100%), 68 (80%), 69 (100%), 103 (80%), 104 (85%), 105 (100%), 106 (100%).

Example O

In Vivo Preventive Test on *Phytophthora infestans*

Tomato Late Blight

The active ingredients tested are prepared by homogenization in a mixture of acetone/tween/DMSO and then diluted with water to obtain the desired active material.

Tomato plants ("Rentita" variety), sown in started cups on a 50/50 peat soil-pozzolana substrate and grown at 20-25° C., are treated at the Z12 leaf stage by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Phytophthora infestans* spores (20 000 spores per ml). The spores are collected from infected plants. The contaminated tomato plants are incubated at 16-18° C., under a humid atmosphere.

Grading (% of efficacy) is carried out 5 days after the contamination, in comparison with the control plants.

Under these conditions, good protection (at least 70%) is observed at a dose of 500 ppm with the following compounds: 72 (75%), 73 (85%), 74 (79%), 75 (95%).

Example P

In Vivo Preventive Test on *Pyrenophora teres*

Net Blotch on Barley

The active ingredients tested are prepared by homogenization in a mixture of acetone/tween/DMSO, and then diluted with water to obtain the desired active material concentration.

Barley plants ("Plaisant" variety), sown in starter cups on a 50/50 peat soil-pozzolana substrate and grown at 22° C. (12 h)/20° C. (12 h), are treated at the 1-leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Pyrenophora teres* spores (12 000 spores per ml). The spores are collected from a 12-day-old culture. The contaminated barley plants are incubated for 48 hours at 20° C. and at 100% relative humidity, and then for 12 days at 80% relative humidity.

Grading (% of efficacy) is carried out 12 days after the contamination, in comparison with the control plants.

Under these conditions, good (at least 70%) or total protection is observed at a dose of 500 ppm with the following compounds: 65 (71%), 69 (79%), 72 (94%), 73 (94%), 74 (81%), 75 (98%), 105 (81%).

Example Q

In Vivo Preventive Test on *Pyricularia oryzae*

Rice Blast

The active ingredients tested are prepared by homogenization in a mixture of acetone/tween/DMSO, and then diluted with water to obtain the desired active material concentration.

Rice plants ("Koshihikari" variety), sown in starter cups on a 50/50 peat soil-pozzolana substrate and grown at 25° C., are treated at the 2-leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Pyricularia oryzae* spores (40 000 spores per ml). The spores are collected from a 17-day-old culture and are suspended in water containing 2.5 g/l of gelatin. The contaminated rice plants are incubated at 25° C. and at 80% relative humidity.

Grading (% of efficacy) is carried out 6 days after the contamination, in comparison with the control plants.

Under these conditions, good (at least 70%) or total protection is observed at a dose of 500 ppm with the following compounds: 64 (80%), 65 (80%), 66 (80%), 68 (80%), 69 (100%), 72 (80%), 73 (90%), 74 (80%), 75 (90%), 89 (75%), 95 (83%), 104 (75%).

Example R

In Vivo Preventive Test on *Puccinia recondita*

Brown Rust on Wheat

The active ingredients tested are prepared by homogenization in a mixture of acetone/tween/DMSO, and then diluted with water to obtain the desired active material concentration.

Wheat plants ("Scipion" variety), sown in starter cups on a 50/50 peat soil-pozzolana substrate and grown at 22° C. (12 h)/20° C. (12 h), are treated at the 1-leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Puccinia recondita* spores (100 000 spores per ml). The spores are collected from an infected plant and are suspended in water containing 2.5 ml/l of Tween 80 at 10%. The contaminated wheat plants are incubated for 24 hours at 20° C. and at 100% relative humidity, and then for 10 days at 20° C. and at 70% relative humidity.

Grading (% of efficacy) is carried out 10 days after the contamination, in comparison with the control plants.

Under these conditions, good (at least 70%) or total protection is observed at a dose of 500 ppm with the following compounds: 64 (81%), 66 (81%), 68 (81%), 69 (81%), 72 (98%), 73 (88%), 74 (88%), 75 (88%), 105 (75%).

Example S

In Vivo Preventive Test on *Septoria tritici*

Leaf Spot on Wheat

The active ingredients tested are prepared by homogenization in a mixture of acetone/tween/DMSO, and then diluted with water to obtain the desired active material concentration.

Wheat plants ("Scipion" variety), sown in starter cups on a 50/50 peat soil-pozzolana substrate and grown at 22° C. (12 h)/20° C. (12 h), are treated at the 1-leaf stage (10 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of cryopreserved *Septoria tritici* spores (500 000 spores per ml). The contaminated wheat plants are incubated for 72 hours at 18° C. and at 100% relative humidity, and then for 21 to 28 days at 90% relative humidity.

Grading (% of efficacy) is carried out 21 to 28 days after the contamination, in comparison with the control plants.

Under these conditions, good (at least 70%) or total protection is observed at a dose of 500 ppm with the following compounds: 64 (86%), 66 (79%), 68 (93%), 72 (75%).

Example T

In Vivo Preventive Test on *Sphaerotheca fuliginea*

Powdery Mildew on Cucurbits

The active ingredients tested are prepared by homogenization in a mixture of acetone/tween/DMSO and then diluted with water to obtain the desired active material.

Gherkin plants ("Vert petit de Paris" variety), sown in starter cups on a 50/50 peat soil-pozzolana substrate and grown at 24° C., are treated at the Z11 cotyledon stage by spraying with the active ingredient prepared as described above. Plants, used as controls, are treated with the mixture of acetone/tween/DMSO/water not containing the active material.

After 24 hours, the plants are contaminated by spraying the cotyledons with an aqueous suspension of *Sphaerotheca fuliginea* spores (100 000 spores per ml). The spores are collected from infected plants. The contaminated gherkin plants are incubated at about 20° C./25° C. and at 60/70% relative humidity.

Grading (% of efficacy) is carried out 12 days after the contamination, in comparison with the control plants.

Under these conditions, good (at least 70%) or total protection is observed at a dose of 500 ppm with the following compounds: 64 (100%), 66 (94%), 68 (89%), 69 (100%), 72 (100%), 73 (100%), 74 (94%), 75 (100%), 106 (98%).

Example U

In Vivo Preventive Test on *Uromyces appendiculatus*

Bean Rust

The active ingredients tested are prepared by homogenization in a mixture of acetone/tween/DMSO, and then diluted with water to obtain the desired active material concentration.

Bean plants ("Saxa" variety), sown in starter cups on a 50/50 peat soil-pozzolana substrate and grown at 24° C., are treated at the 2-leaf stage (9 cm height) by spraying with the active ingredient prepared as described above. Plants, used as controls, are treated with the mixture of acetone/tween/DMSO/water not containing the active material.

After 24 hours, the plants are contaminated by spraying the leaves with an aqueous suspension of *Uromyces appendiculatus* spores (150 000 spores per ml). The spores are collected from an infected plant and are suspended in water containing 2.5 ml/l of Tween 80 at 10%. The contaminated bean plants are incubated for 24 hours at 20° C. and at 100% relative humidity, and then for 10 days at 20° C. and at 70% relative humidity.

Grading (% of efficacy) is carried out 10 days after the contamination, in comparison with the control plants.

Under these conditions, good (at least 70%) or total protection is observed at a dose of 500 ppm with the following compounds: 72 (96%), 73 (86%), 75 (100%), 104 (88%), 105 (96%), 106 (81%).

Example V

Production of DON/Acetyl-DON by *Fusarium graminearum*

Compounds were tested in microtiter plates in 7 concentrations ranging from 0.07 µM to 50 µM in DON-inducing liquid media (1 g $(NH_4)_2HPO_4$, 0.2 g $MgSO_4 \times 7H_2O$, 3 g $KH_2PO_4$, 10 g Glycerin, 5 g NaCl and 40 g Sachharose per liter), supplemented with 10% oat extract, containing 0.5% DMSO, inoculated with a concentrated spore suspension of *Fusarium graminearum* to a final concentration of 2000 spores/ml.

The plate was covered and incubated at high humidity at 28° C. for 7 days.

At start and after 3 days OD measurement at OD620 multiple read per well (square: 3×3) was taken to calculate the growth inhibition.

After 7 days 100 µl 84/16 acetonitrile/water was added to each well and a sample of the liquid medium was taken and diluted 1:100 in 10% acetonitrile. The amounts of DON and Acetyl-DON of the samples were analysed per HPLC-MS/MS and results were used to calculate inhibition of DON/AcDON production in comparison to a control without compound.

HPLC-MS/MS was done with the following parameters:
Ionization mode: ESI negative
Ionspray voltage: −4500V
Spraygas Temperature: 500° C.
Declustering potential: −40V
Collision energy: −22 eV
Collision gas: $N_2$
MRM trace: 355.0>264.9; dwell time 150 ms
HPLC column: Waters Atlantis T3 (trifunctional C18 bonding, fully endcapped)
Particle size: 3 µm
Column size: 50×2 mm
Temperature: 40° C.
Solvent A: Water/2.5 mM $NH_4OAc$+0.05% $CH_3COOH$ (v/v)
Solvent B: Methanol/2.5 mM $NH_4OAc$+0.05% $CH_3COOH$ (v/v)
Flow: 400 µL/min
Injection volume: 11 µL Gradient:

| Time [min] | A % | B % |
|---|---|---|
| 0 | 100 | 0 |
| 0.75 | 100 | 0 |
| 1.5 | 5 | 95 |
| 4 | 5 | 95 |
| 5 | 100 | 0 |
| 10 | 100 | 0 |

Examples for Inhibition of DON/AcDON Production

The compounds listed below showed an activity of >80% of inhibition of DON/AcDON at 50 µM. Growth inhibition of *Fusarium graminearum* of these examples varied from 55 to 100% at 50 µM.

| Ex_no. | Inhibition of DON/AcDON in % | Growth inhibition of Fusarium graminearum in % |
|---|---|---|
| 1 | 98 | 90 |
| 2 | 100 | 57 |
| 3 | 98 | 57 |
| 4 | 99 | 69 |
| 5 | 100 | 62 |
| 9 | 100 | 100 |
| 10 | 100 | 95 |
| 14 | 100 | 95 |
| 22 | 100 | 99 |
| 24 | 94 | 91 |
| 28 | 99 | 94 |
| 35 | 99 | 100 |
| 39 | 99 | 89 |
| 40 | 99 | 85 |
| 43 | 100 | 89 |
| 45 | 100 | 78 |
| 51 | 100 | 90 |
| 53 | 100 | 79 |
| 55 | 100 | 100 |
| 57 | 100 | 76 |
| 62 | 99 | 86 |
| 64 | 98 | 83 |
| 69 | 96 | 83 |
| 70 | 90 | 76 |
| 72 | 100 | 77 |
| 73 | 100 | 83 |
| 75 | 100 | 88 |
| 77 | 100 | 91 |
| 80 | 100 | |
| 82 | 100 | 100 |
| 85 | 99 | |
| 86 | 99 | 100 |
| 88 | 70 | 55 |
| 92 | 99 | |
| 95 | 97 | 77 |
| 101 | 100 | 93 |
| 105 | 99 | 83 |
| 106 | 95 | 65 |

The invention claimed is:

1. Heterocyclylpyri(mi)dinylpyrazole of formula (I)

in which
U represents a structure of formula $X^1$ represents C—H or N,
$X^2$ represents S or O,
Y represents O, S or N with N being optionally substituted by $R^5$,
W represents C, N each of which is optionally substituted by identical or different substituents selected from the group consisting of $R^5$
or represents O if Y equals N,
a,b represent a single or double bond
with the proviso that "a" and "b" represent a single bond if W equals O, "a" represents a single bond if Q equals C=C or C—Si and "b" represents a single bond if Y equals O or S,
n is 0,1,2, 3 or 4,
Q represents C, C—C, C=C, C—Si or C—C—C, each of which is optionally mono or polysubstituted by identical or different substituents selected from the group consisting of $R^5$,
$R^1$ represents H, $C(O)OR^7$, $C(O)SR^7$, $C(S)OR^7$, $C(O)R^7$, $C(S)R^7$, $C(O)NR^7R^8$, $C(S)NR^7R^8$, $C(O)C(O)R7$, $C(=NR^9)R^{10}$, $C(=NR^9)OR^{10}$, $C(=NR^9)NR^9R^{10}$, $SO(=NR^9)R^{10}$, $SO_2NR^7R^8$, $SO_2R^7$
or represents $C_1$-$C_6$-alkyl, $C_3$-$C_8$-cycloalkyl, $C_2$-$C_6$-alkenyl, $C_2$-$C_8$-alkynyl, $C_6$-$C_{14}$-aryl, $C_2$-$C_9$-heterocyclyl, $C_2$-$C_9$-heteroaryl, each of which is optionally mono- or polysubstituted by identical or different substituents selected from the group consisting of $R^{11}$,
$R^2$ represents H, cyano, formyl, $OR^7$, $SR^7$, $C(O)OR^7$, $C(O)SR^7$, $C(S)OR^7$, $C(O)R^7$, $C(S)R^7$
or represents $C_1$-$C_6$-alkyl, $C_3$-$C_8$-cycloalkyl, $C_2$-$C_6$-alkenyl, $C_2$-$C_8$-alkynyl, $C_6$-$C_{14}$-aryl, $C_2$-$C_9$-heterocyclyl, $C_2$-$C_9$-heteroaryl, each of which is optionally mono- or polysubstituted by identical or different substituents selected from the group consisting of $R^{11}$,
with the proviso that $R^1$ is not H, $C_1$-$C_6$-alkyl, $C_3$-$C_8$-cycloalkyl, $C_1$-$C_6$-haloalkyl, $C_3$-$C_8$-halocycloalkyl, $C_1$-$C_4$-alkoxy-$C_1$-$C_6$-alkyl or amino-$C_1$-$C_6$-alkyl if $R^2$ is H, $C_1$-$C_6$-alkyl, $C_3$-$C_8$-cycloalkyl, $C_1$-$C_6$-haloalkyl, $C_3$-$C_8$-halocycloalkyl, $C_1$-$C_4$-alkoxy-$C_1$-$C_6$-alkyl or amino-$C_1$-$C_6$-alkyl and vice-versa, $R^3$ and $R^4$ represent independently of each other H, F, Cl, Br, I, cyano, nitro, OH, SH or represent $C_1$-$C_6$-alkyl, $C_3$-$C_6$-cycloalkyl, $C_2$-$C_6$-alkenyl, $C_2$-$C_6$-alkinyl, $C_6$-$C_{14}$-aryl, $C_1$-$C_4$-alkoxy, O—($C_6$-$C_{14}$-aryl), S—($C_1$-$C_4$-alkyl), S(O)—($C_1$-$C_6$-alkyl), C(O)—($C_1$-$C_6$-alkyl), $C_3$-$C_8$-trialkylsilyl, heteroaryl, heterocyclyl, each of which is optionally mono- or polysubstituted by identical or different substituents selected from the group consisting of $R^{11}$ or form together with the carbon atoms, which they are attached to, an optionally mono- or multi identical or different by halogen, oxygen, cyano or $C_1$-$C_4$-alkyl, $C_1$-$C_4$-alkoxy, $C_1$-$C_6$-haloalkyl, $C_1$-$C_4$-haloalkoxy, $C_3$-$C_6$-cycloalkyl substituted cycle with 5 to 8 ring atoms, whereas the cycle comprises carbon atoms but may also contain 1 to 4 heteroatoms selected from oxygen, sulphur or $NR^{14}$, $R^5$ represents as substituent for C: H, Cyano, Halogen, OH, =O, $C_1$-$C_6$-alkyl, $C_2$-$C_6$-alkenyl, $C_2$-$C_6$-alkinyl, $C_1$-$C_6$-alkoxy, $C_3$-$C_6$-cycloalkyl, $C_3$-$C_8$-allenyl, $C_3$-$C_8$-trialkylsilyl, $C_4$-$C_8$-cycloalkenyl, $C_1$-$C_6$-alkoxy-$C_1$-$C_6$-alkyl, acyloxy-$C_1$-$C_6$-alkyl, heteroaryl-$C_1$-$C_6$-alkyl, aryl-$C_1$-$C_6$-alkyl, $C_1$-$C_6$-alkylthio-$C_1$-$C_6$-alkyl, $C_1$-$C_4$-alkyl-C(O)—$C_1$-$C_6$-alkyl, $C_3$-$C_6$-cycloalkyl-C(O)—$C_1$-$C_4$-alkyl, heterocyclyl-C(O)—$C_1$-$C_4$-alkyl, $C_1$-$C_4$-alkyl-C(O)O—$C_1$-$C_6$-alkyl, $C_3$-$C_6$-cycloalkyl-C(O)O—$C_1$-$C_4$-alkyl, heterocyclyl-C(O)O— $C_1$-$C_4$-alkyl, heterocyclyl-$C_1$-$C_6$-alkyl, $C_6$-$C_{10}$-aryl, heterocyclyl, heteroaryl, each of which is optionally mono- or polysubstituted by identical or different substituents selected from the group consisting of OH, F, Cl, Br, I, cyano, NH—C(O)$R^9$, $NR^9R^{10}$, C(O)$R^9$, C(O)O$R^9$, C(O)$NR^9R^{10}$, SO$_2R^9$, OC(O)$R^9$ or represents C(O)$NR^9R^{10}$, C(O)$R^9$, C(O)O$R^9$, S(O)$_2R^9$, C(S)$NR^9R^{10}$, C(S)$R^9$, S(O)$_2NR^9R^{10}$, =N(O$R^9$)

and represents as substituent for N: H, OH, $C_1$-$C_6$-alkyl, $C_2$-$C_6$-alkenyl-$C_1$-$C_6$-alkyl, $C_2$-$C_6$-alkinyl-$C_1$-$C_6$-alkyl, $C_1$-$C_6$-alkoxy, $C_3$-$C_6$-cycloalkyl, $C_1$-$C_6$-alkoxy-$C_1$-$C_6$-alkyl, acyloxy-$C_1$-$C_6$-alkyl, heteroaryl-$C_1$-$C_6$-alkyl, aryl-$C_1$-$C_6$-alkyl, $C_1$-$C_6$-alkylthio-$C_1$-$C_6$-alkyl, $C_1$-$C_4$-alkyl-C(O)—$C_1$-$C_6$-alkyl, $C_3$-$C_6$-cycloalkyl-C(O)—$C_1$-$C_4$-alkyl, heterocyclyl-C(O)—$C_1$-$C_4$-alkyl, $C_1$-$C_4$-alkyl-C(O)O—$C_1$-$C_6$-alkyl, $C_3$-$C_6$-cycloalkyl-C(O)O—$C_1$-$C_4$-alkyl, heterocyclyl-C(O)O— $C_1$-$C_4$-alkyl, heterocyclyl-$C_1$-$C_6$-alkyl, $C_6$-$C_{10}$-aryl, heterocyclyl, heteroaryl, each of which is optionally mono- or polysubstituted by identical or different substituents selected from the group consisting of OH, F, Cl, Br, I, cyano, NH—C(O)$R^9$, $NR^9R^{10}$, C(O)$R^9$, C(O)O$R^9$, C(O)$NR^9R^{10}$, SO$_2R^9$, OC(O)$R^9$ or represents C(O)$NR^9R^{10}$, C(O)$R^9$, C(O)O$R^9$, S(O)$_2R^9$, C(S)$NR^9R^{10}$, C(S)$R^9$, S(O)$_2NR^9R^{10}$ $R^6$ represents H, cyano, halogen or represents $C_1$-$C_6$-alkyl, $C_3$-$C_6$-cycloalkyl, heterocyclyl, $C_2$-$C_8$-alkenyl, $C_2$-$C_8$-alkinyl, $C_1$-$C_8$-alkoxy, $C_2$-$C_8$-alkynyloxy, $C_1$-$C_8$-alkylthio, $C_3$-$C_8$-trialkylsilyl, each of which is optionally mono- or polysubstituted by identical or different substituents selected from the group consisting of OH, F, Cl, cyano, $R^7$ and $R^8$ represent H, C(S)$R^{12}$, C(O)$R^{12}$, SO$_2R^{12}$, C(O)O$R^{12}$, O$R^{12}$ or C(O)$NR^{12}R^{13}$ or represent $C_1$-$C_6$-alkyl, $C_2$-$C_6$-alkenyl, $C_2$-$C_6$-alkinyl, $C_3$-$C_8$-cycloalkyl, $C_3$-$C_8$-cycloalkenyl, having a two to eight atoms long bridge containing C and O atoms in which two O atoms never follow one another, $C_6$-$C_{14}$-aryl, benzyl, phenethyl, indanyl, aryloxyalkyl, heteroaryloxyalkyl, heterocyclyl or heteroaryl, each of which is optionally mono- or polysubstituted by identical or different substituents selected from the group consisting of F, Cl, Br, OH, =O, cyano, nitro, $C_1$-$C_6$-alkyl, $C_3$-$C_8$-cycloalkyl, $C_1$-$C_6$-halogenalkyl, O—C(O)$R^9$, O—P(O)(O$R^9$)$_2$, O—B(O$R^9$)$_2$ or O—($C_1$-$C_4$-alkyl), O—($C_3$-$C_8$-cycloalkyl), S—($C_1$-$C_4$-alkyl), SO—($C_1$-$C_4$-alkyl), SO$_2$—($C_1$-$C_4$-alkyl), piperidin, $C_1$-$C_6$-alkylsulfinyl, ($C_1$-$C_6$-alkyl ideneamino)oxy, aryl, heteroaryl, heterocyclyl, alkoxyalkyloxy, NHC(O)H, C(O)$R^9$, C(O)O$R^9$ which is optionally mono- or polysubstituted by identical or different substituents selected from the group consisting of F, Cl, Br, OH, cyano, $C_1$-$C_6$-alkyl, $R^9$ and $R^{10}$ represent $C_1$-$C_6$-alkyl, $C_3$-$C_6$-cycloalkyl, $C_2$-$C_6$-alkenyl, $C_2$-$C_6$-alkinyl, aryl, benzyl, phenethyl, each of which is optionally mono- or polysubstituted by identical or different substituents selected from the group consisting of F, Cl, Br, I, OH, carbonyl, cyano or represent H, $R^{11}$ represents OH, F, Cl, Br, I, cyano, =O, NH—C(O)$R^9$, $NR^9R^{10}$, C(O)$R^9$, C(O)O$R^9$, C(O)$NR^9R^{10}$, SO$_2R^9$, OC(O)$R^9$ or represents $C_1$-$C_6$-alkyl, $C_2$-$C_6$-alkenyl, $C_2$-$C_6$-alkinyl, $C_3$-$C_8$-cycloalkyl, $C_1$-$C_4$-alkoxy, $C_1$-$C_4$-alkylthio, O—($C_3$-$C_8$-cycloalkyl), S—($C_3$-$C_8$-cycloalkyl), $C_6$-$C_{14}$-aryl, O—($C_6$-$C_{14}$-aryl), S—($C_6$-$C_{14}$-aryl), heterocyclyl or heteroaryl, each of which is optionally mono- or polysubstituted by identical or different substituents selected from the group consisting of F, Cl, Br, I, OH, carbonyl, cyano, $C_1$-$C_6$-alkyl or $C_1$-$C_4$-alkoxy, $R^{12}$ and $R^{13}$ represent H or represents $C_1$-$C_6$-alkyl, $C_3$-$C_6$-cycloalkyl, $C_2$-$C_6$-alkenyl, $C_2$-$C_6$-alkinyl, $C_3$-$C_8$-cycloalkyl, $C_6$-$C_{14}$-aryl, heterocyclyl oder heteroaryl, each of which is optionally mono- or polysubstituted by identical or different substituents selected from the group consisting of F, Cl, Br, I, OH, carbonyl, cyano, $C_1$-$C_6$-alkyl or $C_1$-$C_4$-alkoxy, $R^{14}$ represents H, $C_1$-$C_6$-alkyl, $C_3$-$C_6$-cycloalkyl, $C_2$-$C_6$-alkenyl, $C_2$-$C_6$-alkinyl, C(S)$R^{15}$, C(O)$R^{15}$, SO$_2R^{15}$, C(O)O$R^{15}$, $R^{15}$ represent H or represents $C_1$-$C_6$-alkyl, $C_3$-$C_6$-cycloalkyl, $C_2$-$C_6$-alkenyl, $C_2$-$C_6$-alkinyl, $C_3$-$C_8$-cycloalkyl, $C_6$-$C_{14}$-aryl, benzyl, phenethyl, phenoxymethyl, heterocyclyl or heteroaryl, each of which is optionally mono- or polysubstituted by identical or different substituents selected from the group consisting of F, Cl, Br, I, OH, carbonyl, cyano, methyl, ethyl, n-propyl, iso-propyl, n-butyl, iso-butyl, sec-butyl, tert-butyl, n-pentyl, cyclopropyl, or methoxy, ethoxy, n-propoxy, iso-propoxy, n-butoxy, tert-butoxy, methylsulfanyl, nitro, trifluormethyl, difluormethyl, C(O)$R^{12}$, C(O)O$R^{12}$, C(O)$NR^{12}R^{13}$, SO$_2R^{12}$, OC(O)$R^{12}$ and/or an agrochemically active salt thereof.

2. The heterocyclylpyri(mi)dinylpyrazole of the formula (I) as claimed in claim 1,
in which
U represents a structure of formula

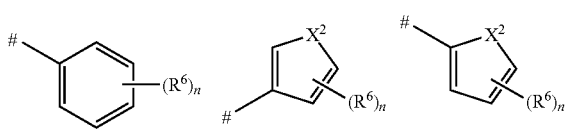

$X^1$ represents C—H, $X^2$ represents S or O,

Y represents 0 or N with N being optionally substituted by $R^5$,

W represents C, N each of which is optionally substituted by identical or different substituents selected from the group consisting of $R^5$ or represents 0 if Y equals N, a,b represent a single or double bond with the proviso that "a" and "b" represent a single bond if W equals 0, "a" represents a single bond if Q equals C=C or C—Si and "b" represents a single bond if Y equals 0, n is 0,1,2, 3 or 4, Q represents C, C—C, C=C, C—Si or C—C—C, each of which is optionally mono or polysubstituted by identical or different substituents selected from the group consisting of $R^5$, $R^1$ represents H, $C(O)OR^7$, $C(O)SR^7$, $C(S)OR^7$, $C(O)R^7$, $C(S)R^7$, $C(O)C(O)R7$, $C(O)NR^7R^8$, $C(S)NR^7R^8$, $C(=NR^9)R^{10}$, $C(=NR^9)OR^{10}$, $C(=NR^9)NR^9R^{10}$, $SO(=NR^9)R^{10}$, $SO_2NR^7R^8$, $SO_2R^7$ or represents methyl, ethyl, n-propyl, iso-propyl, n-butyl, iso-butyl, sec-butyl, tert-butyl, n-pentyl, cyclopropyl, cyclobutyl, cyclopentyl, cyclohexyl, —CH$_2$CH=CH$_2$, —C≡CH, —C≡CCH$_3$, —CH$_2$C≡CH, $C_6$-$C_{14}$-aryl, $C_2$-$C_9$-heterocyclyl, $C_2$-$C_9$-heteroaryl, each of which is optionally mono- or polysubstituted by identical or different substituents selected from the group consisting of $R^{11}$, $R^2$ represents H, $C(O)OR^7$, $C(O)SR^7$, $C(S)OR^7$, $C(O)R^7$, $C(S)R^7$ or represents $C_1$-$C_6$-alkyl, $C_3$-$C_8$-cycloalkyl, $C_2$-$C_6$-alkenyl, $C_2$-$C_8$-alkynyl, $C_6$-$C_{14}$-aryl, $C_2$-$C_9$-heterocyclyl, $C_2$-$C_9$-heteroaryl, each of which is optionally mono- or polysubstituted by identical or different substituents selected from the group consisting of $R^{11}$, with the proviso that $R^1$ is not H, $C_1$-$C_6$-alkyl, $C_3$-$C_8$-cycloalkyl, $C_1$-$C_6$-haloalkyl, $C_3$-$C_8$-halocycloalkyl, $C_1$-$C_4$-alkoxy-C1-$C_6$-alkyl or amino-$C_1$-$C_6$-alkyl if $R^2$ is H, $C_1$-$C_6$-alkyl, $C_3$-$C_8$-cycloalkyl, $C_1$-C6-haloalkyl, $C_3$-$C_8$-halocycloalkyl, $C_1$-$C_4$-alkoxy-$C_1$-$C_6$-alkyl or amino-$C_1$-$C_6$-alkyl and vice-versa, $R^3$ and $R^4$ represent independently of each other H, F, Cl, Br, I, cyano or represents methyl, ethyl, cyclopropyl, —CH=CH$_2$, —CH$_2$CH=CH$_2$, —CH$_2$C≡CH, —C≡CH, phenyl, methoxy, each of which is optionally mono- or polysubstituted by identical or different substituents selected from the group consisting of $R^{11}$, $R^5$ represents as substituent for C: H, Cyano, Halogen, OH, =O, methyl, ethyl, n-propyl, iso-propyl, n-butyl, iso-butyl, sec-butyl, tert-butyl, n-pentyl, cyclopropyl, cyclobutyl, cyclopentyl, cyclohexyl, —CH$_2$CH=CH$_2$, —C≡CH, —C≡CCH$_3$, —CH$_2$C≡CH, methoxy, ethoxy, n-propoxy, iso-propoxy, n-butoxy, tert-butoxy, —O—CH$_2$C≡CH, each of which is optionally mono- or polysubstituted by identical or different substituents selected from the group consisting of OH, F, Cl, cyano or represents $C(O)NR^9R^{10}$, $C(O)R^9$, $C(O)OR^9$, $S(O)_2R^9$, $C(S)NR^9R^{10}$, $C(S)R^9$, $S(O)_2NR^9R^{10}$, =N(OR$^9$) and represents as substituent for N: H, methyl, ethyl, n-propyl, iso-propyl, n-butyl, iso-butyl, sec-butyl, tert-butyl, n-pentyl, cyclopropyl, cyclobutyl, cyclopentyl, cyclohexyl, —CH$_2$CH=CH$_2$, —C≡CH, —C≡CCH$_3$, —CH$_2$C≡CH, each of which is optionally mono- or polysubstituted by identical or different substituents selected from the group consisting of OH, F, Cl, cyano or represents $C(O)NR^9R^{10}$, $C(O)R^9$, $C(O)OR^9$, $S(O)_2R^9$, $C(S)NR^9R^{10}$, $C(S)R^9$, $S(O)_2NR^9R^{10}$ $R^6$ represents H, Cl, F, Cyano or represents methyl, ethyl, n-propyl, iso-propyl, n-butyl, iso-butyl, sec-butyl, tert-butyl, n-pentyl, cyclopropyl, cyclobutyl, cyclopentyl, cyclohexyl, CH=CH$_2$, —CH$_2$CH=CH$_2$, —CH$_2$C≡CH, —C≡CH, methoxy, ethoxy, n-propoxy, iso-propoxy, n-butoxy, tert-butoxy, methylthio, ethylthio, n-propylthio, iso-propylthio, tertbutylthio, n-butylthio, sec-butylthio, iso-butylthio, each of which is optionally mono- or polysubstituted by identical or different substituents selected from the group consisting of $R^{11}$, $R^7$ and $R^8$ represent H, $C(S)R^{12}$, $C(O)R^{12}$, $SO_2R^{12}$, $C(O)OR^{12}$, $OR^{12}$ or $C(O)NR^{12}R^{13}$ or represent methyl, ethyl, n-propyl, iso-propyl, n-butyl, iso-butyl, sec-butyl, tert-butyl, n-pentyl, cyclopropyl, cyclopropylmethyl, cyclobutyl, cyclopentyl, cyclohexyl, cyclopentenyl, cyclohexenyl, —CH=CH$_2$, —CH$_2$CH=CH$_2$, —CH$_2$C≡CH, —C≡CH, phenyl, naphthalenyl, benzyl, phenethyl, phenoxymethyl, pyridinyl, pyrazinyl, pyrimidinyl, furanyl, thienyl, thietanyl, oxetanyl, pyrazolyl, imidazolyl, tetrahydrofuranyl, tetrahydropyranyl, morpholinyl, pyrrolidinyl, piperidinyl, indanyl, dithiolanyl, dioxanyl, dioxolanyl, tetrahydrothiopyranyl, oxazolyl, isoxazolyl triazolyl each of which is optionally mono- or polysubstituted by identical or different substituents selected from the group consisting of F, Cl, Br, OH, =O, cyano, methyl, ethyl, n-propyl, iso-propyl, n-butyl, iso-butyl, sec-butyl, tert-butyl, n-pentyl, cyclopropyl, cyclobutyl, cyclopentyl, or methoxy, ethoxy, n-propoxy, iso-propoxy, n-butoxy, tert-butoxy, methylsulfanyl, methylsulfinyl, nitro, trifluormethyl, difluormethyl, acetyl, methoxycarbonyl, ethoxycarbonyl, O—C(O)R$^9$, ($C_1$-$C_6$-alkylideneamino) oxy, aryl, heteroaryl, heterocyclyl, $C_1$-$C_3$-alkoxyethoxy, NHC(O)H or cyclopropyl, cyclobutyl, cyclopentyl, cyclohexyl bridged by a two to eight atom containing chain, $R^9$ and $R^{10}$ represent methyl, ethyl, n-propyl, iso-propyl, n-butyl, iso-butyl, sec-butyl, tert-butyl, n-pentyl, cyclopropyl, cyclobutyl, cyclopentyl, cyclohexyl, —CH=CH$_2$, —CH$_2$CH=CH$_2$, —CH$_2$C≡CH, —C≡CH, phenyl, benzyl, phenethyl each of which is optionally mono- or polysubstituted by identical or different substituents selected from the group consisting of F, Cl, Br, I, OH, carbonyl, cyano or represent H, $R^{11}$ represents OH, =O, F, Cl, Br, I, cyano, NH—C(O)R$^9$, $NR^9R^{10}$, $C(O)R^9$, $C(O)OR^9$, $C(O)NR^9R^{10}$, $SO_2R^9$, $OC(O)R^9$ or represents methyl, ethyl, n-propyl, iso-propyl, n-butyl, iso-butyl, sec-butyl, tert-butyl, n-pentyl, cyclopropyl, cyclobutyl, cyclopentyl, cyclohexyl, —CH=CH$_2$, —CH$_2$CH=CH$_2$, —CH$_2$C≡CH, —C≡CH, phenyl, methoxy, ethoxy, tetrahydrofuranyl, 3-tetrahydrofuranyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-Isoxazolin-4-yl, 4-Isoxazolin-4-yl, 2-Isoxazolin-5-yl, 3-Isoxazolin-5-yl, 4-isoxazolin-5-yl, 2-isothiazolin-3-yl, 3-isothiazolin-3- yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2-piperidinyl, 3-piperidinyl, 4-piperidinyl, 2-piperazinyl, furan-2-yl, furan-3-yl, thiophen-2-yl, thiophen-3-yl, isoxazol-3-yl, isoxazol-4-yl, isoxazol-5-yl, 1H-pyrrol-1-yl, 1H-pyrrol-2-yl, 1H-pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, Imidazol-1-yl, Imidazol-2-yl, Imidazol-4-yl, Pyridin-2-yl, Pyridin-3-yl, pyridin-4-yl, pyridazin-3-yl, pyridazin-4-yl, pyrimidin-2-yl, pyrimidin-4-yl, pyrimidin-5-yl, pyrazin-2-yl, each of which is optionally mono- or polysubstituted by identical or different substituents selected from the group consisting of F, Cl, Br, I, OH, carbonyl, cyano, methyl, ethyl, methoxy, $R^{12}$ and $R^{13}$ represent H or represents methyl, ethyl, n-propyl, iso-propyl, n-butyl, iso-butyl, sec-butyl, tert-butyl, n-pentyl, cyclopropyl, cyclobutyl, cyclopentyl, cyclohexyl, —CH=CH$_2$, —CH$_2$CH=CH$_2$, —CH$_2$C=CH, —C=CH, phenyl, each of which is optionally mono- or polysubstituted by identical or different sub stituents selected from the group consisting of F, Cl, Br, I, OH, carbonyl, cyano, methyl, ethyl, n-propyl, iso-propyl, n-butyl, iso-butyl, sec-butyl, tert-butyl, n-pentyl or methoxy, ethoxy, n-propoxy, iso-propoxy, n-butoxy, tert-butoxy, and/or an agrochemically active salt thereof.

3. The heterocyclylpyri(mi)dinylpyrazole of the formula (I) as claimed in claim 1,
in which
U represents a structure of formula

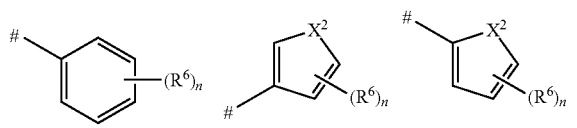

$X^1$ represents C—H,
$X^2$ represents S or O,
Y represents 0 or N with N being optionally substituted by $R^5$,
W represents C, N each of which is optionally substituted by identical or different substituents selected from the group consisting of $R^5$
or represents 0 if Y equals N,
a,b represent a single or double bond
with the proviso that "a" and "b" represent a single bond if W equals 0, "a" represents a single bond if Q equals C=C or C—Si and "b" represents a single bond if Y equals 0,
n is 0,1,2, 3 or 4
Q represents C, C—C, C—Si or C=C each of which is optionally mono or polysubstituted by identical or different substituents selected from the group consisting of $R^5$,
$R^1$ represents formamido, acetyl, n-propionyl, isobutyryl, 2-methylbutanoyl, 3-methylbutanoyl, 3,3-dimethylbutanoyl, methoxyacetyl, (2-methoxyethoxy)acetyl, 3,3,3-trifluoropropanoyl, cyanoacetyl, lactoyl, 2-hydroxy-2-methylpropanoyl, (methylsulfanyl)acetyl, 2-(4-chlorophenoxyl)propanoyl, phenylacetyl, 2-phenylpropanoyl, 2-(4-fluorophenyl)propanoyl, 2-(3-fluorophenyl)propanoyl, 3-phenylpropanoyl, 3-(4-chlorophenyl)propanoyl, 2-(2-fluorophenyl)propanoyl, cyclopentylacetyl, cyclopropylacetyl, cyclopropylcarbonyl, (2-methylcyclopropyl)carbonyl, (1-chlorocyclopropyl)carbonyl, cyclobutylcarbonyl, 2,3-dihydro-1H-inden-2-ylcarbonyl, (2-phenylcyclopropyl)carbonyl, methacryloyl, 3-methylbut-2-enoyl, 4-methylpent-3-enoyl, benzoyl, 4-fluorobenzoyl, 3-thienylcarbonyl, 2-thienylcarbonyl, tetrahydrofuran-2-ylcarbonyl, tetrahydrofuran-3-ylcarbonyl, tetrahydro-2H-pyran-4-ylcarbonyl, tetrahydro-2H-pyran-3-ylcarbonyl, methoxycarbonyl, ethoxycarbonyl, isopropoxycarbonyl, tert-butoxycarbonyl, difluoroacetyl, trifluoroacetyl or $R^1$ represents 1-cyclopropyl-cyclopropylcarbonyl, cyclopentylcarbonyl, bicyclo[2.2.1]heptane-2-carbonyl, bicyclo[4.1.0]heptane-7-carbonyl, 2-propylpentanoyl, 1,3-dithiolan-2-ylcarbonyl, (2,2,3,3-tetramethylcyclopropyl)carbonyl, cyclohex-1-en-1-ylacetyl, (5-methyl-1,2-oxazol-3-yl)carbonyl, 3- (1H-1,2,3-triazol-1-yl)propanoyl, 2-[(isopropylideneamino)oxy]propanoyl, (3,5-dimethyl-1,2-oxazol-4-yl)carbonyl, 5-oxohexanoyl, (1-methylcyclopropyl)carbonyl, [(isopropylideneamino)oxy]acetyl, 1H-pyrazol-1-ylacetyl, tetrahydro-2H-pyran-3-ylacetyl, (1-methylcyclopentyl)carbonyl, (5-methyl-1,3-dioxan-5-yl)carbonyl, (1-cyanocyclopropyl)carbonyl, tetrahydro-2H-thiopyran-4-ylcarbonyl, 1,1'-bi(cyclopropyl)-1-ylcarbonyl, (3S)-3-methylpentanoyl, (3R)-3-methylpentanoyl, 3-fluoro-2-(fluoromethyl)-2-methylpropanoyl, (4-oxocyclohexyl)carbonyl, cyclopent-3-en-1-ylcarbonyl, 2-methyl-3-furoyl, 2,4-dimethylhexanoyl, (2-chloro-2-fluorocyclopropyl)carbonyl, 2-fluoro-2-methylpropanoyl, (5-fluoropyridin-3-yl)carbonyl, 2-fluoropropanoyl, (3-oxocyclopentyl)carbonyl, (1,5-dimethyl-1H-pyrazol-4-yl)carbonyl optionally substituted with OH, F, Cl, CN, O—$C_1$-$C_6$-alkyl, $C_1$-$C_6$-alkyl, $C_2$-$C_6$-alkenyl, $C_2$-$C_6$-alkinyl, $C_1$-$C_6$-haloalkyl, $C_2$-$C_6$-haloalkenyl, $C_1$-$C_6$—S-alkyl, $R^2$ represents H, Methyl, methylsulfanyl, methoxymethyl, difluoromethyl, 2-hydroxypropan-2-yl, hydroxymethyl, 2-hydroxyethyl, 2-cyanoethyl, Ethyl, n-propyl, methoxy, ethoxy, acetyl, n-propionyl, isobutyryl, cyclopropylacetyl, cyclopropylcarbonyl, difluoroacetyl, trifluoroacetyl, methoxycarbonyl, ethoxycarbonyl, isopropoxycarbonyl, propoxycarbonyl, sec-butoxycarbonyl optionally substituted with OH, F, Cl, CN, O—$C_1$-$C_6$-alkyl, $C_1$-$C_6$-alkyl, $C_2$-$C_6$-alkenyl, $C_2$-$C_6$-alkinyl, $C_1$-$C_6$-haloalkyl, $C_2$-$C_6$-haloalkenyl, $C_1$-$C_6$—S-alkyl, $R^3$ represents H, F, Cl, Methyl,
$R^4$ represents H, F, Cl, Methyl,
$R^5$ represents as substituent for C: H, Cyano, F, OH, =O, methyl, ethyl, n-propyl, iso-propyl, n-butyl, iso-butyl, sec-butyl, tert-butyl, cyclopropyl, each of which is optionally mono- or polysubstituted by identical or different substituents from the group consisting of OH, F, Cl, cyano and represents as substituent for N: H, methyl, ethyl, n-propyl, iso-propyl, cyclopropyl, each of which is optionally mono- or polysubstituted by identical or different substituents selected from the group consisting of OH, F, Cl, cyano or represents acetyl, propionyl, isobutyryl, methoxycarbonyl, ethoxycarbonyl, methylcarbamoyl, dimethylcarbamoyl, diethylcarbamoyl, methylsulfonyl, ethylsulfonyl $R^6$ represents H, Cl, F, methyl, ethyl, cyano, difluoromethyl, trifluoromethyl,
and/or an agrochemically active salt thereof.

4. The heterocyclylpyri(mi)dinylpyrazole of the formula (I) as claimed in claim 1,
in which
U represents a structure of formula

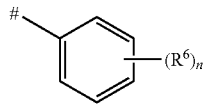

$X^1$ represents C—H,
Y represents O,
W represents C which is optionally substituted by identical or different substituents selected from the group consisting of $R^5$,
a and b represent a single bond,
n is 0, 1 or 2,
Q represents C or C—C, each of which is optionally mono or polysubstituted by identical or different substituents selected from the group consisting of $R^5$,
$R^1$ represents acetyl, n-propionyl, isobutyryl, 2-methylbutanoyl, 3-methylbutanoyl, lactoyl, phenylacetyl, cyclopropylacetyl, cyclopropylcarbonyl, 1-cyclopropyl-cyclopropylcarbonyl, cyclobutylcarbonyl, cyclopentylcarbonyl, bicyclo[2.2.1]heptane-2-carbonyl, bicyclo[4.1.0]heptane-7-carbonyl, (2-methylcyclopropyl)carbonyl, cyclobutylcarbonyl, tetrahydrofuran-3-ylcarbonyl, 3,3,3-trifluoropropanoyl, tetrahydro-2H-pyran-4-ylcarbonyl, 3-phenylpropanoyl, 2-phenylpropanoyl, 1,3-dithiolan-2-ylcarbonyl, 5-oxohexanoyl, (1-methylcyclopropyl)carbonyl, (4-oxocyclohexyl)carbonyl, 2-fluoro-2-methylpropanoyl, 2-fluoropropanoyl,
$R^2$ represents H, acetyl, n-propionyl, isobutyryl, cyclopropylacetyl, cyclopropylcarbonyl, methoxycarbonyl, ethoxycarbonyl, isopropoxycarbonyl, propoxycarbonyl, sec-butoxycarbonyl,
$R^3$ represents H,
$R^4$ represents H, F,
$R^5$ represents H, Cyano, F, OH, =O, methyl, ethyl, n-propyl, Cyclopropyl, Haloalkyl, Cyanoalkyl,
$R^6$ represents H, F
and/or an agrochemically active salt thereof.

5. A composition for controlling phytopathogenic harmful and mycotoxin producing fungi, comprising at least one heterocyclylpyri(mi)dinylpyrazole of the formula (I) and/or salt as claimed in claim 1, in addition to one or more extenders and/or surfactants.

6. A method for controlling phytopathogenic harmful and mycotoxin producing fungi, comprising applying heterocyclylpyri(mi)dinylpyrazole of the formula (I) and/or salt thereof as claimed in claim 1 to one or more microorganisms and/or a habitat thereof.

7. A process for preparing a composition for controlling unwanted microorganisms, comprising mixing heterocyclylpyri(mi)dinylpyrazole of the formula (I) and/or salt thereof according to claim 1 with one or more extenders and/or surfactants.

* * * * *